(12) United States Patent
Zhang et al.

(10) Patent No.: US 10,266,848 B2
(45) Date of Patent: *Apr. 23, 2019

(54) METHODS AND COMPOSITIONS TO INCREASE SOMATIC CELL NUCLEAR TRANSFER (SCNT) EFFICIENCY BY REMOVING HISTONE H3-LYSINE TRIMETHYLATION

(71) Applicant: CHILDREN'S MEDICAL CENTER CORPORATION, Boston, MA (US)

(72) Inventors: Yi Zhang, Boston, MA (US); Shogo Matoba, Boston, MA (US)

(73) Assignee: CHILDREN'S MEDICAL CENTER CORPORATION, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/017,157

(22) Filed: Jun. 25, 2018

(65) Prior Publication Data

US 2018/0363008 A1 Dec. 20, 2018

Related U.S. Application Data

(63) Continuation of application No. 15/511,348, filed as application No. PCT/US2015/050178 on Sep. 15, 2015.

(60) Provisional application No. 62/053,514, filed on Sep. 22, 2014, provisional application No. 62/050,308, filed on Sep. 15, 2014.

(51) Int. Cl.
| | |
|---|---|
| *C12N 5/073* | (2010.01) |
| *A01K 67/027* | (2006.01) |
| *C12N 15/113* | (2010.01) |
| *C12N 15/877* | (2010.01) |
| *C12N 5/0735* | (2010.01) |

(52) U.S. Cl.
CPC ........ *C12N 15/877* (2013.01); *A01K 67/0273* (2013.01); *C12N 5/0604* (2013.01); *C12N 5/0606* (2013.01); *C12N 15/1137* (2013.01); *C12Y 201/01043* (2013.01); *A01K 2227/105* (2013.01); *C12N 2310/14* (2013.01); *C12N 2517/04* (2013.01)

(58) Field of Classification Search
CPC .. C12N 15/877; C12N 5/0604; C12N 5/0606; C12N 15/1137; C12N 2310/14; C12N 2517/04; A01K 67/0273; A01K 2227/105; C12Y 201/0143

See application file for complete search history.

(56) References Cited

U.S. PATENT DOCUMENTS

| | | |
|---|---|---|
| 2009/0055945 A1 | 2/2009 | Kishigami et al. |
| 2011/0136145 A1 | 6/2011 | Song et al. |
| 2011/0172107 A1 | 7/2011 | Katz et al. |
| 2013/0189780 A1 | 7/2013 | Shoemaker et al. |
| 2014/0234968 A1 | 8/2014 | Chung et al. |
| 2017/0327846 A1 | 11/2017 | Zhang et al. |

FOREIGN PATENT DOCUMENTS

| | | |
|---|---|---|
| WO | 2009143421 A2 | 11/2009 |
| WO | 2010033920 A2 | 3/2010 |
| WO | 2014197835 A2 | 12/2014 |
| WO | 2016044271 A2 | 3/2016 |

OTHER PUBLICATIONS

Antony (2011). Manipulation of the epigenetic mark histone 3 lysine 9 tri-methylation (H3K9me3) in donor cells prior to nuclear transfer (Doctoral Dissertation). Retrieved from http://researchspace.auckland.ac.nz.*
Ralf Kuhn, Wolfgang Wurst (eds.), Gene Knockout Protocols: Second Edition, vol. 530, Humana Press, Chapter 13, Cloning of ES Cells and Mice by Nuclear Transfer, pp. 251-265,2009.*
Chung, Y.G. et al., "Histone Demethylase Expression Enhances Human Somatic Cell Nuclear Transfer Efficiency and Promotes Derivation of Pluripotent Stem Cells," Cell Stem Cell, vol. 17, No. 6, Oct. 29, 2015, pp. 758-766.
Matoba, S. et al., "Embryonic Development following Somatic Cell Nuclear Transfer Impeded by Persisting Histone Methylation," Cell, Cell Press, Amsterdam, NL, vol. 159, No. 4, Oct. 20, 2014, pp. 884-895.
Markoulaki, S. et al., "Somatic cell nuclear transfer and derivation of embryonic stem cells in the mouse," Methods, Academic Press, US, vol. 45, No. 2, Jun. 1, 2008, pp. 101-114.
Zhang, M. et al., "Defective Chromatin Structure in Somatic Cell Cloned Mouse Embryos," Journal of Biological Chemistry, vol. 284, No. 37, Jul. 14, 2009, pp. 24981-24987.
Loh, Y.H. et al., "Jmjd1a and Jmjd2c histone H3 Lys 9 demethylases regulate self-renewal in embryonic stem cells," Genes and Development, vol. 21, No. 20, Oct. 15, 2007, pp. 2545-2557.
Roderiguez-Osorio, N. et al., "Reprogramming mammalian somatic cells," Theriogenology, vol. 78, No. 9, Dec. 1, 2012, pp. 1869-1886.
Tachibana, M. et al., "Human Embryonic Stem Cells Derived by Somatic Cell Nuclear Transfer," Cell, vol. 153, No. 6, Jun. 6, 2013, pp. 1228-1238.
European Search Report in corresponding European Patent Application No. 15841324.5, dated Mar. 21, 2013 (8 pages).

(Continued)

*Primary Examiner* — Thaian N Ton
(74) *Attorney, Agent, or Firm* — Melissa Hunter-Ensor; Wade Haaland; Greenberg Traurig, LLP

(57) ABSTRACT

The present invention provides methods and compostions to improve the efficiency of somatic cell nuclear transfer (SCNT) and the consequent production of nuclear transfer ESC (ntESC) and transgenic cells and/or non-human animals. More specifically, the present invention relates to the discovery that trimethylation of Histone H3-Lysine 9 (H3K9me3) in reprogramming resistant regions (RRRs) in the nuclear genetic material of donor somatic cells prevents efficient somatic cell nuclear reprogramming or SCNT. The present invention provide methods and compositions to decrease H3K9me3 in methods to improve efficacy of SCNT by exogenous or overexpression of the demethylase Kdm4 family and/or inhibiting methylation of H3K9me3 by inhibiting the histone methyltransferases Suv39h1 and/or Suv39h2.

8 Claims, 12 Drawing Sheets

Specification includes a Sequence Listing.

(56) References Cited

OTHER PUBLICATIONS

Kishigami, S. et al., "Significant improvement of mouse cloning technique by treatment with trichostatin A after somatic nuclear transfer," Biochemical and Biophysical Research Communications, vol. 340, pp. 183-189 (2006).

Yamada, et al., "Human oocytes reprogram adult somatic nuclei of type 1 diabetic to diploid pluripotent stem cells," Nature, vol. 510, pp. 533-536 (Jun. 26, 2014).

Noggle, et al., Human oocytes reprogram somatic cells to a pluripotent state, Nature, vol. 478, pp. 70-77 (Oct. 6, 2011).

Yamada, et al., "Human oocytes reprogram adult somatic nuclei of type 1 diabetic to diploid pluripotent stem cells," Nature, vol. 510, 16 pages (Jun. 26, 2014).

Chung, et al., "Human somatic cell nuclear transfer using adult cells," Cell Stem Cell, Apr. 17, 2014, vol. 14, pp. 777-780, entire document.

International Search Report and Written Opinion for corresponding PCT/US2016/055890, dated Dec. 27, 2016 (17 pages).

U.S. Appl. No. 15/948,781, filed Apr. 9, 2018.

Chung et al., "Histone Demethylase Expression Enhances Human Somatic Cell Nuclear Transfer Efficiency and Promotes Derivation of Pluripotent Stem Cells", Cell Stem Cell 17, 758-766, Dec. 3, 2015, Elsevier Inc., http://dx.doi.org/10.1016/j.stem.2015.10.001.

Liu et al., "Cloning of Macaque Monkeys by Somatic Cell Nuclear Transfer", Cell, 172:881-87.e7, 2018.

Vassena, R. et al., "Tough beginnings: Alterations in the transcriptome of cloned embryos during the first two cell cycles," ScienceDirect, Development Biology, vol. 304, pp. 75-79 (2007).

Suzuki T., et al., "Zygotically Activated Genes Are Supressed in Mouse Nuclear Transferred Embryos," www.researchgate.net/publication/6604910 (Abstract only).

Inoue, K. et al., "Impeding Xist Expression from the Active X Chromosome Improves Mouse Somatic Cell Nuclear Transfer," www.sciencemag.org (Abstract only).

Inoue, K. et al., "Inefficient reprogramming of the hematopoietic stem cell genome following nuclear transfer," Journal of Cell Science, vol. 119, pp. 1985-1991 (2006).

Matoba, et all., "RNAi-mediated knockdown of Xist can rescue the impaired postimplantation development of cloned mouse embryos," PNAS, vol. 108, No. 51, pp. 20621-20626, Dec. 20, 2011.

Akagi, S., "Treatment with a Histone Deacetylase Inhibitor after Nuclear Transfer Improves the Preimplantation Development of Cloned Bovine Embryos," Journal of Reproductions and Development, vol. 57, No. 1, pp. 120-126, (2011).

Zhao, J. et al., "Significant Improvement in Cloning Efficiency of an Inbred Miniature Pig by Histone Deacetylase Inhibitor Treatment after Somatic Cell Nuclear Transfer," BioOne Research Evolved, vol. 81, pp. 525-530 (2009).

Van Thuan, N. et al., "The histone deacetylase inhibitor scriptaid enhances nascent mRNA production and rescues full-term development in cloned inbred mice," Reproduction, vol. 138, pp. 309-317 (2009).

Antony et al., "Transient JMJD2B-mediated reduction of H3K9me3 levels improves reprogramming of embryonic stem cells into cloned embryos," Mol. Cell. Biol., 33(5), 974-983 (2013).

Thomson, et al., "Embryonic stem cell lines derived from human blastocysts," Science 282(5391) 1145-1147 (1998).

Kim et al., "Regulation of tumor suppressor p53 and HCT116 cell physiology by histone demethlyase JMJD2D/KDM4D," PLoS One 7(4) e34618 (2012).

International Search Report on corresponding PCT Patent Application No. PCT/US2015/050178, dated Mar. 7, 2016, 15 pages.

\* cited by examiner

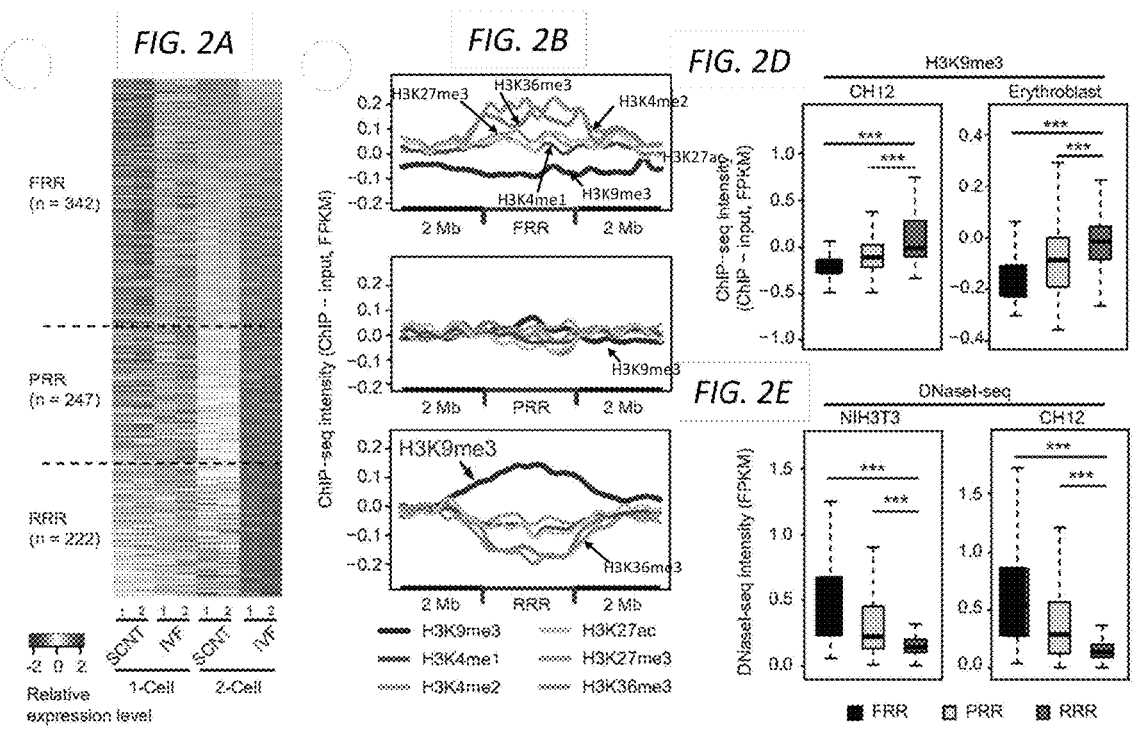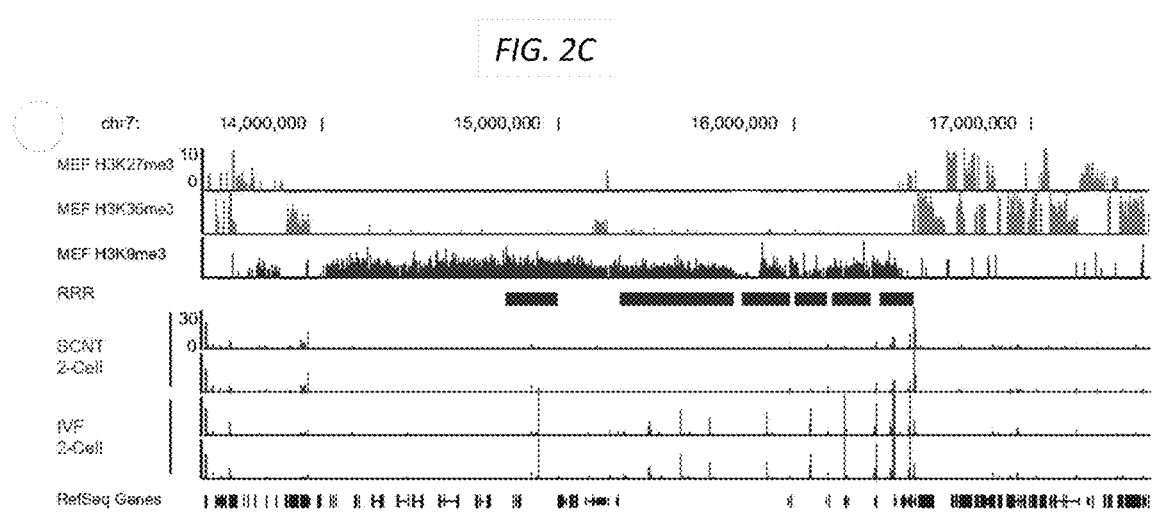

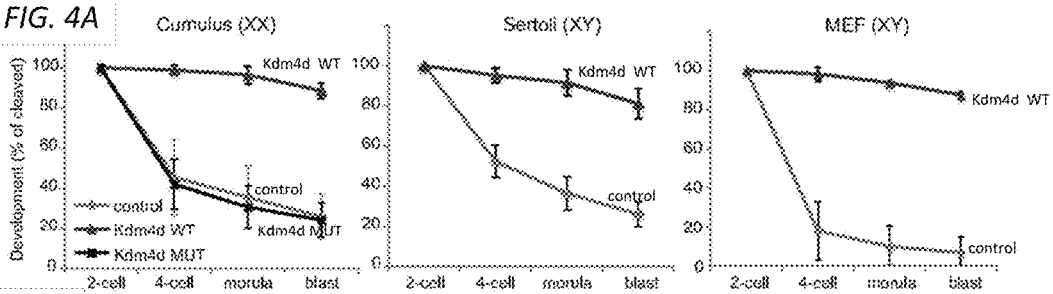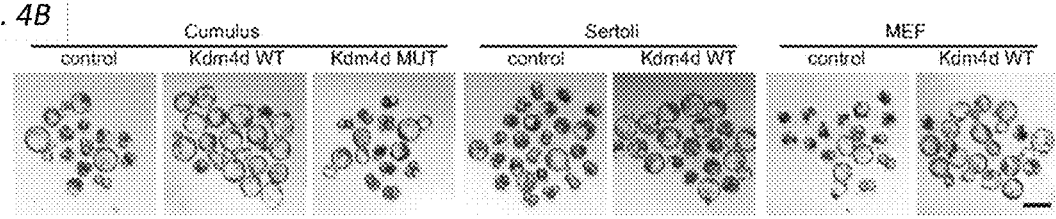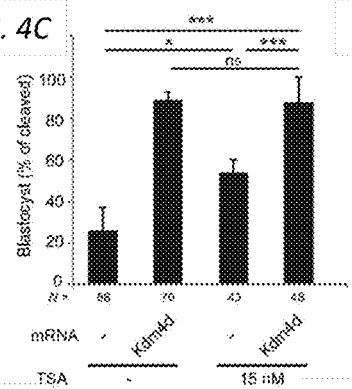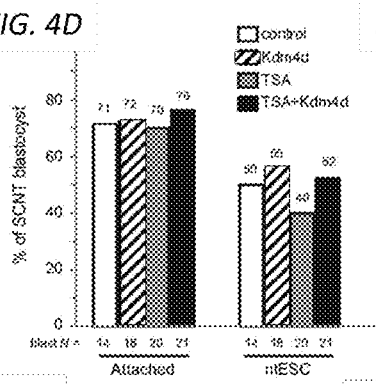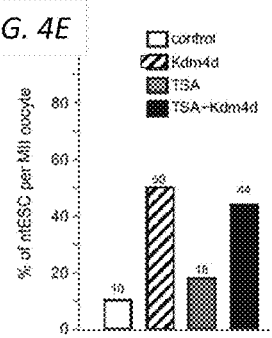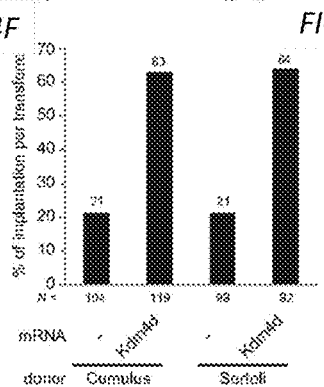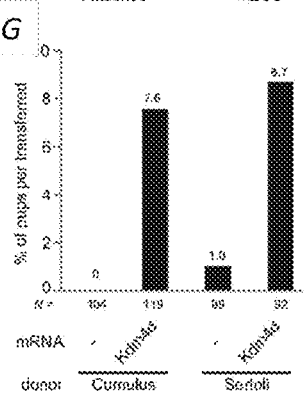

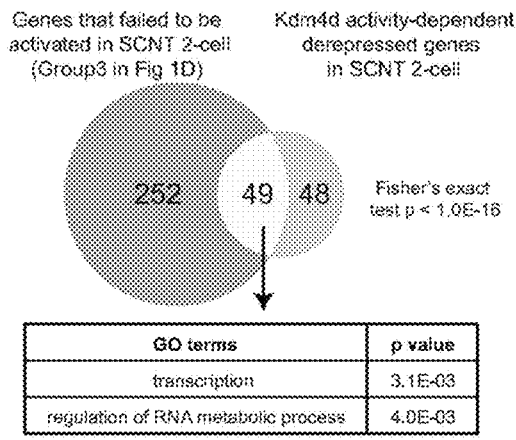
FIG. 5A
FIG. 5B
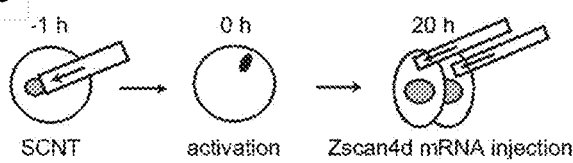
FIG. 5C
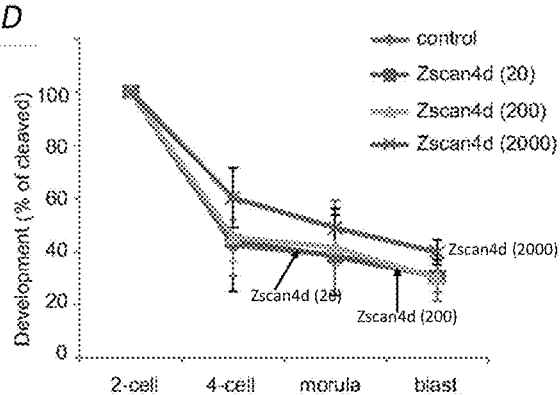
FIG. 5D
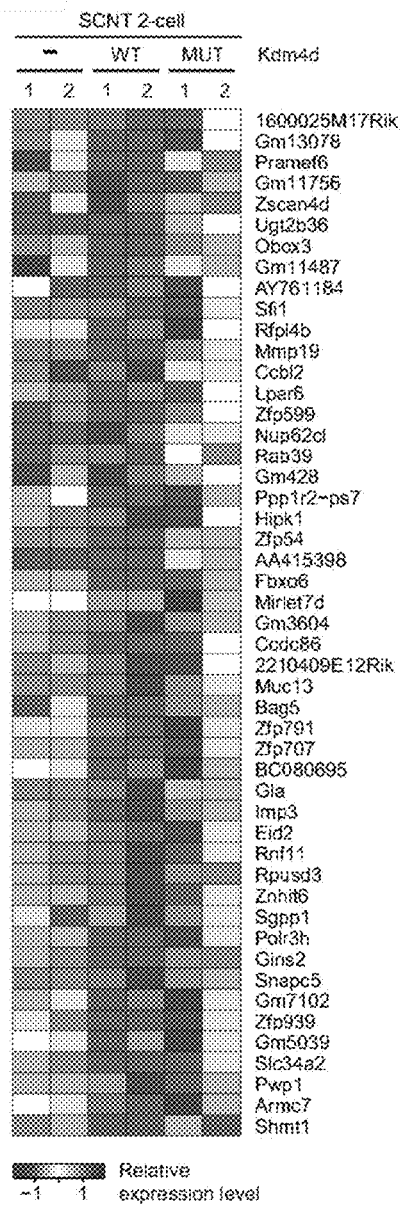

| Samples | replicates | total reads | uniquely mapped reads | uniquely mapped rate |
|---|---|---|---|---|
| Donor | 1 | 4.12E+07 | 3.21E+07 | 0.778 |
|  | 2 | 4.03E+07 | 3.18E+07 | 0.789 |
| IVF 1-Cell | 1 | 7.68E+07 | 5.43E+07 | 0.708 |
|  | 2 | 7.14E+07 | 5.05E+07 | 0.707 |
| SCNT 1-Cell | 1 | 7.47E+07 | 5.24E+07 | 0.702 |
|  | 2 | 7.15E+07 | 5.00E+07 | 0.699 |
| IVF 2-Cell | 1 | 6.40E+07 | 4.23E+07 | 0.661 |
|  | 2 | 6.55E+07 | 4.31E+07 | 0.658 |
| SCNT 2-Cell | 1 | 6.27E+07 | 4.42E+07 | 0.705 |
|  | 2 | 6.65E+07 | 4.73E+07 | 0.711 |
| SCNT 2-Cell Kdm4d WT | 1 | 4.18E+07 | 2.76E+07 | 0.660 |
|  | 2 | 3.36E+07 | 2.26E+07 | 0.672 |
| SCNT 2-Cell Kdm4d MUT | 1 | 3.91E+07 | 2.51E+07 | 0.642 |
|  | 2 | 3.82E+07 | 2.70E+07 | 0.707 |

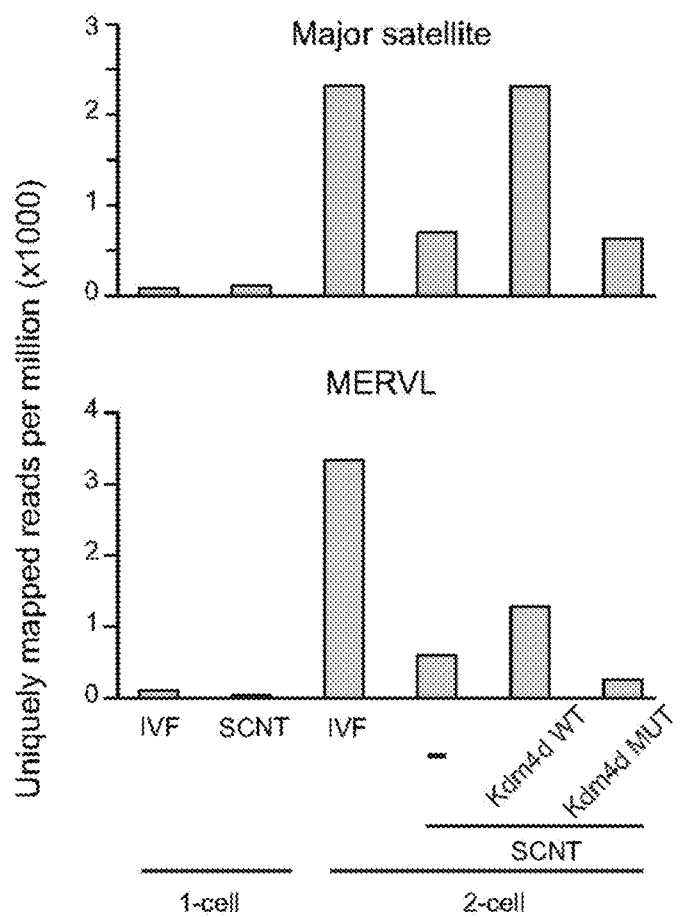

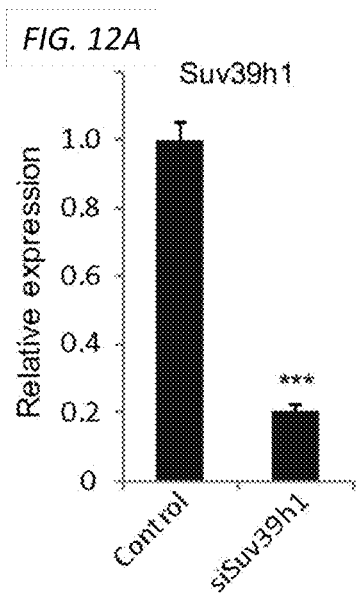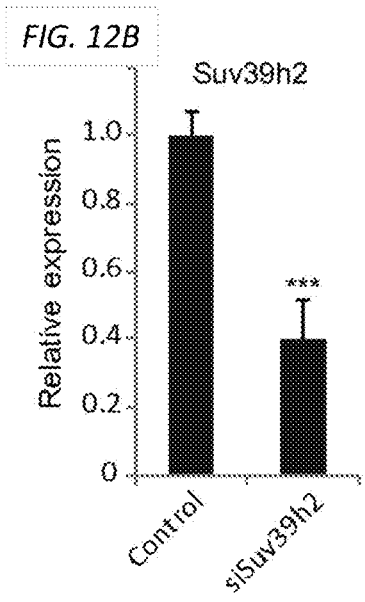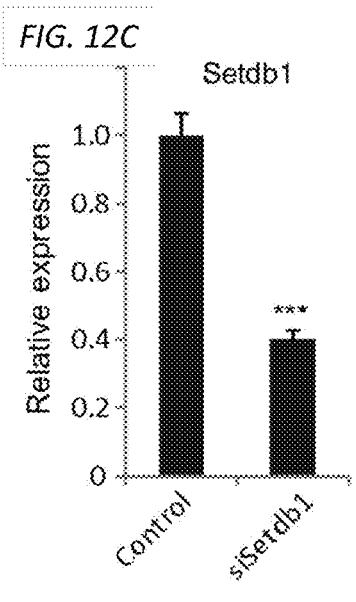

METHODS AND COMPOSITIONS TO INCREASE SOMATIC CELL NUCLEAR TRANSFER (SCNT) EFFICIENCY BY REMOVING HISTONE H3-LYSINE TRIMETHYLATION

CROSS REFERENCE TO RELATED APPLICATIONS

This application is a continuation of U.S. Utility application Ser. No. 15/511,348, filed Mar. 15, 2017, which is the US national stage application of PCT/US2015/050178, filed Sep. 15, 2015, which claims priority under 35 U.S.C. 119(e) of U.S. Provisional Patent Application Ser. No. 62/050,308 filed on Sep. 15, 2014 and U.S. Provisional Patent Application Ser. No. 62/053,514, filed on Sep. 22, 2014, the contents of each are incorporated herein by reference in their entirety.

GOVERNMENT SUPPORT

This invention was made with Government Support under NIH U01DK089565 awarded by the National Institutes of Health (NIH). The Government has certain rights in the invention.

BACKGROUND OF THE INVENTION

Terminally differentiated somatic cells can be reprogrammed to the totipotent state when transplanted into enucleated oocytes by the means of somatic cell nuclear transfer (SCNT) (Gurdon, 1962). Because SCNT allows the generation of an entire animal from a single nucleus of differentiated somatic cell, it has great potential in agriculture, biomedical industry, and endangered species conservation (Yang et al., 2007). Indeed, more than 20 mammalian species have been cloned through SCNT (Rodriguez-Osorio et al., 2012) since the first successful mammalian cloning in sheep in 1997 (Wilmut et al., 1997). Moreover, because pluripotent embryonic stem cells can be established from SCNT-generated blastocysts (Wakayama et al., 2001), SCNT holds great promise in human therapies (Hochedlinger and Jaenisch, 2003). This promise is closer to reality after the recent success in derivation of the first human nuclear transfer embryonic stem cells (ntESCs) (Tachibana et al., 2013), as well as the generation of human ntESCs from aged adult or human patient cells (Chung et al., 2014; Yamada et al., 2014). These ntESCs can serve as valuable cell sources for in vitro disease modeling as well as a source of cells for regenerative therapy and and cell/tissue-replacement therapies.

Despite its tremendous potential, several technical problems have prevented the practical use of SCNT, in particular, it has an extremely low efficiency in producing cloned animals. For example, approximately half of mouse SCNT embryos display developmental arrest prior to implantation, and only 1-2% of embryos transferred to surrogate mothers develop to term (Ogura et al., 2013). With the exception of bovine species, which have a higher rate of reproductive cloning efficiency (5 to 20%), the overall reproductive cloning efficiency in all other species is very low (1 to 5%) (Rodriguez-Osorio et al., 2012). Furthermore, the success rate of human ntESCs establishment is also low owing to their poor preimplantation development (10 to 25% to the blastocyst stage; Tachibana et al., 2013; Yamada et al., 2014).

To realize the application potential of SCNT, efforts have been taken to improve SCNT cloning efficiency. First, transient treatment of 1-cell SCNT embryos with histone deacetylase (HDAC) inhibitors, such as Tricostatin A (TSA) or scriptaid, has been reported to improve reprogramming efficiency of various mammalian species including mouse (Kishigami et al., 2006; Van Thuan et al., 2009), pig (Zhao et al., 2009), bovine (Akagi et al., 2011) and humans (Tachibana et al., 2013; Yamada et al., 2014). Secondly, knockout or knockdown of Xist has been reported to improve postimplantation development of mouse SCNT embryos (Inoue et al., 2010; Matoba et al., 2011). However, neither of these methods improve the cloning efficiency of SCNT enough for SCNT to be useful for reproductive cloning of non-human mammals, or for the generation of human pluripotent stem cells (e.g. human ntESC) for therapeutic cloning or regenerative therapies.

The developmental defects of SCNT embryos start to appear at the time of zygotic gene activation (ZGA), which occurs at the 2-cell stage in mouse and at the 4- to 8-cell stage in pig, bovine and human (Schultz, 2002). SCNT embryos have difficulties in ZGA due to undefined epigenetic barriers pre-existing in the genome of donor cells. Although a number of dysregulated genes in mouse 2-cell SCNT embryos (Inoue et al., 2006; Suzuki et al., 2006; Vassena et al., 2007), and in the late cleavage stage human SCNT embryos (Noggle et al., 2011) have been identified, the nature of the "pre-existing epigenetic barriers" and their relationship with impaired ZGA in SCNT embryos are unknown.

Accordingly, there is a need to improve mammalian cloning efficiency by removing such epigenetic barriers in the genome of the donor cell nuclei so that the SCNT embryo can proceed efficiently through zygotic gene activation (ZGA) and the SCNT embryo can proceed through the 2-, 4- and 8-cell stage to blastocyst without developmental defects or loss of viability.

SUMMARY OF THE INVENTION

Mammalian oocytes can reprogram somatic cells into a totipotent state, which allows animal reproductive cloning through somatic cell nuclear transfer (SCNT), or the production of ES cell lines (ntESC) from blastocyst developed from SCNT embryos. However, the majority of SCNT embryos fail to develop into blastocyst or to term due to undefined reprogramming defects. The inefficiency of mammalian SCNT is a critical limitation to the development of patient-specific hESC lines for regenerative medicine applications.

The production of human SCNT-derived human blastocysts using human donor somatic cells has been reported, but the blastocyst quality and developmental efficiency was insufficient to allow the production of a human embryonic stem cell line (human ntESC) (French A J et al., Stem Cells 26, 485-493 (2008)). Human nuclear transfer embryonic stem cells (ntESCs) have been reported (Tachibana et al., 2013), as well as the generation of human ntESCs from aged adult or human patient cells (Chung et al., 2014; Yamada et al., 2014). However, the success rate for human ntESC establishment is very low due to poor pre-implantation development (only 10 to 25% develop to the blastocyst stage; Tachibana et al., 2013; Yamada et al., 2014). The refinement of human SCNT techniques is therefore critical to improve the development to human SCNT embryos to blastocyst stage, to reduce the number of donor oocytes required for SCNT, and successfully produce human and patient-specific isogenic embryonic stem cell lines for research and cell based therapies.

Herein the inventors have discovered that histone H3 lysine 9 trimethylation (H3K9me3) in the genome of donor nuclei of differentiated somatic cells is a major pre-existing epigenetic barrier for efficient reprogramming by SCNT, and have discovered that decreasing H3K9me3 methylation can increase the efficiency of SCNT, in particular, increase the efficiency of pre-implantation development of SCNT embryos to 2-cell, 4-cell or blastocyst stage. More specifically, through comparative analysis the inventors have discovered genomic domains that are resistant to zygotic gene activation (ZGA) in SCNT embryos. These reprogramming resistant regions (RRRs) are enriched for the repressive histone modification, H3K9me3, in somatic cells and removal of this epigenetic mark either through (i) increased expression of an H3K9me3-specific demethylase, such as, e.g., Kdm4d or members of the Kdm4 family in oocytes and/or (ii) knocking-down or inhibiting a H3K9 methyltransferases, such as, e.g., Suv39h1 or Suv39h2 or both (i.e., Suv39h1/2), in somatic donor nuclei not only attenuates the ZGA defects and reactivates the RRRs, but also greatly improves the efficiency of SCNT, e.g., increases the % of SCNT embryos developing to 2-cell, 4-cell or blastocyst stage. Thus, the inventors have discovered that Suv39h1/2-mediated H3K9me3 is an "epigenetic barrier" of SCNT and have demonstrated that the inhibition and/or removal of the trimethylation of H3K9me3 in either the nuclei of the somatic donor cell, the recipient oocyte or the SCNT embryo can significantly improve SCNT cloning efficiency of mammalian cells, including human SCNT cloning and other non-human mammals.

Accordingly, the present invention is based on the inventor's discovery that H3K9me3 is enriched in the RRRs in somatic cells used in the production of SCNT embryos, and that the H3K9me3 barrier in somatic cells is established by Suv39h1/2. Importantly, the inventors have demonstrated that removal of H3K9me3 by overexpression of Kdm4d (e.g., by introduction of exogenous Kdm4d mRNA or cDNA) in the recipient oocyte, and/or inhibition of Suv39h1/2 in nuclei of the donor somati cell, results in a surprisingly significant increase in the efficiency of SCNT cloning. Interestingly, the inventors suprizingly discovered that removal of H3K9me3 resulted in an unexpected and significant increase in the efficiency of SCNT to more than about 80% of SCNT embryos that progressed to blastocyst stage, whereas the efficiency of normal SCNT embryos without removal of H3K9me3 remained at around 30%, demonstrating an unexpected 50% increase in efficiency of SCNT to blastocyst stage. Moreover, the inventors also demonstrate that H3K9me3 removal resulted in an unexpected and significant improvement of post-implantation development of SCNT embryos, with more than 8-fold of increase in mouse pup generation compared to the absence of artificial H3K9me3 removal.

Accordingly, aspects of the present invention are based on the discovery that the trimethylation of Histone H3-Lysine 9 (H3K9me3) prevents efficient somatic cell nuclear reprogramming or SCNT. The inventors have assessed two ways to improve efficacy of SCNT of mice embryos, (i) promoting demethylation of H3K9me3 by using overexpression (i.e., exogenous expression) of the demethylase Kdm4d (also known as Jmjd2d or Jhdm3d), and by (ii) inhibiting methylation of H3K9me3 by inhibiting the histone methyltransferases Suv39h1 and/or Suv39h2. Thus, overexpression of Kdm4d/Jmjd2d gene, and/or inhibitors of Suv39h1/2 proteins or genes are useful for removing epigenetic barriers in cell reprogramming, in particular SCNT.

Accordingly, aspects of the invention relate to methods, compositions and kits directed to increasing SCNT efficiency by reducing H3K9me3 methylation by either (i) expressing histone demethylases which are capable of demethylating H3K9me3, e.g., for example, members of the Kdm4 family of histone demethylases, such as, for example but not limited to, Jmjd2d/Kdm4d or Jmjd2a/Kdm4a, or Jmjd2b/Kdm4b or Jmjd2c/Kdm4c and/or (ii) inhibiting histone methytransferases that are involved in the methylation of H3K9me3, for example, inhibition of any one or a combination of Suv39h1, Suv39h2 or Setdb1. In some embodiment, the agent which increases the expression or activity of the Kdm4 family of histone demethylases Kdm4d (Jmjd2d), or Kdm4a (Jmjd2a), or Jmjd2b/Kdm4b or Jmjd2c/Kdm4c.

Although demethylation of H3K9me3 (by Kdm4c/Jmjd2c) has been reported to be used to increase the efficiency of somatic cell reprogramming (e.g., the generation of induced pluripotent stem (iPS) cells (Sridharan et al., 2013)), the demethylation of H3K9me3 for increasing the efficiency of SCNT from terminally differentiated somatic cells has not yet been reported. Antony et al. in "Transient JMJD2B-Mediated Reduction of H3K9me3 Levels Improve Reprogramming of Embryonic Stem Cells in Cloned Embryos." Mol. Cell Biol., 2013; 33(5); 974 report using Kdm4b/Jmjd2b in SCNT derived from donor nuclei from pluripotent ES cells. A pluripotent ES cell is a developmentally immature cell that is not the same as a terminally differentiated somatic cell. Importantly, there are significant differences in the global epigenetic status of an embryonic stem (ES) cell or an induced pluripotent stem (iPS) cell as compared to a differentiated somatic cell. Pluripotent ES cells have less epigenetic barriers, (e.g., less methylation, in particular in the reprogramming resistant regions (RRRs)) and therefore the efficiency of SCNT embryos produced when a ES cell nuclei is used as the donor nuclei is very different from the efficiency of SCNT embryos produced when the nuclei from a terminally differentiated somatic cell is used (Rideout et al., 2000, *Nature Genetics*, 24(2), 109-10).

In contrast to the report by Antony et al., the inventors herein demonstrate that decreasing H3K9me3 levels in a terminally differentiated somatic cell nuclei results in a surprising increase in pre-implantation development, with more than 80%, of the SCNT embryos successfully developing into blastocysts when demethylation of H3K9me3 is decreased (e.g., an increase from 26% to 89% when nuclei from Cumulus cells are used: from 26% to 81% when nuclei from Sertoli cells are used, and from 7% to 82% when nuclei from MEF cells are used). This result is highly unexpected given that Antony et al report only a minor improvement (about a 9% improvement) in pre-implantation development, even with ES-cell derived donor nuclei are used.

Furthermore, while Antony et al fail to demonstrate any improvement in post-implantation development by Jmjd2b/Kdm4b induction, the inventors herein demonstrate a more than 8-fold of increase in mouse pup generation from the SCNT embryos. Given that one purpose of SCNT is for reproductive cloning of non-human mammals and the generation of individual animals, which requires completion of postimplantation development, one of ordinary skill in the art reading Antony et al would conclude that Kdm4b injection into the nuclei of donor cells cannot improve SCNT efficiency. Furthermore, Antony et al., do not inhibit Suvh1/2 in the ES cells.

Furthermore, while there have been numerous reports of demethylation of H3K9me3 to increase the efficiency of reprogramming somatic cells to an earlier developmental stage (e.g., the generation of induced pluripotent stem (iPS) cells) (e.g., US applications 2011/0136145 and 2012/0034192 which are incorporated herein in in their entirety by reference), the mechanism of reprogramming somatic cells for the generation of iPS cells is significantly different from the mechanism of reprogramming somatic cells for the generation of SCNT embryos (as discussed in Pasque et al., 2011, Mechanisms of nuclear reprogramming by eggs and oocytes: a deterministic process? Nat. Rev. Mol. Cell Biol. 12, 453-459; and Apostolou, E., and Hochedlinger, K., 2013; Chromatin dynamics during cellular reprogramming. Nature 502, 462-471). Therefore what is learned from the demethylation of H3K9me3 in the generation of iPS cells is not relevant and cannot be transferred to methods for the successful generation of SCNT embryos and increasing both pre- and post-implantation efficiency of SCNT embryos.

In particular, notable differences exist regarding the barrier between SCNT and iPS reprogramming. Firstly, the H3K9me3-barrier in mouse iPSC reprogramming is established primarily by Setdb1 (Chen et al., 2013; Sridharan et al., 2013). In contrast, the inventors' results clearly point to Suv39h1/2, but not Setdb1, as the critical enzymes that establish the H3K9me3 barrier for SCNT reprogramming. Secondly, the downstream gene networks necessary for successful iPSC and SCNT reprogramming are different. For instance, in iPSC reprogramming, key core pluripotency network genes, such as Nanog and Sox2, which are repressed by the H3K9me3 barrier are expressed during relatively late stages of reprogramming (Chen et al., 2013; Sridharan et al., 2013). In contrast, in SCNT reprogramming, key genes repressed by H3K9me3 are expressed and have a critical function at the 2-cell embryonic stage (discussed herein below). This distinction most likely stems from the differences in the set of transcription factors required for successful reprogramming in each context. Indeed, core transcription factors Oct4/Pou5f1 which are required for iPSC reprogramming, have been demonstrated to be dispensable in SCNT reprogramming (Wu et al., 2013). Therefore, although H3K9m3 appears to be a common reprogramming barrier for both iPS cell generation and successful SCNT, its deposition, and how it affects the reprogramming process are very different in the method of reprogramming to generate iPS cells or the method of reprogramming to generate SCNT embryos.

Therefore, even if removal of the H3K9me3 barrier in reprogrammed somatic cells to iPS cells has been demonstrated, as different reprogramming genes and reprogramming mechanisms are used, there is no indication that such a method would work for reprogramming somatic cells for generation of SCNT embryos. In fact, both US applications 2011/0136145 and 2012/0034192 specifically state that their method only applies to reprogramming of somatic cells to iPSC and is not suitable for generation of totipotent cells or for the production of SCNT embryos. Therefore both 2011/0136145 and 2012/0034192 US applications teach away from the present invention.

Furthermore, as well as the very different mechanisms used for somatic cell reprogramming in the generation of iPSC as compared to the generation of SCNT embryos, which are outlined below in Table 1 below, the stem cells produced from reprogramming somatic cells to produce iPSC are markedly different from stem cells obtained from a SCNT embryo (Ma et al., 2014, Abnormalities in human pluripotent cells due to reprogramming mechanisms. Nature, 511(7508), 177-183).

TABLE 1

A summary of key differences between SCNT- and iPS-mediated reprogramming.

| Reprogramming features | iPS | SCNT | Source |
|---|---|---|---|
| Speed | Slow (days or weeks) | Fast (hours) | (Yamanaka & Blau, 2010) |
| Efficiency | Low | High | (Pasque, Miyamoto, & Gurdon, 2010) |
| Factors | Oct4, Sox2, Klf4 | Not yet identified (Not Oct4) | (Apostolou & Hochedlinger, 2013; Jullien, Pasque, Halley-Stott, Miyamoto, & Gurdon, 2011) |
| Mode | Stochastic | Deterministic | (Jullien et al., 2011) |
| Potency | Pluripotency | Totipotency | (Mitalipov & Don Wolf, 2009) |

Accordingly, as discussed above, as the reprogramming genes and mechanisms of reprogramming somatic cells to iPS cells are significantly different from the reprogramming genes and mechanisms of reprogramming somatic cells to SCNT, and as the resulting cells are significantly different, there is no indication or reason to believe that methods which work for reprogramming to produce iPSC would work reprogramming for generation of SCNT.

Accordingly, one aspect of the present invention relates to a method for increasing the efficiency of somatic cell nuclear transfer (SCNT) comprising contacting any one of a donor mammalian somatic cell, a recipient mammalian oocyte or a mammalian SCNT embryo (i.e., after fusion of the donor nuclei with the oocyte) with an agent which decreases H3K9me3 methylation in the donor mammalian cell, recipient mammalian oocyte or mammalian SCNT embryo, thereby increasing the efficiency of SCNT, e.g., increasing pre-implantation development of the SCNT embryo to blastocyst and/or increasing the post-implantation development of the SCNT embryo from blastocyst to viable offspring.

In some embodiments, the present invention provides a method for increasing the efficiency of somatic cell nuclear transfer (SCNT) comprising contacting a donor mammalian somatic cell, recipient mammalian oocyte or a mammalian SCNT embryo with at least one of (i) a Kdm4 family of histone demethylase and/or (ii) a H3K9 methyltransferase-inhibiting agent, to decrease H3K9me3 methylation in the donor mammalian cell, recipient mammalian oocyte or mammalian SCNT embryo, thereby removing the epigenetic barriers in the RRR and increasing the efficiency of the SCNT.

In some embodiments, increasing the efficiency of somatic cell nuclear transfer (SCNT) comprising contacting a donor mammalian somatic cell with at least one of (i) a Kdm4 family of histone demethylase and/or (ii) a H3K9 methyltransferase-inhibiting agent. In some embodiments, increasing the efficiency of somatic cell nuclear transfer (SCNT) comprising contacting an recipient mammalian oocyte, e.g., either nucleated or enucleated with at least one of (i) a Kdm4 family of histone demethylase and/or (ii) a H3K9 methyltransferase-inhibiting agent. In some embodiments, increasing the efficiency of somatic cell nuclear transfer (SCNT) comprising contacting an SCNT embryo, e.g., at least 5 hpa, or between 10-12 hpa (i.e. at 1-cell stage), or at about 20 hpa (i.e., early 2-cell stage) or between 20-28 hpa (i.e., 2-cell stage) with at least one of (i) a Kdm4 family of histone demethylase and/or (ii) a H3K9 methyltransferase-inhibiting agent.

In some embodiments, the reducing the H3K9me3 methylation occurs by overexpressing or exogenous expression of a Kdm4 gene, e.g., Kdm4d, in any one of, or a combination of: the mammalian donor oocyte (either pre-enucleation or after enucleation) or in the SCNT embryo (e.g., after at least 5 hours post activation (5 hpa) or at 1-cell stage, or at 2-cell stage), or the donor mammalian somatic cell. In some embodiments, exogenous expression of a Kdm4 gene, e.g., Kdm4d, occurs in the mammalian donor oocyte. In some embodiments, exogenous expression of a Kdm4 gene, e.g., Kdm4d, occurs in an enucleated mammalian donor oocyte. In some embodiments, exogenous expression of a Kdm4 gene, e.g., Kdm4d, occurs in the SCNT embryo at any one of 5 hpa, between 10-12 hpa (i.e. at 1-cell stage), at about 20 hpa (i.e., early 2-cell stage) or between 20-28 hpa (i.e., 2-cell stage). In some embodiments, where the SCNT embryo is contacted with an agent which inhibits H3K9me3, such agent, e.g., agent that increases exogenous expression of a Kdm4 gene, e.g., Kdm4d, (e.g., Kdm4d mRNA or mod-RNA), each cell of the SCNT embryo (e.g., each cell of the 2-cell embryo) is injected with the Kdm4d activating or overexpressing agent.

In other embodiments, the reducing the H3K9me3 methylation occurs by inhibiting the expression of Suv39h1 and/or Suv39h2, or both (Suv39h1/2), in any one of, or a combination of: the mammalian donor oocyte (either pre-enucleation or after enucleation) or in the SCNT embryo (e.g., after at least 5 hours post activation (5 hpa) or at 1-cell stage, or at 2-cell stage), or the donor mammalian somatic cell. In some embodiments, inhibition of Suv39h1 and/or Suv39h2, or both (Suv39h1/2), occurs in the donor somatic cell, e.g., at least about 24 hours, or at least about 48 hours, or at least about 3-days or at least about 4-days or more than 4-days before removal of the nuclei for transfer to the enucleated mammalian donor oocyte. In some embodiments, inhibiting the expression of Suv39h1 and/or Suv39h2, or both (Suv39h1/2) is by siRNA and occurs for at least 12 hours, or at least 24 hours or more, at the time periods prior to removal of the nuclei.

Another aspect of the present invention relates to a method for increasing the efficiency of somatic cell nuclear transfer (SCNT) comprising contacting or a mammalian SCNT embryo with an agent which decreases H3K9me3 methylation in the recipient mammalian oocyte or mammalian SCNT embryo, thereby increasing the efficiency of the SCNT. In some embodiments, the recipient mammalian oocyte is a mammalian oocyte prior to the injection of a donor nuclei obtained from a terminally differentiated somatic cell. In some embodiments, the recipient mammalian oocyte is an enucleated mammalian oocyte. In some embodiments, the SCNT embryo is a 1-cell stage, or 2-cell stage SCNT embryo. In some embodiments, the agent contacts a recipient mammalian oocyte or enucleated mammalian oocyte prior to nuclear transfer with a nucleus from a terminally differentiated somatic cell.

In some embodiments, the agent which contacts a recipient mammalian oocyte or mammalian SCNT embryo increases the expression or activity of at least one member of the Kdm4 family of histone demethylases, for example, at least one member of the Kdm4 (Jmjd2) family consisting of: Kdm4a, Kdm4b, Kdm4c or Kdm4d. In some embodiment, the agent which increases the expression or activity of the Kdm4 family of histone demethylases increases the expression or activity of Kdm4d (Jmjd2d) or Kdm4a (Jmjd2a) or Kdm4b or Kdm4c. In some embodiment, the agent comprises a nucleic acid sequence of Kdm4 from a mammalian species, e.g., human KDM4d (SEQ ID NO: 1), mouse Kdm4d (SEQ ID NO: 2), rat Kdm4d (SEQ ID NO:3), rabbit Kdm4d (SEQ ID NO:4), pig Kdm4d (SEQ ID NO:5), cattle Kdm4d (SEQ ID NO:6), macaque Kdm4d (SEQ ID NO:7), and chimpanzee Kdm4d (SEQ ID NO:8.), or a biologically active fragment or homologue of at least 80%, or at least about 85%, or at least about 90%, or at least about 95%, or at least about 98%, or at least about 99% sequence identity thereof which increases the efficiency of SCNT to a similar or greater extent (e.g., at least about 110%, or at least about 120%, or at least about 130%, or at least about 140%, or at least about 150%, or more than 150% increased) as compared to the corresponding sequence of SEQ ID NO: 1-8.

In some embodiments, the agent which contacts a recipient mammalian oocyte or mammalian SCNT embryo increases the expression of human KDM4d protein of SEQ ID NO: 55, and/or comprises a human KDM4d nucleic acid sequence corresponding of SEQ ID NO: 1, or a biologically active fragment thereof which increases the efficiency of SCNT to a similar or greater extent (e.g., at least about 110%, or at least about 120%, or at least about 130%, or at least about 140%, or at least about 150%, or more than 150% increased) as compared to the nucleic acid sequence of SEQ ID NO: 1. In some embodiments, a biologically active fragment of SEQ ID NO: 55 comprises amino acids 1-424 of SEQ ID NO: 55, as disclosed in Antony et al., Nature, 2013. In some embodiments, a biologically active fragment of SEQ ID NO: 55 comprises amino acid 1-424 of SEQ ID NO: 55 that also lacks at least 1, or at least 2, or at least between 2-10, or at least between 10-20, or at least between 20-50, or at least between 50-100 amino acids at the C-terminal, or the N-terminal of amino acids 1-424 of SEQ ID NO: 55, or lacks at least 1, or at least 2, or at least between 2-10, or at least between 10-20, or at least between 20-50, or at least between 50-100 amino acids at the C-terminal and the N-terminal of amino acids 1-424 of SEQ ID NO: 55.

In alternative embodiments, an agent which contacts a donor mammalian cell, e.g., a donor nuclei of a terminally differentiated cell, increases the expression or activity of the Kdm4 family of histone demethylases, for example, but not limited to the Kdm4 family consisting of: Kdm4a, Kdm4b, Kdm4c or Kdm4d as discussed above.

Another aspect of the present invention relates to a method for increasing the efficiency of somatic cell nuclear transfer (SCNT) comprising contacting the nuclei of a donor mammalian cell, e.g., a terminally differentiated somatic cell, with an agent which decreases H3K9me3 methylation in the nuclei of the donor mammalian somatic cell, thereby increasing the efficiency of the SCNT.

In some embodiments of all aspects of the present invention, an agent which contacts a donor mammalian somatic cell is an inhibitor of a H3K9 methyltransferase, for example, but not limited to, Suv39h1, Suv39h2 or Setdb1. In some embodiments, at least one or any combination of inhibitors of Suv39h1, Suv39h2 or Setdb1 can be used in the methods to increase the efficiency of SNCT. In some embodiments, an inhibitor of Suv39h1, Suv39h2 or Setdb1 inhibits the expression of Suv39h1, Suv39h2 or Setdb1 nucleic acid sequence of a variety of mammalian species, e.g., human, mouse, rat, cattle (e.g., SEQ ID NO: 9-14), or the activity of the Suv39h1, Suv39h2 or Setdb1 proteins from a variety of different mammals, e.g., e.g., human, mouse, rat, cattle. In some embodiments, an inhibitor of a H3K9 methyltransferase is not an inhibitor of Setdb1.

In some embodiments, an inhibitor of H3K9 methyltransferase is selected from the group consisting of; a RNAi agent, an siRNA agent, shRNA, oligonucleotide, CRISPR/Cas9, neutralizing antibody or antibody fragment, aptamer, small molecule, protein, peptide, small molecule, avidimir, and functional fragments or derivatives thereof etc. In some embodiments, the H3K9 methyltransferase inhibitor is a RNAi agent, e.g., siRNA or shRNA molecule. In some embodiments, the agent comprises a nucleic acid inhibitor to inhibit expression of human SUV39H1 (SEQ ID NO: 9), mouse Suv39h1 (SEQ ID NO: 11), rat Suv39h1 (SEQ ID NO: 13) or cattle Suv39h1 (SEQ ID NO: 15). In some embodiments, the agent comprises a nucleic acid inhibitor to inhibit expression of human SUV39H2 (SEQ ID NO: 10), mouse Suv39h2 (SEQ ID NO: 12), rat Suv39h2 (SEQ ID NO: 14) or cattle Suv39h2 (SEQ ID NO: 16). In some embodiments, a siRNA inhibitor of mouse Suv39h1 is SEQ ID NO: 18 or a fragment of at least 10 consecutive nucleotides thereof, or nucleic acid sequence with at least 80% sequence identity (or at least about 85%, or at least about 90%, or at least about 95%, or at least about 98%, or at least about 99% sequence identity) to SEQ ID NO: 18. In some embodiments, a siRNA or other nucleic acid inhibitor hybridizes to in full or in part, a target sequence of SEQ ID NO: 17 of Suv39h1. In some embodiments, a siRNA inhibitor of mouse Suv39h2 is SEQ ID NO: 20 or a fragment of at least 10 consecutive nucleotides thereof, or nucleic acid sequence with at least 80% sequence identity (or at least about 85%, or at least about 90%, or at least about 95%, or at least about 98%, or at least about 99%) to SEQ ID NO: 20. In some embodiments, a siRNA or other nucleic acid inhibitor hybridizes in full or part, to a target sequence of SEQ ID NO: 19 of Suv39h2.

In some embodiments, an agent can contact the SCNT embryo prior to, or at 5 hours post activation, or when the SCNT embryo is at the 1-cell stage. In alternative embodiments, an agent can contact the SCNT embryo after 5 hours post activation or when the SCNT embryo is at the 2-cell stage. In some embodiments, the recipient mammalian oocyte or SCNT embryo is injected with the agent, for example, by injection into the nuclei or cytoplasm of the recipient mammalian oocyte or SCNT embryo. In some embodiments, the agent increases the expression or activity of the Kdm4 family of histone demethylases.

In some embodiments, the agent contacts the donor mammalian cell, e.g., the nuclei or cytoplasm of a terminally differentiated somatic cell, prior to injection of the nuclei of the donor mammalian cell into an enucleated mammalian oocyte. In some embodiments, such an agent contacts the donor mammalian somatic cell for at least 1 hour, or at least 2 or more hours, where the contact occurs at least 1 day (24 hours), or at least 2 days, or at least 3 days, or more than 3 days, prior to the removal of the nuclei from the donor mammalian somatic cell into an enucleated mammalian oocyte.

In all aspects of the present invention, the SCNT embryo is produced from the injection of a donor somatic cell nuclei from a differentiated somatic cell (often a terminally differentiated cell, but not an ES cell or iPSC) into an enucleated oocyte, where the donor nuclei is not from an embryonic stem (ES) cell or an induced pluripotent stem (iPS) cell, or a fetal cell. In all aspects of the present invention, the SCNT embryo is generated by the injecting a donor nuclei from a terminally differentiated somatic cell into an enucleated mammalian oocyte. In some embodiments, the donor mammalian somatic cell is from a different mammalian species as the mammalian species from which the recipient oocyte.

In all aspects of the present invention, the donor mammalian cell, recipient mammalian oocyte or mammalian SCNT embryo are human cells, e.g., are a human donor cell, a recipient human oocyte or human SCNT embryo. In aspects of the present invention, the donor mammalian cell, recipient mammalian oocyte or mammalian SCNT embryo are non-human cells, e.g., non-human donor cells, a recipient non-human oocytes or non-human SCNT embryos.

In some embodiments, the donor mammalian cell, recipient mammalian oocyte or mammalian SCNT embryo is a non-human mammal, for example, selected from the group consisting of; mouse, rat, rabbit, cow, horse, pig, chicken, dog, cat, macaque, chimpanzee, or a domestic or commercial animals such as a cow, pig, horse, deer, bison, llama, mule, rabbit, reindeer, sheep, water buffalo, yak, poultry, fish and other livestock raised in an agricultural setting for commodities such as food, fiber and labor. In some embodiments, the donor mammalian cell, recipient mammalian oocyte or mammalian SCNT embryo is from a companion animal, for example, but not limited to a dog, cat, rabbit, guinea pig or horse. In some embodiments, the donor mammalian cell, recipient mammalian oocyte or mammalian SCNT embryo is a zoo animal, for example, lion, zebra, giraffe, elephant, rhino etc. In some embodiments, the method can be used to produce animals that are near extinction, and in some embodiments, the donor mammalian cell, recipient mammalian oocyte or mammalian SCNT embryo is from a mammalian species which are endangered species, e.g., animals that are near extinction, for example, Giant panda, polar bear, lion, Javan Rhinoceros, Cross River Gorilla, Sumatran Tiger, Borneo Pygmy Elephant and the like.

Accordingly, in all aspects of the invention, the method results in an at least a 30% increase, or at least a 50% increase, or a 50%-80% increase, or a greater than 80% increase in efficiency of SCNT as compared to SCNT performed in the absence of an agent which decreases H3K9me3 methylation. Stated another way, the methods as disclosed herein increase the efficiency of pre-implantation development of SCNT embryos, whereby at least about a 50%, or at least about a 70%, or at least about a 80%, or a greater than 80% SCNT embryos survive and are viable and develop into blastocysts. In another embodiment, the methods increase the efficiency of post-implantation development of SCNT embryos, for example, at least a 3-fold, or at least a 4-fold, or at least a 5-fold, or at least about a 6-fold, or at least about a 7-fold, or at least about a 8-fold or more than 8-fold increase in the successful post-implantation development of SCNT embryos to produce live animals as compared to in the absence of an agent which decreases H3K9me3 methylation. In some embodiments, an increase in SCNT efficiency provided by the methods and compositions as disclosed herein refers to an increase in the generation of SCNT embryo-derived embryonic stem cells (ntESCs).

Another aspect of the present invention relates to a composition comprising at least one of: a mammalian SCNT embryo, recipient mammalian oocyte or a blastocyst and at least one of: (i) an agent which increases the expression or activity of the Kdm4 family (Jmjd2) of histone demethylases or (ii) an agent which inhibits a H3K9 methyltransferase.

In some embodiments, the composition comprises a recipient mammalian oocyte which is an enucleated mammalian oocyte or a mammalian oocyte prior to the injection of a donor nucleus obtained from a terminally differentiated somatic cell. In some embodiments, the SCNT embryo is a 1-cell stage, or 2-cell stage SCNT embryo. In some embodiments, the composition comprises an agent which increases the expression of at least one gene encoding a member of the Kdm4 family of histone demethylases, or increases the activity of at least one member of the Kdm4 family of histone demethylases, for example, Kdm4a, Kdm4b, Kdm4c or Kdm4d. In some embodiment, the agent increases the expression or activity of Kdm4d (Jmjd2d) or Kdm4a (Jmjd2a). In some embodiment, the agent comprises a nucleic acid sequence of Kdm4d selected from a variety of different mammalian species, e.g., human Kdm4d (SEQ ID NO: 1), mouse Kdm4d (SEQ ID NO: 2), rat Kdm4d (SEQ ID NO:3), rabbit Kdm4d (SEQ ID NO:4), pig Kdm4d (SEQ ID NO:5), cattle Kdm4d (SEQ ID NO:6), macaque Kdm4d (SEQ ID NO:7), and chimpanzee Kdm4d (SEQ ID NO:8.), or is a biologically active fragment or homologue thereof which increases the efficiency of SCNT to a similar or greater extent as compared to the corresponding sequence of SEQ ID NO: 1-8. In some embodiments, the composition comprises a human KDM4 nucleic acid sequence corresponding of SEQ ID NO: 1, or a biologically active fragment thereof which increases the efficiency of SCNT to a similar or greater extent as compared to the nucleic acid sequence of SEQ ID NO: 1.

In some embodiments, the composition comprises an agent which is an inhibitor of a H3K9 methyltransferase, for example, but not limited to, Suv39h1, Suv39h2 or Setdb1. In some embodiments, at least one or any combination of inhibitors of Suv39h1, Suv39h2 or Setdb1 can be used in the methods to increase the efficiency of SNCT. In some embodiments, an inhibitor of Suv39h1, Suv39h2 or Setdb1 inhibits the expression of Suv39h1, Suv39h2 or Setdb1 nucleic acid sequence of a variety of mammalian species, e.g., human, mouse, rat, cattle (e.g., SEQ ID NO: 9-14), or the activity of the Suv39h1, Suv39h2 or Setdb1 proteins from a variety of different mammals, e.g., e.g., human, mouse, rat, cattle.

In some embodiments, the composition comprises an inhibitor of H3K9 methyltransferase selected from the group consisting of; an siRNA, shRNA, neutralizing antibody or antibody fragment, aptamer, small molecule, protein, peptide, small molecule etc. In some embodiments, the H3K9 methyltransferase inhibitor is a siRNA or shRNA molecule which inhibits Suv39h1 or Suv39h2 or Setdb1. In some embodiments, the composition comprises a nucleic acid inhibitor to inhibit expression of human Suv39h1 (SEQ ID NO: 9), mouse Suv39h1 (SEQ ID NO: 11), rat Suv39h1 (SEQ ID NO: 13) or cattle Suv39h1 (SEQ ID NO: 15). In some embodiments, the composition comprises a nucleic acid inhibitor to inhibit expression of human Suv39h2 (SEQ ID NO: 10), mouse Suv39h2 (SEQ ID NO: 12), rat Suv39h2 (SEQ ID NO: 14) or cattle Suv39h2 (SEQ ID NO: 16). In some embodiments, the composition comprises a siRNA inhibitor of mouse Suv39h1 corresponding to SEQ ID NO: 18 or a fragment of at least 10 consecutive nucleotides thereof, or nucleic acid sequence with at least 80% sequence identity (or at least about 85%, or at least about 90%, or at least about 95%, or at least about 98%, or at least about 99% sequence identity) to SEQ ID NO: 18. In some embodiments, the composition comprises a siRNA or other nucleic acid inhibitor which hybridizes to, in full or in part, a target sequence of SEQ ID NO: 17 of Suv39h1. In some embodiments, the composition comprises a siRNA inhibitor of mouse Suv39h2 corresponding to SEQ ID NO: 20 or a fragment of at least 10 consecutive nucleotides thereof, or nucleic acid sequence with at least 80% sequence identity (or at least about 85%, or at least about 90%, or at least about 95%, or at least about 98%, or at least about 99%) to SEQ ID NO: 20. In some embodiments, the composition comprises a siRNA or other nucleic acid inhibitor which hybridizes, in full or part, to a target sequence of SEQ ID NO: 19 of Suv39h2.

In some embodiments, the composition comprises a SCNT embryo that is at the 1-cell or 2-cell stage. In some embodiments, the composition comprises an enucleated mammalian oocyte. In some embodiments, the composition comprises a human SCNT embryo, recipient human oocyte or a human blastocyst, or in alternative embodiments, the composition comprises a non-human mammalian SCNT embryo, a non-human recipient mammalian oocyte or a non-human blastocyst, for example, but not limited to, mouse, rat, rabbit, cow, horse, pig, chicken, dog, cat, macaque, chimpanzee. In some embodiments, the composition comprises donor mammalian cell, recipient mammalian oocyte or mammalian SCNT embryo is from a companion animal, for example, but not limited to a dog, cat, rabbit, guinea pig or horse, or from a zoo animal, for example, lion, zebra, giraffe, elephant, rhino etc. In some embodiments, the composition can be used in a method as disclosed herein to produce animals that are near extinction.

Another embodiment related to a kit comprising (i) an agent which increases the expression or activity of the Kdm4 family of histone demethylases or (ii) an agent which inhibits a H3K9 methyltransferase.

BRIEF DESCRIPTION OF THE DRAWINGS

FIG. 1A is a schematic illustration of the experimental approach. Samples used for RNA-seq are marked by dashed rectangles. FIGS. 1B and 1C are scatter plots comparing gene expression levels between IVF and SCNT mouse embryos at the 1-cell stage (FIG. 1B) and the 2-cell stage (FIG. 1C). Genes expressed higher in IVF embryos (FC>3.0, IVF-high) and higher in SCNT embryos (FC>3.0, SCNT-high) are colored with red and blue, respectively. FIG. 1D is a heatmap illustration showing differentially expressed genes (DEGs) (FC>5.0, FPKM>5 in each replicates) obtained by a pairwise comparison between donor mouse cumulus cells, IVF 2-cell and SCNT 2-cell embryos. A total of 3775 DEGs are classified into 5 groups by unsupervised hierarchical clustering. FIG. 1E shows results of a gene ontology analysis of the 5 groups classified in (FIG. 1D).

FIGS. 2A-2E show that Reprogramming resistant regions (RRRs) are enriched for H3K9me3 in somatic cells. FIG. 2A is a heatmap illustration of the transcripts of IVF and SCNT embryos. Each tile represents an average of peaks within the region obtained by sliding-window analysis. Shown are the 811 regions that are activated from 1-cell (12 h) to 2-cell (28 h) stage IVF embryos compared to cumulus derived SCNT embryos. These regions were classified into three groups based on the fold-change (FC) in transcription levels between SCNT- and IVF 2-cell embryos. FRRs, PRRs, and RRRs indicate fully reprogrammed regions (FRR) (FC<=2), partially reprogrammed regions (PRR) (2<FC<=5) and reprogramming resistant regions (RRR) (FC>5), respectively. FIG. 2B shows the average ChIP-seq intensity of six histone modifications in MEF cells are shown within FRR, PRR and RRR compared with 2 MB flanking regions. Reads counts are normalized by input, total mapped reads and region length. FIG. 2C shows the representative genome browser view of RRRs on chromosome 7. FIGS. 2D and 2E are box plots comparing the average intensity of H3K9me3-ChIP-seq (FIG. 2D) or DNaseI-seq (FIG. 2E) within FRR, PRR and RRR in different somatic cell types. ChIP-seq and DNaseI-seq datasets shown in (FIGS. 2B-2E) were obtained from ENCODE projects (Bernstein et al., 2012; The Encode Consortium Project, 2011). Abreviations: fully reprogrammed regions (FRR), partially reprogrammed regions (PRR) and reprogramming resistant regions (RRR).

FIG. 3A is a schematic illustration of the experimental procedure. SCNT embryos derived from cumulus cells were injected with wild-type or a catalytic defective Kdm4d mRNA at 5 hours post activation (hpa). Samples used for RNA-seq are marked by dashed rectangles. FIG. 3B shows representative nuclear images of 1-cell and 2-cell stage SCNT embryos stained with anti-H3K9me3 and DAPI. Shown in each panel is a nucleus of a single blastomere. Scale bar, 10 FIG. 3C is a heatmap comparing transcription levels of the 222 RRRs at the 2-cell stage. The expression level of 184 out of the 222 RRRs are significantly (FC>2) increased in response to wild-type, but not the catalytic mutant, Kdm4d injection. FIG. 3D shows a genome browser view of an example of RRRs on chromosome 7. FIG. 3E shows the hierarchical clustering of all samples used in this study. Note that 2-cell SCNT embryos injected with wild-type Kdm4d were clustered together with 2-cell IVF embryos based on their transcriptome analysis. FIG. 3F is a bar graph that illustrates the reduced number of differentially expressed genes (FC>3) between IVF and SCNT 2-cell embryos after Kdm4d injection.

FIGS. 4A-4H show that injection of Kdm4d mRNA improves developmental potential of SCNT embryos. FIG. 4A shows that Kdm4d mRNA injection greatly improves pre-implantation development of SCNT embryos into blastocysts derived from cumulus donor cells, Sertoli donor cells and MEF donor cells. Shown is the percentage of mouse SCNT embryos that reaches the indicated stages. XX and XY indicate the sex of donor mice. Error bars indicate s.d. FIG. 4B shows representative images of SCNT embryos after 120 hours of culturing in vitro. Scale bar, 100 μm. FIG. 4C shows that Kdm4d mRNA injection has additional effect over the treatment with Trichostatin A (TSA; 15 nM). Shown is the percentage of embryos that reached the blastocyst stage at 96 hpa. * P<0.05,  P<0.01, * P<0.001. ns, not significant. FIG. 4D is a bar graph showing the efficiency of attachment to the feeder cells and ntESC derivation of mouse SCNT blastocysts. FIG. 4E is a bar graph showing the efficiency of mouse ntESC derivation. The efficiency was calculated based on the total number of MII oocytes used for the generation of SCNT embryos. FIG. 4F shows the implantation rate, and FIG. 4G shows birth rate of SCNT embryos examined by caesarian section on E19.5. FIG. 4H is an image of an adult female mouse derived by SCNT of a cumulus cell with Kdm4d mRNA injection and its pups generated through natural mating with a wild-type male. See also Tables 2-4.

FIGS. 5A-5D show the candidate genes responsible for the poor developmental phenotype of SCNT embryos. FIG. 5A is a venn diagram showing the overlap between the genes that failed to be activated in SCNT 2-cell embryos (Group3 in FIG. 1D) and Kdm4d enzyme activity-dependently derepressed genes in SCNT 2-cell embryos. Gene ontology (GO) enrichment analysis was performed on the 49 overlap genes. FIG. 5B is a heatmap showing the expression pattern of 49 overlap genes in FIG. 5A. FIG. 5C is a schematic illustration of the experimental procedure. Zscan4d mRNA was injected into both cells of 2-cell blastomeres of SCNT embryos at 20 hpa (early 2-cell stage). FIG. 5D shows the pre-implantation development rate of SCNT embryos injected with Zscan4d mRNA at 0, 20, 200 or 2000 ng/μl injected per cell. Error bars indicate s.d. of three biological replicates. See also FIG. 11 and Table 6.

FIG. 6A shows a schematic illustration of SCNT using siRNA transfected MEF cells. FIG. 6B shows representative images of MEF cells stained with anti-H3K9me3 antibody and DAPI at day 6 of transfection (see Methods for details). Scale bar, 10 μm FIG. 6C shows preimplantation development rate of SCNT embryos derived from different knockdown MEF cells. Error bars indicate s.d. of three biological replicates. FIG. 6D shows representative images of SCNT embryos after 120 hours of culturing in vitro. Scale bar, 100 μm.

FIG. 8A is a summary of total and uniquely mapped reads for each sample of the seven types of samples with two biological replicates used in this study. FIG. 8B shows a scatter plot evaluation of the reproducibility of different biological replicates.

FIG. 9A shows a genome browser view of an example of RRRs on chromosome 13 showing ChIP-seq data of histone modifications in MEF cells and RNA-seq data of 2-cell embryos. Note that this RRR overlaps with a large block of H3K9me3 peaks and is located within a gene-poor region. FIG. 9B is a box plot comparing the average percentage of exonic sequences, which represents the density of protein coding genes, in FRR, PRR and RRR. * P<0.001. FIG. 9C is a box plot comparing the average percentage of repetitive sequence within FRR, PRR and RRR. * P<0.001. FIG. 9D is a box plot comparing the average values of ChIP-seq for H3K9me3 in megakaryocyte and whole brain. ChIP-seq data were obtained from ENCODE projects (Bernstein et al., 2012). H3K9me3 is significantly enriched in RRRs compared to FRRs and PRRs. FIG. 9E is a box plot comparing the average values of sequence intensity after DNaseI treatment in whole brain, T-regulatory cells, Cell_416b and Mel cells. DNaseI-seq data were obtained from ENCODE projects (The Encode Consortium Project, 2011). RRR is significantly less sensitive to DNaseI than FRR or PRR in all four types of cells/tissues.  P<0.01, * P<0.001. Abreviations: fully reprogrammed regions (FRR), partially reprogrammed regions (PRR) and reprogramming resistant regions (RRR)

FIG. 10A shows a genome browser view of representative RRRs on chromosome 7. FIG. 10B shows a genome browser view of an example of RRRs on chromosome 13. FIG. 10C is a scatter plot comparing gene expression of Kdm4d WT injected SCNT 2-cell embryos with that of IVF 2-cell embryos. Genes expressed higher (FC>3) in IVF (IVF-high) or SCNT (SCNT-high) embryos were colored as grey and black, respectively.

FIG. 11 (is related to FIG. 5) and shows the expression levels of candidate non-genic transcripts potentially responsible for the poor developmental phenotype of SCNT embryos. Bar graphs indicate the expression level (uniquely mapped read numbers) of the major satellite DNA and the mouse endogenous retrotransposon MERVL in IVF and SCNT embryos.

FIG. 12A-12C (is related to FIG. 6) and shows results from RT-qPCR analysis of the knockdown efficiency. RT-qPCR analysis of Suv39h1 (FIG. 12A), Suv39h2 (FIG. 12B) and Setdb1 (FIG. 12C) mRNA levels in MEF cells at 48 hours after transfection of each siRNA. Data shown are mean expression values relative to Gapdh. The value in control was set as 1.0. Error bars represents s.d. with three biological replicates. *** P<0.001 by Student's T-test.

DETAILED DESCRIPTION OF THE INVENTION

Figure 1A:
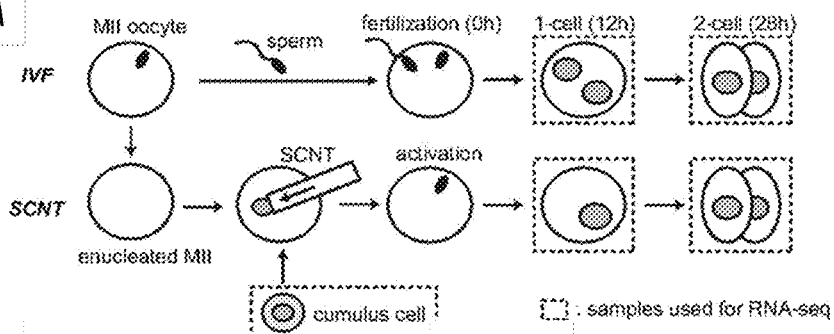
FIGS. 1A-1E show abnormal gene expression of SCNT embryos at the 1- and 2-cell stages.

Despite its enormous potential for both basic science and therapeutic use, the efficiency of mammalian cloning by somatic cell nuclear transfer (SCNT) remains very low. The birth rate of live young after SCNT is less than 10% regardless of species, donor cell type, protocols, or techniques used. Similarly the development rate of cloned embryos is lower than that of normal fertilized embryos, resulting in poor development to blastocyst and smaller cell number at blastocyst. These deficits also contribute to the infrequent successful ES cell line establishment from cloned mouse SCNT embryos, which is approximately 5% irrespective of the mouse strain or donor cell type, compared to approximate 30% success rate when normal embryos are used. The incompetence of the cloned embryos is largely due to incomplete nuclear programming and/or epigenetic barriers in the donor nuclei.

The present invention is based on the discovery that the trimethylation of Histone H3-Lysine 9 (H3K9me3) on reprogramming resistant regions (RRR) in the nuclei of the donor cell is an epigenetic barrier which prevents efficient somatic cell nuclear reprogramming by SCNT. As disclosed herein, the inventors have demonstrated two ways to improve efficacy of SCNT, firstly by promoting demethylation of H3K9me3 by using exogenous or increased expression of the demethylase Kdm4d (also known as Jmjd2d or Jhdm3d), and/or by inhibiting methylation of H3K9me3 by inhibiting the histone methyltransferases Suv39h1 or Suv39h2. Accordingly, the present invention relates to methods, compositions and kits comprising H3K9me3 histone demethylase activators, e.g., activators of the Kdm4/Jmjd2 family and/or H3K9me3 methyltransferase inhibitors, e.g., inhibitors of Suv39h1 or Suv39h2 or Setdb1 to remove the epigenetic barriers and increase the efficiency of SCNT. This can be done in any one of: the donor somatic cell (e.g., in the cytoplasm or nuclei) and/or in the recipient oocyte (e.g., nucleated or enucleated oocyte) and/or SCNT embryo (e.g., at 5 hpa, or 10-12 hpa, or 20-28 hpa, 1-cell stage, 2-cell stage SCNT embryo).

Accordingly, aspects of the invention relate to methods, compositions and kits directed to increasing SCNT efficiency by reducing H3K9me3 methylation by either (i) expressing histone demethylases which are capable of demethylating H3K9me3, e.g., for example, members of the Kdm4 family of histone demethylases, such as, for example but not limited to, Jmjd2b/Kdm4b or Jmjd2a/Kdm4a, or Jmjd2c/Kdm4c or Jmjd2d/Kdm4d and/or (ii) inhibiting histone methytransferases that are involved in the methylation of H3K9me3, for example, inhibition of any one or a combination of Suv39h1, Suv39h2 or Setdb1. In some embodiment, the agent which increases the expression or activity of the Kdm4 family of histone demethylases increases the expression or activity of Kdm4d (Jmjd2d), Kdm4c (Jmjd2c), Kdm4b (Jmjd2b) or Kdm4a (Jmjd2a).

Another aspect relates to uses of the SCNT-embryos produced using the methods and compositions as disclosed herein to develop into one or more blastomeres, which can be removed or biopsied and/or used to generate ES cells (i.e., ntESCs) or for reproductive cloning of non-human mammals.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The phrase "Somatic Cell Nuclear Transfer" or "SCNT" is also commonly referred to as therapeutic or reproductive cloning, is the process by which a somatic cell is fused with an enucleated oocyte. The nucleus of the somatic cell provides the genetic information, while the oocyte provides the nutrients and other energy-producing materials that are necessary for development of an embryo. Once fusion has occurred, the cell is totipotent, and eventually develops into a blastocyst, at which point the inner cell mass is isolated.

The term "nuclear transfer" as used herein refers to a gene manipulation technique allowing an identical characteristics and qualities acquired by artificially combining an enucleated oocytes with a cell nuclear genetic material or a nucleus of a somatic cell. In some embodiments, the nuclear transfer procedure is where a nucleus or nuclear genetic material from a donor somatic cell is transferred into an enucleated egg or oocyte (an egg or oocyte from which the nucleus/pronuclei have been removed). The donor nucleus can come from a somatic cell.

The term "nuclear genetic material" refers to structures and/or molecules found in the nucleus which comprise polynucleotides (e.g., DNA) which encode information about the individual. Nuclear genetic material includes the chromosomes and chromatin. The term also refers to nuclear genetic material (e.g., chromosomes) produced by cell division such as the division of a parental cell into daughter cells. Nuclear genetic material does not include mitochondrial DNA.

The term "SCNT embryo" refers to a cell, or the totipotent progeny thereof, of an enucleated oocyte which has been fused with the nucleus or nuclear genetic material of a somatic cell. The SCNT embryo can develop into a blastocyst and develop post-implantation into living offspring. The SCNT embryo can be a 1-cell embryo, 2-cell embryo, 4-cell embryo, or any stage embryo prior to becoming a blastocyst.

The term "parental embryo" is used to refer to a SCNT embryo from which a single blastomere is removed or biopsied. Following biopsy, the remaining parental embryo (the parental embryo minus the biopsied blastomere) can be cultured with the blastomere to help promote proliferation of the blastomere. The remaining, viable parental SCNT embryo may subsequently be frozen for long term or perpetual storage or for future use. Alternatively, the viable parental embryo may be used to create a pregnancy.

The term "donor mammalian cell" or "donor mammalian somatic cell" refers to a somatic cell or a nucleus of cell which is transferred into a recipient oocyte as a nuclear acceptor or recipient.

The term "somatic cell" refers to a plant or animal cell which is not a reproductive cell or reproductive cell precursor. In some embodiments, a differentiated cell is not a germ cell. A somatic cell does not relate to pluiripotent or totipotent cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

The term "differentiated cell" as used herein refers to a any cell in the process of differentiating into a somatic cell lineage or having terminally differentiated. For example, embryonic cells can differentiate into an epithelial cell lining the intestine. Differentiated cells can be isolated from a fetus or a live born animal, for example.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "oocyte" as used herein refers to a mature oocyte which has reached metaphase II of meiosis. An oocyte is also used to describe a female gamete or germ cell involved in reproduction, and is commonly also called an egg. A mature egg has a single set of maternal chromosomes (23, X in a human primate) and is halted at metaphase II. A "hybrid" oocyte has the cytoplasm from a first primate oocyte (termed a "recipient") but does not have the nuclear genetic material of the recipient; it has the nuclear genetic material from another oocyte, termed a "donor."

The term "enucleated oocyte" as used herein refers to an oocyte which its nucleus has been removed.

The "recipient mammalian oocyte" as used herein refers to a mammalian oocyte that receives a nucleus from a mammalian nuclear donor cell after removing its original nucleus.

The term "fusion" as used herein refers to a combination of a nuclear donor cell and a lipid membrane of a recipient oocyte. For example, the lipid membrane may be the plasma membrane or nuclear membrane of a cell. Fusion may occur upon application of an electrical stimulus between a nuclear donor cell and a recipient oocyte when they are placed adjacent to each other or when a nuclear donor cell is placed in a perivitelline space of a recipient oocyte.

The term "activation" as used herein refers to stimulation of a cell to divide, before, during or after nuclear transfer. Preferably, in the present invention, it means stimulation of a cell to divide after nuclear transfer.

The term "living offspring" as used herein means an animal that can survive ex utero. Preferably, it is an animal that can survive for one second, one minute, one day, one week, one month, six months or more than one year. The animal may not require an in utero environment for survival.

The term "prenatal" refers to existing or occurring before birth. Similarly, the term "postnatal" is existing or occurring after birth.

The term "blastocyst" as used herein refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst consists of a sphere made up of a layer of cells (the trophectoderm), a fluid-filled cavity (the blastocoel or blastocyst cavity), and a cluster of cells on the interior (the inner cell mass, or ICM). The ICM, consisting of undifferentiated cells, gives rise to what will become the fetus if the blastocyst is implanted in a uterus. These same ICM cells, if grown in culture, can give rise to embryonic stem cell lines. At the time of implantation the mouse blastocyst is made up of about 70 trophoblast cells and 30 ICM cells.

The term "blastula" as used herein refers to an early stage in the development of an embryo consisting of a hollow sphere of cells enclosing a fluid-filled cavity called the blastocoel. The term blastula sometimes is used interchangeably with blastocyst.

The term "blastomere" is used throughout to refer to at least one blastomere (e.g., 1, 2, 3, 4, etc) obtained from a preimplantation embryo. The term "cluster of two or more blastomeres" is used interchangeably with "blastomere-derived outgrowths" to refer to the cells generated during the in vitro culture of a blastomere. For example, after a blastomere is obtained from a SCNT embryo and initially cultured, it generally divides at least once to produce a cluster of two or more blastomeres (also known as a blastomere-derived outgrowth). The cluster can be further cultured with embryonic or fetal cells. Ultimately, the blastomere-derived outgrowths will continue to divide. From these structures, ES cells, totipotent stem (TS) cells, and partially differentiated cell types will develop over the course of the culture method.

The term "karyoplast" as used herein refers to a cell nucleus, obtained from the cell by enucleation, surrounded by a narrow rim of cytoplasm and a plasma membrane.

The term "cell couplet" as used herein refers to an enucleated oocyte and a somatic or fetal karyoplast prior to fusion and/or activation.

The term "cleavage pattern" as used herein refers to the pattern in which cells in a very early embryo divide; each species of organism displays a characteristic cleavage pattern that can be observed under a microscope. Departure from the characteristic pattern usually indicates that an embryo is abnormal, so cleavage pattern is used as a criterion for preimplantation screening of embryos.

The term "clone" as used herein refers to an exact genetic replica of a DNA molecule, cell, tissue, organ, or entire plant or animal, or an organism that has the same nuclear genome as another organism.

The term "cloned (or cloning)" as used herein refers to a gene manipulation technique for preparing a new individual unit to have a gene set identical to another individual unit. In the present invention, the term "cloned" as used herein refers to a cell, embryonic cell, fetal cell, and/or animal cell has a nuclear DNA sequence that is substantially similar or identical to the nuclear DNA sequence of another cell, embryonic cell, fetal cell, differentiated cell, and/or animal cell. The terms "substantially similar" and "identical" are described herein. The cloned SCNT embryo can arise from one nuclear transfer, or alternatively, the cloned SCNT embryo can arise from a cloning process that includes at least one re-cloning step.

The term "transgenic organism" as used herein refers to an organism into which genetic material from another organism has been experimentally transferred, so that the host acquires the genetic traits of the transferred genes in its chromosomal composition.

The term "embryo splitting" as used herein refers to the separation of an early-stage embryo into two or more embryos with identical genetic makeup, essentially creating identical twins or higher multiples (triplets, quadruplets, etc.).

The term "morula" as used herein refers to the preimplantation embryo 3-4 days after fertilization, when it is a solid mass composed of 12-32 cells (blastomeres). After the eight-cell stage, the cells of the preimplantation embryo begin to adhere to each other more tightly, becoming "compacted". The resulting embryo resembles a mulberry and is called a morula (Latin:morus=mulberry).

The term "enucleation" as used herein refers to a process whereby the nuclear material of a cell is removed, leaving only the cytoplasm. When applied to an egg, enucleation refers to the removal of the maternal chromosomes, which are not surrounded by a nuclear membrane. The term "enucleated oocyte" refers to an oocyte where the nuclear material or nuclei is removed.

The term "embryonic stem cells" (ES cells) refers to pluripotent cells derived from the inner cell mass of blastocysts or morulae that have been serially passaged as cell lines. The ES cells may be derived from fertilization of an egg cell with sperm or DNA, nuclear transfer, e.g., SCNT, parthenogenesis etc. The term "human embryonic stem cells" (hES cells) refers to human ES cells. The term "ntESC" refers to embryonic stem cells obtained from the inner cell mass of blastocysts or morulae produced from SCNT. The generation of ESC is disclosed in U.S. Pat. Nos. 5,843,780, 6,200,806, and ESC obtained from the inner cell mass of blastocysts derived from somatic cell nuclear transfer are described in U.S. Pat. Nos. 5,945,577, 5,994,619, 6,235,970, which are incorporated herein in their entirety by reference. The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Such cells include hES cells, human embryo-derived cells (hEDCs), human SCNT-embryo derived stem cells and adult-derived stem cells. Pluripotent stem cells may be genetically modified or not genetically modified. Genetically modified cells may include markers such as fluorescent proteins to facilitate their identification. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

The term "totipotent" as used herein in reference to SCNT embryos refers to SCNT embryos that can develop into a live born animal.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "reprogramming" as used herein refers to the process that alters or reverses the differentiation state of a somatic cell, such that the developmental clock of a nucleus is reset; for example, resetting the developmental state of an adult differentiated cell nucleus so that it can carry out the genetic program of an early embryonic cell nucleus, making all the proteins required for embryonic development. In some embodiments, the donor mammalian cell is terminally differentiated prior to the reprogramming by SCNT. Reprogramming as disclosed herein encompasses complete reversion of the differentiation state of a somatic cell to a pluripotent or totipotent cell. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult. In somatic cell nuclear transfer (SCNT), components of the recipient oocyte cytoplasm are thought to play an important role in reprogramming the somatic cell nucleus to carry out the functions of an embryonic nucleus.

The term "culturing" as used herein with respect to SCNT embryos refers to laboratory procedures that involve placing an embryo in a culture medium. The SCNT embryo can be placed in the culture medium for an appropriate amount of time to allow the SCNT embryo to remain static but functional in the medium, or to allow the SCNT embryo to grow in the medium. Culture media suitable for culturing embryos are well-known to those skilled in the art. See, e.g., U.S. Pat. No. 5,213,979, entitled "In vitro Culture of Bovine Embryos," First et al., issued May 25, 1993, and U.S. Pat. No. 5,096,822, entitled "Bovine Embryo Medium," Rosenkrans, Jr. et al., issued Mar. 17, 1992, incorporated herein by reference in their entireties including all figures, tables, and drawings.

The term "culture medium" is used interchangeably with "suitable medium" and refers to any medium that allows cell proliferation. The suitable medium need not promote maximum proliferation, only measurable cell proliferation. In some embodiments, the culture medium maintains the cells in a pluripotent or totipotent state.

The term "implanting" as used herein in reference to SCNT embryos as disclosed herein refers to impregnating a surrogate female animal with a SCNT embryo described herein. This technique is well known to a person of ordinary skill in the art. See, e.g., Seidel and Elsden, 1997, Embryo Transfer in Dairy Cattle, W. D. Hoard & Sons, Co., Hoards Dairyman. The embryo may be allowed to develop in utero, or alternatively, the fetus may be removed from the uterine environment before parturition.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "contacting" (i.e., contacting a mammalian donor cell, a mammalian recipient oocyte or a SCNT embryo with an agent) is intended to include incubating the agent and the cell, oocyte or SCNT-embryo together in vitro (e.g., adding the agent to the donor cell, oocyte or SCNT-embryo in culture or in a container). In some embodiments, the term "contacting" is not intended to include the in vivo exposure of cells to the agent as disclosed herein that may occur naturally in a subject (i.e., exposure that may occur as a result of a natural physiological process). The step of contacting a mammalian donor cell, a mammalian recipient oocyte or a SCNT embryo with an agent as disclosed herein can be conducted in any suitable manner. For example, a mammalian donor cell, a mammalian recipient oocyte or a SCNT embryo may be treated in adherent culture, or in suspension culture. It is understood that a mammalian donor cell, a mammalian recipient oocyte or a SCNT embryo can be contacted with an agent as disclosed herein can also be simultaneously or subsequently contacted with another agent, such as a growth factor or other differentiation agent or environments to stabilize the cells, or to differentiate the cells further. Similarly, a mammalian donor cell, a mammalian recipient oocyte or a SCNT embryo can be contacted with an agent as disclosed herein (e.g., a Kdm4 histone demethylase activator) and then with a second agent as disclosed herein (e.g., a H3K9 methyltransferase inhibitor) or vice versa. In some embodiments, a mammalian donor cell, a mammalian recipient oocyte, a SCNT embryo is contacted with an agent as disclosed herein and a second agent as disclosed herein and the contact is temporally separated. In some embodiments, a mammalian donor cell, a mammalian recipient oocyte, a SCNT embryo is contacted with one or more agents as disclosed herein substantially simultaneously (e.g., contacted with a Kdm4 histone demethylase activator and a H3K9 methyltransferase inhibitor substantially simultaneously).

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system or cell at that time. For instance, "exogenous Kdm4d" refers to the introduction of Kdm4d mRNA or cDNA which is not normally found or expressed in the cell or organism at that time.

The term "expression" refers to the cellular processes involved in producing RNA and proteins as applicable, for example, transcription, translation, folding, modification and processing. "Expression products" include RNA transcribed from a gene and polypeptides obtained by translation of mRNA transcribed from a gene.

A "genetically modified" or "engineered" cell refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "identity" refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI. In some embodiments, a nucleic acid or amino acid sequence has at least 80%, or at least about 85%, or at least about 90%, or at least about 95%, or at least about 98% or at least about 99% sequence identity to the nucleic acid or amino acid sequence.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated". An "isolated cell" is a cell that has been removed from an organism in which it was originally found or is a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of definitive endoderm cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not definitive endoderm cells or their progeny as defined by the terms herein. In some embodiments, the present invention encompasses methods to expand a population of definitive endoderm cells, wherein the expanded population of definitive endoderm cells is a substantially pure population of definitive endoderm cells. Similarly, with regard to a "substantially pure" or "essentially purified" population of SCNT-derived stem cells or pluripotent stem cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not stem cell or their progeny as defined by the terms herein.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "lineages" as used herein describes a cell with a common ancestry or cells with a common developmental fate. In the context of a cell that is of endoderm origin or is "endodermal linage" this means the cell was derived from an endoderm cell and can differentiate along the endoderm lineage restricted pathways, such as one or more developmental lineage pathways which give rise to definitive endoderm cells, which in turn can differentiate into liver cells, thymus, pancreas, lung and intestine.

As used herein, the term "xenogeneic" refers to cells that are derived from different species.

The term "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

The term "RNA interference" or "RNAi" is used herein consistently with its meaning in the art to refer to a phenomenon whereby double-stranded RNA (dsRNA) triggers the sequence-specific degradation or translational repression of a corresponding mRNA having complementarity to a strand of the dsRNA. It will be appreciated that the complementarity between the strand of the dsRNA and the mRNA need not be 100% but need only be sufficient to mediate inhibition of gene expression (also referred to as "silencing" or "knockdown"). For example, the degree of complementarity is such that the strand can either (i) guide cleavage of the mRNA in the RNA-induced silencing complex (RISC); or (ii) cause translational repression of the mRNA. In certain embodiments the double-stranded portion of the RNA is less than about 30 nucleotides in length, e.g., between 17 and 29 nucleotides in length. In mammalian cells, RNAi may be achieved by introducing an appropriate double-stranded nucleic acid into the cells or expressing a nucleic acid in cells that is then processed intracellularly to yield dsRNA therein. Nucleic acids capable of mediating RNAi are referred to herein as "RNAi agents". Exemplary nucleic acids capable of mediating RNAi are a short hairpin RNA (shRNA), a short interfering RNA (siRNA), and a microRNA precursor. These terms are well known and are used herein consistently with their meaning in the art. siRNAs typically comprise two separate nucleic acid strands that are hybridized to each other to form a duplex. They can be synthesized in vitro, e.g., using standard nucleic acid synthesis techniques. They can comprise a wide variety of modified nucleosides, nucleoside analogs and can comprise chemically or biologically modified bases, modified backbones, etc. Any modification recognized in the art as being useful for RNAi can be used. Some modifications result in increased stability, cell uptake, potency, etc. In certain embodiments the siRNA comprises a duplex about 19 nucleotides in length and one or two 3' overhangs of 1-5 nucleotides in length, which may be composed of deoxyribonucleotides. shRNA comprise a single nucleic acid strand that contains two complementary portions separated by a predominantly non-selfcomplementary region. The complementary portions hybridize to form a duplex structure and the non-selfcomplementary region forms a loop connecting the 3' end of one strand of the duplex and the 5' end of the other strand. shRNAs undergo intracellular processing to generate siRNAs.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or Renilla luciferase) are also of use. As will be evident to one of skill in the art, the term "selectable marker" as used herein can refer to a gene or to an expression product of the gene, e.g., an encoded protein.

The term "small molecule" refers to an organic compound having multiple carbon-carbon bonds and a molecular weight of less than 1500 daltons. Typically such compounds comprise one or more functional groups that mediate structural interactions with proteins, e.g., hydrogen bonding, and typically include at least an amine, carbonyl, hydroxyl or carboxyl group, and in some embodiments at least two of the functional chemical groups. The small molecule agents may comprise cyclic carbon or heterocyclic structures and/or aromatic or polyaromatic structures substituted with one or more chemical functional groups and/or heteroatoms.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term "variant" in referring to a polypeptide or nucleic acid sequence could be, e.g., a polypeptide or nucleic acid sequence which has at least 80%, 85%, 90%, 95%, 98%, or 99% sequence identity to the full length polypeptide or nucleic acid sequence. In some embodiments, a variant can be a fragment of a full length polypeptide or nucleic acid sequence. In some embodiments, a variant could be a naturally occurring splice variant. A variant could be a polypeptide or nucleic acid sequence which has at least 80%, 85%, 90%, 95%, 98%, or 99% sequence identity to a fragment of at least 50% the length of the full-length polypeptide or full-length nucleic acid sequence, wherein the fragment is at least 50%, 60%, 70%, 80%, 85%, 90%, 95%, 98%, or 99% as long as the full length wild type polypeptide or nucleic acid sequence having an activity of interest. For example, a variant of Kdm4d that has the ability to increase the efficiency of SCNT to the same, or similar extent, as compared to the Kdm4d polypeptide or Kdm4d nucleic acid sequence.

The term "functional fragment" or "biologically active fragment" are used interchangeably herein refers to a polypeptide having amino acid sequence which is smaller in size than the polypeptide from which it is a fragment of, where the functional fragment polypeptide has about at least 50%, or 60% or 70% or at 80% or 90% or 100% or greater than 100%, for example 1.5-fold, 2-fold, 3-fold, 4-fold or greater than 4-fold the same biological action as the polypeptide from which it is a fragment of. Functional fragment polypeptides may have additional functions that can include decreased antigenicity, increased DNA binding (as in transcription factors), or altered RNA binding (as in regulating RNA stability or degradation). In some embodiments, the biologically active fragment is substantially homologous to the polypeptide it is a fragment of Without being limited to theory, an exemplary example of a functional fragment of the Kdm4 histone demethylase activator of Kdm4d comprises a fragment of SEQ ID NO:55, (e.g., wherein the fragment is at least 50%, 60%, 70%, 80%, 85%, 90%, 95%, 98%, or 99% as long as SEQ ID NO: 55) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a Kdm4d polypeptide comprising the amino acids of SEQ ID NO: 1, using the same method and under the same conditions. In some embodiments, a biologically active fragment of SEQ ID NO: 55 comprises amino acids 1-424 of SEQ ID NO: 55, as disclosed in Antony et al., Nature, 2013. In some embodiments, a biologically active fragment of SEQ ID NO: 55 comprises amino acid 1-424 of SEQ ID NO: 55 that also lacks at least 1, or at least 2, or at least between 2-10, or at least between 10-20, or at least between 20-50, or at least between 50-100 amino acids at the C-terminal, or the N-terminal of amino acids 1-424 of SEQ ID NO: 55. In some embodiments, a biologically active fragment of SEQ ID NO: 55 comprises amino acid 1-424 of SEQ ID NO: 55 that also lacks at least 1, or at least 2, or at least between 2-10, or at least between 10-20, or at least between 20-50, or at least between 50-100 amino acids at both the C-terminal and the N-terminal of amino acids 1-424 of SEQ ID NO: 55.

The term "functional fragment" or "biologically active fragment" as used herein with respect to a nucleic acid sequence refers to a nucleic acid sequence which is smaller in size than the nucleic acid sequence which it is a fragment of, where the nucleic acid sequence has about at least 50%, or 60% or 70% or at 80% or 90% or 100% or greater than 100%, for example 1.5-fold, 2-fold, 3-fold, 4-fold or greater than 4-fold the same biological action as the biologically active fragment from which it is a fragment of Without being limited to theory, an exemplary example of a functional fragment of the nucleic acid sequence of the Kdm4 histone demethylase activator of Kdm4d comprises a fragment of SEQ ID NO:1 (e.g., wherein the fragment is at least 50%, 60%, 70%, 80%, 85%, 90%, 95%, 98%, or 99% as long as SEQ ID NO: 1) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a Kdm4d nucleic acid sequence of SEQ ID NO: 1, using the same method and under the same conditions.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill (suffers from a disease or other condition warranting medical/surgical attention) or injured, or at increased risk of becoming ill relative to an average member of the population and in need of such attention, care, or management. "Individual" is used interchangeably with "subject" herein. In any of the embodiments of the invention, the "individual" may be a human, e.g., one who suffers or is at risk of a disease for which cell therapy is of use ("indicated").

The term "synchronized" or "sychronous" as used herein in reference to estrus cycle, refers to assisted reproductive techniques well known to a person of ordinary skill in the art. These techniques are fully described in the reference cited in the previous paragraph. Typically, estrogen and progesterone hormones are utilized to synchronize the estrus cycle of the female animal with the developmental cycle of the embryo. The term "developmental cycle" as used herein refers to embryos of the invention and the time period that exists between each cell division within the embryo. This time period is predictable for embryos, and can be synchronized with the estrus cycle of a recipient animal.

The term "substantially similar" as used herein in reference to nuclear DNA sequences refers to two nuclear DNA sequences that are nearly identical. The two sequences may differ by copy error differences that normally occur during the replication of a nuclear DNA. Substantially similar DNA sequences are preferably greater than 97% identical, more-preferably greater than 98% identical, and most preferably greater than 99% identical. Identity is measured by dividing the number of identical residues in the two sequences by the total number of residues and multiplying the product by 100. Thus, two copies of exactly the same sequence have 100% identity, while sequences that are less highly conserved and have deletions, additions, or replacements have a lower degree of identity. Those of ordinary skill in the art will recognize that several computer programs are available for performing sequence comparisons and determining sequence identity.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Kdm4 Histone Demethylase Activators

In one aspect, the invention provides a method of increasing the efficiency of SCNT comprising: contacting the nuclei or cytoplasm of a donor mammalian cell, or a SCNT embryo, or an oocyte with an agent that inhibits histone methylation, in particular, inhibits H3K9 methylation, in particular, inhibits H3H9me3 trimethylation. In some embodiments, the agent is a Kdm4 histone demethylase activator.

In some embodiments, a Kdm4 histone demethylase activator useful in the methods, compositions and kits as disclosed herein is an agent which increases the expression of genes encoding the Kdm4 family of histone demethylases, or increases the activity of Kdm4 family of histone demethylases, for example, Kdm4a, Kdm4b, Kdm4c or Kdm4d. In some embodiment, the agent increases the expression or activity of Kdm4d (Jmjd2d) or Kdm4a (Jmjd2a).

In some embodiment, the agent comprises a nucleic acid sequence of Kdm4d selected from a variety of different mammalian species, e.g., human KDM4D (SEQ ID NO: 1), mouse Kdm4d (SEQ ID NO: 2), rat Kdm4d (SEQ ID NO:3), rabbit Kdm4d (SEQ ID NO:4), pig Kdm4d (SEQ ID NO:5), cattle Kdm4d (SEQ ID NO:6), macaque Kdm4d (SEQ ID NO:7), and chimpazee Kdm4d (SEQ ID NO:8.), or is a biologically active fragment or homologue or variant thereof of at least 80% sequence identity (or at least about 85%, or at least about 90%, or at least about 95%, or at least about 98%, or at least about 99% sequence identity) thereto which increases the efficiency of SCNT to a similar or greater extent as compared to the corresponding sequence of SEQ ID NO: 1-8. In some embodiments, the composition comprises a human KDM4D nucleic acid sequence corresponding of SEQ ID NO: 1, or a biologically active fragment thereof which increases the efficiency of SCNT to a similar or greater extent as compared to the nucleic acid sequence of SEQ ID NO: 1.

In some embodiments, the Kdm4 histone demethylase activator useful in the methods, compositions and kits as disclosed herein is a nucleic acid agent which encodes the KDM4A polypeptide, or a KDM4A polypeptide, or a variant or biological active fragment thereof. As used herein, the human Kdm4a nucleotide sequence corresponds to Genbank Accession No. NM_014663.2, and refers to SEQ ID NO: 49. KDM4A is also known as lysine (K)-specific demethylase 4A, JMJD2, JMJD2A, "jumonji domain containing 2", or "jumonji domain containing 2A". The human KDM4A protein corresponds to Genebank Accession no. NP_055478.2 (SEQ ID NO: 50). Accordingly, the protein sequence of KDM4A is as follows:

```
                                             (SEQ ID NO: 50)
MASESETLNPSARIMTFYPTMEEFRNFSRYIAYIESQGAHRAGLAKVVPP

KEWKPRASYDDIDDLVIPAPIQQLVTGQSGLFTQYNIQKKAMTVREFRKI

ANSDKYCTPRYSEFEELERKYWKNLTFNPPIYGADVNGTLYEKHVDEWNI

GRLRTILDLVEKESGITIEGVNTPYLYFGMWKTSFAWHTEDMDLYSINYL

HFGEPKSWYSVPPEHGKRLERLAKGFFPGSAQSCEAFLRHKMTLISPLML

KKYGIPFDKVTQEAGEFMITFPYGYHAGFNHGFNCAESTNFATRRWIEYG

KQAVLCSCRKDMVKISMDVFVRKFQPERYKLWKAGKDNTVIDHTLPTPEA

AEFLKESELPPRAGNEEECPEEDMEGVEDGEEGDLKTSLAKHRIGTKRHR

VCLEIPQEVSQSELFPKEDLSSEQYEMTECPAALAPVRPTHSSVRQVEDG

LTFPDYSDSTEVKFEELKNVKLEEEDEEEEQAAAALDLSVNPASVGGRLV

FSGSKKKSSSSLGSGSSRDSISSDSETSEPLSCRAQGQTGVLTVHSYAKG

DGRVTVGEPCTRKKGSAARSFSERELAEVADEYMFSLEENKKSKGRRQPL

SKLPRHHPLVLQECVSDDETSEQLTPEEEAEETEAWAKPLSQLWQNRPPN

FEAEKEFNETMAQQAPHCAVCMIFQTYHQVEFGGFNQNCGNASDLAPQKQ

RTKPLIPEMCFTSTGCSTDINLSTPYLEEDGTSILVSCKKCSVRVHASCY

GVPPAKASEDWMCSRCSANALEEDCCLCSLRGGALQRANDDRWVHVSCAV

AILEARFVNIAERSPVDVSKIPLPRFKLKCIFCKKRRKRTAGCCVQCSHG

RCPTAFHVSCAQAAGVMMQPDDWPFVVFITCFRHKIPNLERAKGALQSIT

AGQKVISKHKNGRFYQCEVVRLTTETFYEVNFDDGSFSDNLYPEDIVSQD

CLQFGPPAEGEVVQVRWTDGQVYGAKFVASHPIQMYQVEFEDGSQLVVKR

DDVYTLDEELPKRVKSRLSVASDMRFNEIFTEKEVKQEKKRQRVINSRYR

EDYIEPALYRAIME
```

In some embodiments, the Kdm4 histone demethylase activator useful in the methods, compositions and kits as disclosed herein is a nucleic acid agent which encodes the KDM4B polypeptide, or a KDM4B polypeptide, or a variant or biological active fragment thereof. As used herein, the human KDM4B nucleic acid corresponds to Genbank Accession No. NM_015015.2, and refers to SEQ ID NO: 51 as disclosed herein. KDM4B is also known as lysine (K)-specific demethylase 4B, JMJD2B or "jumonji domain containing 2B", KIAA0876, TDRD14B, or "tudor domain containing 14B. The human KDM4B protein corresponds to Genebank Accession no. NP_055830.1 (SEQ ID NO: 52). Accordingly, the protein sequence of KDM4B is as follows:

```
                                             (SEQ ID NO: 52)
MGSEDHGAQNPSCKIMTFRPTMEEFKDFNKYVAYIESQGAHRAGLAKIIP

PKEWKPRQTYDDIDDVVIPAPIQQVVTGQSGLFTQYNIQKKAMTVGEYRR

LANSEKYCTPRHQDFDDLERKYWKNLTFVSPIYGADISGSLYDDDVAQWN

IGSLRTILDMVERECGTIIEGVNTPYLYFGMWKTTFAWHTEDMDLYSINY

LHFGEPKSWYAIPPEHGKRLERLAIGFFPGSSQGCDAFLRHKMTLISPII

LKKYGIPFSRITQEAGEFMITFPYGYHAGFNHGFNCAESTNFATLRWIDY

GKVATQCTCRKDMVKISMDVFVRILQPERYELWKQGKDLTVLDHTRPTAL
```

TSPELSSWSASRASLKAKLLRRSHRKRSQPKKPKPEDPKFPGEGTAGAAL

LEEAGGSVKEEAGPEVDPEEEEEEPQPLPHGREAEGAEEDGRGKLRPTKA

KSERKKKSFGLLPPQLPPPPAHFPSEEALWLPSPLEPPVLGPGPAAMEES

PLPAPLNVVPPEVPSEELEAKPRPIIPMLYVVPRPGKAAFNQEHVSCQQA

FEHFAQKGPTWKEPVSPMELTGPEDGAASSGAGRMETKARAGEGQAPSTF

SKLKMEIKKSRRHPLGRPPTRSPLSVVKQEASSDEEASPFSGEEDVSDPD

ALRPLLSLQWKNRAASFQAERKFNAAAARTEPYCAICTLFYPYCQALQTE

KEAPIASLGEGCPATLPSKSRQKTRPLIPEMCFTSGGENTEPLPANSYIG

DDGTSPLIACGKCCLQVHASCYGIRPELVNEGWTCSRCAAHAWTAECCLC

NLRGGALQMTTDRRWIHVICAIAVPEARFLNVIERHPVDISAIPEQRWKL

KCVYCRKRMKKVSGACIQCSYEHCSTSFHVTCAHAAGVLMEPDDWPYVVS

ITCLKHKSGGHAVQLLRAVSLGQVVITKNRNGLYYRCRVIGAASQTCYEV

NFDDGSYSDNLYPESITSRDCVQLGPPSEGELVELRWTDGNLYKAKFISS

VTSHIYQVEFEDGSQLTVKRGDIFTLEEELPKRVRSRLSLSTGAPQEPAF

SGEEAKAAKPRVGTPLATEDGRSQDYVAFVESLLQVQGRPGAPF

In some embodiments, the Kdm4 histone demethylase activator useful in the methods, compositions and kits as disclosed herein is a nucleic acid agent which encodes the KDM4C polypeptide, or a KDM4C polypeptide, or a variant or biological active fragment thereof. As used herein, the human KDM4C nucleic acid sequence corresponds to Genbank Accession No. NM_015061.3 (SEQ ID NO: 53) as disclosed herein. KDM4C is also known as lysine (K)-specific demethylase C, JMJD2C or "jumonji domain containing 2C"GASC1, KIAA0780, TDRD14C or "tudor domain containing 14 C. The human KDM4C protein corresponds to Genebank Accession no. NP_055876.2 (SEQ ID NO: 54). Accordingly, the protein sequence of KDM4C is as follows:

(SEQ ID NO: 54)
MEVAEVESPLNPSCKIMTFRPSMEEFREFNKYLAYMESKGAHRAGLAKVI

PPKEWKPRQCYDDIDNLLIPAPIQQMVTGQSGLFTQYNIQKKAMTVKEFR

QLANSGKYCTPRYLDYEDLERKYWKNLTFVAPIYGADINGSIYDEGVDEW

NIARLNTVLDVVEEECGISIEGVNTPYLYFGMWKTTFAWHTEDMDLYSIN

YLHFGEPKSWYAIPPEHGKRLERLAQGFFPSSSQGCDAFLRHKMTLISPS

VLKKYGIPFDKITQEAGEFMITFPYGYHAGFNHGFNCAESTNFATVRWID

YGKVAKLCTCRKDMVKISMDIFVRKFQPDRYQLWKQGKDIYTIDHTKPTP

ASTPEVKAWLQRRRKVRKASRSFQCARSTSKRPKADEEEEVSDEVDGAEV

PNPDSVTDDLKVSEKSEAAVKLRNTEASSEEESSASRMQVEQNLSDHIKL

SGNSCLSTSVTEDIKTEDDKAYAYRSVPSISSEADDSIPLSSGYEKPEKS

DPSELSWPKSPESCSSVAESNGVLTEGEESDVESHGNGLEPGEIPAVPSG

ERNSFKVPSIAEGENKTSKSWRHPLSRPPARSPMTLVKQQAPSDEELPEV

LSIEEEVEETESWAKPLIHLWQTKSPNFAAEQEYNATVARMKPHCAICTL

LMPYHKPDSSNEENDARWETKLDEVVTSEGKTKPLIPEMCFIYSEENIEY

SPPNAFLEEDGTSLLISCAKCCVRVHASCYGIPSHEICDGWLCARCKRNA

WTAECCLCNLRGGALKQTKNNKWAHVMCAVAVPEVRFTNVPERTQIDVGR

IPLQRLKLKCIFCRHRVKRVSGACIQCSYGRCPASFHVTCAHAAGVLMEP

DDWPYVVNITCFRHKVNPNVKSKACEKVISVGQTVITKHRNTRYYSCRVM

AVTSQTFYEVMFDDGSFSRDTFPEDIVSRDCLKLGPPAEGEVVQVKWPDG

KLYGAKYFGSNIAHMYQVEFEDGSQIAMKREDIYTLDEELPKRVKARFST

ASDMRFEDTFYGADIIQGERKRQRVLSSRFKNEYVADPVYRTFLKSSFQK

KCQKRQ

In some embodiments, the Kdm4 histone demethylase activator useful in the methods, compositions and kits as disclosed herein is a nucleic acid agent which encodes the KDM4D polypeptide, or a KDM4D polypeptide, or a variant or biological active fragment thereof. As used herein, the human KDM4D nucleic acid sequence corresponds to Genbank Accession No. NM_018039.2, and refers to SEQ ID NO: 1 as disclosed herein. KDM4D is also known as lysine (K)-specific demethylase 4D, FLJ10251, JMJD2D or "jumonji domain containing 2D". The human KDM4D protein corresponds to Genebank Accession no. NP_060509.2" (SEQ ID NO: 55). Accordingly, the protein sequence of KDM4D is as follows:

(SEQ ID NO: 55)
METMKSKANCAQNPNCNIMIFHPTKEEFNDFDKYIAYMESQGAHRAGLAK

IIPPKEWKARETYDNISEILIATPLQQVASGRAGVFTQYHKKKKAMTVGE

YRHLANSKKYQTPPHQNFEDLERKYWKNRIYNSPIYGADISGSLFDENTK

QWNLGHLGTIQDLLEKECGVVIEGVNTPYLYFGMWKTTFAWHTEDMDLYS

INYLHLGEPKTWYVVPPEHGQRLERLARELFPGSSRGCGAFLRHKVALIS

PTVLKENGIPFNRITQEAGEFMVTFPYGYHAGFNHGFNCAEAINFATPRW

IDYGKMASQCSCGEARVTFSMDAFVRILQPERYDLWKRGQDRAVVDHMEP

RVPASQELSTQKEVQLPRRAALGLRQLPSHWARHSPWPMAARSGTRCHTL

VCSSLPRRSAVSGTATQPRAAAVHSSKKPSSTPSSTPGPSAQIIHPSNGR

RGRGRPPQKLRAQELTLQTPAKRPLLAGTTCTASGPEPEPLPEDGALMDK

PVPLSPGLQHPVKASGCSWAPVP

In some embodiments, the agent which contacts a recipient mammalian oocyte or mammalian SCNT embryo increases the expression of human KDM4d protein of SEQ ID NO: 55, and/or comprises a human KDM4d nucleic acid sequence corresponding of SEQ ID NO: 1, or a biologically active fragment thereof which increases the efficiency of SCNT to a similar or greater extent (e.g., at least about 110%, or at least about 120%, or at least about 130%, or at least about 140%, or at least about 150%, or more than 150% increased) as compared to the nucleic acid sequence of SEQ ID NO: 1.

In some embodiments, a biologically active fragment of SEQ ID NO: 55 comprises amino acids 1-424 of SEQ ID NO: 55, as disclosed in Antony et al., Nature, 2013. In some embodiments, a biologically active fragment of SEQ ID NO: 55 comprises amino acid 1-424 of SEQ ID NO: 55 that also lacks at least 1, or at least 2, or at least between 2-10, or at least between 10-20, or at least between 20-50, or at least between 50-100 amino acids at the C-terminal, or the N-terminal of amino acids 1-424 of SEQ ID NO: 55. In some embodiments, a biologically active fragment of SEQ ID NO:

55 comprises amino acid 1-424 of SEQ ID NO: 55 that also lacks at least 1, or at least 2, or at least between 2-10, or at least between 10-20, or at least between 20-50, or at least between 50-100 amino acids at both the C-terminal and the N-terminal of amino acids 1-424 of SEQ ID NO: 55. In some embodiments, a biologically active fragment of SEQ ID NO: 55 comprises SEQ ID NO: 64, wherein the protein sequence of SEQ ID NO: 64 comprises:

(SEQ ID NO: 64)
METMKSKANCAQNPNCNIMIFHPTKEEFNDFDKYIAYMESQGAHRAGLAK

IIPPKEWKARETYDNISEILIATPLQQVASGRAGVFTQYHKKKKAMTVGE

YRHLANSKKYQTPPHQNFEDLERKYWKNRIYNSPIYGADISGSLFDENTK

QWNLGHLGTIQDLLEKECGVVIEGVNTPYLYFGMWKTTFAWHTEDMDLYS

INYLHLGEPKTWYVVPPEHGQRLERLARELFPGSSRGCGAFLRHKVALIS

PTVLKENGIPFNRITQEAGEFMVTFPYGYHAGFNHGFNCAEAINFATPRW

IDYGKMASQCSCGEARVTFSMDAFVRILQPERYDLWKRGQDRAVVDHMEP

RVPASQELSTQKEVQLPRRAALGLRQLPSHWARHSPWPMAARSGTRCHTL

VCSSLPRRSAVSGTATQPRAAAV

In some embodiments, a biologically active fragment of SEQ ID NO: 55 comprises amino acids of SEQ ID NO: 64 that also lacks at least 1, or at least 2, or at least between 2-10, or at least between 10-20, or at least between 20-50 amino acids at the C-terminal of SEQ ID NO: 64. In some embodiments, a biologically active fragment of SEQ ID NO: 55 comprises amino acids of SEQ ID NO: 64 that also lacks at least 1, or at least 2, or at least between 2-10, or at least between 10-20, or at least between 20-50 amino acids at the N-terminal of SEQ ID NO: 64.

In some embodiments, a histone demethylase activator for use in the methods as disclosed herein is selected from a nucleic acid agent which encodes any mammalian KDM4A polypeptide, or encodes a variant or biological active fragment of a mammalian KDM4A polypeptide. In some embodiments, a histone demethylase activator for use in the methods as disclosed herein is selected from any mammalian KDM4A polypeptide, or a variant or biological active fragment of such a mammalian KDM4A polypeptide. It is encompassed in the present invention that one of ordinary skill in the art can identify an appropriate mammalian homologue of human KDM4A polypeptide, and the nucleic acid encoding such a mammalian homologue for use in the methods and composition as disclosed herein.

In some embodiments, a histone demethylase activator for use in the methods as disclosed herein is selected from a nucleic acid agent which encodes any mammalian KDM4B polypeptide, or encodes a variant or biological active fragment of a mammalian KDM4B polypeptide. In some embodiments, a histone demethylase activator for use in the methods as disclosed herein is selected from any mammalian KDM4B polypeptide, or a variant or biological active fragment of such a mammalian KDM4B polypeptide. It is encompassed in the present invention that one of ordinary skill in the art can identify an appropriate mammalian homologue of human KDM4B polypeptide, and the nucleic acid encoding such a mammalian homologue for use in the methods and composition as disclosed herein.

In some embodiments, a histone demethylase activator for use in the methods as disclosed herein is selected from a nucleic acid agent which encodes any mammalian KDM4C polypeptide, or encodes a variant or biological active fragment of a mammalian KDM4C polypeptide. In some embodiments, a histone demethylase activator for use in the methods as disclosed herein is selected from any mammalian KDM4C polypeptide, or a variant or biological active fragment of such a mammalian KDM4C polypeptide. It is encompassed in the present invention that one of ordinary skill in the art can identify an appropriate mammalian homologue of human KDM4C polypeptide, and the nucleic acid encoding such a mammalian homologue for use in the methods and composition as disclosed herein.

In some embodiments, a histone demethylase activator for use in the methods as disclosed herein is selected from a nucleic acid agent which encodes any mammalian KDM4D polypeptide, or encodes a variant or biological active fragment of a mammalian KDM4D polypeptide. In some embodiments, a histone demethylase activator for use in the methods as disclosed herein is selected from any mammalian KDM4D polypeptide, or a variant or biological active fragment of such a mammalian KDM4D polypeptide. It is encompassed in the present invention that one of ordinary skill in the art can identify an appropriate mammalian homologue of human KDM4D polypeptide, and the nucleic acid encoding such a mammalian homologue for use in the methods and composition as disclosed herein.

As used in some embodiments, a histone demethylase activator for use in the methods as disclosed herein is selected from any of the group consisting of; AOF (LSD1), AOF1 (LSD2), FBXL11 (JHDM1A), Fbx110 (JHDM1B), FBXL19 (JHDM1C), KIAA1718 (JHDM1D), PHF2 (JHDM1E), PHF8 (JHDM1F), JMJD1A (JHDM2A), JMJD1B (JHDM2B), JMJD1C (JHDM2C), KDM4A (JMJD2A; JHDM3A), KDM4B (JMJD2B; JHDM3B), KDM4C (JMJD2C; JHDM3C),KDM4D (JMJD2D; JHDM3D), RBP2 (JARID1A), PLU1 (JARID1B), SMCX (JARID1C), SMCY (JARID1D), Jumonji (JARID2), UTX (UTX), UTY (UTY), JMJD3 (JMJD3), JMJD4 (JMJD4), JMJD5 (JMJD5), JMJD6 (JMJD6), JMJD7 (JMJD7), JMJD8 (JMJD8). Such histone demethylase activators are disclosed in US Application 2011/0139145, which is incorporated herein in its entirety by reference.

In some embodiments, a KDM4 histone demethylase activator is a polypeptide variant, or a nucleic acid sequence that encodes a polypeptide variant of at least 80%, 85%, 90%, 95%, 98%, or 99% identical to the full-length polypeptide, or a fragment of the polypeptide of any human Kdm4 polypeptides of SEQ ID NOs: 50, 52, 54, 55 (human KDM4A-KDM4D) or encoded by any one of the nucleic acid sequences corresponding to SEQ ID NO: 1-8.

In some embodiments, a KDM4 histone demethylase activator is a polypeptide variant, or a nucleic acid sequence that encodes a polypeptide variant, of at least 80%, 85%, 90%, 95%, 98%, or 99% identical to the full-length polypeptide, or a fragment of the polypeptide of Kdm4 polypeptides of SEQ ID NOs: 50, 52, 54, 55 (human KDM4A-KDM4D). In some embodiments, a Kdm4 histone demethylase is a fragment of at least 20 consecutive amino acids of SEQ ID NOs: 50, 52, 54, 55 (human KDM4A-KDM4D), or a fragment of human KDM4A, KDM4B, KDM4C or KDM4D which is at least 50%, 60%, 70%, 80%, 85%, 90%, 95%, 98%, or 99% as long as the full length wild type polypeptide or a domain thereof having an activity of interest, such as at least 80% or greater in ability to increase the efficiency of SCNT as compared to the efficiency of a protein of SEQ ID NOs: 50, 52, 54, 55 (human KDM4A-KDM4D) respectively.

In some embodiments, a biologically active fragment of human KDM4A comprises a fragment of SEQ ID NO:50, (e.g., wherein the fragment is at least 50%, 60%, 70%, 80%, 85%, 90%, 95%, 98%, or 99% as long as SEQ ID NO: 50) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4A polypeptide comprising the amino acids of SEQ ID NO: 50, using the same method and under the same conditions.

In some embodiments, a biologically active fragment of human KDM4B comprises a fragment of SEQ ID NO:52, (e.g., wherein the fragment is at least 50%, 60%, 70%, 80%, 85%, 90%, 95%, 98%, or 99% as long as SEQ ID NO: 52) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4B polypeptide comprising the amino acids of SEQ ID NO: 52, using the same method and under the same conditions.

In some embodiments, a biologically active fragment of human KDM4C comprises a fragment of SEQ ID NO:54, (e.g., wherein the fragment is at least 50%, 60%, 70%, 80%, 85%, 90%, 95%, 98%, or 99% as long as SEQ ID NO: 54) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4C polypeptide comprising the amino acids of SEQ ID NO: 54, using the same method and under the same conditions.

In some embodiments, a biologically active fragment of human KDM4D comprises a fragment of SEQ ID NO:55, (e.g., wherein the fragment is at least 50%, 60%, 70%, 80%, 85%, 90%, 95%, 98%, or 99% as long as SEQ ID NO: 55) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4D polypeptide comprising the amino acids of SEQ ID NO: 55, using the same method and under the same conditions. In some embodiments, a biologically active fragment of SEQ ID NO: 55 comprises amino acids 1-424 of SEQ ID NO: 55, as disclosed in Antony et al., Nature, 2013. In some embodiments, a biologically active fragment of SEQ ID NO: 55 comprises amino acid 1-424 of SEQ ID NO: 55 that also lacks at least 1, or at least 2, or at least between 2-10, or at least between 10-20, or at least between 20-50, or at least between 50-100 amino acids at the C-terminal, or the N-terminal of amino acids 1-424 of SEQ ID NO: 55. In some embodiments, a biologically active fragment of SEQ ID NO: 55 comprises amino acid 1-424 of SEQ ID NO: 55 that also lacks at least 1, or at least 2, or at least between 2-10, or at least between 10-20, or at least between 20-50, or at least between 50-100 amino acids at both the C-terminal and the N-terminal of amino acids 1-424 of SEQ ID NO: 55. In some embodiments, a biologically active fragment of SEQ ID NO: 55 comprises SEQ ID NO: 64, wherein the protein sequence of SEQ ID NO: 64 comprises:

(SEQ ID NO: 64)
METMKSKANCAQNPNCNIMIFHPTKEEFNDFDKYIAYMESQGAHRAGLAK

IIPPKEWKARETYDNISEILIATPLQQVASGRAGVFTQYHKKKKAMTVGE

YRHLANSKKYQTPPHQNFEDLERKYWKNRIYNSPIYGADISGSLFDENTK

QWNLGHLGTIQDLLEKECGVVIEGVNTPYLYFGMWKTTFAWHTEDMDLYS

INYLHLGEPKTWYVVPPEHGQRLERLARELFPGSSRGCGAFLRHKVALIS

-continued
PTVLKENGIPFNRITQEAGEFMVTFPYGYHAGFNHGFNCAEAINFATPRW

IDYGKMASQCSCGEARVTFSMDAFVRILQPERYDLWKRGQDRAVVDHMEP

RVPASQELSTQKEVQLPRRAALGLRQLPSHWARHSPWPMAARSGTRCHTL

VCSSLPRRSAVSGTATQPRAAAV

In some embodiments, a biologically active fragment of SEQ ID NO: 55 comprises amino acids of SEQ ID NO: 64 that also lacks at least 1, or at least 2, or at least between 2-10, or at least between 10-20, or at least between 20-50 amino acids at the C-terminal of SEQ ID NO: 64. In some embodiments, a biologically active fragment of SEQ ID NO: 55 comprises amino acids of SEQ ID NO: 64 that also lacks at least 1, or at least 2, or at least between 2-10, or at least between 10-20, or at least between 20-50 amino acids at the N-terminal of SEQ ID NO: 64.

In some embodiments, a biologically active variant of human KDM4A comprises a variant of SEQ ID NO:50 which has at least 80% sequence identity (or at least about 85%, or at least about 90%, or at least about 95%, or at least about 98%, or at least about 99% sequence identity) to SEQ ID NO: 50, (e.g., wherein the variant is at least 85%, 90%, 95%, 98%, or 99% identical SEQ ID NO: 50) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4A polypeptide comprising the amino acids of SEQ ID NO: 50, using the same method and under the same conditions.

In some embodiments, a biologically active variant of human KDM4B comprises a variant of SEQ ID NO:52 which has at least 80% sequence identity (or at least about 85%, or at least about 90%, or at least about 95%, or at least about 98%, or at least about 99% sequence identity) to SEQ ID NO: 52, (e.g., wherein the variant is at least 85%, 90%, 95%, 98%, or 99% identical SEQ ID NO: 52) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4B polypeptide comprising the amino acids of SEQ ID NO: 52, using the same method and under the same conditions.

In some embodiments, a biologically active variant of human KDM4C comprises a variant of SEQ ID NO:54 which has at least 80% sequence identity (or at least about 85%, or at least about 90%, or at least about 95%, or at least about 98%, or at least about 99% sequence identity) to SEQ ID NO: 54, (e.g., wherein the variant is at least 85%, 90%, 95%, 98%, or 99% identical SEQ ID NO: 54) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4C polypeptide comprising the amino acids of SEQ ID NO: 54, using the same method and under the same conditions.

In some embodiments, a biologically active variant of human KDM4D comprises a variant of SEQ ID NO:55 which has at least 80% sequence identity (or at least about 85%, or at least about 90%, or at least about 95%, or at least about 98%, or at least about 99% sequence identity) to SEQ ID NO: 55, (e.g., wherein the variant is at least 85%, 90%, 95%, 98%, or 99% identical SEQ ID NO: 55) which has about at least 50%, or 60% or 70% or at 80% or 90% or 100% or greater than 100%, for example 1.5-fold, 2-fold, 3-fold, 4-fold or greater than 4-fold the ability to increase the efficiency of SCNT as compared to a KDM4D polypeptide comprising the amino acids of SEQ ID NO: 55, using the same method and under the same conditions.

In some embodiments, the Kdm4 histone demethylase activator useful in the methods and compositions and kits as disclosed herein is a nucleic acid agent, such as a RNA or modified RNA (modRNA) as disclosed in US Patent Application US2012/03228640, which encodes a polypeptide of SEQ ID NO: 50, 52, 54 or 55, or a biologically active variant or fragment thereof. In some embodiments, a KDM4 histone demethylase activator comprises a nucleic acid agent selected from any of SEQ ID NO: 1-8, 49, 51 or 53, or a nucleic acid variant which is has at least 80% sequence identity (or at least about 85%, or at least about 90%, or at least about 95%, or at least about 98%, or at least about 99% sequence identity) SEQ ID NO: 1-8, 49, 51 or 53. In some embodiments, a KDM4 histone demethylase activator comprises a nucleic acid which is a fragment of at least 20 consecutive amino acids of any one of SEQ ID NO: 1-8, 49, 51 or 53, e.g., a fragment of at least 20-, or at least 30- or at least 40- or at least 50 nucleic acids of SEQ ID NO: 1-8, 49, 51 or 53. In some embodiments, a KDM4 histone demethylase activator which is a nucleic acid agent useful in the methods and compositions and kits is expressed from a vector, e.g., a viral vector.

In alternative embodiments, a KDM4 histone demethylase activator encompassed for use herein is a synthetic modified RNA (modRNA) encoding SEQ ID NO: 1-8, 49, 51 or 53. Synthetic modified RNA (modRNA) are described in U.S. applications US2012/03228640; US2009/0286852 and US2013/0111615 and U.S. Pat. Nos. 8,278,036; 8,691, 966; 8,748,089; 8,835,108, which are incorporated herein in their entirety by reference. In some embodiments, the synthetic, modified RNA molecule is not expressed in a vector, and the synthetic, modified RNA molecule can be a naked synthetic, modified RNA molecule. In some embodiments, a composition can comprises at least one synthetic, modified RNA molecule present in a lipid complex.

In some embodiments, the synthetic, modified RNA molecule comprises at least two modified nucleosides, for example, at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2'deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2, N2, 7-trimethylguanosine (m2,2,7G), and inosine (I). In some embodiments, the synthetic, modified RNA molecule further comprises a 5' cap, such as a 5' cap analog, e.g., a 5' diguanosine cap. In some embodiments, a synthetic, modified RNA molecule for use in the methods and compositions as disclosed herein does not comprise a 5' triphosphate. In some embodiments, a synthetic, modified RNA molecule for use in the methods and compositions as disclosed herein further comprises a poly(A) tail, a Kozak sequence, a 3' untranslated region, a 5' untranslated region, or any combination thereof, and in some embodiments, the a synthetic, modified RNA molecule can optionally treated with an alkaline phosphatase.

H3K9 Methyltransferase Inhibitors.

In one aspect, the invention provides a method of increasing the efficiency of SCNT comprising: contacting the nuclei or cytoplasm of a donor mammalian cell, or a SCNT embryo, or an oocyte with an agent that inhibits histone methylation, in particular, inhibits H3K9 methylation, in particular, inhibits H3H9me3 trimethylation. In certain embodiments of the invention the agent inhibits histone methyltransferase activity. In certain embodiments of the invention the agent inhibits expression of a histone methyltransferase. In certain embodiments of the invention the inhibitor is an inhibitor of H3K9 methyltransferase. As discussed herein, the inventors have discovered that inhibition of a H3K9 methyltransferase protein can be used to increase the efficiency of SCNT. In some embodiments, an H3K9 methyltransferase inhibitor is a protein inhibitor, and in some embodiments, the inhibitor is any agent which inhibits the function of a H3K9 methyltransferase protein or the expression of a H3K9 methyltransferase from its gene.

In certain embodiments of the invention, the agent inhibits the histone methyltransferase Suv39h1. In certain embodiments of the invention, the agent inhibits the histone methyltransferase Suv39h2. In certain embodiments of the invention, the agent is an inhibitor of the histone methyltransferase Ehmt1. In certain embodiments of the invention, the agent inhibits the histone methyltransferase Setdb1. In certain embodiments at least two H3K9 methyltransferases (e.g., 2, 3, 4, etc.) are inhibited. In certain embodiments of the invention, both Suv39h1 and Suv39h2 are inhibited by the same agent (e.g., a Suv39h1/2 inhibitor) or by 2 or more separate agents. In certain embodiments of the invention the agent is a RNAi agent, e.g., a siRNA or shRNA that inhibits expression of a histone methyltransferase, e.g., an H3K9 methyltransferase, e.g., Suv39h1, Suv39h2, or Setdb1.

As used herein the term "Suv39h1" or "H3K9-histone methyltransferase Suv39h1" has its general meaning in the art and refers to the histone methyltransferase "suppressor of variegation 3-9 homolog 1 (*Drosophila*)" that methylates Lys-9 of histone H3 (Aagaard L, Laible G, Selenko P, Schmid M, Dorn R, Schotta G, Kuhfittig S, Wolf A, Lebersorger A, Singh P B, Reuter G, Jenuwein T (June 1999). "Functional mammalian homologues of the *Drosophila* PEV-modifier Su(var)3-9 encode centromere-associated proteins which complex with the heterochromatin component M31". EMBO J 18 (7): 1923-38.). Said histone methyltransferase is also known as MG44, KMT1A, SUV39H, histone-lysine N-methyltransferase SUV39H1, H3-K9-HMTase 1, OTTHUMP00000024298, Su(var)3-9 homolog 1, lysine N-methyltransferase 1A, histone H3-K9 methyltransferase 1, position-effect variegation 3-9 homolog, histone-lysine N-methyltransferase, or H3 lysine-9 specific 1. The term encompasses all orthologs of Suv39h1 such as SU(VAR)3-9.

According to the invention, the inhibitor of the Suv39h1 is selected from the group consisting of inhibitors of H3K9-histone methyltransferase Suv39h1; inhibitors of H3K9-histone methyltransferase Suv39h1 gene expression.

The term "inhibitor of H3K9-histone methyltransferase Suv39h1" refers to any compound natural or not having the ability of inhibiting the methylation of Lys-9 of histone H3 by H3K9-histone methyltransferase Suv39h1. The term "inhibitor of H3K9-histone methyltransferase Suv39h2" refers to any compound natural or not having the ability of inhibiting the methylation of Lys-9 of histone H3 by H3K9-histone methyltransferase Suv39h2.

The inhibiting activity of a compound may be determined using various methods as described in Greiner D. Et al. Nat Chem Biol. 2005 August; 1(3):143-5 or Eskeland, R. et al. Biochemistry 43, 3740-3749 (2004).

In some embodiments, inhibition of a H3K9 methyltransferase is by an agent. One can use any agent, for example but are not limited to nucleic acids, nucleic acid analogues, peptides, phage, phagemids, polypeptides, peptidomimetics, ribosomes, aptamers, antibodies, small or large organic or inorganic molecules, or any combination thereof.

In some embodiments, an inhibitor of H3K9 methyltransferase is selected from the group consisting of; a RNAi agent, an siRNA agent, shRNA, oligonucleotide, CRISPR/Cas9, neutralizing antibody or antibody fragment, aptamer, small molecule, protein, peptide, small molecule, avidimir, avimir, and functional fragments or derivatives thereof etc. Commerically available sequences to knockout Suv39h1 and/or Suv39h2 via a CRISPR/Cas9 system are available from Origene (product numbers KN202428 and KN317005) and Santa Cruz Biotechnology (product number: sc-401717) and are encompassed for use in the methods and compostions as disclosed herein.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include, but are not limited to a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues, for example but are not limited to peptide nucleic acid (PNA), pseudo-complementary PNA (pc-PNA), locked nucleic acids (LNA) and derivatives thereof etc. Nucleic acid agents also include, for example, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligonucleotides, etc.

In some embodiments of all aspects of the present invention, an agent which contacts a donor mammalian cell is an inhibitor of a H3K9 methyltransferase, for example, but not limited to, Suv39h1, Suv39h2 or Setdb1. In some embodiments, at least one or any combination of inhibitors of Suv39h1, Suv39h2 or Setdb1 can be used in the methods to increase the efficiency of SNCT. In some embodiments, an inhibitor of Suv39h1, Suv39h2 or Setdb1 inhibits the expression of Suv39h1, Suv39h2 or Setdb1 nucleic acid sequence of a variety of mammalian species, e.g., human, mouse, rat, cattle (e.g., SEQ ID NO: 9-14), or the activity of the Suv39h1, Suv39h2 or Setdb1 proteins from a variety of different mammals, e.g., e.g., human, mouse, rat, cattle.

In the context of the present invention, inhibitors of H3K9-histone methyltransferase Suv39h1/2 are preferably selective for H3K9-histone methyltransferase Suv39h1/2 as compared to other molecues. By "selective" it is meant that the affinity of the inhibitor is at least 10-fold, preferably 25-fold, more preferably 100-fold, still preferably 500-fold higher than the affinity for other histone methyltransferases.

Typically, the inhibitor of H3K9-histone methyltransferase Suv39h1 and/or Suv39h2 is a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

In a particular embodiment, the inhibitor of H3K9-histone methyltransferase Suv39h1 is chaetocin (CAS 28097-03-2) as described by Greiner D, Bonaldi T, Eskeland R, Roemer E, Imhof A. Identification of a specific inhibitor of the histone methyltransferase SU(VAR)3-9. Nat Chem Biol. 2005 August; 1(3):143-5. Epub 2005 Jul. 17.; Weber, H. P., et al., The molecular structure and absolute configuration of chaetocin. Acta Cryst., B28, 2945-2951 (1972); Udagawa, S., et al., The production of chaetoglobosins, sterigmatocystin, O-methylsterigmatocystin, and chaetocin by *Chaetomium* spp. and related fungi. Can. J. microbiol., 25, 170-177 (1979).; Gardiner, D. M., et al., The epipolythiodioxopiperazine (ETP) class of fungal toxins: distribution, mode of action, functions and biosynthesis. Microbiol., 151, 1021-1032 (2005). For example, chaetocin is commercially available from Sigma Aldrich.

In another embodiment, the inhibitor of H3K9-histone methyltransferase Suv39h1 is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Inhibitors of expression for use in the present invention may be based on anti-sense oligonucleotide constructs. Anti-sense oligonucleotides, including anti-sense RNA molecules and anti-sense DNA molecules, would act to directly block the translation of H3K9-histone methyltransferase Suv39h1 or HP1α mRNA by binding thereto and thus preventing protein translation or increasing mRNA degradation, thus decreasing the level of H3K9-histone methyltransferase Suv39h1 or HP1α, and thus activity, in a cell. For example, antisense oligonucleotides of at least about 15 bases and complementary to unique regions of the mRNA transcript sequence encoding H3K9-histone methyltransferase Suv39h1 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Inhibitors of Suv39h1 are disclosed in US Patent Application 2015/0038496, which is incorporated herein in its entirety by reference. The small molecule, Veticillin is identified as a selective inhibitor for both Suv39h1 and Suv39h2 (i.e., inhibits Suv39h1/2), as disclosed in US application 2014/0161785, which is incorporated herein in its entirety by reference.

Inhibitors of Suv39h2 and method of their identification are disclosed in US Patent Application US2014/0094387, which is incorporated herein in its entirety by reference.

RNAi Inhibitors of H3K9 Methyltransferases.

In some embodiments, the H3K9 methyltransferase inhibitor is a RNAi agent, e.g., siRNA or shRNA molecule. RNAi agents of Suv39h1, Suv39h2, Setdb1, Ehmt1, and PRDM2 are well known in the art. In some embodiments an inhibitor of a H3K9 methyltransferase is a RNAi agent. In some embodiments, a RNAi agent inhibits the expression of any one of the proteins of Suv39h1, Suv39h2 or Setdb1 as disclosed herein Inhibition of a H3K9 methyltransferase gene can be by gene silencing RNAi molecules according to methods commonly known by a skilled artisan. In some embodiments, the H3K9 methyltransferase inhibitor is a RNAi agent is any one or a combination of siRNA agents selected from Table 2.

For example, a gene silencing siRNA oligonucleotide duplexes targeted specifically to human Suv39h1 corresponding to NM_003173.3 (SEQ ID NO: 43) can readily be used to knockdown Suv39h1 expression. Suv39h1 mRNA can be successfully targeted using siRNAs; and other siRNA molecules may be readily prepared by those of skill in the art based on the known sequence of the target mRNA. To avoid doubt, the sequence of a human Suv39h1 is provided at, for example, GenBank Accession Nos. NM_003173.3 (SEQ ID NO: 43). One of ordinary skill can select a RNAi agent to be used which inhibits the expression of mRNA which encodes proteins human Suv39h1 (SEQ ID NO: 9), mouse Suv39h1 (SEQ ID NO: 11), rat Suv39h1 (SEQ ID NO: 13) or cattle Suv39h1 (SEQ ID NO: 15) or inhibits the expression of any other mammalian Suv39h1 protein.

To avoid doubt, the sequence of a human Suv39h1 cDNA is provided at, for example, GenBank Accession Nos.: NM_003173.3 (SEQ ID NO: 43) and can be used to design a gene silencing RNAi modulator which inhibits human Suv39h1 mRNA expression for use as a H3K9 methyltransfer inhibitor in the methods and compositions as disclosed herein. In some embodiments, an inhibitor of Suv39h1 is a siRNA agent, for example, but not limited to: GAAACGA-GUCCGUAUUGAAtt (SEQ ID NO: 17) or GAAACGA-GUCCGUAUUGAAtt (SEQ ID NO: 18) and fragments or derivatives of at least 80% sequence identity thereof.

As used herein, the term "Suv39h1 protein" refers to the nucleic acid of SEQ ID NO: 9 as disclosed herein, and homologues thereof, including conservative substitutions, additions, deletions therein not adversely affecting the structure of function. As used herein, the Suv39h1 protein is encoded by the nucleic acid sequence for human Suv39h1 transcript (SEQ ID NO: 43) is as follows:

```
   1 cgctcttctc gcgaggccgg ctaggcccga atgtcgttag ccgtggggaa agatggcgga
  61 aaatttaaaa ggctgcagcg tgtgttgcaa gtcttcttgg aatcagctgc aggacctgtg
 121 ccgcctggcc aagctctcct gccctgccct cggtatctct aagaggaacc tctatgactt
 181 tgaagtcgag tacctgtgcg attacaagaa gatccgcgaa caggaatatt acctggtgaa
 241 atggcgtgga tatccagact cagagagcac ctgggagcca cggcagaatc tcaagtgtgt
 301 gcgtatcctc aagcagttcc acaaggactt agaaagggag ctgctccggc ggcaccaccg
 361 gtcaaagacc ccccggcacc tggacccaag cttggccaac tacctggtgc agaaggccaa
 421 gcagaggcgg gcgctccgtc gctgggagca ggagctcaat gccaagcgca gccatctggg
 481 acgcatcact gtagagaatg aggtggacct ggacggccct ccgcgggcct tcgtgtacat
 541 caatgagtac cgtgttggtg agggcatcac cctcaaccag gtggctgtgg gctgcgagtg
 601 ccaggactgt ctgtgggcac ccactggagg ctgctgcccg ggggcgtcac tgcacaagtt
 661 tgcctacaat gaccagggcc aggtgcggct tcgagccggg ctgcccatct acgagtgcaa
 721 ctcccgctgc cgctgcggct atgactgccc aaatcgtgtg gtacagaagg gtatccgata
 781 tgacctctgc atcttccgca cggatgatgg gcgtggctgg ggcgtccgca ccctggagaa
 841 gattcgcaag aacagcttcg tcatggagta cgtgggagag atcattacct cagaggaggc
 901 agagcggcgg ggccagatct acgaccgtca gggcgccacc tacctctttg acctggacta
 961 cgtggaggac gtgtacaccg tggatgccgc ctactatggc aacatctccc actttgtcaa
1021 ccacagttgt gacccccaacc tgcaggtgta caacgtcttc atagacaacc ttgacgagcg
1081 gctgccccgc atcgctttct ttgccacaag aaccatccgg gcaggcgagg agctcaccct
1141 tgattacaac atgcaagtgg accccgtgga catggagagc acccgcatgg actccaactt
1201 tggcctggct gggctccctg gctccctaa gaagcgggtc cgtattgaat gcaagtgtgg
1261 gactgagtcc tgccgcaaat acctcttcta gcccttagaa gtctgaggcc agactgactg
1321 aggggcctg aagctacatg cacctccccc actgctgccc tcctgtcgag aatgactgcc
1381 agggcctcgc ctgcctccac ctgcccccac ctgctcctac ctgctctacg ttcagggctg
1441 tggccgtggt gaggaccgac tccaggagtc cctttccct gtcccagccc catctgtggg
1501 ttgcacttac aaaccccccac ccaccttcag aaatagtttt tcaacatcaa gactctctgt
1561 cgttgggatt catggcctat taaggaggtc caagggtga gtcccaaccc agccccagaa
```

```
-continued
1621 tatatttgtt tttgcacctg cttctgcctg gagattgagg ggtctgctgc aggcctcctc 1681 cctgctgccc caaaggtatg gggaagcaac cccagagcag gcagacatca gaggccagag 1741 tgcctagccc gacatgaagc tggttcccca accacagaaa ctttgtacta gtgaaagaaa 1801 ggggtccct gggctacggg ctgaggctgg tttctgctcg tgcttacagt gctgggtagt 1861 gttggcccta agagctgtag ggtctcttct tcagggctgc atatctgaga agtggatgcc 1921 cacatgccac tggaagggaa gtgggtgtcc atgggccact gagcagtgag aggaaggcag 1981 tgcagagctg gccagccctg gaggtaggct gggaccaagc tctgccttca cagtgcagtg 2041 aaggtaccta gggctcttgg gagctctgcg gttgctaggg gccctgacct ggggtgtcat 2101 gaccgctgac accactcaga gctggaacca agatctagat agtccgtaga tagcacttag 2161 gacaagaatg tgcattgatg gggtggtgat gaggtgccag gcactgggta gagcacctgg 2221 tccacgtgga ttgtctcagg gaagccttga aaaccacgga ggtggatgcc aggaaagggc 2281 ccatgtggca gaaggcaaag tacaggccaa gaattggggg tgggggagat ggcttcccca 2341 ctatgggatg acgaggcgag agggaagccc ttgctgcctg ccattcccag acccagccc 2401 tttgtgctca ccctggttcc actggtctca aaagtcacct gcctacaaat gtacaaaagg 2461 cgaaggttct gatggctgcc ttgctccttg ctcccccacc cctgtgagg acttctctag 2521 gaagtccttc ctgactacct gtgcccagag tgccctaca tgagactgta tgccctgcta 2641 tcagatgcca gatctatgtg tctgtctgtg tgtccatccc gccggccccc cagactaacc 2641 tccaggcatg gactgaatct ggttctcctc ttgtacaccc ctcaaccta tgcagcctgg 2701 agtgggcatc aataaaatga actgtcgact gaacaaaaaa aaaaaaaaaa aa
```

In some embodiments, the agent comprises a nucleic acid inhibitor that inhibits or reduces the expression of human Suv39h1 (SEQ ID NO: 9), mouse Suv39h1 (SEQ ID NO: 11), rat Suv39h1 (SEQ ID NO: 13) or cattle Suv39h1 (SEQ ID NO: 15) by at least 50% (as compared to in the ansence of the Suv39h1 inhibitor). In some embodiments, the agent comprises a nucleic acid inhibitor that inhibits or decreases the protein expression of human Suv39h2 (SEQ ID NO: 10), mouse Suv39h2 (SEQ ID NO: 12), rat Suv39h2 (SEQ ID NO: 14) or cattle Suv39h2 (SEQ ID NO: 16). In some embodiments, a siRNA inhibitor of mouse Suv39h1 is SEQ ID NO: 18 or a fragment of at least 10 consecutive nucleotides thereof, or nucleic acid sequence with at least 80% sequence identity (or at least about 85%, or at least about 90%, or at least about 95%, or at least about 98%, or at least about 99% sequence identity) to SEQ ID NO: 18. In some embodiments, a siRNA or other nucleic acid inhibitor hybridizes to in full or in part, a target sequence of SEQ ID NO: 17 of Suv39h1. In some embodiments, a siRNA inhibitor of mouse Suv39h2 is SEQ ID NO: 20 or a fragment of at least 10 consecutive nucleotides thereof, or nucleic acid sequence with at least 80% sequence identity (or at least about 85%, or at least about 90%, or at least about 95%, or at least about 98%, or at least about 99%) to SEQ ID NO: 20. In some embodiments, a siRNA or other nucleic acid inhibitor hybridizes in full or part, to a target sequence of SEQ ID NO: 19 of Suv39h2.

Inhibition of a H3K9 methyltransferase gene can be by gene silencing RNAi molecules according to methods commonly known by a skilled artisan. Inhibition of Suv39h1, Suv39h2, Setdb1, Ehmt1, and PRDM2 are well known in the art. In some embodiments, the H3K9 methyltransferase inhibitor is a RNAi agent is any one or a combination of siRNA agents selected from Table 2.

In some embodiments, Suv39h1 can be targeted and inhibited by hsa-mir-98-5p (MIRT027407), hsa-mir-615-3p (MIRT040438), hsa-mir-331-3p (MIRT043442) or miR variants of at least 85% sequence identity thereto. Commercially available siRNA, RNAi and shRNA products that inhibit Suv39h1 and/or Suv39h2 in human, mouse and rat are available from Origene, Qiagen and Santa Cruz Biotechnilogy, and can be used by one of ordinary skill in the art.

For example, a gene silencing siRNA oligonucleotide duplexes targeted specifically to human Suv39h2 corresponding to NM_024670.3 (SEQ ID NO: 43) can readily be used to knockdown Suv39h2 expression. Suv39h2 mRNA can be successfully targeted using siRNAs; and other siRNA molecules may be readily prepared by those of skill in the art based on the known sequence of the target mRNA. To avoid doubt, the sequence of a human Suv39h2 is provided at, for example, GenBank Accession Nos. NM_024670.3 ((SEQ ID NO: 44). To avoid doubt, the sequence of a human Suv39h2 cDNA is provided at, for example, GenBank Accession Nos.: NM_024670.3 (SEQ ID NO: 44) and can be used to design a gene silencing RNAi modulator which inhibits human Suv39h2 mRNA expression for use as a H3K9 methyltransfer inhibitor in the methods and compositions as disclosed herein. In some embodiments, an inhibitor of Suv39h2 is a siRNA agent, for example, but not limited to: GCUCACAUGUAAAUCGAUUtt (SEQ ID NO: 19) or AAUCGAUUUACAUGUGAGCtt (SEQ ID NO: 20) and a fragment or derivative of at least 80% sequence identity thereof.

As used herein, the term "Suv39h2 protein" refers to the nucleic acid of SEQ ID NO: 10 as disclosed herein, and homologues thereof, including conservative substitutions, additions, deletions therein not adversely affecting the structure of function. As used herein, the Suv39h2 protein is encoded by the nucleic acid sequence for human Suv39h2 transcript (SEQ ID NO: 44) is as follows:

```
   1 cggggccgag gcgcgaggag gtgaggctgg agcgcggccc cctcgccttc cctgttccca
  61 ggcaagctcc caaggccggg gcggcggggc cgtcccgcgg gccagccaga tggcgacgtg
 121 gcggttcccc gcccgccgcg acccaactc cgggacgcac gctgcggacg cctatcctcc
 181 cccaggccgc tgacccgcct ccctgccgg ccggctcccg ccgcggagga tatggaatat
 241 tatcttgtaa aatggaaagg atggccagat tctacaaata cttgggaacc tttgcaaaat
 301 ctgaagtgcc cgttactgct tcagcaattc tctaatgaca agcataatta tttatctcag
 361 gtaaagaaag gcaaagcaat aactccaaaa gacaataaca aaactttgaa acctgccatt
 421 gctgagtaca ttgtgaagaa ggctaaacaa aggatagctc tgcagagatg gcaagatgaa
 481 ctcaacagaa gaaagaatca taaaggaatg atatttgttg aaaatactgt tgatttagag
 541 ggcccacctt cagacttcta ttacattaac gaatacaaac cagctcctgg aatcagctta
 601 gtcaatgaag ctacctttgg ttgttcatgc acagattgct tctttcaaaa atgttgtcct
 661 gctgaagctg gagttctttt ggcttataat aaaaaccaac aaattaaaat cccacctggt
 721 actcccatct atgaatgcaa ctcaaggtgt cagtgtggtc ctgattgtcc aataggatt
 781 gtacaaaaag gcacacagta ttcgctttgc atctttcgaa ctagcaatgg acgtggctgg
 841 ggtgtaaaga cccttgtgaa gattaaaaga atgagttttg tcatggaata tgttggagag
 901 gtaatcacaa gtgaagaagc tgaaagacga ggacagttct atgacaacaa gggaatcacg
 961 tatctctttg atctggacta tgagtctgat gaattcacag tggatgcggc tcgatacggc
1021 aatgtgtctc attttgtgaa tcacagctgt gacccaaatc ttcaggtgtt caatgttttc
1081 attgataacc tcgatactcg tcttccccga atagcattgt tttccacaag aaccataaat
1141 gctggagaag agctgacttt tgattatcaa atgaaaggtt ctggagatat atcttcagat
1201 tctattgacc acagcccagc caaaagagg gtcagaacag tatgtaaatg tggagctgtg
1261 acttgcagag gttacctcaa ctgaactttt tcaggaaata gagctgatga ttataatatt
1321 ttttttcctaa tgttaacatt tttaaaaata catatttggg actcttatta tcaaggttct
1381 acctatgtta atttacaatt catgtttcaa gacatttgcc aaatgtatta ccgatgcctc
1441 tgaaaagggg gtcactgggt ctcatagact gatatgaagt cgacatattt atagtgctta
1501 gagaccaaac taatggaagg cagactattt acagcttagt atatgtgtac ttaagtctat
1561 gtgaacagag aaatgcctcc cgtagtgttt gaaagcgtta agctgataat gtaattaaca
1621 actgctgaga gatcaaagat tcaacttgcc atacacctca aattcggaga aacagttaat
1681 ttgggcaaat ctacagttct gttttgcta ctctattgtc attcctgttt aatactcact
1741 gtacttgtat ttgagacaaa taggtgatac tgaatttat actgttttct acttttccat
1801 taaaacattg gcacctcaat gataaagaaa tttaaggtat aaaattaaat gtaaaaatta
1861 atttcagctt catttcgtat ttcgaagcaa tctagactgt tgtgatgagt gtatgtctga
1921 acctgtaatt cttaaaagac ttcttaatct tctagaagaa aaatctccga agagctctct
1981 ctagaagtcc aaaatggcta gccattatgc ttctttgaaa ggacatgata atgggaccag
2041 gatggttttt tggagtacca agcaagggga atggagcact ttaagggcgc tgttagtaa
2101 catgaattgg aaatctgtgt cgagtacctc tgatctaaac ggtaaaacaa gctgcctgga
2161 gagcagctgt acctaacaat actgtaatgt acattaacat tacagcctct caatttcagg
2221 caggtgtaac agttcctttc caccagattt aatattttta tacttcctgc aggttcttct
2281 taaaaagtaa tctatatttt tgaactgata cttgttttat acataaattt tttttagatg
```

```
2341 tgataaagct aaacttggcc aaagtgtgtg cctgaattat tagaccttt tattagtcaa 2401 cctacgaaga ctaaaataga atatattagt tttcaaggga gtgggaggct tccaacatag 2461 tattgaatct caggaaaaac tattctttca tgtctgattc tgagatttct aattgtgttg 2521 tgaaaatgat aaatgcagca aatctagctt tcagtattcc taatttttac ctaagctcat 2581 tgctccaggc tttgattacc taaaataagc ttggataaaa ttgaaccaac ttcaagaatg 2641 cagcacttct taatctttag ctctttcttg ggagaagcta gactttattc attatattgc 2701 tatgacaact tcactctttc ataatatata ggataaattg tttacatgat tggaccctca 2761 gattctgtta accaaaattg cagaatgggg ggccaggcct gtgtggtggc tcacacctgt 2821 gatcccagca ctttgggagg ctgaggtagg aggatcacgt gaggtcggga gttcaagacc 2881 agcctggcca tcatggtgaa accctgtctc tactgaaaat acaaaaatta gccgggcgtg 2941 gtggcacacg cctgtagtcc cagctactca ggaggctgag gcaggagaat cacttgaatt 3001 caggaggcgg aggttgcagt gagccaagat cataccactg cactgcagcc tgagtgacac 3061 agtaagactg tctccaaaaa aaaaaaaaa aaa
```

In some embodiments, or inhibits the mRNA expression of SEQ ID NO:2 as disclosed herein. In some embodiments, one of ordinary skill can select a RNAi agent to be used which inhibits the expression of mRNA which encodes proteins of human Suv39h2 (SEQ ID NO: 10), mouse Suv39h2 (SEQ ID NO: 12), rat Suv39h2 (SEQ ID NO: 14) or cattle Suv39h2 (SEQ ID NO: 16) or inhibits the expression of any other mammalian Suv39h2 protein.

Other exemplary siRNA sequences for Suv39h1 and Suv39h2 are disclosed in US application 2012/0034192 which is incorporated herein in its entirety by reference.

TABLE 2 exemplary siRNA sequences to inhibit H3K9 methyltransfersases:

| Gene | SEQ ID NO: | siRNA sequence |
|---|---|---|
| Human Suv39h1 | 17 | GAAACGAGUCCGUAUUGAAtt, (sense) |
| Human Suv39h1 | 18 | UUCAAUACGGACUCGUUUCtt (antisense) |
| Human Suv39h2 | 19 | GCUCACAUGUAAAUCGAUUtt (sense) |
| Human Suv39h2 | 20 | AAUCGAUUUACAUGUGAGCtt (antisense) |
| Human Suv39h1 | 21 | GGUGUACAACGUAUUCAUAtt (sense) |
| Human Suv39h1 | 22 | UAUGAAUACGUUGUACACCtg (antisense) |
| Human Suv39h1 | 23 | GGUCCUUUGUCUAUAUCAAtt (sense) |
| Human Suv39h1 | 24 | UUGAUAUAGACAAAGGACCtt (antisense) |
| Human Suv39h2 | 25 | GCUCACAUGUAAAUCGAUUtt (sense) |
| Human Suv39h2 | 26 | AAUCGAUUUACAUGUGAGCtt (antisense) |
| Human Suv39h2 | 27 | GUGUCGAUGUGGACCUGAAtt (sense) |
| Human Suv39h2 | 28 | UUCAGGUCCACAUCGACACct (antisense) |
| Human Setdb1 (ESET) | 29 | GGACUACAGUAUCAUGACAtt (sense) |
| Human Setdb1 (ESET) | 30 | UGUCAUGAUACUGUAGUCCca (antisense) |
| Human Setdb1 (ESET) | 31 | GGACGAUGCAGGAGAUAGAtt (sense) |
| Human Setdb1 (ESET) | 32 | UCUAUCUCCUGCAUCGUCCga (antisense) |
| Human Setdb1 (ESET) | 33 | GGAUGGGUGUCGGGAUAAAtt (sense) |
| Human Setdb1 (ESET) | 34 | UUUAUCCCGACACCCAUCCtt (antisense) |
| Human Ehmt1(GLP) | 35 | GCACCUUUGUCUGCGAAUAtt (sense) |

TABLE 2-continued exemplary siRNA sequences to inhibit H3K9 methyltransfersases:

| Gene | SEQ ID NO: | siRNA sequence |
|---|---|---|
| Human Ehmt1(GLP) | 36 | UAUUCGCAGACAAAGGUGCcc (antisense) |
| Human Ehmt1(GLP) | 37 | GAUCAAACCUGCUCGGAAAtt (sense) |
| Human Ehmt1(GLP) | 38 | UUUCCGAGCAGGUUUGAUCca (antisense) |
| Human PRDM2/Riz1 | 39 | GAAUUUGCCUUCUUAUGCAtt (sense) |
| Human PRDM2/Riz1 | 40 | UGCAUAAGAAGGCAAAUUCtt (antisense) |
| Human PRDM2/Riz1 | 41 | GAGGAAUUCUAGUCCCGUAtt (sense) |
| Human PRDM2/Riz1 | 42 | UACGGGACUAGAAUUCCUCaa (antisense) |

To avoid doubt, the sequence of a human Setdb1 cDNA is provided at, for example, GenBank Accession Nos.: NM_001145415.1 (SEQ ID NO: 45) and can be used by one of ordinary skill in the art to design a gene silencing RNAi modulator which inhibits human Setdb1 mRNA expression for use as a H3K9 methyltransfer inhibitor in the methods and compositions as disclosed herein.

To avoid doubt, the sequence of a human Ehmt1 cDNA is provided at, for example, GenBank Accession Nos.: NM_024757.4 (SEQ ID NO: 46) and can be used by one of ordinary skill in the art to design a gene silencing RNAi modulator which inhibits human Ehmt1 mRNA expression for use as a H3K9 methyltransfer inhibitor in the methods and compositions as disclosed herein.

To avoid doubt, the sequence of a human PRDM2 cDNA is provided at, for example, GenBank Accession Nos.: NM_012231.4 (SEQ ID NO: 47) and can be used by one of ordinary skill in the art to design a gene silencing RNAi modulator which inhibits human PRDM2 mRNA expression for use as a H3K9 methyltransfer inhibitor in the methods and compositions as disclosed herein.

In some embodiments, an inhibitor of H3K9 methyltransferase is selected from the group consisting of; a RNAi agent, an siRNA agent, shRNA, oligonucleotide, CRISPR/Cas9, neutralizing antibody or antibody fragment, aptamer, small molecule, protein, peptide, small molecule, avidimir, and functional fragments or derivatives thereof etc. In some embodiments, the H3K9 methyltransferase inhibitor is a RNAi agent, e.g., siRNA or shRNA molecule. In some embodiments, the agent comprises a nucleic acid inhibitor that reduces protein expression of human Suv39h1 (SEQ ID NO: 9), mouse Suv39h1 (SEQ ID NO: 11), rat Suv39h1 (SEQ ID NO: 13) or cattle Suv39h1 (SEQ ID NO: 15). In some embodiments, the agent comprises a nucleic acid inhibitor to inhibit expression of human Suv39h2 (SEQ ID NO: 10), mouse Suv39h2 (SEQ ID NO: 12), rat Suv39h2 (SEQ ID NO: 14) or cattle Suv39h2 (SEQ ID NO: 16). In some embodiments, a siRNA inhibitor of mouse Suv39h1 is SEQ ID NO: 18 or a fragment of at least 10 consecutive nucleotides thereof, or nucleic acid sequence with at least 80% sequence identity (or at least about 85%, or at least about 90%, or at least about 95%, or at least about 98%, or at least about 99% sequence identity) to SEQ ID NO: 18. In some embodiments, a siRNA or other nucleic acid inhibitor hybridizes to in full or in part, a target sequence of SEQ ID NO: 17 of Suv39h1. In some embodiments, a siRNA inhibitor of mouse Suv39h2 is SEQ ID NO: 20 or a fragment of at least 10 consecutive nucleotides thereof, or nucleic acid sequence with at least 80% sequence identity (or at least about 85%, or at least about 90%, or at least about 95%, or at least about 98%, or at least about 99%) to SEQ ID NO: 20. In some embodiments, a siRNA or other nucleic acid inhibitor hybridizes in full or in part, to a target sequence of SEQ ID NO: 19 or SEQ ID NO: 44 of Suv39h2.

In other embodiments of the above aspects, a H3K9 methyltransferase inhibitor inhibits any one of the following histone methyltransferases selected from the group consisting of: SUV39H1, SUV39H2, G9A (EHMT2), EHMT1, ESET (SETDB1), SETDB2, MLL, MLL2, MLL3, SETD2, NSD1, SMYD2, DOT1L, SETD8, SUV420H1, SUV420H2, EZH2, SETD7, PRDM2, PRMT1, PRMT2, PRMT3, PRMT4, PRMT5, PRMT6, PRMT7, PRMT8, PRMT9, PRMT10, PRMT11, CARM1.

In some embodiments, a agent that inhibits a H3K9 methyltransferase, e.g., Suv39h1, Suv39h2 or Setdb1 is a nucleic acid. Nucleic acid inhibitors of H3K9 methyltransferases, e.g., Suv39h1, Suv39h2 or Setdb1 include, for example, but are not limited to, RNA interference-inducing (RNAi) molecules, for example but are not limited to siRNA, dsRNA, stRNA, shRNA and modified versions thereof, where the RNA interference (RNAi) molecule silences the gene expression from any one of Suv39h1, Suv39h2 or Setdb1 genes.

Accordingly, in some embodiments, inhibitors of H3K9 methyltransferases, e.g., Suv39h1, Suv39h2 or Setdb1 can inhibit by any "gene silencing" methods commonly known by persons of ordinary skill in the art. In some embodiments, a nucleic acid inhibitor of H3K9 methyltransferases, e.g., Suv39h1, Suv39h2 or Setdb1 is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. a H3K9 methyltransferase gene sequence of Suv39h1, Suv39h2 or Setdb1 gene sequence. A siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target sequence.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting H3K9 methyltransferases, e.g., Suv39h1, Suv39h2 or Setdb1 gene can be readily designed and tested. Accordingly, siRNAs useful for the methods described herein include siRNA molecules of about 15 to about 40 or about 15 to about 28 nucleotides in length, which are homologous to the specific H3K9 methyltransferase gene, e.g., Suv39h1, Suv39h2 or Setdb1 gene. In some embodiments, a H3K9 methyltransferase targeting agent, e.g., Suv39h1, Suv39h2 or Setdb1 targeting siRNA molecules have a length of about 25 to about 29 nucleotides. In some embodiments, a H3K9 methyltransferase targeting siRNA, e.g., a Suv39h1, a Suv39h2 or a Setdb1 targeting siRNA molecules have a length of about 27, 28, 29, or 30 nucleotides. In some embodiments, a H3K9 methyltransferase targeting RNAi, e.g., Suv39h1, Suv39h2 or Setdb1 targeting siRNA molecules can also comprise a 3' hydroxyl group. In some embodiments, a H3K9 methyltransferase targeting siRNA, e.g., a Suv39h1, a Suv39h2 or Setdb1 targeting siRNA molecules can be single-stranded or double stranded; such molecules can be blunt ended or comprise overhanging ends (e.g., 5', 3'). In specific embodiments, the RNA molecule can be a double stranded and either blunt ended or comprises overhanging ends.

In one embodiment, at least one strand of the H3K9 methyltransferases, e.g., Suv39h1, Suv39h2 or Setdb1 targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the Suv39h1/2, Setdb1, Ehmt1 or PRDM2 targeting RNA molecule is double stranded—one strand has a 3' overhang and the other strand can be blunt-ended or have an overhang. In the embodiment in which a H3K9 methyltransferase, e.g., Suv39h1, Suv39h2 Setdb1, Ehmt1 or PRDM2 RNAi agent is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

As disclosed herein in the Examples, siRNAs to H3K9 methyltransferases Suv39h1, Suv39h2 and Setdb1 have been successfully used to increase the efficiency of SCNT. In some embodiments, where gene silencing RNAi of H3K9 methyltransferases, e.g., Suv39h1, Suv39h2 Setdb1, Ehmt1 or PRDM2 are not commercially available, gene silencing RNAi agents targeting inhibition of H3K9 methyltransferases, e.g., Suv39h1, Suv39h2 Setdb1, Ehmt1 or PRDM2 can be produced by one of ordinary skill in the art and according to the methods as disclosed herein. In some embodiments, the assessment of the expression and/or knock down of a H3K9 methyltransferases, e.g., Suv39h1, Suv39h2 Setdb1, Ehmt1 or PRDM2 mRNA and/or protein can be determined using commercially available kits known by persons of ordinary skill in the art. Others can be readily prepared by those of skill in the art based on the known sequence of the target mRNA.

In some embodiments, an inhibitor of the H3K9 methyltransferases is a gene silencing RNAi agent which downregulates or decreases any one or more of Suv39h1, Suv39h2 Setdb1, Ehmt1 or PRDM2 mRNA levels and can be a 25-nt hairpin sequence. In some embodiments, a H3K9 methyltransferase inhibitor is a gene silencing RNAi, such as, for example, a shRNA sequence of any one or more of Suv39h1, Suv39h2 Setdb1, Ehmt1 or PRDM2.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.).

The terms "antimir" "microRNA inhibitor" or "miR inhibitor" are synonymous and refer to oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands.

In some embodiments, an agent is protein or polypeptide or RNAi agent which inhibits the expression of any one or a combination of the H3K9 methyltransferases such as Suv39h1, Suv39h2 Setdb1, Ehmt1 and/or PRDM2. In such embodiments cells can be modified (e.g., by homologous recombination) to provide increased expression of such an agent, for example by replacing, in whole or in part, the naturally occurring promoter with all or part of a heterologous promoter so that the cells express an inhibitor of a H3K9 methyltransferase such as Suv39h1, Suv39h2 Setdb1, Ehmt1 and/or PRDM2, for example a protein or RNAi agent (e.g. gene silencing-RNAi agent). Typically, a heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also can be engineered to express an endogenous gene comprising the inhibitor agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. The agent can be prepared by culturing transformed host cells under culture conditions suitable to express the miRNA. The resulting expressed agent can then be purified from such culture (i.e., from culture medium or cell extracts) using known purification processes, such as gel filtration and ion exchange chromatography. The purification of the peptide or nucleic acid agent inhibitor of a H3K9 methyltransferase such as Suv39h1, Suv39h2 Setdb1, Ehmt1 and/or PRDM2 can also include an affinity column containing agents which will bind to the protein; one or more column steps over such affinity resins as concanavalin A-agarose, HEPARIN-TOYOPEARL™ or Cibacrom blue 3GA Sepharose; one or more steps involving hydrophobic interaction chromatography using such resins as phenyl ether, butyl ether, or propyl ether; immunoaffinity chromatography, or complementary cDNA affinity chromatography.

In one embodiment, a nucleic acid inhibitor of a H3K9 methyltransferase such as Suv39h1, Suv39h2 Setdb1, Ehmt1 and/or PRDM2, e.g. (gene silencing RNAi agent) can be obtained synthetically, for example, by chemically synthesizing a nucleic acid by any method of synthesis known to the skilled artisan. A synthesized nucleic acid inhibitor of a H3K9 methyltransferase such as Suv39h1, Suv39h2 Setdb1, Ehmt1 and/or PRDM2 can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability of a nucleic acid inhibitor is desired, nucleic acids having nucleic acid analogs and/or modified internucleoside linkages can be used. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy-2'fluoro' phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

Synthetic siRNA molecules, including shRNA molecules, can also easily be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

In some embodiments, an inhibitor of a H3K9 methyltransferase is a gene silencing siRNA molecule which targets any one of Suv39h1, Suv39h2 Setdb1, Ehmt1 and/or PRDM2 genes and in specific embodiments, targets the coding mRNA sequence of H3K9 methyltransferase such as Suv39h1, Suv39h2 Setdb1, Ehmt1 and/or PRDM2, beginning from about 25 to 50 nucleotides, from about 50 to 75 nucleotides, or from about 75 to 100 nucleotides downstream of the start codon. One method of designing a siRNA molecule of the present invention involves identifying the 29 nucleotide sequence motif AA(N29)TT (where N can be any nucleotide) (SEQ ID NO: 48), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis software such as OLIGOENGINE®, can also be used to select siRNA sequences against EST libraries to ensure that only one gene is targeted.

siRNAs useful for the methods described herein include siRNA molecules of about 15 to about 40 or about 15 to about 28 nucleotides in length, which are homologous to any one of the H3K9 methyltransferase such as Suv39h1, Suv39h2 Setdb1, Ehmt1 and/or PRDM2. Preferably, a targeting siRNA molecule to a H3K9 methyltransferase gene such as Suv39h1, Suv39h2 Setdb1, Ehmt1 and/or PRDM2 has a length of about 19 to about 25 nucleotides. More preferably, the targeting siRNA molecules have a length of about 19, 20, 21, or 22 nucleotides. The targeting siRNA molecules can also comprise a 3' hydroxyl group. The targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of a H3K9 methyltransferase RNAi targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the targeting RNA molecule is double stranded—one strand has a 3' overhang and the other strand can be blunt-ended or have an overhang. In the embodiment in which the targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Oligonucleotide Modifications

Unmodified oligonucleotides can be less than optimal in some applications, e.g., unmodified oligonucleotides can be prone to degradation by e.g., cellular nucleases. Nucleases can hydrolyze nucleic acid phosphodiester bonds. However, chemical modifications to one or more of the subunits of oligonucleotide can confer improved properties, and, e.g., can render oligonucleotides more stable to nucleases.

Modified nucleic acids and nucleotide surrogates can include one or more of: (i) alteration, e.g., replacement, of one or both of the non-linking phosphate oxygens and/or of one or more of the linking phosphate oxygens in the phosphodiester backbone linakge. (ii) alteration, e.g., replacement, of a constituent of the ribose sugar, e.g., of the 2' hydroxyl on the ribose sugar; (iii) wholesale replacement of the phosphate moiety with "dephospho" linkers; (iv) modification or replacement of a naturally occurring base with a non-natural base; (v) replacement or modification of the ribose-phosphate backbone; (vi) modification of the 3' end or 5' end of the oligonucelotide, e.g., removal, modification or replacement of a terminal phosphate group or conjugation of a moiety, e.g., a fluorescently labeled moiety, to either the 3' or 5' end of oligonucleotide; and (vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can only occur at a 3' or 5' terminal position, can only occur in the internal region, can only occur in a terminal regions, e.g. at a position on a terminal nucleotide or in the last 2, 3, 4, 5, or 10 nucleotides of an oligonucleotide. A modification can occur in a double strand region, a single strand region, or in both. A modification can occur only in the double strand region of an oligonucleotide or can only occur in a single strand region of an oligonucleotide. E.g., a phosphorothioate modification at a non-bridging oxygen position can only occur at one or both termini, can only occur in a terminal regions, e.g., at a position on a terminal nucleotide or in the last 2, 3, 4, 5, or 10 nucleotides of a strand, or can occur in double strand and single strand regions, particularly at termini. The 5' end or ends can be phosphorylated.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific Modifications to Oligonucleotide
The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, BR3 (R is hydrogen, alkyl, aryl), C (i.e. an alkyl group, an aryl group, etc. . . . ), H, NR2 (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non-phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine and peptide nucleic acid (PNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=NH2; alkylamino, dialkylamino, heterocyclyl, arylamino, diaryl amino, heteroaryl amino, or diheteroaryl amino, ethylene diamine, polyamino) and aminoalkoxy, O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), (OCH2CH2OCH3, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; thioalkyl; and alkyl, cycloalkyl, aryl, alkenyl and alkynyl, which can be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Preferred substitutents are 2'-O-Me (2'-O-methyl), 2'-O-MOE (2'-O-methoxyethyl), 2'-F, 2'-O-[2-(methylamino)-2-oxoethyl] (2'-O—NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP) and 2'-O-dimethylaminoethyloxyethyl (2'-O-DMAEOE).

Terminal Modifications

The 3-prime (3') and 5-prime (5') ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');

5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-). Other embodiments include replacement of oxygen/sulfur with BH3, BH3- and/or Se.

Terminal modifications can also be useful for monitoring distribution, and in such cases the preferred groups to be added include fluorophores, e.g., fluorscein or an ALEXA® dye, e.g., ALEXA® 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-(halo)adenine, 2-(alkyl)adenine, 2-(propyl)adenine, 2 (amino)adenine, 2-(aminoalkyll)adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl)adenine, 8 (thioalkyl)adenine, 8-(thiol)adenine, N6-(isopentyl)adenine, N6 (methyl)adenine, N6, N6 (dimethyl) adenine, 2-(alkyl)guanine, 2 (propyl)guanine, 6-(alkyl) guanine, 6 (methyl)guanine, 7 (alkyl)guanine, 7 (methyl) guanine, 7 (deaza)guanine, 8 (alkyl)guanine, 8-(alkenyl) guanine, 8 (alkynyl)guanine, 8-(amino)guanine, 8 (halo) guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl) cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl) uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo) uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, N2-substituted purines, N6-substituted purines, 06-substituted purines, substituted 1,2,4-triazoles, or any O-alkylated or N-alkylated derivatives thereof;

Further purines and pyrimidines include those disclosed in U.S. Pat. No. 3,687,808, hereby incorporated by reference, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=NH2; alkylamino, dialkylamino, heterocyclyl, arylamino, diaryl amino, heteroaryl amino, or diheteroaryl amino, ethylene diamine, polyamino); aminoalkoxy, e.g., O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino); amino (e.g. NH2; alkylamino, dialkylamino, heterocyclyl, arylamino, diaryl amino, heteroaryl amino, diheteroaryl amino, or amino acid); or NH(CH2CH2NH)nCH2CH2-AMINE (AMINE=NH2; alkylamino, dialkylamino, heterocyclyl, arylamino, diaryl amino, heteroaryl amino, or diheteroaryl amino).

Placement within an Oligonucleotide

Some modifications can preferably be included on an oligonucleotide at a particular location, e.g., at an internal position of a strand, or on the 5' or 3' end of an oligonucleotide. A preferred location of a modification on an oligonucleotide, can confer preferred properties on the agent. For example, preferred locations of particular modifications can confer optimum gene silencing properties, or increased resistance to endonuclease or exonuclease activity.

One or more nucleotides of an oligonucleotide can have a 2'-5' linkage. One or more nucleotides of an oligonucleotide can have inverted linkages, e.g. 3'-3', 5'-5', 2'-2' or 2'-3' linkages.

An oligonucleotide can comprise at least one 5'-pyrimidine-purine-3' (5'-PyPu-3') dinucleotide wherein the pyrimidine is modified with a modification chosen independently from a group consisting of 2'-O-Me (2'-O-methyl), 2'-O-MOE (2'-O-methoxyethyl), 2'-F, 2'-O-[2-(methylamino)-2-oxoethyl] (2'-O—NMA), 2'-S-methyl, 2'-O—CH2-(4'-C) (LNA) and 2'-O—CH2CH2-(4'-C) (ENA).

In one embodiment, the 5'-most pyrimidines in all occurrences of sequence motif 5'-pyrimidine-purine-3' (5'-PyPu-3') dinucleotide in the oligonucleotide are modified with a modification chosen from a group consisting of 2"-O-Me (2'-O-methyl), 2'-O-MOE (2'-O-methoxyethyl), 2'-F, 2'-O-[2-(methylamino)-2-oxoethyl] (2'-O—NMA), 2'-S-methyl, 2'-O—CH2-(4'-C) (LNA) and 2'-O—CH2CH2-(4'-C) (ENA).

A double-stranded oligonucleotide can include at least one 5'-uridine-adenine-3' (5'-UA-3') dinucleotide wherein the uridine is a 2'-modified nucleotide, or a 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

General References

The oligoribonucleotides and oligoribonucleosides used in accordance with this invention can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL, Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., Helv. Chim. Acta, 1995, 78, 486-504; Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. J. Org. Chem. 2001, 66, 2789-2801. Preparation of sulfur bridged nucleotides is described in Sproat et al. Nucleosides Nucleotides 1988, 7,651 and Crosstick et al. Tetrahedron Lett. 1989, 30, 4693.

Sugar Group References

Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083 which is incorporated herein in its entirety by reference.

Terminal Modification References.

Terminal modifications are described in Manoharan, M. et al. Antisense and Nucleic Acid Drug Development 12, 103-128 (2002) and references therein.

Nuclebases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications Oligonucleotide Production The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other oligonucleotides, such as the phosphorothioates, phosphorodithioates and alkylated derivatives. The double-stranded oligonucleotide compounds of the invention can be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotiode can then be resuspended in a solution appropriate for the intended formulation process.

Teachings regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Delivery of RNA Interfering Agents:

Methods of delivering RNAi agents, e.g., an siRNA, or vectors containing an RNAi agent, to the target cells (e.g., basal cells or cells of the lung ad/or respiratory system or other desired target cells) are well known to persons of ordinary skill in the art. In some embodiments, a RNAi agent (e.g. gene silencing-RNAi agent) which is an inhibitor of H3K9 methyltransferase, such as an RNAi agent which inhibits any one or Suv39h1, Suv39h2 Setdb1, Ehmt1 and/or PRDM2 can be administered to a subject via aerosol means, for example using a nebulizer and the like. In alternative embodiments, administration of a RNAi agent (e.g. gene silencing-RNAi agent) which is a H3K9 methyltransferase inhibitor, e.g., an inhibitor of any one of Suv39h1, Suv39h2 Setdb1, Ehmt1 and/or PRDM2 can include, for example (i) injection of a composition containing the RNA interfering agent, e.g., an siRNA, or (ii) directly contacting the cell, (e.g., the donor mammalian cell, the recipient oocyte, or SCNT embryo) with a composition comprising an RNAi agent, e.g., an siRNA.

In some embodiments, administration the cell, oocyte or embryo can be by a single injection or by two or more injections. In some embodiments, a RNAi agent is delivered in a pharmaceutically acceptable carrier. One or more RNAi agents can be used simultaneously, e.g. one or more gene silencing RNAi agent inhibitors of a H3K9 methyltransferase such as Suv39h1, Suv39h2 Setdb1, Ehmt1 and/or PRDM2 can be administered together. The RNA interfering agents, e.g., the siRNA H3K9 methyltransferase inhibitors such as inhibitors of Suv39h1, Suv39h2 Setdb1, Ehmt1 and/or PRDM21, can be delivered singly, or in combination with other RNA interfering agents, e.g., siRNAs, such as, for example siRNAs directed to other cellular genes.

In some embodiments, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNAi effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen which is identified by the antibody.

In some embodiments, a siRNA or RNAi binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

In some embodiments, a viral-mediated delivery mechanism can also be employed to deliver siRNAs, e.g. siRNAs (e.g. gene silencing RNAi agents) inhibitors of H3K9 methyltransferase such as Suv39h1, Suv39h2 Setdb1, Ehmt1 and/or PRDM2, to cells in vitro as described in Xia, H. et al. (2002) Nat Biotechnol 20(10):1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501). Alternatively, in other embodiments, a RNAi agent, e.g., a gene silencing-RNAi agent inhibitor of a H3K9 methyltransferase such as Suv39h1, Suv39h2 Setdb1, Ehmt1 and/or PRDM2 can also be introduced into cells via the culturing the cells, oocyte or SCNT embryo with the RNAi agent inhibitor alone or a viral vector expressing the RNAi agent.

In general, any method of delivering a nucleic acid molecule can be adapted for use with an RNAi interference molecule (see e.g., Akhtar S. and Julian R L. (1992) Trends Cell. Biol. 2(5):139-144; WO94/02595, which are incorporated herein by reference in their entirety).

RNA interference molecules can be modified by chemical conjugation to lipophilic groups such as cholesterol to enhance cellular uptake and prevent degradation. In an alternative embodiment, the RNAi molecules can be delivered using drug delivery systems such as e.g., a nanoparticle, a dendrimer, a polymer, liposomes, or a cationic delivery system. Positively charged cationic delivery systems facilitate binding of an RNA interference molecule (negatively charged) and also enhance interactions at the negatively charged cell membrane to permit efficient uptake of an siRNA by the cell. Cationic lipids, dendrimers, or polymers can either be bound to an RNA interference molecule, or induced to form a vesicle or micelle (see e.g., Kim S H., et al (2008) Journal of Controlled Release 129(2):107-116) that encases an RNAi molecule. The formation of vesicles or micelles further prevents degradation of the RNAi molecule when administered systemically. Methods for making and administering cationic-RNAi complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety).

The dose of the particular RNAi agent will be in an amount necessary to effect RNA interference, e.g., gene silencing of the H3K9 methyltransferase gene, thereby leading to decrease in the H3K9 methyltransferase gene expression level, such as Suv39h1, Suv39h2 Setdb1, Ehmt1 and/or PRDM2 gene expression level and subsequent decrease in the respective protein expression level.

It is also known that RNAi molecules do not have to match perfectly to their target sequence. Preferably, however, the 5' and middle part of the antisense (guide) strand of the siRNA is perfectly complementary to the target nucleic acid sequence of the H3K9 methyltransferase gene such as Suv39h1, Suv39h2 Setdb1, Ehmt1 and/or PRDM2 genes.

Accordingly, the RNAi molecules functioning as gene silencing-RNAi agents inhibitors H3K9 methyltransferase such as Suv39h1, Suv39h2 Setdb1, Ehmt1 and/or PRDM2 as disclosed herein are for example, but are not limited to, unmodified and modified double stranded (ds) RNA molecules including short-temporal RNA (stRNA), small interfering RNA (siRNA), short-hairpin RNA (shRNA), micro-RNA (miRNA), double-stranded RNA (dsRNA), (see, e.g. Baulcombe, Science 297:2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length.

In some embodiments, a gene silencing RNAi nucleic acid inhibitors of a H3K9 methyltransferase such as Suv39h1, Suv39h2 Setdb1, Ehmt1 and/or PRDM2 is any agent which binds to and inhibits the expression of the H3K9 methyltransferase gene, e.g., Suv39h1, Suv39h2 Setdb1, Ehmt1 and/or PRDM2 gene, where the expression of the respective methyltransferase gene is inhibited.

In another embodiment of the invention, an inhibitor of a H3K9 methyltransferase such as Suv39h1, Suv39h2 Setdb1, Ehmt1 and/or PRDM2 can be a catalytic nucleic acid construct, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example for cleavage of a H3K9 methyltransferase such as Suv39h1, Suv39h2 Setdb1, Ehmt1 and/or PRDM2 by techniques well known to those skilled in the art (for example Lleber and Strauss, (1995) Mol Cell Biol 15:540.551, the disclosure of which is incorporated herein by reference).

Proteins and Peptide Inhibitors of H3K9 Methyltransferases

In some embodiments, a H3K9 methyltransferase inhibitor is a protein and/or peptide inhibitor of any one of H3K9 methyltransferases such as Suv39h1, Suv39h2, Setdb1, Ehmt1 or PRDM2 for example, but are not limited to mutated proteins; therapeutic proteins and recombinant proteins of H3K9 methyltransferases such as Suv39h1, Suv39h2, Setdb1, Ehmt1 or PRDM2 as well as dominant negative inhibitors (e.g., non-functional proteins of the H3K9 methyltransferase, or non-functional ligands of H3K9 methyltransferase which bind to, and competitively H3K9 methyltransferase). Proteins and peptides inhibitors can also include for example mutated proteins, genetically modified proteins, peptides, synthetic peptides, recombinant proteins, chimeric proteins, antibodies, humanized proteins, humanized antibodies, chimeric antibodies, modified proteins and fragments thereof.

As used herein, agents useful in the method as inhibitors of H3K9 methyltransferases, e.g., Suv39h1, Suv39h2 or Setdb1 gene expression and/or inhibition of Suv39h1, Suv39h2 or Setdb1 protein function can be any type of entity, for example but are not limited to chemicals, nucleic acid sequences, nucleic acid analogues, proteins, peptides or fragments thereof. In some embodiments, the agent is any chemical, entity or moiety, including without limitation, synthetic and naturally-occurring non-proteinaceous entities. In certain embodiments the agent is a small molecule having a chemical moiety.

In alternative embodiments, agents useful in the methods as disclosed herein are proteins and/or peptides or fragment thereof, which inhibit the gene expression or function of H3K9 methyltransferases, e.g., Suv39h1, Suv39h2 or Setdb1. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof.

Alternatively, agents useful in the methods as disclosed herein as inhibitors of H3K9 methyltransferases, e.g., Suv39h1, Suv39h2 or Setdb1 can be a chemicals, small molecule, large molecule or entity or moiety, including without limitation synthetic and naturally-occurring non-proteinaceous entities. In certain embodiments the agent is a small molecule having the chemical moieties as disclosed herein.

In some embodiments, a H3K9 methyltransferase inhibitor for use in the methods and compostions as disclosed herein is a dominant negative variants of a H3K9 methyltransferase, for example a non-functional variant of a H3K9 methyltransferase such as Suv39h1, Suv39h2 Setdb1, Ehmt1 and/or PRDM2, e.g., a protein such SEQ ID NO: 9 or 10 or a fragment of at least about 50, or at least about 60, or at least about 70, or at least about 80 or at least about 90 or more than 90 amino acids of SEQ ID NO: 9 or 10. In some embodiments, a dominant negative inhibitor of a H3K9 methyltransferase protein, such as Suv39h1, Suv39h2 Setdb1, Ehmt1 and/or PRDM2 protein is a soluble extracellular domain of the H3K9 methyltransferase protein.

Protein inhibitors, such as the gene product or protein of the DBC1 (Deleted Breast Cancer 1) gene binds to the SUV39H1 catalytic domain and inhibits its ability to methylate histone H3 in vitro and in vivo (Lu et al., Inhibition of SUV39H1 Methyltransferase Activity by DBC1, JBC, 2009, 284; 10361-10366), and is encompassed for use in the methods and compositions as disclosed herein.

Antibodies

In some embodiments, a H3K9 methyltransferase inhibitor useful in the methods of the present invention include, for example, antibodies, including monoclonal, chimeric humanized, and recombinant antibodies and antigen-binding fragments thereof. In some embodiments, neutralizing antibodies can be used as a H3K9 methyltransferase inhibitor. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. Commercially available antibody inhibitors of Suv39h1 and/or Suv39h2 are encompassed for use in the present invention, for example, are available from Santa Cruz biotechnology and the like.

In one embodiment of this invention, the inhibitor to the gene products identified herein can be an antibody molecule or the epitope-binding moiety of an antibody molecule and the like. Antibodies provide high binding avidity and unique specificity to a wide range of target antigens and haptens. Monoclonal antibodies useful in the practice of the present invention include whole antibody and fragments thereof and are generated in accordance with conventional techniques, such as hybridoma synthesis, recombinant DNA techniques and protein synthesis.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, (scFv)2, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys (SEQ ID NO: 19) sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In preferred embodiment of this invention, ligands and/or chimeric inhibitors can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively, two or more active agents and or inhibitors attached to targeting moieties can be administered, wherein each conjugate includes a targeting moiety, for example, a different antibody. Each antibody is reactive with a different target site epitope (associated with the same or a different target site antigen). The different antibodies with the agents attached accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Small Molecules

All of the applications set out in the above paragraphs are incorporated herein by reference. In some embodiments, one of ordinary skill in the art can use other agents as a H3K9 methyltransferase inhibitor, for example antibodies, decoy antibodies, or RNAi are effective in the methods, compounds and kits for increasing the efficiency of SCNT as disclosed herein.

In some embodiments, a H3K9 methyltransferase inhibitor is gliotoxin or a related epipolythiodioxopiperazines, or BIX-01294 (diazepin-quinazolin-amine derivative as disclosed in Takahashi et al., 2012, J. Antibiotics 65, 263-265 or Shaabam et al., Chemistry & Biology, Volume 14, Issue 3, March 2007, Pages 242-244, which are incorporated herein in their entirety by reference. BIX-01294 has the following chemical structure:

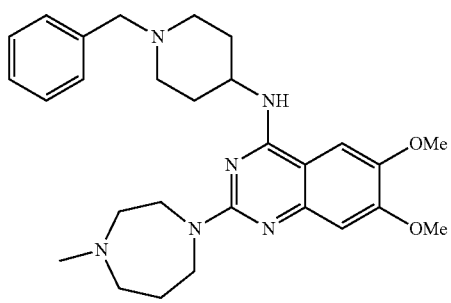

BIX-01294

Quinazoline, also known as UNC0638 also inhibits G9a, and is encompassed for use in the methods and compostions as disclosed herein. UNC0638 has the following structure:

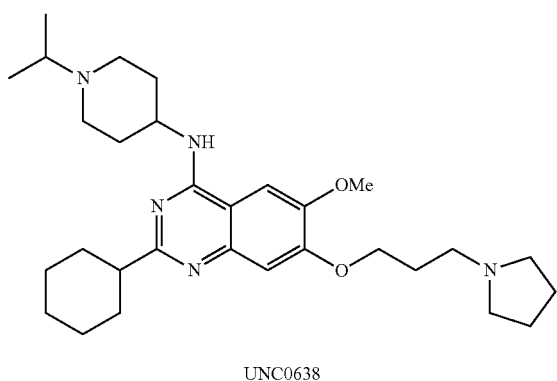

UNC0638

Small molecule inhibitors of Suv39h1 are disclosed in US Patent Application 2015/0038496, which is incorporated herein in its entirety by reference. The small molecule, verticillin A is identified as a selective inhibitor for both Suv39h1 and Suv39h2 (i.e., inhibits Suv39h1/2), as disclosed in US application 2014/0161785, which is incorporated herein in its entirety by reference, and is encompassed for use in the methods and compositions as disclosed herein.

Other small molecule inhibitors of Suv39h1 include Chaetocin (chemical name: (3S,3'S,5aR,5aR,10bR,10'bR,11aS,11'aS)-2,2',3,3',5a,5'a,6,6'-octahydro-3,3'-bis(hydroxymethyl)-2,2'-dimethyl-[10b,10'b(11H,11'H)-bi3,11a-epidithio-11aH-pyrazino[1',2':1,5]pyrrolo[2,3-b]indole]-1,1',4,4'-tetrone) (see Bernhard et al., FEBS Letts, 2011, 585 (22); 3549-3554), which has the following chemical structure, and is encompassed for use in the methods and compositions as disclosed herein.

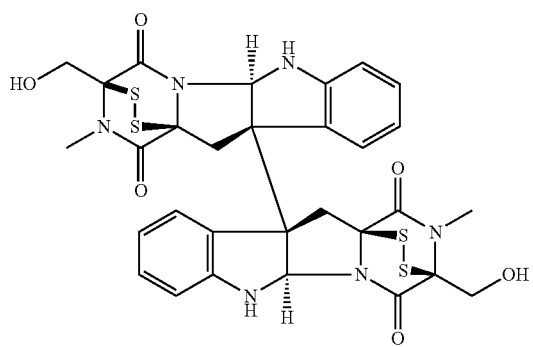 [SMILES: CN1C(=O)[C@@]23C[C@]4([C@]56C[C@@]78SS[C@@](CO)(C(=O)N7[C@H]5Nc5ccccc56)N(C)C8=O)c5ccccc5N[C@@H]4N2C(=O)[C@]1(CO)SS3]

The compound A-366 (also referred to as CHEMBL3109630) (PubChem CID: 76285486), has also been found to be a potent inhibitor of EHMT2 (Euchromatic histone methyltransferase 2) also known as G9a, with a $IC_{50}$ of 3.3 nM, and having a greater than 1000-fold selectivity over 21 other methyltransferases (see: Sweis et al., Discovery and development of potent and selective inhibitors of histone methyltransferase G9a. ACS medical Chem Letts, 2014; 5(2); 205-209), and is encompassed for use in the methods and compositions as disclosed herein. The small molecule A-366 has the following structure;

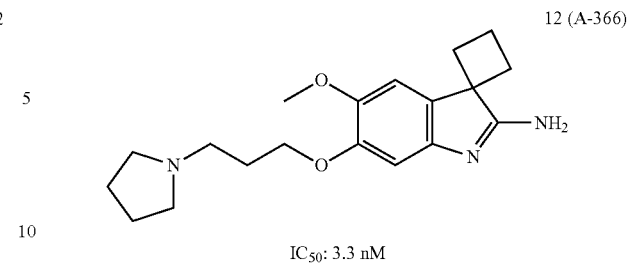

$IC_{50}$: 3.3 nM

3-Deazaneplanocin A (DZNep) (CAS No: 102052-95-9) results in the decrease of SetDB1 H3K9me3 HMTase and results in the decrease in reduced levels of both H3K27me3 and H3K9me3 (Lee et al., Biochem Biophys Res Comm, 2013, 438(4); 647-652), and is encompassed for use in the methods and compostions as disclosed herein. DZNp has the formula as follows:

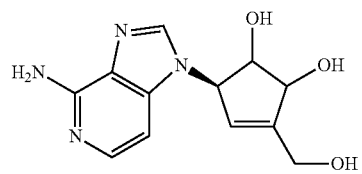 [SMILES: Nc1nccc2c1ncn2[C@@H]1C=C(CO)C(O)C1O]

The HMTase Inhibitor IV, UNC0638 (available from Calbiochem) minimally inhibits Suv39h2 ($IC_{50}$>10 μM) (see: Vedadi, M., et al. 2011. Nat. Chem. Biol. 7, 566; and Liu, F., et al. 2011. J. Med. Chem. 54, 6139), and is encompassed for use in the methods and compositions as disclosed herein. The HMTase Inhibitor IV is also known by synonyms: 2-Cyclohexyl-N-(1-isopropylpiperidin-4-yl)-6-methoxy-7-(3-(pyrrolidin-1-yl)propoxy)quinazolin-4-amine, DNA Methyltransferase Inhibitor III, DNA MTase Inhibitor III, EHMT1/GLP Inhibitor II, EHMT2/G9a Inhibitor IV and has a chemical formula as follows:

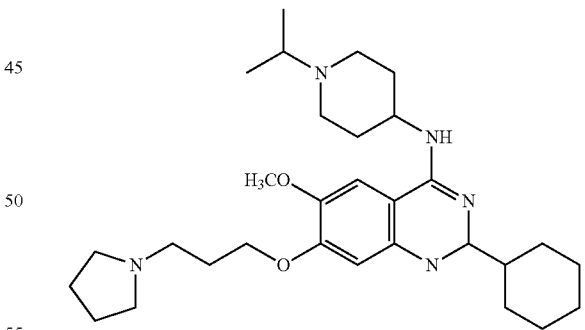

SCNT

An objective of the present invention is to provide a means of increasing the efficiency of SCNT and cloning somatic cells more efficiently using SCNT. The methods of the disclosure may be used for cloning a mammal, for obtaining totipotent or pluripotent cells, or for reprogramming a mammalian cell.

Recipient Mammalian Oocyte:

In certain embodiments, a recipient oocyte for use in the methods, kits and compositions of the invention may be from any mammalian species. In certain embodiments, cryopreserved oocytes are used as recipient oocyte cells. In certain embodiments, a recipient oocyte is human. Cryogenic preservation and thawing of oocytes are known to those skilled in the art (see Tucker et al., Curr Opin Obstet Gynecol. 1995 June; 7(3):188-92). In some embodiments, the recipient oocyte is obtained from a willing female donor, for example a egg donor. In some embodiments, the oocyte is obtained from a female mammalian subject who has ondergone ovarian stimulation or overstimulation of the ovaries (i.e. ovulation induction or controlled ovarian hyperstimulation). Methods of controlled ovarian hyperstimulationare well known in the art, for example, as disclosed in U.S. Pat. No. 8,173,592, and international patent application WO2000/059542, and incorporated herein in their entirety by reference.

In some embodiments, a recipient oocyte is an enucleated oocyte. Enucleation of the donor oocyte may be effected by known methods, such as described in U.S. Pat. No. 4,994,384 which is incorporated by reference herein. For example, metaphase II (MII) oocytes are either placed in HECM, optionally containing 7.5 micrograms per milliliter cytochalasin B, for immediate enucleation, or may be placed in a suitable medium, for example CR1aa, plus 10% estrus cow serum, and then enucleated later. Enucleation can also be accomplished microsurgically using a micropipette to remove the polar body and the adjacent cytoplasm. The cells may then be screened to identify those of which have been successfully enucleated. This screening may be effected by staining the cells with 1 microgram per milliliter 33342 Hoechst dye in HECM, and then viewing the cells under ultraviolet irradiation for less than 10 seconds. Cells that have been successfully enucleated can then be placed in a suitable culture medium.

In some embodiments, non-invasive approaches for oocyte enucleation can be used, for example, similar to a procedure for enucleation of oocytes from amphibians, where irradiation with ultraviolet light is used as a routine procedure (Gurdon Q. J. Microsc. Soc. 101 299-311 (1960)). In some embodiments, oocyte enucleation of mammalian oocyte can be done using DNA-specific fluorochrome, with exposure of mouse oocytes to ultraviolet light for more than 30 seconds reduced the developmental potential of the cell (Tsunoda et al., J. Reprod. Fertil. 82 173 (1988)).

In some embodiments, an enucleated mammalian oocyte has undergone "induced enucleation" which refers to enucleation of the oocyte by disrupting the meiotic spindle apparatus through the destabilization (e.g., depolymerization) of the microtubules of the meiotic spindle (see U.S. Patent Application No. 2006/0015950, which is incorporate herein in its entirety by reference). Destabilization of the microtubules prevents the chromatids from separating (e.g., prevents successful karyokinesis), and induces the oocyte genome (e.g., nuclear chromatin) to segregate unequally (e.g., skew) during meiotic maturation, whereby essentially all endogenous chromatin of the oocyte collects in the second polar body.

In some embodiments, oocyte donations are from a healthy woman, e.g., a healthy human female oocyte donor. In some embodiments, to bypass the need for human oocyte donors, cross-species SCNT has been explored where non-human oocytes have been reported for nuclear reprogramming of human donor somatic cell (Chung et al., Cloning and Stem Cells 11, 1-11 (2009)). Accordingly, in some embodiments, the donor oocyte is bovine, or any other non-human mammalian species, which can be a recipient oocyte for the nuclei or nuclear genetic material obtained from a human donor somatic cell.

In some embodiments, the oocyte is obtained from a female subject who does not have a mitochondrial disease. In some embodiments, the oocyte is obtained from a female subject who has a mitochondrial disease. Mitochondrial diseases are typically carried in the mitochondrial DNA (mtDNA) are well known by one of ordinary skill in the art.

Accordingly, in some embodiments, the recipient oocyte is obtained from a different subject or individual, but who is of the same mammalian species, as the subject/individual whom the donor somatic cell is obtained. In some embodiments, the recipient oocyte is obtained from a different subject or individual, who is of a different mammalian species to the subject/individual whom the donor somatic cell is obtained. In some embodiments, the recipient oocyte is obtained from the same subject that the SCNT embryo is implanted into for post-implantation development.

In some embodiments, if the female subject has a mitochondrial DNA defect, or mutation in the mtDNA, mitochondrial transfer can occur such that an ooplasm with healthy mitochondria and wildtype mtDNA can be introduced into a recipient oocyte via cytoplasmic transfer, also called ooplasmic transfer to result in a heteroplasmy oocyte (see: Sterneckert et al., Nat Reviews Genetics, Genetics 15, 625-639 (2014) and Ma et al., 2015; *Metabolic rescue in pluripotent cells from patients with mtDNA disease*, Nature 524, 234-238). Methods for cytoplasmic transfer are well known, e.g., are described in US patent application 2004/0268422, which is incorporated herein in its entirety by reference. Such a heteroplasmy oocyte can then be enucleated and used as the recipient oocyte for injection of the nuclear genetic material from the donor somatic cell. Accordingly, in some embodiments, the resultant SCNT embryo can be derived from 3 separate individuals; i.e., contain nuclear genetic material from the donor somatic cell, the cytoplasm from the recipient oocye and wild type or mutant mtDNA from a third individual or donor subject).

Donor Mammalian Cells

The methods, kits and compositions as disclosed herein comprise a donor mammalian cell, from which the nuclei is injected into an enucleated oocyte to generate a SCNT embryo. In some embodiments, the donor mammalian cell is a terminally differentiated somatic cell. In some embodiments, the donor mammalian cell is not an embryonic stem cell or an adult stem cell or an iPS cell. In some embodiments, the donor mammalian cell is a human or animal cell for use in the methods as disclosed herein as donor mammalian cells where the nuclei from the donor cell is transferred into an enucleated oocyte. In some embodiments, the donor somatic cell is obtained from a male mammalian subject, e.g., XY subject. In alternative embodiments, the donor of a somatic cell is obtained from a female subject, e.g., XX subject. In some embodiments, the donor of the somatic cell is obtained from a XXY subject.

Human and animal/mammalian donor somatic cells useful in the present invention include, by way of example, epithelial, neural cells, epidermal cells, keratinocytes, hematopoietic cells, melanocytes, chondrocytes, lymphocytes (B and T lymphocytes), other immune cells, erythrocytes, macrophages, melanocytes, monocytes, mononuclear cells, fibroblasts, cardiac muscle cells, cumulus cells and other muscle cells, etc. Moreover, the human cells used for nuclear transfer may be obtained from different organs, e.g., skin, lung, pancreas, liver, stomach, intestine, heart, reproductive organs, bladder, kidney, urethra and other urinary organs, etc. These are just some examples of suitable mammalian donor cells. Suitable donor cells, i.e., cells useful in the subject invention, may be obtained from any cell or organ of the body. This includes all somatic and in some embodiments, germ cells e.g., primordial germ cells, sperm cells. In some embodiments, the donor cell or nucleus (i.e., nuclear genetic material) from the donor cell is actively dividing, i.e., non-quiescent cells, as this has been reported to enhance cloning efficacy. Such donor somatic cells include those in the G1, G2 S or M cell phase. Alternatively, quiescent cells may be used. In some embodiments, such donor cells will be in the G1 cell cycle. In certain embodiments, donor and/or recipient cells of the application do not undergo a 2-cell block.

In some embodiments, the nuclear genetic material (i.e., the nucleus) of a mammalian donor somatic cell is obtained from a cumulus cell, Sertoli cells or from a embryonic fibroblast or adult fibroblast cell.

In some embodiments, the nuclear genetic material is genetically modified, e.g., to correct for a genetic mutation or abnormality, or to introduce a genetic modification, for example, to study the effect of the genetic modification in a disease model, e.g., in ntESCs obtained from the SCNT embryo. In some embodiments, the nuclear genetic material is genetically modified, e.g., to introduce a desired characteristic into the somatic donor cell. Methods to genetically modify a somatic cell are well known by persons of ordinary skill in the art and are encompassed for use in the methods and compositions as disclosed herein.

In some embodiments, a donor somatic cell is selected according to the methods as disclosed in US patent Application US2004/0025193, which is incorporated herein in its entirety by reference, which discloses introducing a desired transgene into the donor somatic cell and selecting the somatic cells having the transgene prior to obtaining the nucleus for injection into the recipient oocyte.

In certain embodiments, donor nuclei (e.g., the nuclear genetic material from the donor somatic cell) may be labeled. Cells may be genetically modified with a transgene encoding a easily visualized protein such as the Green Fluorescent protein (Yang, M., et al., 2000, Proc. Natl. Acad. Sci. USA, 97:1206-1211), or one of its derivatives, or modified with a transgene constructed from the Firefly (*Photinus pyralis*) luciferase gene (Fluc) (Sweeney, T. J., et al. 1999, Proc. Natl. Acad. Sci. USA, 96: 12044-12049), or with a transgene constructed from the Sea Pansey (*Renilla reniformis*) luciferase gene (Rluc) (Bhaumik, S., and Ghambhir, S. S., 2002, Proc. Natl. Acad. Sci. USA, 99:377-382).

One or more transgenes introduced into the nuclear genetic material of the donor somatic cell may be constitutively expressed using a "house-keeping gene" promoter such that the transgene(s) are expressed in many or all cells at a high level, or the transgene(s) may be expressed using a tissue specific and/or specific developmental stage specific gene promoter, such that only specific cell lineages or cells that have located into particular niches and developed into specific tissues or cell types express the transgene(s) and visualized (if the transgene is a reporter gene). Additional reporter transgenes or labeling reagents include, but are not limited to, luminescently labeled macromolecules including fluorescent protein analogs and biosensors, luminescent macromolecular chimeras including those formed with the green fluorescent protein and mutants thereof, luminescently labeled primary or secondary antibodies that react with cellular antigens involved in a physiological response, luminescent stains, dyes, and other small molecules. Labeled cells from a mosaic blastocyst can be sorted for example by flow cytometry to isolate the cloned population.

In some embodiments, mammalian donor somatic cell can be from healthy donors, e.g., healthy humans, or donors with pre-existing medical conditions (e.g., Parkinson's Disease (PD) and Age Related Macular Degeneration (AMD), diabetes, obesity, cystic fibrosis, an autoimmune disease, a neurodegenerative disease, any subject with a genetic or acquired disease) or any subject whom is in need to a regenerative therapy or a stem cell transplantation to treat an existing, or pre-existing or developing condition or disease. For example, in some embodiments, a donor mammalian somatic cell is obtained from a subject who is to be a recipient of a stem cell transplant of SCNT-derived human ES cells (ntESCs), thereby allowing autologous transplantation of patient-specific hES cells. Accordingly, in some embodiments, the methods and compositions allow for the production of patient-specific isogenic embryonic stem cell lines (i.e., isogenic ntESC lines).

In some embodiments, the donor somatic cell or nuclei (i.e., nuclear genetic material) are treated with a H3K9 methyltransferase inhibitor as disclosed herein, for example, any one of an inhibitor of Suv39h1, Suv39h2 or Setdb1 according to the methods as disclosed herein. In certain embodiments, donor mammalian cells or nuclei are not pretreated before nuclear transfer, and the SCNT embryo is treated with a H3K9 methyltransferase inhibitor and/or Kdm4 histone demethylase activator according to the methods as disclosed herein. In certain embodiments, a donor cell or nuclei are not pretreated with spermine, protamine, or putrescine before nuclear transfer or collection of the genetic material (or nucleus) for injection into the enucleated recipient oocyte.

Contacting the Donor Mammalian Cell, Recipient Mammalian Oocyte or SCNT with an Agent which Decreases H3K9Me3 Methylation.

In some embodiments, a donor mammalian somatic cell is treated with, or contacted with a H3K9 methyltransferase inhibitor and/or Kdm4 histone demethylase activator. In some embodiments, the nuclei (or nuclear genetic material) of the donor mammalian cell is treated with, or contacted with, a H3K9 methyltransferase inhibitor and/or Kdm4 histone demethylase activator. In some embodiments, the cytoplasm and/or nuclei of the donor mammalian cell is treated with, or contacted with, a H3K9 methyltransferase inhibitor as disclosed herein, for example, an inhibitor of any one or a combination of Suv39h1, Suv39h2 and/or Setdb1. In some embodiments, the contact is microinjection of the H3K9 methyltransferase inhibitor and/or Kdm4 histone demethylase activator into the cytoplasm and/or nucleus of the donor mammalian somatic cell.

In some embodiments, the donor somatic cell is contacted with an inhibitor of Suv39h1 and/or Suv39h2, or both (Suv39h1/2) at least about 24 hours, or at least about 48 hours, or at least about 3-days or at least about 4-days or more than 4-days before removal of the nuclei for transfer to the enucleated mammalian donor oocyte. In some embodiments, an inhibitor of Suv39h1 and/or Suv39h2, or both (Suv39h1/2) is by siRNA and inhibition of the expression of Suv39h1 and/or Suv39h2, or both (Suv39h1/2) occurs for a time period of at least 12 hours, or at least 24 hours or more prior to removal of the nuclei for injection into the recipient oocyte. In some embodiments, inhibition of Suv39h1 and/or Suv39h2, or both (Suv39h1/2), occurs in the donor somatic cell, e.g., at least about 24 hours, or at least about 48 hours, or at least about 3-days or at least about 4-days or more than 4-days before removal of the nuclei for transfer to the enucleated mammalian donor oocyte. In some embodiments, inhibiting the expression of Suv39h1 and/or Suv39h2, or both (Suv39h1/2) is by siRNA and occurs for at least 12 hours, or at least 24 hours or more, at the time periods prior to removal of the nuclei.

In some embodiments, in some embodiments, a mammalian oocyte is treated with or contacted with a H3K9 methyltransferase inhibitor and/or Kdm4 histone demethylase activator. In some embodiments, a mammalian oocyte is an enucleated oocyte which is treated with or contacted with a H3K9 methyltransferase inhibitor and/or Kdm4 histone demethylase activator, e.g., by direct injection into the cytoplasm of the enucleated oocyte. In some embodiments, a mammalian oocyte, or enucleated mammalian oocyte is treated with or contacted with a Kdm4 histone demethylase activator, for example, but not limited to, an agent which activates a member of the Kdm4 family of histone demethylases, such as any one or a combination of Kdm4A, Kdm4B, Kdm4C or Kdm4D. In some embodiments, the enucleated oocyte has not been injected with, or received, the donor nuclear genetic material.

In alternative embodiments, a recipient oocyte will be treated with a H3K9 methyltransferase inhibitor and/or Kdm4 histone demethylase activator within the timeframe of about 40 hours prior to nuclear transfer (i.e., prior to being injected with the donor nuclear genetic material). Such contact can occur about 40 hours before nuclear transfer, or more preferably within the timeframe of about 12 or 24 hours before nuclear transfer, and most preferably from within the timeframe of about 4 to 9 hours before nuclear transfer. In some embodiments, a recipient oocyte is contacted with a H3K9 methyltransferase inhibitor and/or Kdm4 histone demethylase activator when the recipient oocyte is a hybrid oocyte (i.e., comprises the nuclear genetic material from the donor somatic cell, but is not yet activated). Such contact can occur about 40 hours after nuclear transfer, or more preferably within the timeframe of about 1-4, or 4-12 or any time within 24 hours after nuclear transfer, and most preferably from within the timeframe of about 1-4, or 4 to 9 hours after nuclear transfer, but before fusion or activation.

The recipient oocyte can be treated with a H3K9 methyltransferase inhibitor and/or Kdm4 histone demethylase activator either before, simultaneous, or after nuclear transfer. In general, a recipient oocyte will be treated within 5 hours of nuclei transfer or within 5 hours of activation or fusion (e.g., 5 hpa; 5 hours post activation). In some embodiments, activation (or fusion) occurs within 1-2 or 2-4 hours after injection of the genetic material from the donor somatic cell into an enuclated oocyte, and in that case, the SCNT embryo is contacted with a H3K9 methyltransferase inhibitor and/or Kdm4 histone demethylase activator.

In some embodiments, the SCNT embryo is treated with a H3K9 methyltransferase inhibitor and/or Kdm4 histone demethylase activator. The SCNT embryo is generated from the injection of a nuclei (e.g., nuclear genetic material) from a donor somatic cell into an enucleated recipient oocyte to form a "hybrid oocyte", which is activated (or fused) to generate a SCNT embryo. The SCNT embryo is generated after activation (also known as fusion) of the donor nucleus with the cytoplasm of the recipient oocyte. In some embodiments, either, or both the cytoplasm or nuclei from a donor cell and/or the enucleated oocyte have been treated or contacted with a H3K9 methyltransferase inhibitor and/or Kdm4 histone demethylase activator as disclosed herein. In some embodiments, neither the donor cell and/or enucleated oocyte has been treated with a H3K9 methyltransferase inhibitor and/or Kdm4 histone demethylase activator.

In some embodiments, increasing the efficiency of somatic cell nuclear transfer (SCNT) comprising contacting a SCNT embryo, e.g., at least 5 hpa, or between 10-12 hpa (i.e. at 1-cell stage), or at about 20 hpa (i.e., early 2-cell stage) or between 20-28 hpa (i.e., 2-cell stage) with at least one of (i) a Kdm4 family of histone demethylase and/or (ii) a H3K9 methyltransferase-inhibiting agent. In some embodiments, exogenous expression of a Kdm4 gene, e.g., Kdm4d, occurs in the SCNT embryo at any one of 5 hpa, between 10-12 hpa (i.e. at 1-cell stage), at about 20 hpa (i.e., early 2-cell stage) or between 20-28 hpa (i.e., 2-cell stage). In some embodiments, where the SCNT embryo is contacted with an agent which inhibits H3K9me3, such agent, e.g., agent that increases exogenous expression of a Kdm4 gene, e.g., Kdm4d, (e.g., Kdm4d mRNA or mod-RNA), each cell of the SCNT embryo (e.g., each cell of the 2-cell embryo) is injected with the Kdm4d activating or overexpressing agent. In some embodiments, exogenous expression of a Kdm4 gene, e.g., Kdm4d, occurs in the SCNT embryo at any one of 5 hpa, between 10-12 hpa (i.e. at 1-cell stage), at about 20 hpa (i.e., early 2-cell stage) or between 20-28 hpa (i.e., 2-cell stage). In some embodiments, where the SCNT embryo is contacted with an agent which inhibits H3K9me3, such agent, e.g., agent that increases exogenous expression of a Kdm4 gene, e.g., Kdm4d, (e.g., Kdm4d mRNA or mod-RNA), each cell of the SCNT embryo (e.g., each cell of the 2-cell embryo) is injected with the Kdm4d activating or overexpressing agent.

Method of Nuclear Transfer

One objective of the present invention is to provide a means of cloning somatic cells more efficiently. The methods and compositions of the disclosure may be used for cloning a mammal, e.g., a non-human mammal, for obtaining mammalian (e.g., human and non-human mammalian) pluripotent and totipotent cells, and for reprogramming a mammalian cell.

Nuclear transfer techniques or nuclear transplantation techniques are known in the literature. See, in particular, Campbell et al, Theriogenology, 43:181 (1995); Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation. See, also Cibelli et al, Science, Vol. 280:1256-1258 (1998).

Transferring the donor nucleus into a recipient fertilized embryo may be done with a microinjection device. In certain embodiments, minimal cytoplasm is transferred with the nucleus. Transfer of minimal cytoplasm is achievable when nuclei are transferred using microinjection, in contrast to transfer by cell fusion approaches. In one embodiment, the microinjection device includes a piezo unit. Typically, the piezo unit is operably attached to the needle to impart oscillations to the needle. However, any configuration of the piezo unit which can impart oscillations to the needle is included within the scope of the invention. In certain instances the piezo unit can assist the needle in passing into the object. In certain embodiments, the piezo unit may be used to transfer minimal cytoplasm with the nucleus. Any piezo unit suitable for the purpose may be used. In certain embodiments a piezo unit is a Piezo micromanipulator controller PMM150 (PrimeTech, Japan).

In some embodiments, the method includes a step of fusing the donor nuclei with enucleated oocyte. Fusion of the cytoplasts with the nuclei is performed using a number of techniques known in the art, including polyethylene glycol (see Pontecorvo "Polyethylene Glycol (PEG) in the Production of Mammalian Somatic Cell Hybrids" Cytogenet Cell Genet. 16(1-5):399-400 (1976), the direct injection of nuclei, Sendai viral-mediated fusion (see U.S. Pat. No. 4,664,097 and Graham Wistar Inst. Symp. Monogr. 9 19 (1969)), or other techniques known in the art such as electrofusion. Electrofusion of cells involves bringing cells together in close proximity and exposing them to an alternating electric field. Under appropriate conditions, the cells are pushed together and there is a fusion of cell membranes and then the formation of fusate cells or hybrid cells. Electrofusion of cells and apparatus for performing same are described in, for example, U.S. Pat. Nos. 4,441,972, 4,578, 168 and 5,283,194, International Patent Application No. PCT/AU92/00473 [published as WO1993/05166], Pohl, "Dielectrophoresis", Cambridge University Press, 1978 and Zimmerman et al., Biochimica et Bioplzysica Acta 641: 160-165, 1981.

Methods of SCNT, and activation (i.e. fusion) of the donor nuclear genetic material with the cytoplasm of the recipient oocyte are disclosed in US application 2004/0148648, which is incorporated herein in its entirety by reference.

Oocyte Collection.

Oocyte donors can be synchronized and superovulated as previously described (Gavin W. G., 1996), and were mated to vasectomized males over a 48-hour interval. After collection, oocytes were cultured in equilibrated M199 with 10% FBS supplemented with 2 mM L-glutamine and 1% penicillin/streptomycin (10,000 I.U. each/ml). Nuclear transfer can also utilize oocytes that could have been matured in vivo or in vitro. In vivo matured oocytes are derived as explained above, and in vitro matured oocytes are allowed to develop in vitro to a specific cell stage before they are harvested for use in the nuclear transfer.

Cytoplast Preparation and Enucleation.

Oocytes with attached cumulus cells are typically discarded. Cumulus-free oocytes were divided into two groups: arrested Metaphase-II (one polar body) and Telophase-II protocols (no clearly visible polar body or presence of a partially extruding second polar body). The oocytes in the arrested Metaphase-II protocol are enucleated first. The oocytes allocated to the activated Telophase-II protocols were prepared by culturing for 2 to 4 hours in M199/10% FBS. After this period, all activated oocytes (presence of a partially extruded second polar body) were grouped as culture-induced, calcium-activated Telophase-II oocytes (Telophase-II-Ca) and enucleated. Oocytes that had not activated during the culture period were subsequently incubated 5 minutes in M199, 10% FBS containing 7% ethanol to induce activation and then cultured in M199 with 10% FBS for an additional 3 hours to reach Telophase-II (Telophase-II-EtOH protocol). All oocytes are treated with cytochalasin-B 15 to 30 minutes prior to enucleation. Metaphase-II stage oocytes were enucleated with a glass pipette by aspirating the first polar body and adjacent cytoplasm surrounding the polar body (~30% of the cytoplasm) to remove the metaphase plate. Telophase-II-Ca and Telophase-II-EtOH oocytes were enucleated by removing the first polar body and the surrounding cytoplasm (10 to 30% of cytoplasm) containing the partially extruding second polar body. After enucleation, all oocytes were immediately reconstructed.

Nuclear Transfer and Reconstruction

Donor cell injection was conducted in the same medium used for oocyte enucleation. One donor cell was placed between the zona pellucida and the ooplasmic membrane using a glass pipet. The cell-oocyte couplets were incubated in M199 for 30 to 60 minutes before electrofusion and activation procedures. Reconstructed oocytes were equilibrated in fusion buffer (300 mM mannitol, 0.05 mM $CaCl_2$, 0.1 mM $MgSO_4$, 1 mM $K_2HPO_4$, 0.1 mM glutathione, 0.1 mg/ml BSA) for 2 minutes. Electrofusion and activation were conducted at room temperature, in a fusion chamber with 2 stainless steel electrodes fashioned into a "fusion slide" (500 µm gap; BTX-Genetronics, San Diego, Calif.) filled with fusion medium.

Fusion (e.g., activation) is performed using a fusion slide. The fusion slide is placed inside a fusion dish, and the dish was flooded with a sufficient amount of fusion buffer to cover the electrodes of the fusion slide. Couplets were removed from the culture incubator and washed through fusion buffer. Using a stereomicroscope, couplets were placed equidistant between the electrodes, with the karyoplast/cytoplast junction parallel to the electrodes. It should be noted that the voltage range applied to the couplets to promote activation and fusion can be from 1.0 kV/cm to 10.0 kV/cm. Preferably however, the initial single simultaneous fusion and activation electrical pulse has a voltage range of 2.0 to 3.0 kV/cm, most preferably at 2.5 kV/cm, preferably for at least 20 µsec duration. This is applied to the cell couplet using a BTX ECM 2001 Electrocell Manipulator. The duration of the micropulse can vary from 10 to 80 µsec. After the process the treated couplet is typically transferred to a drop of fresh fusion buffer. Fusion treated couplets were washed through equilibrated SOF/FBS, then transferred to equilibrated SOF/FBS with or without cytochalasin-B. If cytocholasin-B is used its concentration can vary from 1 to 15 µg/ml, most preferably at 5 µg/ml. The couplets were incubated at 37-39° C. in a humidified gas chamber containing approximately 5% $CO_2$ in air. It should be noted that mannitol may be used in the place of cytocholasin-B throughout any of the protocols provided in the current disclosure (HEPES-buffered mannitol (0.3 mm) based medium with Ca+2 and BSA). Starting at between 10 to 90 minutes post-fusion, most preferably at 30 minutes post-fusion, the presence of an actual karyoplast/cytoplast fusion is determined for the development of a transgenic embryo for later implantation or use in additional rounds of nuclear transfer.

Following cycloheximide treatment, couplets are washed extensively with equilibrated SOF medium supplemented with at least 0.1% bovine serum albumin, preferably at least 0.7%, preferably 0.8%, plus 100 U/ml penicillin and 100 µg/ml streptomycin (SOF/BSA). Couplets were transferred to equilibrated SOF/BSA, and cultured undisturbed for 24-48 hours at 37-39° C. in a humidified modular incubation chamber containing approximately 6% $O_2$, 5% $CO_2$, balance Nitrogen. Nuclear transfer embryos with age appropriate development (1-cell up to 8-cell at 24 to 48 hours) were transferred to surrogate synchronized recipients.

Nuclear Transfer Embryo Culture and Transfer to Recipients.

Culture of SCNT Embryos

It has been suggested that embryos derived by SCNT may benefit from, or even require culture conditions in vivo other than those in which embryos are usually cultured (at least in vivo). In routine multiplication of bovine embryos, reconstituted embryos (many of them at once) have been cultured in sheep oviducts for 5 to 6 days (as described by Willadsen, In Mammalian Egg Transfer (Adams, E. E., ed.) 185 CRC Press, Boca Raton, Fla. (1982)). In certain embodiments, the SCNT embryo may be embedded in a protective medium such as agar before transfer and then dissected from the agar after recovery from the temporary recipient. The function of the protective agar or other medium is twofold: first, it acts as a structural aid for the SCNT embryo by holding the zona pellucida together; and secondly it acts as barrier to cells of the recipient animal's immune system. Although this approach increases the proportion of embryos that form blastocysts, there is the disadvantage that a number of embryos may be lost. In some embodiments, SCNT embryos can be co-cultured on monolayers of feeder cells, e.g., primary goat oviduct epithelial cells, in 50 µl droplets. Embryo cultures can be maintained in a humidified 39° C. incubator with 5% $CO_2$ for 48 hours before transfer of the embryos to recipient surrogate mothers.

SCNT expreiments showed that nuclei from adult differentiated somatic cells can be reprgrammed to a totipotent state. Accordingly, a SCNT embryo generated using the methods as disclosed herein can be cultured in a suitable in vitro culture medium for the generation of totipotent or embryonic stem cell or stem-like cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum or steer serum. A preferred maintenance medium includes TCM-199 with Earl salts, 10% fetal calf serum, 0.2 Ma pyruvate and 50 ug/ml gentamicin sulphate. Any of the above may also involve co-culture with a variety of cell types such as granulosa cells, oviduct cells, BRL cells and uterine cells and STO cells.

In particular, human epithelial cells of the endometrium secrete leukemia inhibitory factor (LIF) during the preimplantation and implantation period. Therefore, in some embodiments, the addition of LIF to the culture medium is encompassed to enhancing the in vitro development of the SCNT-derived embryos. The use of LIF for embryonic or stem-like cell cultures has been described in U.S. Pat. No. 5,712,156, which is herein incorporated by reference.

Another maintenance medium is described in U.S. Pat. No. 5,096,822 to Rosenkrans, Jr. et al., which is incorporated herein by reference. This embryo medium, named CR1, contains the nutritional substances necessary to support an embryo. CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Also, suitable culture medium for maintaining human embryonic stem cells in culture as discussed in Thomson et al., Science, 282:1145-1147 (1998) and Proc. Natl. Acad. Sci., USA, 92:7844-7848 (1995).

In some embodiments, the feeder cells will comprise mouse embryonic fibroblasts. Means for preparation of a suitable fibroblast feeder layer are described in the example which follows and is well within the skill of the ordinary artisan.

Methods of deriving ES cells (e.g., ntESCs) from blastocyst-stage SCNT embryos (or the equivalent thereof) are well known in the art. Such techniques can be used to derive ES cells from SCNT embryos. Additionally or alternatively, ES cells can be derived from cloned SCNT embryos during earlier stages of development.

Applications

Obtaining Totipotent Cells.

In certain embodiments, blastomeres generated from SCNT embryos may be dissociated using a glass pipette to obtain totipotent cells. In some embodiments, dissociation may occur in the presence of 0.25% trypsin (Collas and Robl, 43 BIOL. REPROD. 877-84, 1992; Stice and Robl, 39 BIOL. REPROD. 657-664, 1988; Kanka et al., 43 MOL. REPROD. DEV. 135-44, 1996).

In certain embodiments, the resultant blastocysts, or blastocyst-like clusters from the SCNT embryos can be used to obtain embryonic stem cell lines, eg., nuclear transfer ESC (ntESC) cell lines. Such lines can be obtained, for example, according to the culturing methods reported by Thomson et al., Science, 282:1145-1147 (1998) and Thomson et al., Proc. Natl. Acad. Sci., USA, 92:7544-7848 (1995), incorporated by reference in their entirety herein.

Pluripotent embryonic stem cells can also be generated from a single blastomere removed from a SCNT embryo without interfering with the embryo's normal development to birth. See U.S. application Nos. 60/624,827, filed Nov. 4, 2004; 60/662,489, filed Mar. 14, 2005; 60/687,158, filed Jun. 3, 2005; 60/723,066, filed Oct. 3, 2005; 60/726,775, filed Oct. 14, 2005; Ser. No. 11/267,555 filed Nov. 4, 2005; PCT application no. PCT/US05/39776, filed Nov. 4, 2005, the disclosures of which are incorporated by reference in their entirety; see also Chung et al., Nature, Oct. 16, 2005 (electronically published ahead of print) and Chung et al., Nature V. 439, pp. 216-219 (2006), the entire disclosure of each of which is incorporated by reference in its entirety).

In one aspect of the invention, the method comprises the utilization of cells derived from the SCNT embryo in research and in therapy. Such pluripotent or totipotent cells may be differentiated into any of the cells in the body including, without limitation, skin, cartilage, bone, skeletal muscle, cardiac muscle, renal, hepatic, blood and blood forming, vascular precursor and vascular endothelial, pancreatic beta, neurons, glia, retinal, inner ear follicle, intestinal, lung, cells.

In another embodiment of the invention, the SCNT embryo, or blastocyst, or pluripotent or totipotent cells obtained from a SCNT embryo (e.g., ntESCs) can be exposed to one or more inducers of differentiation to yield other therapeutically-useful cells such as retinal pigment epithelium, hematopoietic precursors and hemangioblastic progenitors as well as many other useful cell types of the ectoderm, mesoderm, and endoderm. Such inducers include but are not limited to: cytokines such as interleukin-alpha A, interferon-alpha A/D, interferon-beta, interferon-gamma, interferon-gamma-inducible protein-10, interleukin-1-17, keratinocyte growth factor, leptin, leukemia inhibitory factor, macrophage colony-stimulating factor, and macrophage inflammatory protein-1 alpha, 1-beta, 2, 3 alpha, 3 beta, and monocyte chemotactic protein 1-3, 6 kine, activin A, amphiregulin, angiogenin, B-endothelial cell growth factor, beta cellulin, brain-derived neurotrophic factor, C10, cardiotrophin-1, ciliary neurotrophic factor, cytokine-induced neutrophil chemoattractant-1, eotaxin, epidermal growth factor, epithelial neutrophil activating peptide-78, erythropoietin, estrogen receptor-alpha, estrogen receptor-beta, fibroblast growth factor (acidic and basic), heparin, FLT-3/FLK-2 ligand, glial cell line-derived neurotrophic factor, Gly-His-Lys, granulocyte colony stimulating factor, granulocytemacrophage colony stimulating factor, GRO-alpha/MGSA, GRO-beta, GRO-gamma, HCC-1, heparin-binding epidermal growth factor, hepatocyte growth factor, heregulin-alpha, insulin, insulin growth factor binding protein-1, insulin-like growth factor binding protein-1, insulin-like growth factor, insulin-like growth factor II, nerve growth factor, neurotophin-3,4, oncostatin M, placenta growth factor, pleiotrophin, rantes, stem cell factor, stromal cell-derived factor 1B, thromopoietin, transforming growth factor--(alpha, beta 1,2,3,4,5), tumor necrosis factor (alpha and beta), vascular endothelial growth factors, and bone morphogenic proteins, enzymes that alter the expression of hormones and hormone antagonists such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagons, gonadotropin, L-3',5'-triiodothyronine, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxin-binding globulin, and vasopressin, extracellular matrix components such as fibronectin, proteolytic fragments of fibronectin, laminin, tenascin, thrombospondin, and proteoglycans such as aggrecan, heparan sulphate proteoglycan, chontroitin sulphate proteoglycan, and syndecan. Other inducers include cells or components derived from cells from defined tissues used to provide inductive signals to the differentiating cells derived from the reprogrammed cells of the present invention. Such inducer cells may derive from human, non-human mammal, or avian, such as specific pathogen-free (SPF) embryonic or adult cells.

In certain embodiments of the invention, pluripotent or totipotent cells obtained from a SCNT embryo (e.g., ntESCs) can be optionally differentiated, and introduced into the tissues in which they normally reside in order to exhibit therapeutic utility. For example, pluripotent or totipotent cells obtained from a SCNT embryo can be introduced into the tissues. In certain other embodiments, pluripotent or totipotent cells obtained from a SCNT embryo can be introduced systemically or at a distance from a cite at which therapeutic utility is desired. In such embodiments, the pluripotent or totipotent cells obtained from a SCNT embryo can act at a distance or may hone to the desired cite.

In certain embodiments of the invention, cloned cells, pluripotent or totipotent cells obtained from a SCNT embryo can be utilized in inducing the differentiation of other pluripotent stem cells. The generation of single cell-derived populations of cells capable of being propagated in vitro while maintaining an embryonic pattern of gene expression is useful in inducing the differentiation of other pluripotent stem cells. Cell-cell induction is a common means of directing differentiation in the early embryo. Many potentially medically-useful cell types are influenced by inductive signals during normal embryonic development including spinal cord neurons, cardiac cells, pancreatic beta cells, and definitive hematopoietic cells. Single cell-derived populations of cells capable of being propagated in vitro while maintaining an embryonic pattern of gene expression can be cultured in a variety of in vitro, in ovo, or in vivo culture conditions to induce the differentiation of other pluripotent stem cells to become desired cell or tissue types.

The pluripotent or totipotent cells obtained from a SCNT embryo (e.g., ntESCs) can be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing an donor adult terminally differentiated somatic cells of a cancer or AIDS patient, e.g., epithelial cells or lymphocytes with a recipient enucleated oocyte, e.g., but not limited to bovine oocyte, obtaining a SCNT embryo according to the methods as disclosed herein which can then be used to obtain pluripotent or totipotent cells or stem-like cells as described above, and culturing such cells under conditions which favor differentiation, until hematopoietic stem cells are obtained. Such hematopoietic cells may be used in the treatment of diseases including cancer and AIDS. As discussed herein, the adult donor cell, or the recipient oocyte or SCNT embryo can be treated with a Kdm4 histone dimethylase activator and/or H3K9 methyltransferase inhibitor according to the methods as disclosed herein.

Alternatively, the donor mammalian cells can be adult somatic cells from a patient with a neurological disorder, and the generated SCNT embryos can be used to produce pluripotent or totipotent cells which can be cultured under differentiation conditions to produce neural cell lines. Specific diseases treatable by transplantation of such human neural cells include, by way of example, Parkinson's disease, Alzheimer's disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms.

In some embodiments, the pluripotent or totipotent cells obtained from the SCNT embryo (e.g., ntESCs) can be differentiated into cells with a dermatological prenatal pattern of gene expression that is highly elastogenic or capable of regeneration without causing scar formation. Dermal fibroblasts of mammalian fetal skin, especially corresponding to areas where the integument benefits from a high level of elasticity, such as in regions surrounding the joints, are responsible for synthesizing de novo the intricate architecture of elastic fibrils that function for many years without turnover. In addition, early embryonic skin is capable of regenerating without scar formation. Cells from this point in embryonic development from pluripotent or totipotent cells obtained from the SCNT embryo are useful in promoting scarless regeneration of the skin including forming normal elastin architecture. This is particularly useful in treating the symptoms of the course of normal human aging, or in actinic skin damage, where there can be a profound elastolysis of the skin resulting in an aged appearance including sagging and wrinkling of the skin.

To allow for specific selection of differentiated cells, in some embodiments, donor mammalian cells may be transfected with selectable markers expressed via inducible promoters, thereby permitting selection or enrichment of particular cell lineages when differentiation is induced. For example, CD34-neo may be used for selection of hematopoietic cells, Pw1-neo for muscle cells, Mash-1-neo for sympathetic neurons, Mal-neo for human CNS neurons of the grey matter of the cerebral cortex, etc.

The great advantage of the present invention is that by increasing the efficiency of SCNT, it provides an essentially limitless supply of isogenic or synegenic human cells, particularly pluripotent that are not induced pluripotent stem cells, which are suitable for transplantation. In some embodiments, these are patient-specific pluripotent obtained from SCNT embryos, where the donor mammalian cell was obtained from a subject to be treated with the pluripotent stem cells or differentiated progeny thereof. Therefore, it will obviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs, such as cyclosporine, imulan, FK-506, glucocorticoids, and rapamycin, and derivatives thereof.

Other diseases and conditions treatable by isogenic cell therapy include, by way of example, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

Reproductive Cloning of Non-Human Animals

In some embodiments, the methods and compositions can be used to increase the efficiency of production of SCNT embryos for cloning a non-human mammal. Methods for cloning a non-human mammal from a SCNT embryo derived from the methods and compositions as disclosed herein are well known in the art. The two main procedures used for cloning mammals are the Roslin method and the Honolulu method. These procedures were named after the generation of Dolly the sheep at the Roslin Institute in Scotland in 1996 (Campbell, K. H. et al. (1996) Nature 380:64-66) and of Cumulina the mouse at the University of Hawaii in Honolulu in 1998 (Wakayama, T. et al. (1998) Nature 394:369-374).

In other embodiments, the methods of the invention can be used to produce cloned cleavage stage embryos or morula stage embryos that can be used as parental embryos. Such parental embryos can be used to generate ES cells. For example, a blastomere (1, 2, 3, 4 blastomeres) can be removed or biopsied from such parental embryos and such blastomeres can be used to derive ES cells.

In particular, the present invention is applicable to use SCNT to generate non-human mammals having certain desired traits or characteristics, such as increased weight, milk content, milk production volume, length of lactation interval and disease resistance have long been desired. Traditional breeding processes are capable of producing animals with some specifically desired traits, but often these traits these are often accompanied by a number of undesired characteristics, are time-consuming, costly and unreliable. Moreover, these processes are completely incapable of allowing a specific animal line from producing gene products, such as desirable protein therapeutics that are otherwise entirely absent from the genetic complement of the species in question (i.e., spider silk proteins in bovine milk).

In some embodiments, the methods and composition as disclosed herein can be used to generate transgenic non-human mammals, e.g., with an introduced desired characteristic, or absent or lacking (e.g., by gene knockout) of a particular undesirable characteristic. The development of technology capable of generating transgenic animals provides a means for exceptional precision in the production of animals that are engineered to carry specific traits or are designed to express certain proteins or other molecular compounds. That is, transgenic animals are animals that carry a gene that has been deliberately introduced into somatic and/or germline cells at an early stage of development. As the animals develop and grow the protein product or specific developmental change engineered into the animal becomes apparent.

Alternatively, the methods and compositions can be used to clone non-human mammals, e.g., produce genetically identical offspring of a particular non-human mammal. Such methods are useful in cloning of, for example, industrial or commercial animal with desirable characteristics (e.g. a cow/cattle with quality milk production and/or muscle for meat production), or cloning or producing genetically identical companion animals, e.g., pets or animals near extinction.

Briefly stated, one advantage of the present invention allows the increased efficiency of the production of transgenic non-human mammals homozygous for a selected trait. In some embodiments, where a non-human donor somatic cell has been genetically modified by transfecting the non-human mammalian cell-line with a given transgene construct containing at least one DNA encoding a desired gene; selecting a cell line(s) in which the desired gene has been inserted into the genome of that cell or cell-line; performing a nuclear transfer procedure to generate a transgenic animal heterozygous for the desired gene; characterizing the genetic composition of the heterozygous transgenic animal; selecting cells homozygous for the desired transgene through the use of selective agents; characterizing surviving cells using known molecular biology methods; picking surviving cells or cell colonies cells for use in a second round of nuclear transfer or embryo transfer; and producing a homozygous animal for a desired transgene.

An additional step that may performed according to the invention is to expand the cell-line obtained from the heterozygous animal in cell and/or cell-line in culture. An additional step that may performed according to the invention is to biopsy the heterozygous transgenic animal.

Alternatively a nuclear transfer procedure can be conducted to generate a mass of transgenic cells useful for research, serial cloning, or in vitro use. In some embodiments of the current invention, surviving SCNT embryos are characterized by one of several known molecular biology methods including without limitation FISH, Southern Blot, PCR. The methods provided above will allow for the accelerated production of herd homozygous for desired transgene(s) and thereby the more efficient production of a desired biopharmaceutical.

In some embodiments, the current invention allows for the production of genetically desirable livestock or non-human mammals. For instance, in some embodiments, one or more multiple proteins can be integrated into the genome of the donor somatic cell used in the SCNT process to produce a transgenic cell line. Successive rounds of transfection with additional DNA transgenes for additional genes/molecules of interest (e.g., molecules that could be so produced, without limitation, include antibodies, biopharmaceuticals). In some embodiments, these molecules could utilize different promoters that would be actuated under different physiological conditions or would lead to production in different cell types. The beta casein promoter is one such promoter turned on during lactation in mammary epithelial cells, while other promoters could be turned on under different conditions in other cellular tissues.

In addition, the methods of the current invention will allow the accelerated development of one or more homozygous animals that carry a particularly beneficial or valuable gene, enabling herd scale-up and potentially increasing herd yield of a desired protein much more quickly than previous methods. Likewise the methods of the current invention will also provide for the replacement of specific transgenic animals lost through disease or their own mortality. It will also facilitate and accelerate the production of transgenic animals constructed with a variety of DNA constructs so as to optimize the production and lower the cost of a desirable biopharmaceutical. In another embodiment, homozygous transgenic animals are more quickly developed for xenotransplantation purposes or developed with humanized Ig loci.

Accordingly, one aspect of the present invention relates to a method of producing a SCNT embryo comprising contacting at least one of; a donor mammalian cell, a recipient mammalian oocyte or a mammalian somatic cell nuclear transfer (SCNT) embryo with at least one agent which decreases H3K9me3 methylation in the donor mammalian cell, the recipient mammalian oocyte or the mammalian SCNT embryo, wherein the recipient mammalian oocyte is a nucleated or enucleated oocyte; enucleating the recipient mammalian oocyte if the mammalian oocyte is nuclated; transferring the nuclei from the donor mammalian cell to the enuclated occyte; and incubating the recipient oocyte for a sufficient amount of time to form the mammalian SCNT embryo.

Blastomere Culturing.

In one embodiment, the SCNT embryos can be used to generate blastomeres and utilize in vitro techniques related to those currently used in pre-implantation genetic diagnosis (PGD) to isolate single blastomeres from a SCNT embryo, generated by the methods as disclosed herein, without destroying the SCNT embryos or otherwise significantly altering their viability. As demonstrated herein, pluripotent human embryonic stem (hES) cells and cell lines can be generated from a single blastomere removed from a SCNT embryo as disclosed herein without interfering with the embryo's normal development to birth.

Therapeutic Cloning

The discoveries of Wilmut et al. (Wilmut, et al, Nature 385, 810 (1997) in sheep cloning of "Dolly", together with those of Thomson et al. (Thomson et al., Science 282, 1145 (1998)) in deriving hESCs, have generated considerable enthusiasm for regenerative cell transplantation based on the establishment of patient-specific hESCs derived from SCNT-embryos or SCNT-engineered cell masses generated from a patient's own nuclei. This strategy, aimed at avoiding immune rejection through autologous transplantation, is perhaps the strongest clinical rationale for SCNT. By the same token, derivations of complex disease-specific SCNT-hESCs may accelerate discoveries of disease mechanisms. For cell transplantations, innovative treatments of murine SCID and PD models with the individual mouse's own SCNT-derived mESCs are encouraging (Rideout et al, Cell 109, 17 (2002); Barberi, Nat. Biotechnol. 21, 1200 (2003)). Ultimately, the ability to create banks of SCNT-derived stem cells with broad tissue compatibility would reduce the need for an ongoing supply of new oocytes.

The methods and composition as described herein for increasing the efficiency of SCNT have numerous important uses that will advance the field of stem cell research and developmental biology. For example, the SCNT embryos can be used to generate ES cells, ES cell lines, totipotent stem (TS) cells and cell lines, and cells differentiated therefrom can be used to study basic developmental biology, and can be used therapeutically in the treatment of numerous diseases and conditions. Additionally, these cells can be used in screening assays to identify factors and conditions that can be used to modulate the growth, differentiation, survival, or migration of these cells. Identified agents can be used to regulate cell behavior in vitro and in vivo, and may form the basis of cellular or cell-free therapies.

The isolation of pluripotent human embryonic stem cells and breakthroughs in SCNT in mammals have raised the possibility of performing human SCNT to generate potentially unlimited sources of undifferentiated cells for use in research, with potential applications in tissue repair and transplantation medicine.

This concept, sometimes called "therapeutic cloning," refers to the transfer of the nucleus of a somatic cell into an enucleated donor oocyte (Lanza, et al., Nature Med. 5,975 (1999)). In theory, the oocyte's cytoplasm would reprogram the transferred nucleus by silencing all of the somatic cell genes and activating the embryonic ones. ES cells (i.e., ntESCs) are isolated from the inner cell mass (ICM) of the cloned pre-implantation stage embryos. When applied in a therapeutic setting, these cells would carry the nuclear genome of the patient; therefore, it is proposed that after directed cell differentiation, the cells could be transplanted without immune rejection to treat degenerative disorders such as diabetes, osteoarthritis, and Parkinson's disease (among others). Previous reports have described the generation of bovine ES-like cells (Cibelli et al., Nature Biotechnol. 16, 642 (1998)), and mouse ES cells from the ICMs of cloned blastocysts (Munsie et al., Curro Bio! 10, 989 (2000); Kawase, et al., Genesis 28, 156 (2000); Wakayama et al., Science 292, 740 (2001)) and the development of cloned human embryos to the 8- to 10-cell stage and blastocysts (Cibelli et al., Regen. Med. 26, 25 (2001); Shu, et al., Fertil. Steril. 78, S286 (2002)). Here, the present invention can be used to generate human, patient-specific ES cells from SCNT-engineered cell masses generated by the methods as disclosed herein. Such ES cells generated from SCNTs are referred to herein as "ntESCs" and can include patient-specific isogenic embryonic stem cell lines.

The present technique for producing human lines of hESCs utilizes excess IVF clinic embryos, and does not yield patient-specific ES cells. Patient-specific, immune-matched hESCs are anticipated to be of great biomedical importance for studies of disease and development and to advance methods of therapeutic stem cell transplantation. Accordingly, the present invention can be used to establish hESC lines from SCNT generated from human donor skin cells, human donor cumulus cells, or other human donor somatic cells from informed donors whose nucleus is inserted into a donated, enucleated oocytes. These lines of SCNT-derived hESCs will be grown on animal protein-free culture media.

The major histocompatibility complex identity of each SCNT-derived hESCs can be compared to the patient's own to show immunological compatibility, which is important for eventual transplantation. With the generation of these SCNT-derived hESCs, evaluations of genetic and epigenetic stability will be made.

Many human injuries and diseases result from defects in a single cell type. If defective cells could be replaced with appropriate stem cells, progenitor cells, or cells differentiated in vitro, and if immune rejection of transplanted cells could be avoided, it might be possible to treat disease and injury at the cellular level in the clinic (Thomson et al., Science 282, 1145 (1998)). By generating hESCs from human SCNT embryos or SCNT-engineered cell masses, in which the somatic cell nucleus comes from the individual patient—a situation where the nuclear (though not mitochondrial DNA (mtDNA) genome is identical to that of the donor—the possibility of immune rejection might be eliminated if these cells were to be used for human treatment (Jaenisch, N. Engl. Med. 351, 2787 (2004); Drukker, Benvenisty, Trends Biotechnol. 22, 136 (2004)). Recently, mouse models of severe combined immunodeficiency (SCID) and Parkinson's disease (PD) (Barberi et al., Nat. Biotechnol. 21, 1200 (2003) have been successfully treated through the transplantation of autologous differentiated mouse embryonic stem cells (mESCs) derived from NT blastocysts, a process also referred to as therapeutic cloning.

Generating hESCs from human SCNT embryos or SCNT-engineered cell masses generated using the methods as disclosed herein can be assessed for the expression of hESC pluripotency markers, including alkaline phosphatase (AP), stage-specific embryonic antigen 4 (SSEA-4), SSEA-3, tumor rejection antigen 1-81 (Tra-I-81), Tra-I-60, and octamer-4 (Oct-4). DNA fingerprinting with human short tandem-repeat probes can also be used to show with high certainty that every NT-hESC line derived originated from the respective donor of the somatic mammalian cell and that these lines were not the result of enucleation failures and subsequent parthenogenetic activation. Stem cells are defined by their ability to self-renew as well as differentiate into somatic cells from all three embryonic germ layers: ectoderm, mesoderm, and endoderm. Differentiation will be analyzed in terms of teratoma formation and embryoid body (EB) formation as demonstrated by IM injection into appropriate animal models.

In summary, the present method to increase the efficiency of SCNT provides an alternative to the current methods for deriving ES cells. However, unlike current approaches, SCNT can be used to generate ES cell lines histocompatible with donor tissue. As such, SCNT embryos produced by the methods as disclosed herein may provide the opportunity in the future to develop cellular therapies histocompatible with particular patients in need of treatment.

In some embodiments, the methods, systems, kits and devices as disclosed herein can be performed by a service provider, for example, where an investigator can request a service provider to provide a SCNT embryo, or pluripotent stem cells, or totipotent stem cells derived from a SCNT embryo which has been generated using the methods as disclosed herein in a laboratory operated by the service provider. In such an embodiment, after obtaining a donor mammalian cell, the service provider can performs the method as disclosed herein to produce the SCNT embryo, or blastocysts derived from such a SCNT-embryo and provide the investigator with the SCNT embryo, or blastocysts derived from such a SCNT-embryo. In some embodiments, the investigator can send the donor mammalian cell samples to the service provider via any means, e.g., via mail, express mail, etc., or alternatively, the service provider can provide a service to collect the donor mammalian cell samples from the investigator and transport them to the diagnostic laboratories of the service provider. In some embodiments, the investigator can deposit the donor mammalian cell samples to be used in the SCNT method at the location of the service provider laboratories. In alternative embodiments, the service provider provides a stop-by service, where the service provider send personnel to the laboratories of the investigator and also provides the kits, apparatus, and reagents for performing the SCNT method methods and systems of the invention as disclosed herein of the investigators desired donor mammalian cell in the investigators laboratories. Such a service is useful for reproductive cloning of non-human mammals, e.g., for companion pets and animals as disclosed herein, or for therapeutic cloning, e.g., for obtaining pluripotent stem cells from blastocyst from the SCNT-embryos, e.g., for patient-specific pluripotent stem cells for transplantation into a subject in need of regenerative cell or tissue therapy.

Compositions and Kits.

Another aspect of the present invention relates to a population of ntESCs obtained from a SCNT produced by the methods as disclosed herein. In some embodiments, the ntESC are human ntESCs, for example patient-specific ntESC, and/or patient-specific isogenic ntESCs. In some embodiments, the ntESC are present in culture medium, such as a culture medium which maintains the ntESC in a totipotent or pluripotent state. In some embodiments, the culture medium is a medium suitable for cryopreservation. In some embodiments, the population of nt ESC are cryopreserved. Cryogenic preservation is useful, for example, to store the ntESC for future use, e.g., for therapeutic use of for other uses, e.g., research use. The ntESC may be amplified and a portion of the amplified ntESCs may be used and another portion may be cryogenically preserved. The ability to amplify and preserve ntESC allows considerable flexibility, for example, production of multiple patient-specific human ntESC as well sa the choice of donor somatic cells for use in the SCNT procedure. For example, cells from a histocompatible donor, may be amplified and used in more than one recipient. Cryogenic preservation of ntESC can be provided by a tissue bank. ntESC may be cryopreserved along with histocompatibility data. ntESC produced using the methods as disclosed herein can be cryopreserved according to routine procedures. For example, cryopreservation can be carried out on from about one to ten million cells in "freeze" medium which can include a suitable proliferation medium, 10% BSA and 7.5% dimethylsulfoxide. ntESCs are centrifuged. Growth medium is aspirated and replaced with freeze culture medium. ntESCs are resuspended as spheres. Cells are slowly frozen, by, e.g., placing in a container at −80° C. Frozen ntESCs are thawed by swirling in a 37° C. bath, resuspended in fresh stem cell medium, and grown as described above.

In some embodiments, the ntESC are generated from a SCNT embryo that was generated from injection of nuclear genetic material from a donor somatic cell into the cytoplasm of a recipient oocyte, where the recipient oocyte comprises mtDNA from a third donor subject.

The present invention also relates to a SCNT embryo produced by the methods as disclosed herein. In some embodiments, the SCNT embryo is a human embryo, and in some embodiments, the SCNT embryo is a non-human mammalian embryo. In some embodiments, the non-human mammalian SCNT embryo is genetically modified, e.g., at least one transgene was modified (e.g., introduced or deleted or changed) in the genetic material of the donor nucleus prior to the SCNT procedure (i.e., prior to collecting the donor nucleus and fusing with the cytoplasm of the recipient oocyte). In some embodiments, the SCNT embryo comprises nuclear DNA from the donor somatic cell, cytoplasm from the recipient oocyte, and mtDNA from a third donor subject.

The present invention also relates to a viable or living offspring of a mammal, e.g., a non-human mammal, where the living offspring is developed from the SCNT embryo produced by the methods as disclosed herein.

Another aspect of the present invention relates to a composition comprising at least one of st one of; a mammalian SCNT embryo or a blastocyst thereof, or a recipient mammalian oocyte (nucleated or enucleated) and at least one of; (i) an agent which increases the expression or activity of the Kdm4 family of histone demethylases; or (ii) an agent which inhibits an H3K9 methyltransferase.

In another embodiment, this invention provides kits for the practice of the methods of this invention. Another aspect of the present invention relates to a kit, including one or more containers comprising (i) an agent which increases the expression or activity of the Kdm4 family of histone demethylases and/or an agent which inhibits an H3K9 methyltransferase, and (ii) a mammalian oocyte. The kit may optionally comprise culture medium for the recipient oocyte, and/or the SCNT embryo, as well as one or more reagents for activation (e.g., fusion) of the donor nuclear genetic material with the cytoplasm of the recipient oocyte. In some embodiments, the mammalian oocyte is an enucleated oocyte. In some embodiments, the mammalian oocyte is a non-human oocyte or a human oocyte. In some embodiments, the oocyte is frozen and/or present in a cryopreservation freezing medium. In some embodiments, the oocyte is obtained from a donor female subject that has a mitochondrial disease or has a mutation or abnormality in a mtDNA. In some embodiments, the oocyte is obtained from a donor female subject that does not has a mitochondrial disease, or does not have a mutation in mtDNA. In some embodiments, the oocyte comprises mtDNA from a third subject.

The kit may also optionally include appropriate systems (e.g. opaque containers) or stabilizers (e.g. antioxidants) to prevent degradation of the agent which increases the expression or activity of the Kdm4 family of histone demethylases and/or the agent which inhibits an H3K9 methyltransferaseby light or other adverse conditions.

The kit may optionally include instructional materials containing directions (i.e., protocols) for performing SCNT procedure (e.g., for enucleating an oocyte, and/or injecting the nuclear genetic material of the donor somatic cell into the recipient oocyte and/or fusion/activation, and/or culturing the SCNT embryo), as well as instructions of contacting at least one of a donor somatic cell and/or recipient oocyte, and/or SCNT embryo with at least one of an agent which increases the expression or activity of the Kdm4 family of histone demethylases and/or an agent which inhibits an H3K9 methyltransferase.

In order that the invention herein described may be fully understood, the following detailed description is set forth.

In Some Embodiments of the Present Invention May be Defined in any of the Following Numbered Paragraphs:

1. A method for increasing the efficiency of somatic cell nuclear transfer (SCNT) comprising contacting a donor mammalian cell, recipient mammalian oocyte or a mammalian SCNT embryo with an agent which decreases H3K9me3 methylation in the donor mammalian cell, recipient mammalian oocyte or mammalian SCNT embryo, thereby increasing the efficiency of the SCNT.
2. A method for producing a mammalian somatic cell nuclear transfer (SCNT) embryo, comprising: (a) contacting at least one of; a donor mammalian cell, a recipient mammalian oocyte or a mammalian somatic cell nuclear transfer (SCNT) embryo with at least one agent which decreases H3K9me3 methylation in the donor mammalian cell, the recipient mammalian oocyte or the mammalian SCNT embryo, wherein the recipient mammalian oocyte is a nucleated or enucleated oocyte; (b) enucleating the recipient mammalian oocyte if the mammalian oocyte is nuclated; (c) transferring the nuclei from the donor mammalian cell to the enuclated occyte; and (d) incubating the recipient oocyte for a sufficient amount of time to form the mammalian SCNT embryo.
3. The method of paragraphs 1 or 2, wherein the agent increases the expression or activity of the Kdm4 (Jmjd2) family of histone demethylases.
4. The method of any of paragraphs 1 to 3, wherein the agent increases the expression or activity of at least one of: Kdm4a (Jmjd2a), Kdm4b (Jmjd2b), Kdm4c (Jmjd2c) or Kdm4d (Jmjd2d).
5. The method of any of paragraphs 1 to 4, wherein the agent increases the expression or activity of Kdm4d (Jmjd2D) or Kdm4A (Jmjd2A)
6. The method of any of paragraphs 1 to 5, wherein the agent comprises a nucleic acid sequence corresponding to SEQ ID NO: 1-8, or a biologically active fragment thereof which increases the efficiency of SCNT to a similar or greater extent as compared to the corresponding sequence of SEQ ID NO: 1-8.
7. The method of paragraph 6, wherein the agent comprises a nucleic acid sequence corresponding to SEQ ID NO: 1, or a biologically active fragment thereof which increases the efficiency of SCNT to a similar or greater extent as compared to the nucleic acid sequence of SEQ ID NO: 1.
8. The method of any of paragraphs 1 to 7, wherein the agent is an inhibitor of a H3K9 methyltransferase.
9. The method of paragraph 8, wherein the H3K9 methyltransferase is Suv39h1 or Suv39h2.
10. The method of paragraph 8, wherein the H3K9 methyltransferase is Setdb1.
11. The method of paragraph 8, wherein two or more of Suv39h1, Suv39h2 and Setdb1 are inhibited.
12. The method of paragraph 8, wherein the agent which inhibits H3K9 methyltransferase is selected from the group consisting of; an RNAi agent, CRISPR/Cas9, oligonucleotide, neutralizing antibody or antibody fragment, aptamer, small molecule, peptide inhibitor, protein inhibitor, avidimir, and functional fragments or derivatives thereof
13. The method of paragraph 12, wherein the RNAi agent is a siRNA or shRNA molecule.
14. The method of any of paragraphs 1 to 13, wherein the agent comprises a nucleic acid inhibitor to inhibit the expression of any of SEQ ID NO: 9, 11, 13 or 15.
15. The method of any of paragraphs 1 to 13, wherein the agent comprises a nucleic acid inhibitor to inhibit the expression of any of SEQ ID NO: 10, 12, 14 or 16.
16. The method of paragraph 15, wherein the RNAi agent hybridizes to at least a portion of SEQ ID NO: 17 or SEQ ID NO: 19.
17. The method of paragraph 16, wherein the RNAi agent comprises SEQ ID NO: 18 or SEQ ID NO: 20 or a fragment of at least 10 consecutive nucleic acid thereof, or a homologue having a sequence that is at least 80% identical to SEQ ID NO: 18 or SEQ ID NO: 20.
18. The method of any of paragraphs 1 to 17, wherein the recipient mammalian oocyte is an enucleated mammalian oocyte.
19. The method of any of paragraphs 1 to 18, wherein the SCNT embryo is selected from any of; a 1-cell stage SCNT embryo, a SCNT embryo 5 hours post activation (5 hpa), a SCNT embryo between 10-12 hours post activation (10-12 hpa), a SCNT embryo 20-28 hours post activation (20-28 hpa), a 2-cell stage SCNT embryo.

20. The method of any of paragraphs 1 to 19, wherein the agent contacts a recipient mammalian oocyte or enucleated mammalian oocyte prior to nuclear transfer.
21. The method of any of paragraphs 1 to 19, wherein the agent contacts the SCNT embryo prior to, or at 5 hours post activation, or when the SCNT embryo is at the 1-cell stage.
22. The method of any of paragraphs 1 to 19, wherein the agent contacts the SCNT embryo after 5 hours post activation (5 hpa), or 12 hours post activation (hpa), or 20 hours post activation (20 hpa), or when the SCNT embryo is at the 2-cell stage, or any time between 5 hpa and 28 hpa.
23. The method of any of paragraphs 1 to 22, wherein the contacting the recipient mammalian oocyte or SCNT embryo with the agent comprises injecting the agent into the nuclei or cytoplasm of the recipient mammalian oocyte or SCNT embryo.
24. The method of any of paragraphs 1 to 23, wherein the agent increases the expression or activity of the Kdm4 family of histone demethylases.
25. The method of any of paragraphs 1 to 24, wherein the agent contacts the cytoplasm of the donor mammalian cell or the nuclei of the donor mammalian cell prior to injection of the nuclei of the donor mammalian cell into an enucleated mammalian oocyte.
26. The method of any of paragraph 25, wherein the donor mammalian cell is contacted at least 24 hours prior to, or for at least 1 day prior to, injection of the nuclei of the donor mammalian cell into an enucleated mammalian oocyte.
27. The method of any of paragraph 25, wherein the agent contacts the donor mammalian cell for at least 24 hours, or at least 48 hours, or at least 3 days, prior to injection of the nuclei of the donor mammalian cell into an enucleated mammalian oocyte.
28. The method of any of paragraphs 25 to 27, wherein the agent inhibits H3K9 methyltransferase.
29. The method of any of paragraphs 25 to 28, wherein the H3K9 methyltransferase is Suv39h1 or Suv39h2, or Suv39h1 and Suv39h2 (Suv39h1/2).
30. The method of any of paragraphs 1 to 29, wherein the donor mammalian cell is a terminally differentiated somatic cell.
31. The method of any of paragraphs 1 to 30, wherein the donor mammalian cell is not an embryonic stem cell, or an induced pluripotent stem (iPS) cell, or a fetal cell, or an embryonic cell.
32. The method of any of paragraphs 1 to 32, wherein the donor mammalian cell is selected from the group consisting of cumulus cell, epithelial cell, fibroblast, neural cell, keratinocyte, hematopoietic cell, melanocyte, chondrocyte, erythrocyte, macropharge, monocyte, muscle cell, B lymphocyte, T lymphocyte, embryonic stem cell, embryonic germ cell, fetal cell, placenta cell, and adult cell.
33. The method of any of paragraphs 1 to 32, wherein the donor mammalian cell is a fibroblast or a cumulus cell.
34. The method of any of paragraphs 1 or 33, wherein the agent contacts the nuclei of the donor mammalian cell prior to removal of the nuclei from the donor mammalian cell for injection into an enucleated recipient mammalian oocyte.
35. The method of any of paragraphs 1 to 34, wherein the donor mammalian cell, recipient mammalian oocyte or mammalian SCNT embryo is a human donor cell, a recipient human oocyte or human SCNT embryo.
36. The method of any of paragraphs 1 to 34, wherein donor mammalian cell, recipient mammalian oocyte or mammalian SCNT embryo is a non-human donor cell, a recipient non-human oocyte or non-human SCNT embryo.
37. The method of paragraph 36, wherein the donor non-human mammalian cell, recipient non-human mammalian oocyte or non-human mammalian SCNT embryo is selected from the group consisting of; mouse, rat, rabbit, cow, horse, pig, chicken, dog, cat, cow, macaque, chimpanze.
38. The method of paragraph 36, wherein the donor mammalian cell, recipient mammalian oocyte or mammalian SCNT embryo is from a domestic or commercial animal.
39. The method of paragraph 38, wherein the domestic animal is a working animal or sports animal, or livestock animal, or laboratory animal selected from the group consisting of; Alpaca, bison, camel, cat, cattle, deer, elephant, rodent, dog, donkey, gayal, goat, guinna pig, llama, horse, monkey, mule, oxen, pig, pigeon, non-human primates, rabbit, reindeer, sheep, water buffalo or yak.
40. The method of paragraph 36, wherein the donor mammalian cell, recipient mammalian oocyte or mammalian SCNT embryo is from a companion animal or pet.
41. The method of paragraph 41, wherein the companion animal is selected from the group consisting of; dog, cat, cow, hamster, reptile, rabbit, rodent, ferret, chinchilla, avian pet, guinea pig, aquatic pet or horse.
42. The method of paragraph 36, wherein the donor mammalian cell, recipient mammalian oocyte or mammalian SCNT embryo is from a mammalian species which is near extinction.
43. The method of any of paragraphs 1 to 42, wherein the method results in an at least a 50% increase in efficiency of SCNT to blastocyst stage as compared to SCNT performed in the absence of an agent which decreases H3K9me3 methylation.
44. The method of any of paragraphs 1 to 43, wherein the method results in a 50%-80% increase in efficiency of SCNT as compared to SCNT performed in the absence of an agent which decreases H3K9me3 methylation.
45. The method of any of paragraphs 1 to 44, wherein the method results in a greater than 80% increase in efficiency of SCNT as compared to SCNT performed in the absence of an agent which decreases H3K9me3 methylation.
46. The method of any of paragraphs 44 to 45, wherein the increase in SCNT efficiency is an increase in the development of the SCNT embryo to blastocyst stage.
47. The method of any of paragraphs 44 to 46, wherein the increase in SCNT efficiency is an increase in post-implantation development of the SCNT embryo.
48. The method of any of paragraphs 44 to 47, wherein the increase in SCNT efficiency is an increase in the derivation of SCNT embryo-derived embryonic stem cells (ntESCs).
49. The method of any of paragraphs 1 to 48, wherein the donor mammalian cell is a genetically modified donor mammalian cell.
50. The method of paragraph 2, further comprising in vitro culturing the SCNT embryo to form a blastocyst.
51. The method of paragraph 50, wherein the SCNT embryo is at least a 1-celled SCNT embryo.

52. The method of paragraph 50, wherein the SCNT embryo is at least a 2-celled SCNT embryo.
53. The method of paragraph 50, further comprising isolating a cell from an inner cell mass from the blastocyst; and culturing the cell from the inner cell mass in an undifferentiated state to form a mammalian embryonic stem (ES) cell.
54. The method of paragraph 1 or 2, wherein any one or more of the donor mammalian cell, recipient mammalian oocyte or mammalian SCNT embryo have been frozen and thawed.
55. A population of mammalian SCNT embryo derived embryonic stem cells (ntESCs) produced from the methods of any of paragraphs 1 to 54.
56. The population of mammalian ntESCs of paragraph 55, wherein the ntESCs are human ntESCs.
57. The population of mammalian ntESCs of paragraph 55, wherein the ntESCs are genetically modified ntESCs.
58. The population of mammalian ntESCs of paragraph 55, wherein the ntESCs are pluripotent stem cells.
59. The population of mammalian ntESCs of paragraph 55, wherein the ntESCs are present in a culture medium.
60. The population of mammalian ntESCs of paragraph 59, wherein the culture medium maintains the ntESC in a pluripotent or totipotent state.
61. The population of mammalian ntESCs of paragraph 59, wherein the culture medium is a medium suitable for freezing or cryopreservation of the ntESC.
62. The population of mammalian ntESCs of paragraph 61, wherein the population of mammalian ntESCs are frozen or cryopreserved.
63. A mammalian SCNT embryo produced by the methods of paragraph 1 to 54.
64. The mammalian SCNT embryo of paragraph 63, wherein the mammalian SCNT embryo is genetically modified.
65. The mammalian SCNT embryo of paragraph 63, wherein the mammalian SCNT embryo is a non-human mammalian SCNT embryo.
66. The mammalian SCNT embryo of paragraph 65, wherein the mammalian SCNT embro comprises mitochondrial DNA that is not from the recipient mammalian oocyte.
67. The mammalian SCNT embryo of paragraph 63, wherein the SCNT embryo is present in a culture medium.
68. The mammalian SCNT embryo of paragraph 67, wherein the culture medium is a medium suitable for freezing or cryopreservation of the mammalian SCNT.
69. The mammalian SCNT embryo of paragraph 68, wherein the SCNT embryo is frozen or cryopreserved.
70. A method for producing a non-human mammal offspring from a somatic cell nuclear transfer (SCNT) embryo comprising; (a) contacting at least one of; a donor non-human mammalian cell, a recipient non-human mammalian oocyte or a non-human mammalian somatic cell nuclear transfer (SCNT) embryo with at least one agent which decreases H3K9me3 methylation in the donor non-human mammalian cell, the recipient non-human mammalian oocyte or the non-human mammalian SCNT embryo, wherein the recipient non-human mammalian oocyte is a nucleated or enucleated oocyte; (b) enucleating the recipient non-human mammalian oocyte if the mammalian oocyte is nuclated; (c) transferring the nuclei from the donor non-human mammalian cell to the non-human mammalian enuclated occyte, fusing the nuclei with the enuclated oocyte and activating the fused oocyte; (d) incubating the recipient oocyte for a sufficient amount of time to form the non-human mammalian SCNT embryo; (e) implanting the non-human mammalian SCNT embryo into the oviduct of a non-human surrogate mother and allowing development of the non-human mammalian SCNT into the non-human mammal offspring.
71. The method of paragraph 70, wherein the non-human mammalian SCNT embryo is implanted into the non-human surrogate at a one-celled embro stage, a 2-celled embryo stage, a four celled embryo stage, morula, or blastocyst embryo stage.
72. The method of paragraph 71, wherein non-human surrogate mother is not the source of the donor cell or recipient occocyte.
73. The method of claim 70, further comprising allowing the non-human surrogate to carry the SCNT embryo to term.
74. A non-human mammal offspring produced from a SCNT embryo produced by the method of any of paragraphs 1 to 47 or 70 to 73.
75. A composition comprising at least one of; a mammalian SCNT embryo, recipient mammalian oocyte or a blastocyst and at least one of; (a) an agent which increases the expression or activity of the Kdm4 family of histone demethylases; or (b) an agent which inhibits an H3K9 methyltransferase.
76. The composition of paragraph 75, wherein the agent that increases the expression or activity of the Kdm4 (Jmjd2) family of histone demethylases increases the expression or activity of at least one of: Kdm4a (Jmjd2a), Kdm4b (Jmjd2b), Kdm4c (Jmjd2c) or Kdm4d (Jmjd2d).
77. The composition of paragraph 76, wherein the agent increases the expression or activity of Kdm4d (Jmjd2d) or Kdm4a (Jmjd2a).
78. The composition of paragraph 77, wherein the agent comprises a nucleic acid corresponding to SEQ ID NO: 1-8, or a biologically active fragment thereof which increases the efficiency of SCNT to a similar or greater extent as compared to the corresponding sequence of SEQ ID NO: 1-8.
79. The composition of paragraph 75, wherein the agent comprises a nucleic acid corresponding to SEQ ID NO: 1, or a biologically active fragment thereof which increases the efficiency of SCNT to a similar or greater extent as compared to the nucleic acid sequence of SEQ ID NO: 1.
80. The composition of paragraph 75, wherein the inhibitor of the H3K9 methyltransferase inhibits at least one or any combination of Suv39h1, Suv39h2, or Setdb1.
81. The composition of paragraph 75, wherein the mammalian SCNT embryo is at 1-cell or 2-cell stage.
82. The composition of paragraph 75, wherein the recipient mammalian oocyte is an enucleated recipient mammalian oocyte.
83. The composition of paragraph 75, wherein the mammalian SCNT embryo is produced from the injection of the nuclei of a terminally differentiated somatic cell, or wherein the blastocyst is developed from a mammalian SCNT embryo produced from the injection of the nuclei of a terminally differentiated somatic cell into an enucleated mammalian oocyte.
84. The composition of any of paragraphs 75 to 83, wherein the mammalian SCNT embryo, recipient mammalian oocyte or a blastocyst is a human SCNT embryo, recipient human oocyte or a human blastocyst.

85. The composition of any of paragraphs 75 to 84, wherein the mammalian SCNT embryo, recipient mammalian oocyte or blastocyst is from a non-human mammal.
86. The composition of paragraph 85, wherein the non-human mammal is selected from selected from the group consisting of; mouse, rat, rabbit, cow, horse, pig, chicken, dog, cat, macaque, chimpanzee.
87. The composition of paragraph 85, wherein the non-human mammal is a domestic or commercial animal.
88. The composition of paragraph 87, wherein the domestic animal or commercial animal is a working animal, or a sports animal, or a livestock animal, or a laboratory animal selected from the group consisting of; Alpaca, bison, camel, cat, cattle, deer, elephant, rodent, dog, donkey, gayal, goat, guinna pig, llama, horse, monkey, mule, oxen, pig, pigeon, non-human primate, rabbit, reindeer, sheep, water buffalo or yak.
89. The composition of paragraph 85, wherein the non-human mammal is a companion animal or pet.
90. The composition of paragraph 89, wherein the companion animal is selected from the group consisting of; dog, cat, cow, hamster, reptile, rabbit, rodent, ferret, chinchilla, avian pet, guinea pig, aquatic pet or horse.
91. The composition of paragraph 85, wherein the non-human mammal is a mammalian species that is near extinction.
92. A kit comprising (i) an agent which increases the expression or activity of the Kdm4 family of histone demethylases and/or an agent which inhibits an H3K9 methyltransferase, and (ii) a mammalian oocyte.
93. The kit of paragraph 92, wherein the mammalian oocyte is an enucleated oocyte.
94. The kit of paragraph 92, wherein the mammalian oocyte is a non-human oocyte.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

All publications, patents, patent publications and applications and other documents mentioned herein are incorporated by reference in their entirety.

As summarized above, the present invention provides methods for deriving ES cells, ES cell lines, and differentiated cell types from single blastomeres of an early stage embryo without necessarily destroying the embryo. Various features of the method a described in detail below. All of the combinations of the various aspects and embodiments of the invention detailed above and below are contemplated.

EXAMPLES

The examples presented herein relate to methods and compositions to increase the efficiency of SCNT by decreasing or reducing H3K9me3 by either (i) increasing the expression or activity of the Kdm4 family of histone demethylases and/or (ii) inhibiting any one of the methyl transferases Suv39h1 or Suv39h2 or Setdb1 in the SCNT embryo and/or in the donor nuclei. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Experimental Procedures

Animals

C57BL/6J female mice were mated with DBA/2J males to produce B6D2F1/J (BDF1) mice. BDF1 and CD-1 (ICR) adult females were used for the collection of recipient oocytes and embryo transfer recipients, respectively. BDF1 mice were used for the collection of donor somatic cells for the analyses of development. (C57BL/6×CAST/EiJ) F1 mice were used for the collection of donor cells for RNA-seq. E13.5 embryos harboring GOF18 delta-PE (Jackson Laboratory, 004654: Tg(Pou5f1-EGFP)2Mnn, C57BL/6J background) were used for the isolation of mouse embryonic fibroblasts (MEF). All animal experiments were approved by the Institutional Animal Care and Use Committee of Harvard Medical School.

Preparation of Donor Cells

Cumulus cells were collected from adult BDF1 females through superovulation by injecting 7.5 IU of pregnant mare serum gonadotropin (PMSG; Harbor) and 7.5 IU of human chorionic gonadotropin (hCG; Millipore). Fifteen hours after the hCG injection, cumulus-oocyte complexes (COCs) were collected from the oviducts and briefly treated with Hepes-buffered potassium simplex-optimized medium (KSOM) containing 300 U/ml bovine testicular hyaluronidase (Calbiochem #385931) to obtain dissociated cumulus cells. Sertoli cells were collected from testes of 3- to 5-day-old BDF1 male mice as described (Matoba et al., 2011). Testicular masses were incubated in PBS containing 0.1 mg/ml collagenase (Life Technologies #17104-019) for 30 min at 37° C. followed by 5 min treatment with 0.25% Trypsine with 1 mM EDTA (Life Technologies #25200-056) at room temperature. After washing for four times with PBS containing 3 mg/ml bovine serum albumin, the dissociated cells were suspended in Hepes-KSOM medium.

Primary mouse embryonic fibroblast (MEF) cells were established from GOF18 delta-PE mouse embryos at 13.5 dpc. After removal of head and all organs, minced tissue from remaining corpus was dissociated in 500 µl of 0.25% Trypsine with 1 mM EDTA for 10 min at 37° C. Cell suspension was diluted with equal amount of DMEM (Life Technologies #11995-073) containing 10% FBS and Penicillin/Streptomycin (Life Technologies #15140-022) and pipetted up and down for 20 times. The cell suspension was diluted with fresh medium and plated onto 100 mm dishes and cultured at 37° C. Two days later, MEF cells were harvested and frozen. Frozen stocks of MEF cells were thawed and used for experiments after one passage.

Knockdown of Histone Methyltransferases in MEF Cells by siRNA Transfection siRNAs against mouse Suv39h1 (Life Technologies # s74607), Suv39h2 (Life Technologies # s82300) and Setdb1 (Life Technologies # s96549) were diluted in nuclease free water at 50 µM stock solutions. siRNAs were introduced to MEFs with Lipofectamine RNAi Max (Life technologies #35050-061) following manufacturer's protocol. Briefly, $1 \times 10^5$ MEF cells were seeded onto 24-well plate (day 0; see FIG. 5A). Twenty-four hours later, 5 pM siRNAs were transfected into MEF cells using Lipofectamine RNAi Max (day 1). Twenty-four hours after the first transfection, the culture media was changed to fresh M293T media [DMEM supplemented with 10% FBS, 0.1 mM non-essential amino acids (Life technologies #11140-050), 2 mM GlutaMAX (Life technologies #35050-079), 50 U/ml penicillin-streptomycin and 0.1 mM 2-mercaptoethanol (Life technologies #21985-023)] (day 2). On day 3, MEF cells were reseeded onto 24-well plates at the density of $1 \times 10^5$ cells. Then transfection was repeated once as described above (day 4). Forty-eight hours after the second transfection (day 6), MEF cells were used for immunostaing, RT-qPCR or SCNT.

SCNT and mRNA Injection

Somatic cell nuclear transfer was carried out as described previously (Matoba et al., 2011). Briefly, recipient MII oocytes were collected from superovulated adult BDF1 females by brief treatment with 300 U/ml bovine testicular hyaluronidase (Calbiochem). Isolated MII oocytes were enucleated in Hepes-buffered KSOM medium containing 7.5 µg/ml of cytochalasin B (Calbiochem #250233). The nuclei of donor cumulus cells or Sertoli cells were injected into the enucleated oocytes using a Piezo-driven micromanipulator (Primetech # PMM-150FU). MEF cells were fused with enucleated oocytes by inactivated Sendai virus envelope (HVJ-E; Ishihara Sangyo, Japan). After 1 h incubation in KSOM, reconstructed SCNT oocytes were activated by incubation in Ca-free KSOM containing 5 µg/ml cytochalasin B for 1 h and further cultured in KSOM with cytochalasin B for 4 h. Activated SCNT embryos were washed 5 h after the onset of $SrCl_2$ treatment (hours post activation, hpa) and cultured in KSOM in a humidified atmosphere of 5% $CO_2$ at 37.8° C. In some experiments, SCNT embryos were injected with ~10 pl of water (control), 1800 ng/µl wild-type or mutant (H189A) Kdm4d mRNA at 5-6 hpa by using a Piezo-driven micromanipulator (Primetech). In some experiments, trichostatin A (TSA) was added to the culture medium at 15 nM from the beginning of the activation for a total of 8 hours. Preimplantation developmental rates were statistically analyzed by Student's T-test. Further details on donor cell preparation, embryo transfer, mRNA preparation and other procedures are included in the Extended Experimental Procedures In Vitro Transcription of Kdm4d mRNA To make template plasmids for in vitro transcription of full length Kdm4d mRNA, mouse Kdm4d open reading frame was amplified by PCR from cDNA library derived from ES cells and cloned into pcDNA3.1-poly(A)83 plasmid (Inoue & Zhang, 2014) by using an In-Fusion kit (Clonetech #638909). The catalytic defective mutant Kdm4d (H188A) was generated using PrimeSTAR mutagenesis basal kit (TAKARA # R045A). mRNA was synthesized from the linearized template plasmids by in vitro transcription using a mMESSAGE mMACHINE T7 Ultra Kit (Life technologies # AM1345) following manufacturer's instructions. The synthesized mRNA was precipitated by lithium chloride and dissolved in nuclease-free water. After measuring the concentration by NanoDrop ND-1000 spectrophotometer (NanoDrop Technologies), aliquots were stored at −80° C. until use.

Knockdown of Histone Methyltransferases in MEF Cells by siRNA Transfection siRNAs against mouse Suv39h1 (Life Technologies # s74607), Suv39h2 (Life Technologies # s82300) and Setdb1 (Life Technologies # s96549) were diluted in nuclease free water at 50 µM stock solutions. siRNAs were introduced to MEFs with Lipofectamine RNAi Max (Life technologies #35050-061) following manufacturer's protocol. Briefly, $1 \times 10^5$ MEF cells were seeded onto 24-well plate (day 0; see FIG. 5A). Twenty-four hours later, 5 pM siRNAs were transfected into MEF cells using Lipofectamine RNAi Max (day 1). Twenty-four hours after the first transfection, the culture media was changed to fresh M293T media [DMEM supplemented with 10% FBS, 0.1 mM non-essential amino acids (Life technologies #11140-050), 2 mM GlutaMAX (Life technologies #35050-079), 50 U/ml penicillin-streptomycin and 0.1 mM 2-mercaptoethanol (Life technologies #21985-023)] (day 2). On day 3, MEF cells were reseeded onto 24-well plates at the density of $1 \times 10^5$ cells. Then transfection was repeated once as described above (day 4). Forty-eight hours after the second transfection (day 6), MEF cells were used for immunostaing, RT-qPCR or SCNT.

Reverse Transcription and Real-Time PCR

Total RNA was purified from MEF cells using RNeasy mini kit (Qiagen) according to manufacturer's instruction. cDNA was synthesized with oligo-dT primer and ImProm-II Reverse Transcription Syetem (Promega). Real-time PCR was performed on a CFX384 Real-Time PCR detection system (Bio-Rad) using Ssofast Evagreen Supermix (Bio-Rad). Relative gene expression levels were analyzed using comparative Ct methods and normalized to Gapdh on CFX Manager software (Bio-Rad). The results were statistically analyzed by Student's T-test. Following primers were used: Gapdh-F, 5'-CATGGCCTTCCGTGTTCCTA-3' (SEQ ID NO: 56); Gapdh-R, 5'-GCCTGCTTCACCACCTTCTT-3' (SEQ ID NO: 57); Suv39h1-F, 5'-TGTGATGCCAG-GCACTTGGT-3' (SEQ ID NO: 58); Suv39h1-R, 5'-TGGGCTCCACCTTTGTGGTT-3' (SEQ ID NO: 59); Suv39h2-F, 5'-TTGGAGTCCAGGCAGAGTG-3' (SEQ ID NO: 60); Suv39h2-R, 5'-CACTGTCATCGGGGCTTGTG-3' (SEQ ID NO: 61); Setdb1-F, 5'-TTTCTGGTTGGCTGT-GACTG-3'(SEQ ID NO: 62); Setdb1-R, 5'-GAGT-TAGGGTTGACTTGGCC-3'(SEQ ID NO: 63).

Embryo Transfer

Two-cell stage embryos generated by SCNT or in vitro fertilization were transferred to the oviducts of pseudopregnant (E0.5) ICR females. The pups were recovered by caesarian section on the day of delivery (E19.5) and nursed by lactating ICR females.

ntESC Establishment

Blastocysts were denuded by acid tyrode treatment and cultured on mitomycin treated MEF feeder cells and in DMEM supplemented with 5% FBS, 10% KnockOut serum replacement (Life Technologies #10828-028), 0.1 mM non-essential amino acids, 2 mM GlutaMAX, 50 U/ml penicillin-streptomycin, 0.1 mM 2-mercaptoethanol and 2000 U leukemia inhibitory factor (LIF, Millipore #ESG1107) at 37° C. 5% CO2. Four to five days later, outgrowths from attached embryos were dissociated with 0.25% trypsin and passaged all onto new feeder cells. On the following day, the medium was replaced with N2B27-LIF media [DMEM/F12 (Life Technologies #10565-042) supplemented with 0.1 mM non-essential amino acids, 2 mM GlutaMAX, 50 U/ml penicillin-streptomycin, 0.1 mM 2-mercaptoethanol, 0.5× N2 supplement (Life technologies #17502-048), 0.5×B27 supplement (Life technologies #17504-044), 3 µM CHIR99021 (STEMGENT #04-0004), 0.5 µM PD0325901 (STEMGENT #04-0006) and 1000 U LIF]. Five days later, expanded cells were reseeded as established ntESC.

Immunostaining

Embryos or MEF cells were fixed with 3.7% paraformaldehyde (PFA) for 20 min at room temperature. After washing with PBS containing 10 mg/ml BSA (PBS/BSA), the fixed embryos or cells were permeabilized by 15 min incubation with 0.5% Triton-X 100. After blocking in PBS/BSA for 1 h at room temperature, they were incubated in a mixture of first antibodies at 4° C. overnight. The antibodies include mouse anti-H3K9me3 (1/500: Abcam # ab71604), rabbit anti-H3K9me3 (1/500: Millipore #07-442), rabbit anti-H3K27me3 (1/500: Millipore #07-449), goat anti-Oct4 (1/500: Santa Cruz # SC8628), and mouse anti-Cdx2 (1/100: BioGenex # AM392-5M). Following three washes with PBS/BSA, the embryos or cells were incubated with secondary antibodies that include fluorescein isothiocyanate-conjugated donkey anti-mouse IgG (1/400, Jackson Immuno-Research), Alexa Flour 568 donkey anti-rabbit IgG (1/400, Life technologies), and/or Alexa Flour 647 donkey anti-goat IgG (1/400, Life technologies) for 1 h at room temperature. Finally, they were mounted with Vectashield with 4',6-diamidino-2-phenylindole (DAPI) (Vector Laboratories # H-1200). The fluorescent signals were observed using a laser-scanning confocal microscope (Zeiss LSM510) and an EM-CCD camera (Hamamatsu ImagEM).

RNA-Sequencing Analysis

The embryos were directly lysed and used for cDNA synthesis using SMARTer Ultra Low Input RNA cDNA preparation kit (Clontech). After amplification, the cDNA samples were fragmented using Covaris sonicator (Covaris). Sequencing libraries were made with the fragmented DNA using NEBNext Ultra DNA Library Prep Kit for Illumina according to manufacturer's instruction (New England Biolabs). Single end 50 bp sequencing was performed on a HiSeq 2500 sequencer (Illumina). Sequencing reads were mapped to the mouse genome (mm9) with NovoalignV3.02.00. All programs were performed with default settings (unless otherwise specified). Uniquely mapped reads (about 70% of total reads) were subsequently assembled into transcripts guided by the reference annotation (UCSC gene models) with Cufflinks v2.0.2. Expression level of each gene was quantified with normalized FPKM (fragments per kilobase of exon per million mapped fragments). Functional annotation of significantly different transcripts and enrichment analysis was performed with DAVID. Statistical analyses were implemented with R (world wide web at www.r-project.org/). Independent 2-group Wilcoxon rank sum test were used to compare distributions using the wilcox. test function in R. Pearson's r coefficient was calculated using the cor function with default parameters. The hierarchical clustering analysis of the global gene expression pattern in different samples was carried out using hearmap.2 function (gplots package) in R.

Identification of Reprogramming Resistant Regions

A sliding window (size 100 kb, step size 20 kb) was used to assess the genome-wide expression level of 1-cell and 2-cell embryos. For each window, the expression level was quantified with normalized RPM (reads per millions of uniquely mapped reads). The significantly activated regions in 2-cell relative to 1-cell IVF embryos were identified with stringent criteria (FC>5, Fisher's exact test p value <0.01, RPM>10 in 2-cell IVF embryos), and the overlapping regions were merged. These activated regions were classed into three groups based on their expression differences in SCNT and IVF 2-cell embryos.

Analysis of Published DNAi and ChIP-Seq Data Sets

To perform the histone modification and DNaseI hypersensitivity enrichment analyses in FIG. 2 and S2, we used the following published ChIP-seq and DNaseI-seq data sets: H3K9me3 and H3K96me3 in MEF cells (Pedersen et al., 2014); H3K4me2, H3K27me3 in MEF cells (Chang et al., 2014); H3K4me1 and H3K27ac in MEF cells (ENCODE/LICR project); H3K9me3 in CH12, Erythroblast, Megakaryo (ENCODE/PSU project) and whole brain (ENCODE/LICR project); DNaseI-seq in NIH3T3, CH12, MEL, Treg, 416B and whole brain (ENCODE/UW project). The ChIP-seq intensity was quantified with normalized FPKM. The position-wise coverage of the genome by sequencing reads was determined and visualized as custom tracks in the UCSC genome browser.

Example 1

Abnormal ZGA in 2-Cell SCNT Embryos

Figure 1B:
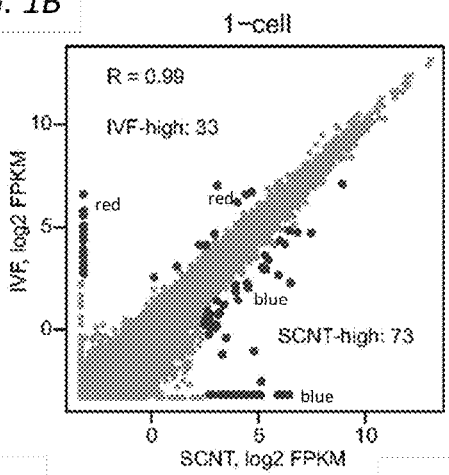
Figures 8A, 8B:
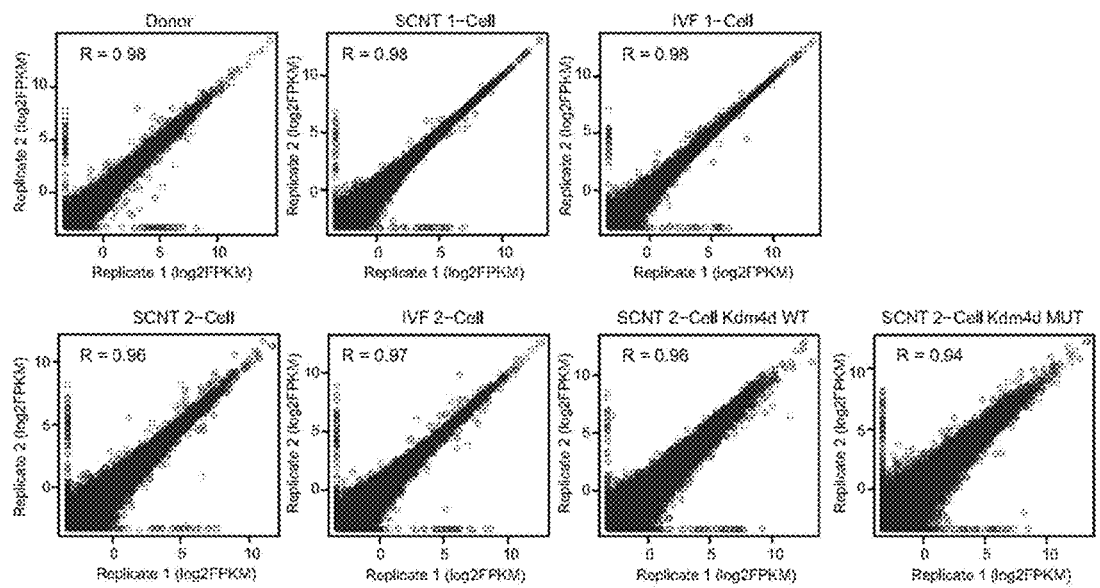
FIGS. 8A-8B (is related to FIG. 1) and shows a summary of RNA-seq information.

To identify the earliest transcriptional differences between mouse embryos derived through in vitro fertilization (IVF) and SCNT, the inventors performed RNA-seq experiments using pooled embryos (25-40 embryos/sample) at 1-cell (12 hours post-activation: hpa), and late 2-cell (28 hpa) stages (FIG. 1A). More than 30 million uniquely mapped reads were obtained for each sample, with the two biological replicates of each sample being highly reproducible (FIGS. 8A and 8B). Analysis of the 1-cell stage transcriptome revealed that SCNT and IVF embryos feature nearly identical transcriptomes (R=0.99; FIG. 1B). Specifically, among the 5517 genes detected (FPKM>5 in at least one sample), only 106 genes showed more than 3-fold difference between SCNT and IVF embryos (FIG. 1B). This is consistent with the fact that ZGA largely begins after the first cleavage in mouse embryos (Schultz, 2002) and that the majority of transcripts present in 1-cell stage embryos, regardless of IVF or SCNT, are maternally stored transcripts. Therefore the inventors focused their analyses on the late 2-cell stage where the major ZGA becomes apparent in mouse embryos.

Figure 1C:
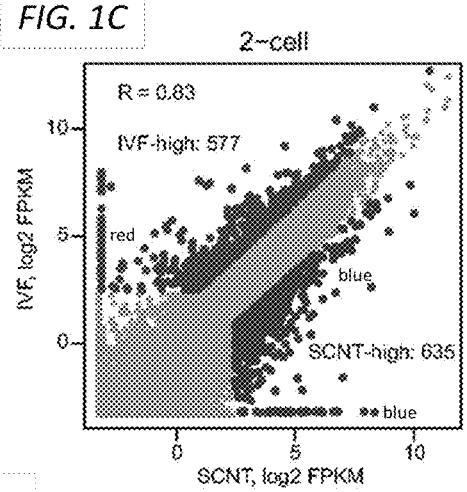
Figure 1D:
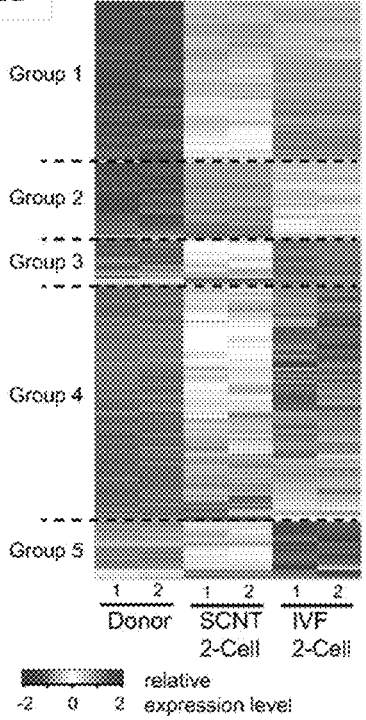
Figure 1E:
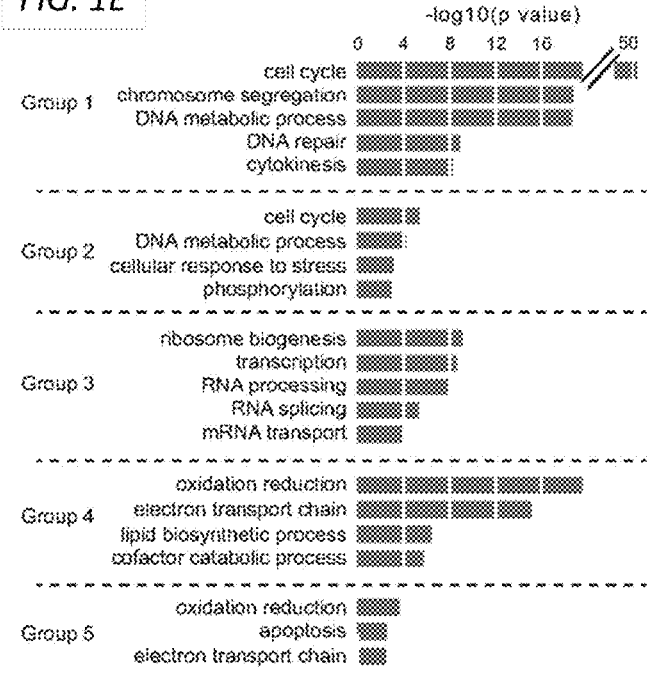

Transcriptome comparison between IVF and SCNT embryos at the 2-cell stage identified 1212 genes that showed more than 3-fold expression difference (FIG. 1C, FPKM>5 in at least one sample). Pairwise comparison of the transcriptome of donor cumulus cells, 2-cell IVF and 2-cell SCNT embryos identified 3775 differentially expressed genes [fold change (FC)>5, FPKM>5] that can be classified into 5 groups by unsupervised hierarchical cluster analysis (FIG. 1D). Of these 3775 differentially expressed genes, 1549 were activated in both SCNT and IVF embryos (Groups 1 and 2). Gene ontology (GO) analysis revealed that these genes were significantly enriched in cell cycle related biological processes (FIG. 1E), demonstrating that SCNT embryos are as transcriptionally prepared for proper cell cycle progression as IVF embryos. Despite a portion of the highly expressed genes in donor cumulus cells still being expressed in 2-cell SCNT embryos (372 genes; Group 5), the majority of these genes were silenced following SCNT, similar to those in IVF embryos (1553 genes; Group 4). Genes in Group 4 were significantly enriched in cell metabolism related biological processes, such as oxidation/reduction and electron transport chain, demonstrating that cumulus cell-specific metabolic processes are quickly terminated after SCNT. Interestingly, a group of 301 genes failed to be properly activated in SCNT embryos compared to IVF embryos (Group 3). GO analysis revealed that these genes were enriched in transcription or mRNA processing, suggesting a possible defect in activation of developmentally important regulators in SCNT embryos (FIG. 1E). Given that proper activation of zygotic genes in 2-cell embryos is believed to be important for embryonic development, we focused our analysis on this group of genes and related genomic loci.

Example 2

Identification of Reprogramming Resistant Regions (RRRs) in 2-Cell SCNT Embryos

Figure 9A:
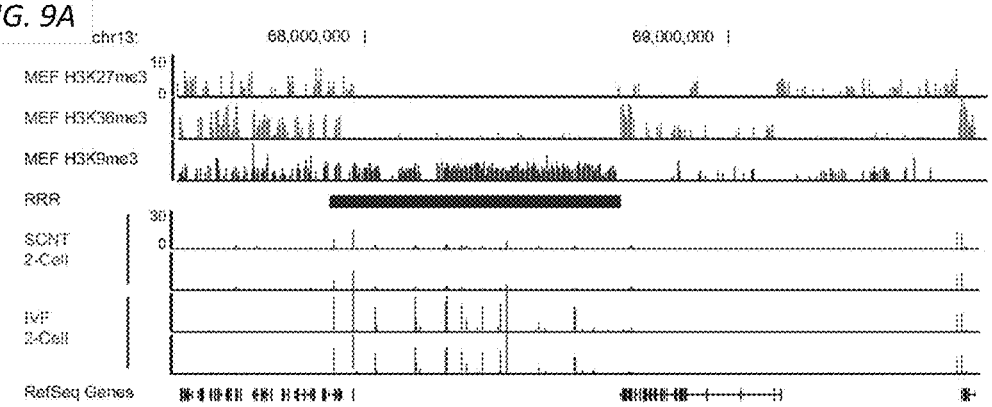
FIGS. 9A-9E (is related to FIG. 2) and shows that RRRs possess heterochromatin features in somatic cells.
Figure 9B:
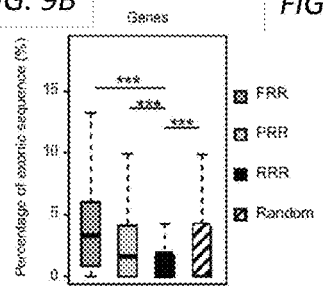
Figure 9C:
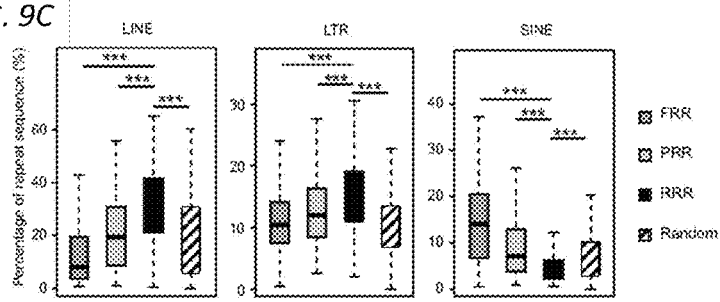

In addition to protein coding genes, previous studies have revealed that non-genic repetitive elements, such as LTR class III retrotransposons and major satellite repeats, are highly expressed in mouse preimplantation embryos, especially at the 2-cell stage (Evsikov et al., 2004; Peaston et al., 2004; Probst et al., 2010). To comprehensively characterize the transcriptome difference between IVF and SCNT 2-cell stage embryos, the inventors applied a sliding window strategy to identify all genomic regions associated with detectable transcripts. First, the inventors identified 811 genomic regions, ranging from 100 to 800 kb, that were significantly activated (Fisher's exact test p value<0.01) in 2-cell stage IVF embryos and compared to 1-cell stage IVF embryos [FIG. 2A, FC>5, RPM (reads per millions of uniquely mapped reads)>10 in IVF 2-cell embryos]. Among the 811 genomic regions, 342 regions were activated in SCNT embryos at a similar level as those in IVF embryos (FC<=2 comparing IVF with SCNT 2-cell embryos), and these regions were termed as fully reprogrammed regions (FRRs). The inventors also identified 247 regions, termed "partially reprogrammed regions" (PRRs), that were partially activated (FC>2 and FC<=5) in SCNT embryos compared to IVF embryos (FIG. 2A). Interestingly, the remaining 222 regions, herein revered to "reprogramming resistant regions" (RRRs), failed to be activated in SCNT embryos (FC>5, FIG. 2A). Notably, transcripts generated within RRRs are largely unannotated as exemplified in a representative region on chromosome 13 (FIG. 9A). Indeed, RRRs are relatively gene-poor regions when compared to FRR and PRR (FIG. 9B). However, RRRs are enriched for specific repeat sequences, such as LINE and LTR, but are depleted of SINE (FIG. 9C). Thus, comparative transcriptome analysis allowed the inventors to identify 222 RRRs that are refractory to transcriptional activation in 2-cell embryos generated by SCNT.

RRRs are Enriched for H3K9Me3 in Somatic Cells

Figure 9D:
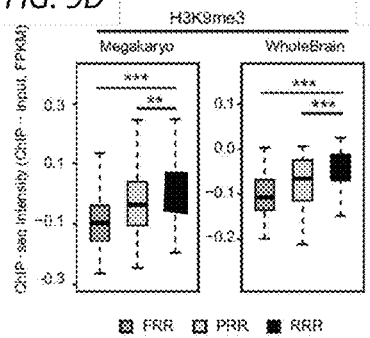

The fact that RRRs are refractory to transcriptional activation in 2-cell SCNT embryos indicates that RRRs may possess certain epigenetic modifications that serve as a barrier for SCNT-mediated reprogramming. Given that developmental failure of SCNT embryos has been observed in different donor somatic cell types, including mouse embryonic fibroblast (MEF) cells (Ono et al., 2001), the inventors assessed whether such epigenetic barriers for SCNT-mediated reprogramming is common to different somatic cell types. Because MEF cells are one of the few somatic cell types with comprehensive histone modification datasets (Bernstein et al., 2012; Chang et al., 2014; Pedersen et al., 2014), the inventors assessed whether any of the six major histone modifications are specifically enriched in the RRRs. The inventors discovered that H3K9me3, but not any other modifications analyzed, was specifically enriched at RRRs, while no obvious enrichment of any histone modifications was observed in FRRs or PRRs (FIG. 2B). Indeed, a careful examination of a representative region on chromosome 7 indicated that RRRs failed to activate in 2-cell SCNT embryos were clearly enriched for the H3K9me3 mark, and regions outside of H3K9me3-enriched regions were properly activated in 2-cell SCNT embryos (FIG. 2C). This observation is not unique to MEF cells as similar enrichment of H3K9me3 in the RRRs was also observed in four other somatic cell- or tissue-types (CH12, Erythroblast, Megakaryocyte and whole brain) following analysis (FIGS. 2D and 9D) of the H3K9me3 ChIP-seq datasets from the ENCODE project (Bernstein et al., 2012). Therefore, we conclude that RRRs in somatic cells are enriched for H3K9me3.

Figure 9E:
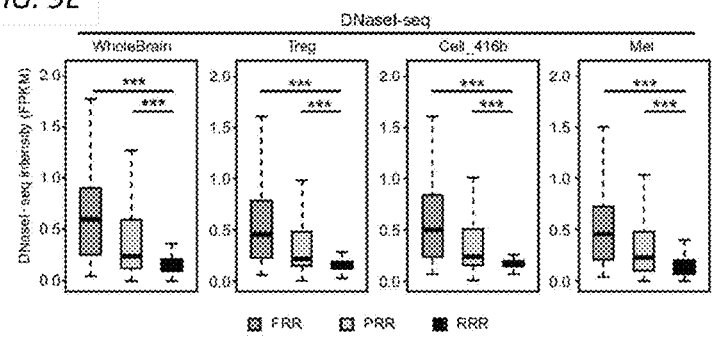

Previous studies have also shown that H3K9me3 is generally enriched in tightly-packaged large domains of so-called heterochromatin regions (Lachner et al., 2001). One possible explanation for the failure of RRRs to be activated in 2-cell SCNT embryos is its chromatin inaccessibility. To test this possibility, the inventors analyzed the DNaseI hypersensitivity of six different somatic cell types using the data derived from the ENCODE project. Remarkably, we found that RRRs were significantly less sensitive to DNaseI compared to FRR and PRR in all somatic cell- or tissue-types analyzed (FIGS. 2E and 9E). Collectively, these results demonstrate that RRRs possess features of heterochromatin that generally exist in somatic cell types.

Example 3

Figure 3A:
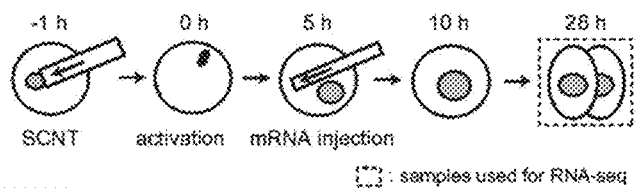
FIGS. 3A-3F show the injection of Kdm4d mRNA into mouse SCNT embryos results in exogenous expression of Kmd4d and removes H3K9me3 which was transferred from the donor nuclei of the somatic cell and results in derepression of silenced genes in 2-cell SCNT embryos.
Figure 3B:
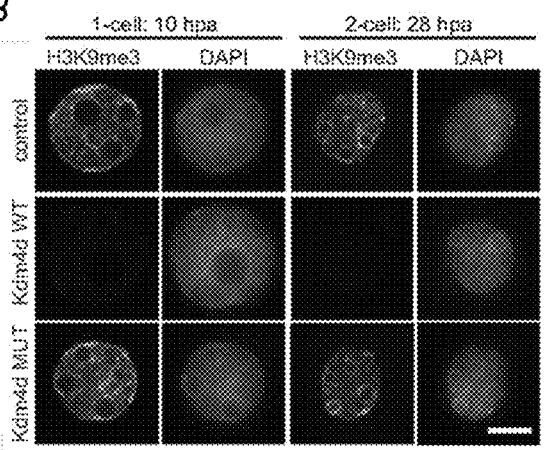

Removal of H3K9Me3 by Kdm4d Restores Transcriptional Reprogramming in SCNT Embryos Having established a correlation between RRRs and H3K9me3 enrichment, the inventors next attempted to address whether removal of H3K9me3 can facilitate transcriptional reprogramming of RRRs in SCNT embryos. To this end, the inventors synthesized mRNAs encoding an H3K9me3-specific histone demethylase, Kdm4d (Krishnan and Trievel, 2013), and injected the mRNAs into SCNT embryos at 5 hpa (FIG. 3A). Immunostaining revealed that injection of wild-type, but not a catalytic defective mutant, Kdm4d mRNAs greatly reduced H3K9me3 levels in SCNT embryos (FIG. 3B).

Figure 3C:
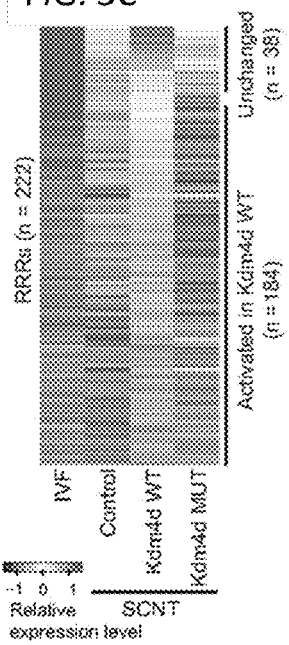
Figure 3D:
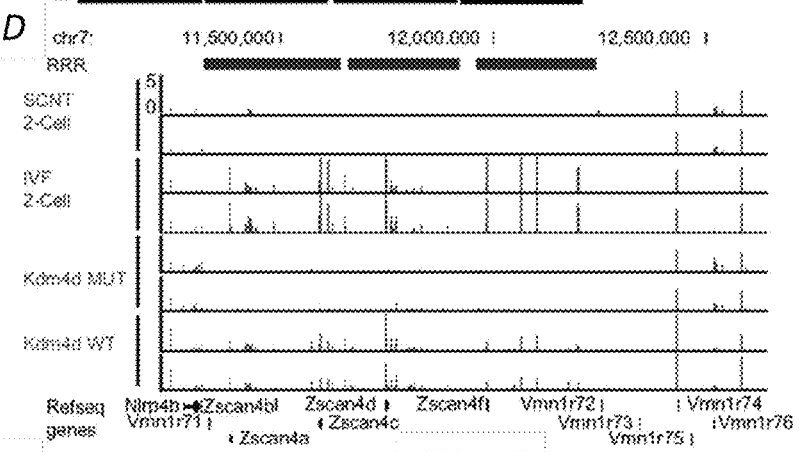
Figure 3E:
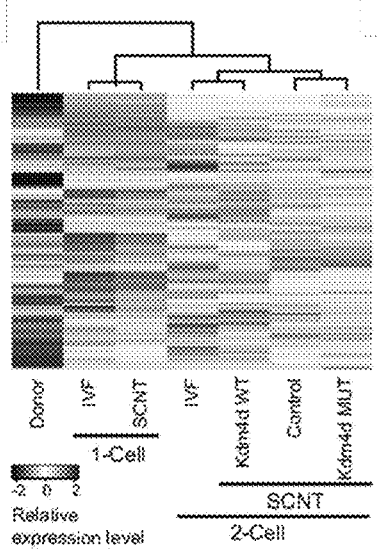
Figure 3F:
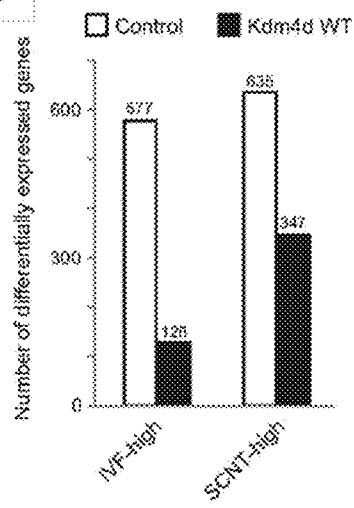
Figure 10A:
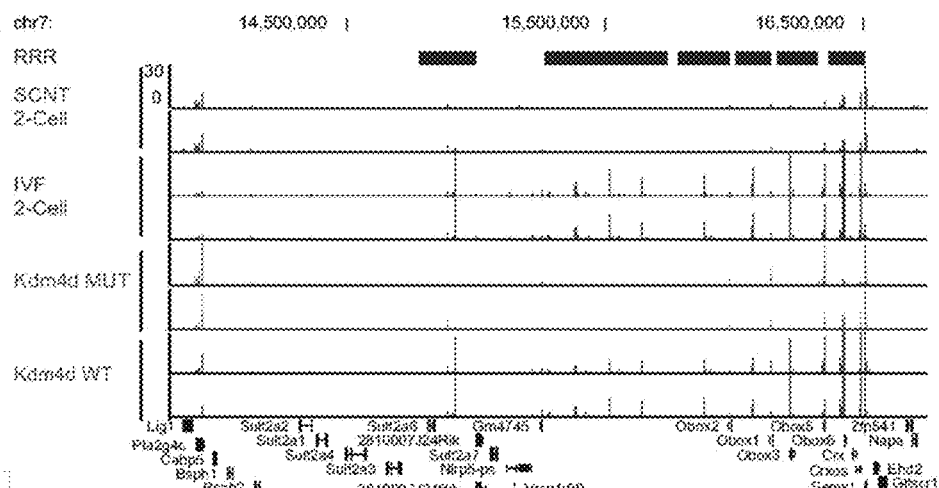
FIGS. 10A-10C (related to FIG. 3) show the transcription of RRRs can be restored by Kdm4d mRNA injection.
Figure 10B:
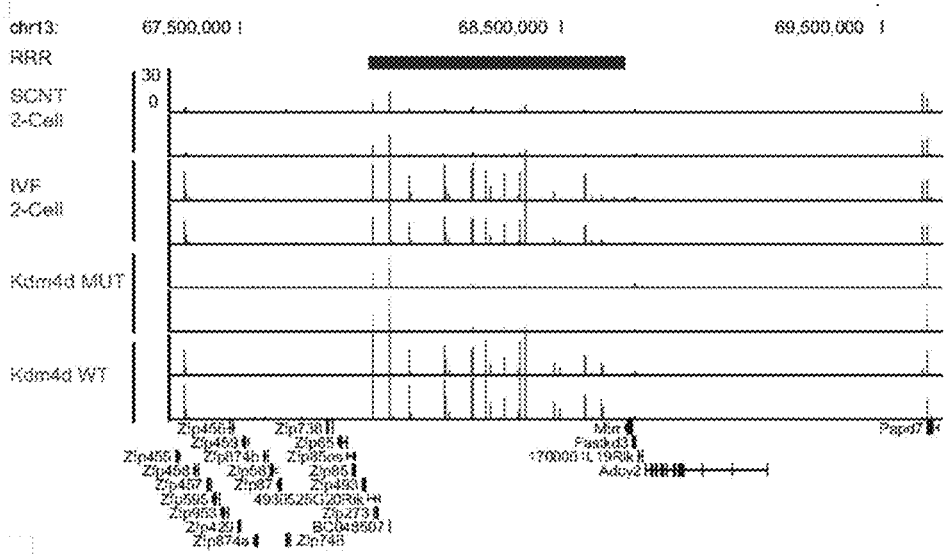
Figure 10C:
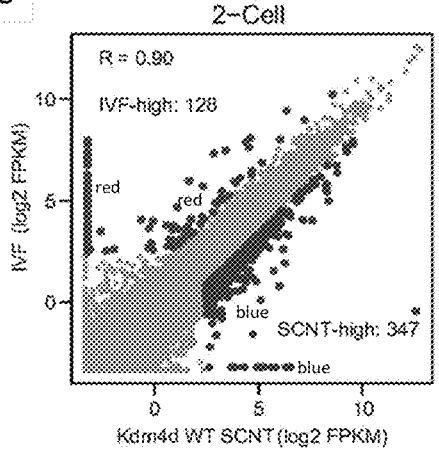

To examine the effects of Kdm4d-mediated H3K9me3 removal on the transcriptional outcome of 2-cell SCNT embryos, the inventors performed RNA-seq analysis focusing on the 222 RRRs that failed to be activated in SCNT. Compared to the control SCNT embryos, 83% (184/222) of RRRs were activated by the injection of wild-type, but not a catalytic defective mutant, Kdm4d (FIG. 3C, FC>2). This result indicates that erasure of H3K9me3 facilitates transcriptional activation within RRRs. As exemplified in FIG. 3D, an RRR on chromosome 7 containing the Zscan4 gene cluster was markedly activated by injection of wild-type Kdm4d, but not a catalytic defective mutant. Notably, not only protein coding genes, but also the majority of non-annotated transcripts from RRRs were also activated upon Kdm4d mRNA injection (FIGS. 10A and 10B). Interestingly, hierarchical clustering transcriptome analysis revealed that the transcriptome of SCNT embryos injected with wild-type Kdm4d was more similar to that of IVF embryos than that of control SCNT embryos, or of mutant Kdm4d injected embryos (FIG. 3E). Indeed, the total number of differentially expressed genes (FC>3) between SCNT and IVF 2-cell embryos decreased from 1212 to 475 by Kdm4d injection (FIGS. 3F and 10C), suggesting that removal of H3K9me3 from transferred somatic nuclei not only restores transcriptional activation of RRRs but also the global transcriptome of SCNT embryos.

Injection of Kdm4d mRNA Greatly Improves Development of SCNT Embryos

To examine the biological consequence of transcriptional restoration of SCNT embryos following Kdm4d injection, we first analyzed the developmental potential of SCNT embryos with Kdm4d mRNA injection using cumulus cells as donor cells. In control SCNT embryos, the developmental rate began to decline after the first cleavage with only 26.0% of cleaved embryos successfully develop to the blastocyst stage after 96 h of culturing (FIGS. 4A and 4B, and Table S1), a finding consistent with previous studies (Kishigami et al., 2006). Strikingly, SCNT embryos injected with wild-type Kdm4d mRNA rarely arrest during 2- to 4-cell and 4-cell to morula stage transition, and develop to the blastocyst stage with high efficiency (88.6%; FIGS. 4A and 4B, and Table 3). In contrast, injection of a catalytic defective mutant Kdm4d mRNAs has no significant impact on the developmental rate of the SCNT embryos, indicating the improvement of Kdm4d injection on SCNT embryo development depends on its enzymatic activity. Given that H3K9me3 enrichment in RRRs appears to be a general phenomenon in different somatic cell types, we anticipated that the positive effect of Kdm4d on SCNT embryo development should be able to be extended to other somatic donor cell types. Indeed, Kdm4d mRNA injection also significantly improved the developmental efficiency of SCNT embryos when Sertoli cells or C57BL/6 background MEF cells were used as donor cells (FIGS. 4A and 4B, Table 3). Together, these results demonstrate that H3K9me3 removal by Kdm4d mRNA injection can significantly improve pre-implantation development of SCNT embryos regardless of the somatic donor cell type.

Previous studies have demonstrated that temporal treatment with histone deacetylase (HDAC) inhibitors can also significantly improve developmental efficiency of SCNT embryos (Kishigami et al., 2006; Van Thuan et al., 2009). To explore a possible relationship between HDAC inhibitors and Kdm4d, the inventors performed a combinatorial treatment of SCNT embryos with the HDAC inhibitor, TSA, and Kdm4d. Treatment of TSA alone improved the blastocyst rate from 26.0% to 53.8% (FIG. 4C and Table 3), similar to previous report (Kishigami et al., 2006). Kdm4d mRNA injection combined with TSA further increased the blastocyst rate to 87.5%, which is statistically similar to Kdm4d injection alone (88.6%; FIG. 4C and Table 3). This result demonstrates that TSA treatment and Kdm4d mRNA injection does not have synergistic effect on SCNT reprogramming, at least in the preimplantation stage, and that TSA treatment may exert its effects through a similar pathway as that by Kdm4d.

The inventors also examined the efficiency of ntESC derivation from the blastocysts. When control SCNT blastocysts were cultured on feeder MEF cells with ES cell derivation medium, 71% of the blastocysts attached to the feeder cells and 50% of the blastocysts eventually gave rise to the established ntESC lines (FIG. 4D and Table 4). Blastocysts generated through Kdm4d mRNA injection, TSA treatment, or a Kdm4d/TSA combination did not show any significant difference in efficiency of attachment or ntESC derivation when compared to control (FIG. 4D and Table 4). Importantly, efficiency was greatly improved by Kdm4d injection when calculations were based on the total number of MII oocytes used for SCNT (FIG. 4E and Table 4)

TABLE 3

Preimplantation development of SCNT embryos injected with Kdm4d mRNA (related to FIGS. 4 and 6).

| Donor cell Cell-type | background | Sex | TSA treatment (nM/h) | mRNA injected | siRNA treated to donor cells | No. of replicates |
|---|---|---|---|---|---|---|
| Cumulus | BDF1 | Female | — | water | — | 5 |
|  |  |  | — | Kdm4d WT | — | 4 |
|  |  |  | — | Kdm4d MUT | — | 3 |
|  |  |  | 15/8 | water | — | 3 |
|  |  |  | 15/8 | Kdm4d WT | — | 3 |
| Sertoli | BDF1 | Male | — | water | — | 3 |
|  |  |  | — | Kdm4d WT | — | 4 |
| MEF | C57BL/6 | Male | — | water | control# | 5 |
|  |  |  | — | Kdm4d WT | control# | 4 |
|  |  |  | — | — | Setdb1 | 3 |
|  |  |  | — | — | Suv39h1/h2 | 3 |
|  |  |  | — | — | Suv39h1/h2, Setdb1 | 3 |

| Donor cell Cell-type | No. of reconstructed 1-cell embryos | % cleaved per 1-cell ± SD | % 4-cell per 2-cell ± SD | % morula per 2-cell ± SD | % blast per 2-cell ± SD |
|---|---|---|---|---|---|
| Cumulus | 91 | 94.8 ± 2.9 | 45.6 ± 18.9 | 35.8 ± 5.6 | 26.0 ± 11.3 |
|  | 76 | 92.7 ± 6.2 | 98.9 ± 2.3* | 96.5 ± 4.4* | 88.6 ± 3.9* |
|  | 62 | 98.6 ± 2.5 | 42.2 ± 12.3 | 30.8 ± 10.5 | 24.4 ± 8.6 |
|  | 44 | 98.0 ± 3.4 | 72.1 ± 10.9* | 60.8 ± 6.8* | 53.8 ± 6.2* |
|  | 51 | 94.1 ± 0.0 | 95.8 ± 0.0* | 93.8 ± 6.3* | 87.5 ± 12.5* |
| Sertoli | 72 | 87.6 ± 4.3 | 52.6 ± 8.0 | 36.8 ± 8.2 | 26.4 ± 6.3 |
|  | 102 | 89.3 ± 8.4 | 95.3 ± 3.6* | 91.6 ± 6.4* | 81.2 ± 7.5* |
| MEF | 124 | 82.0 ± 5.0 | 17.9 ± 15.2 | 10.0 ± 11.0 | 6.7 ± 8.2 |
|  | 56 | 86.9 ± 8.8 | 95.4 ± 5.5* | 89.6 ± 7.9* | 82.0 ± 10.3* |
|  | 77 | 84.7 ± 6.6 | 12.5 ± 11.9 | 4.8 ± 8.2 | 3.2 ± 5.5 |
|  | 80 | 77.3 ± 4.7 | 59.9 ± 8.8* | 53.8 ± 9.6* | 49.9 ± 9.0* |
|  | 77 | 68.5 ± 13.2 | 77.4 ± 12.9* | 74.1 ± 15.8* | 65.6 ± 9.8* |

Concentration of injected mRNAs was 1800 ng/µl.
Concentration of siRNAs was 5 pM each.
treated with transfection reagent alone.
*P < 0.01 as compared with water-injected control.

TABLE 4

In vivo development of SCNT embryos injected with Kdm4d (related to FIG. 4).

| Donor cell | | | TSA treatment | mRNA | No. of MII | No. of reconstructed 1-cell | No. of blastocyst (% per | ntESC derivation | | |
|---|---|---|---|---|---|---|---|---|---|---|
| | | | | | | | | No. of blastocyst attached to feeder cells | No. of established ntESC lines | No. of established ntESC lines (% per MII |
| Cell-type | background | Sex | (nM/h) | injected | oocytes | embryos | 1-cell) | (% per blast) | (% per blast) | oocyte) |
| Cumulus | BDF1 | Female | — | water | 69 | 62 | 14 (22.6) | 10 (71.4) | 7 (50.0) | 7 (10.1) |
| | | | — | Kdm4d WT | 20 | 19 | 18 (94.7) | 13 (72.2) | 10 (55.6) | 10 (50.0) |
| | | | 15/8 | water | 44 | 39 | 20 (51.3) | 14 (70.0) | 8 (40.0) | 8 (18.2) |
| | | | 15/8 | Kdm4d WT | 25 | 22 | 21 (95.5) | 16 (76.2) | 11 (52.3) | 11 (44.0) |

Concentration of injected mRNAs was 1800 ng/µl.

To examine whether the positive effect of Kdm4d on preimplantation development can be maintained through postimplantation development, the inventors transferred 2-cell stage SCNT embryos generated from cumulus cells into the oviducts of pseudopregnant female mice. Caesarian section at E19.5 (the day of term) revealed that the rate of implantation, evidenced by implantation sites, was 3-fold higher in Kdm4d-injected SCNT embryos (63.0%) than in control SCNT embryos (21.2%, FIG. 4F). Importantly, 7.6% (9/119) of transferred Kdm4d-injected 2-cell SCNT embryos developed to term, while none of the 104 transferred control embryos developed to term under the same conditions (FIG. 4G and Table 5). Similar experiments using Sertoli cell-derived SCNT embryos also demonstrated the positive effect of Kdm4d on the implantation rate (21% vs 64%) and the development to term rate (1% vs 8.7%) (FIGS. 4F, G and Table S3). Furthermore, SCNT pups generated through Kdm4d-injection grew normally to adulthood and generated offspring by natural mating (FIG. 4H). These results demonstrate that H3K9me3 in somatic cells is a barrier for oocyte-mediated genomic reprogramming and removal of H3K9me3 by Kdm4d injection at very early stages of SCNT embryo development can significantly improve the overall efficiency of mouse reproductive cloning.

phenotype of SCNT embryos. Given that Kdm4d overexpression greatly increases the rate of SCNT embryos reaching the blastocyst stage, the responsible genes must be derepressed in the wild-type Kdm4d-injected SCNT embryos. Analysis of the genes that failed to be activated in the 2-cell SCNT embryos (Group 3 genes in FIG. 1D), and the genes derepressed in wild-type Kdm4d-injected, but not the mutant Kdm4d-injected 2-cell SCNT embryos, allowed us to identify 49 common genes (FIGS. 5A and 5B, FC>5). GO analysis indicated that this group of genes are enriched for genes involved in transcription and RNA metabolic processes (FIG. 5A). While the function of most of the 49 genes in preimplantation development is unknown, the 2-cell specific Zscan4 family member, Zscan4d, has been shown to be important for preimplantation development (Falco et al., 2007). Therefore, the inventors examined whether supplement of exogenous Zscan4d mRNA could enhance the developmental efficiency of SCNT embryos.

The inventors microinjected mRNA encoding full-length Zscan4d into SCNT embryos at the early 2-cell stage (20 hpa: FIG. 5C) following the expression pattern of endogenous Zscan4d. However, injection of Zscan4d mRNA failed to rescue the poor developmental phenotype of SCNT

TABLE 5

In vivo development of SCNT embryos injected with Kdm4d (related to FIG. 4).

| method | cell type | Donor cell background | Sex | mRNA injected | No. of recipients | No. of 2-cell embryos transferred | No. of implanted (% per ET) | No. of pups (% per ET) | Body weight at birth (g + SD) | Placenta weight at birth (g + SD) |
|---|---|---|---|---|---|---|---|---|---|---|
| SCNT | Cumulus | BDF1 | Female | water | 6 | 104 | 22 (21.2) | 0 (0.0) | N/A | N/A |
| | | | | Kdm4d WT | 8 | 119 | 75 (63.0) | 9 (7.6) | 1.60 ± 0.15 | 0.32 ± 0.03 |
| | Sertoli | BDF1 | Male | Water | 5 | 99 | 21 (21.2) | 1 (1.0) | 1.53 | 0.40 |
| | | | | Kdm4d WT | 7 | 92 | 59 (64.1) | 8 (8.7) | 1.48 ± 0.11 | 0.26 ± 0.10 |
| IVF[#] | | | | | 4 | 72 | 54 (75.0) | 41 (56.9) | 1.47 ± 0.11 | 0.10 ± 0.02 |

Concentration of injected Kdm4d mRNA was 1800 ng/µl.
N/A, not applicable.
ET, embryo transfer.
[#]IVF embryos were produced from BDF1 sperms and oocytes.

Example 4

Candidate Genes Responsible for the Poor Developmental Phenotype of SCNT Embryos.

The inventors next assessed which of the genes repressed by H3K9me3 are responsible for the poor developmental embryos, regardless of concentration (FIG. 5D and Table 6). Therefore, a defect in Zscan4d activation in 2-cell SCNT embryos is unlikely to be solely responsible for the poor preimplantation development of SCNT embryos. Rather, complicated gene networks including transcripts derived from non-genic repetitive elements (FIG. 11) may underlie the defects of SCNT embryonic development.

TABLE 6

Preimplantaiton development of SCNT embryos injected with Zscan4d mRNA (related to FIG. 5). All experiments were done on donor cells which were; Cumulus cell type, BDF1 background, female cell donor cells.

| Concentration of injected Zscan4d mRNA (ng/μl) | No of replicates | No. of reconstructed 1-cell ± SD | % 4-cell per 2-cell ± SD | % morula per 2-cell ± SD | % blactocytes per 2-cell± |
|---|---|---|---|---|---|
| 0 | 3 | 98.0 ± 3.4 | 42.5 ± 17.5 | 38.8 ± 15.2 | 30.8 ± 6.3 |
| 20 | 3 | 100.0 ± 0.0 | 44.2 ± 7.9 | 38.3 ± 3.4 | 30.4 ± 6.0 |
| 200 | 3 | 98.0 ± 3.4 | 45.4 ± 14.4 | 41.7 ± 17.6 | 30.0 ± 8.7 |
| 2000 | 3 | 98.2 ± 3.0 | 60.3 ± 11.1 | 48.9 ± 7.3 | 39.9 ± 4.6 |

Example 5

Figure 6A:
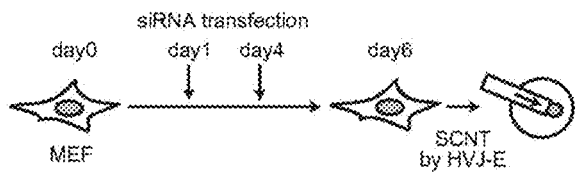
FIGS. 6A-6D shows that Suv39h1/2 is responsible for the establishment of the H3K9me3 barrier.
Figure 6B:
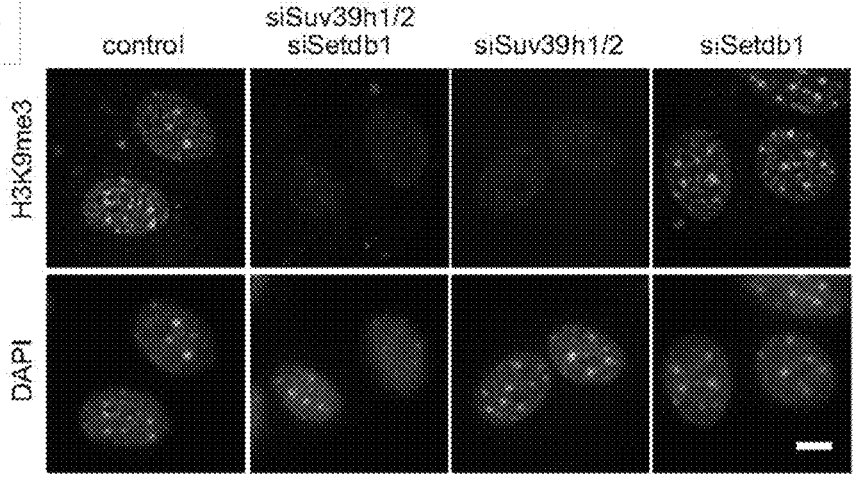
Figure 6C:
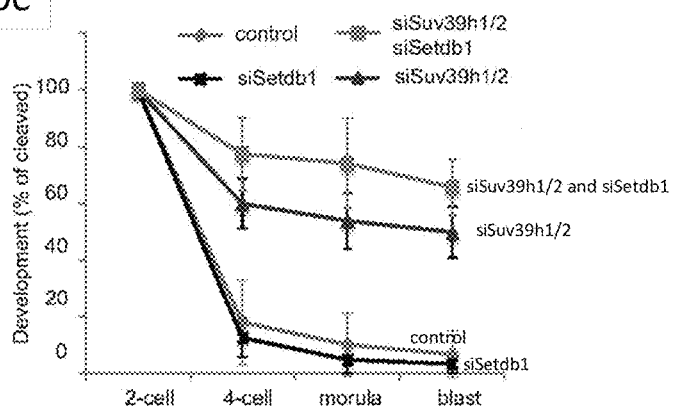
Figure 6D:
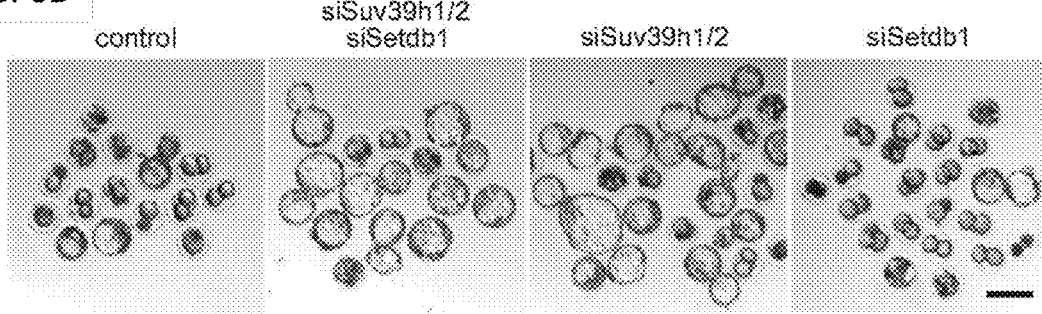

Suv39h1/2 are Responsible for the Establishment of the H3K9Me3 Barrier in Somatic Cells Having demonstrated that H3K9me3 is an epigenetic barrier of SCNT-mediated reprogramming, we next attempted to identify the histone methyltransferase(s) responsible for the deposition of H3K9me3 within RRRs in somatic genomes. Previous studies have reported that at least three histone lysine methyltransferases (KMTs), Suv39h1, Suv39h2 and Setdb1, can catalyze the generation of H3K9me3 in mammalian cells (Matsui et al., 2010; Peters et al., 2001). First, the inventors depleted the three H3K9me3 methyltransferases in MEF cells by transfecting a mixture of short interfering RNAs (siRNAs) targeting Suv39h1, Suv39h2 and Setdb1 (FIG. 6A). RT-qPCR analysis confirmed a knockdown efficiency of 80-60% was achieved 48 hours after transfection (FIG. 12A-12B). Immunostaining showed that transfection of these siRNAs (twice within 6-days of cell culture) could greatly reduce H3K9me3 levels in MEF cells (FIGS. 6A and 6B), demonstrating the three H3K9me3 methyltransferases, and not other unidentified enzymes, as the responsible factors for the H3K9me3 deposition in the somatic cells. Using triple KD MEF cells as donors, we generated SCNT embryos and examined their preimplantation development. The inventors discovered that while only 6.7% of control SCNT embryos developed to the blastocyst stage after 96 h culture (FIGS. 6C, 6D, and Table 3), 65.6% of the triple knockdown MEF-derived embryos developed to blastocyst stage (FIGS. 6C, 6D and Table 3). This result not only confirms that somatic H3K9me3 is an epigenetic barrier of SCNT-mediated reprogramming, but also demonstrates that these three enzymes are responsible for generating this epigenetic barrier.

The inventors next examined which of the three histone methyltransferases is responsible for establishing the H3K9me3 reprogramming barrier by individually depleting them in MEF cells. Since Suv39h1 and Suv39h2 have redundant functions in H3K9 trimethylation (Peters et al., 2001), we knocked down both genes at the same time. Immunostaining at day 6 of knockdown demonstrated that Suv39 KD reduced global H3K9me3 levels, especially at pericentric regions, while Setdb1 knockdown did not cause a global change in H3K9me3 levels (FIG. 6B), a finding consistent with a previous report (Matsui et al., 2010). When these knockdown MEF cells were used as donors for SCNT analysis, the developmental rate to the blastocyst stage was greatly improved from 6.7% in control to 49.9% in the Suv39h KD MEF group, very close to that of triple knockdown MEF group (FIGS. 6C, 6D, and Table 3). In contrast, knockdown of Setdb1 did not significantly alter the developmental rate (FIGS. 6C, 6D, and Table 3). Collectively, these results demonstrate that while Setdb1 can be used to increase the efficiency of SCNT, Suv39h1/2 are primarily responsible for establishing H3K9me3 in somatic cells, which functions as a barrier in genomic reprogramming of SCNT embryos.

Example 6

Figure 7:
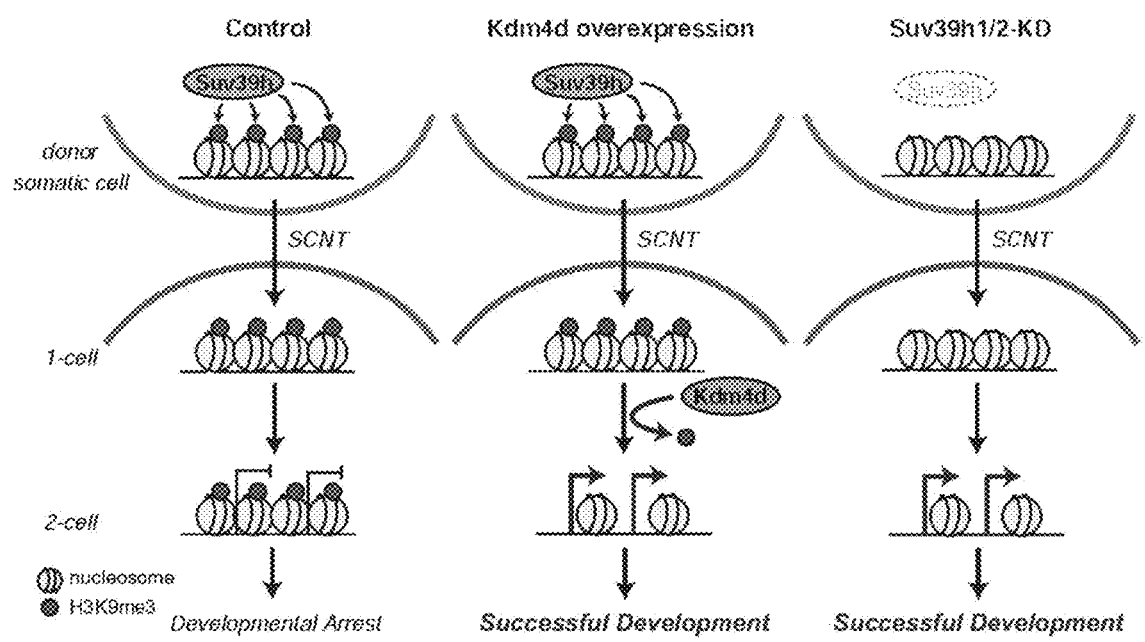
FIG. 7 is a model illustrating how the H3K9me3 reprogramming barrier can be overcome. Suv39h-deposited H3K9me3 in somatic differentiated cells serves as a transcriptional barrier for SCNT-mediated reprogramming which affects normal embryonic development and results in developmental arrest (Left). Removal of this barrier either by the expression of exogenous Kdm4d (Middle) or through preventing H3K9me3 establishment by inhibiting Suv39h or by Suv39h knockdown (Right) can lead to activation of developmental regulators in SCNT embryos, resulting in successful embryonic development and prevents developmental arrest.

More than 50 years have passed since the first demonstration of animal cloning through somatic cell nuclear transfer in *Xenopus* eggs (Gurdon, 1962). Despite tremendous efforts, cloning efficiency has remained relatively low in most of the species, and the mechanism underlying epigenetic reprogramming following SCNT has remained poorly understood. In this study, through comparative transcriptome and integrated epigenomic analysis, the inventors have discovered that Suv39h1/2-deposited H3K9me3 in donor somatic cells functions as an epigenetic barrier of somatic cell nuclear reprogramming in human and mouse oocytes. By comparing to the transcriptome of IVF embryos, the inventors identified 222 genomic regions, termed as RRRs (reprogramming resistant regions), resistant to transcriptional reprogramming in SCNT embryos. RRRs are characterized by significant enrichment of Suv39h1/2-deposited H3K9me3 and low DNase I accessibility, both of which are general features of heterochromatin, in several somatic cell types analyzed. Efficient activation of transcripts within RRRs appears to be important for the development of SCNT embryos as removal of H3K9me3 either by Suv39h1/2 knockdown or by expression of exogenous Kdm4d results in activation of RRRs and significant improvement of the development of SCNT embryos. Thus, the inventors have demonstreated herein a model where Suv39h1/2-deposited H3K9me3 in somatic cells serves as a barrier for the activation of developmentally important genes in oocytes, leading to developmental arrest of SCNT embryos (FIG. 7). Removal of this epigenetic barrier either by exogenous Kdm4d after SCNT or by depletion of Suv39h1/2 in donor cells allows the expression of developmental genes and improvement of the development of SCNT embryos (FIG. 7).

How does H3K9me3 impede reprogramming? Previous studies have reported that H3K9me3 can be recognized and bound by the heterochromatin protein, HP1 (Bannister et al., 2001; Lachner et al., 2001), which can nucleate the formation of heterochromatin (Canzio et al., 2013). Interaction between heterochromatin and nuclear lamina can tether heterochromatin to the nuclear periphery leading to epigenetic silencing (Poleshko and Katz, 2014). Therefore, H3K9me3-initiated heterochromatin assembly can prevent access to reprogramming and transcriptional factors, and thereby prevent the activation of developmentally important genes in RRRs. In addition to preventing reprogramming and transcriptional factor access, H3K9me3 has been reported to inhibit subsequent deposition of activation marks, such as H3K9 acetylation and H3K4 methylation as we have demonstrated previously (Wang et al., 2001).

The inventors demonstrate herein that H3K9me3-mediated heterochromatin formation functions as a general reprogramming barrier, which is consistant with the report that both H3K9me3 (Chen et al., 2013; Soufi et al., 2012) and HP1 (Sridharan et al., 2013) in MEF cells inhibit iPS cell generation. Nonetheless, several important differences exist regarding the barrier between SCNT and iPS reprogramming. First, the H3K9me3-barrier in mouse iPS reprogramming is established primarily by Setdb1(Chen et al., 2013; Sridharan et al., 2013). In contrast, the inventors clearly demonstrate herein that Suv39h1/2, but not Setdb1, as critical enzymes that establish H3K9me3-barrier of SCNT reprogramming. Secondly, the downstream gene networks necessary for successful reprogramming in iPS and SCNT reprogramming, which are repressed by the H3K9me3-barrier, are very different. In particular, in iPS reprogramming, the key downstream factors within the H3K9me3-barrier are the core pluripotency network genes, such as Nanog and Sox2, which operate during relatively late stages of reprogramming (Chen et al., 2013; Sridharan et al., 2013). In contrast, in SCNT reprogramming, transcripts that play a critical function at the 2-cell stage are the key factors repressed by H3K9me3 (as discussed herein). This key distinction is due to differences in the set of transcription factors required for successful reprogramming in iPS and SCNT, respectively. Indeed, Oct4/Pou5f1 which are core transcription factor required for iPS reprogramming have been found to be dispensable in SCNT reprogramming (Wu et al., 2013). Therefore, although H3K9m3 appears to be important in reprogramming in iPS, because of the key mechanistic differences in iPS and SCNT reprogramming, one cannot apply what works for iPS reprogramming to SCNT reprogramming.

Accordingly, as discussed herein, while demethylation of H3K9me3 (by Kdm4d/JmjdJmjd2D) has been reported to be used to increase the efficiency of the generation of iPS cells from somatic cell reprogramming, because there are many key and significant differences in the generation and global epigenetic status of iPSC cells as compared to ES cells (see Table 1 herein), as well as significantly different mechanisms in reprogramming cells in the generation of iPS cells as compared to the mechanism of reprogramming cells in the generation of SCNT embryos (Table 1), one of ordinary skill in the art would not know that demethylation of H3K9me3 in the generation of iPS cells can be transferred to methods for the successful generation and pre- and post-implantation efficiency of SCNT embryos.

The inventors have listed 49 candidate genes that are potentially responsible for the poor developmental phenotype of SCNT embryos. Unexpectedly, the overexpression of one of the candidate genes, Zscan4d, did not improve the blastocyst rate. It was also suprizing that Suv39h1 and Suv39h2 increased the efficiency of SCNT, but not the other histone lysine methyltransferase Setdb1. Therefore, one can envision that other factors activated at 2-cell stage IVF embryos are necessary for SCNT embryos to successfully develop to the blastocyst stage. In addition to the protein coding genes disclosed herein, the deregulated RRRs also harbor many un-annotated transcripts and repeat sequences whose repression in 2-cell SCNT embryos exhibits H3K9me3 dependency. For example, expression of the major satellite repeats were greatly suppressed in 2-cell SCNT embryos, and this repression was completely restored by the wild type, but not the catalytic mutant, Kdm4d injection (FIG. 11). Similarly, Kdm4d injection also partly relieved SCNT-induced repression of class III retrotransposon elements, such as MERVL, in 2-cell SCNT embryos (FIG. 11). Given that activation of both repeat sequences is important for preimplantation development (Kigami, 2003; Probst et al., 2010), transcriptional deregulation of these repeat sequences in 2-cell SCNT embryos may also contribute to the developmental defects observed in these embryos. Therefore, it is likely that defective activation of protein coding genes and repeat sequences that harbor the H3K9me3 mark inherited from somatic cells is collectively responsible for the developmental failure of SCNT embryos.

The inventors indicate that the methods and compositions as disclosed herein to increase SCNT efficiency can be generally applied to other animal and mammalian species. Similar to mice, developmental defects of SCNT embryos appear concurrently with ZGA in other mammalian species such as rabbit (Li et al., 2006), pig (Zhao et al., 2009), bovine (Akagi et al., 2011) and human (Noggle et al., 2011), with abnormal heterochromatin or H3K9me3 status observed in the SCNT embryos of these species (Pichugin et al., 2010; Santos et al., 2003; Yang et al., 2009). Therefore, the H3K9me3 reprogramming barrier is likely to be conserved among different species. Accordingly, Kdm4d mRNA injection can be used to enhance and improve the cloning efficiency in a broad range of mammals, including humans and domestic animals. Importantly, the inventors demonstrate herein that the injection of Kdm4d mRNA greatly enhanced ntESC derivation efficiency in mice. Accordingly, Kdm4d mRNA can be used to enhance ntESC derivation efficiency from human cells, providing a significant source of human cells for human therapeutic cloning (Hochedlinger and Jaenisch, 2003; Yang et al., 2007). The simplicity of Kdm4d mRNA injection into human oocytes during SCNT can be performed by one of ordinary skill in the art. Furthermore, an ordinary skilled artisan can alternatively use a Suv39h-specific inhibitor in a simple incubation with the donor cells prior to transferring or injecting the nuclei into the enucleated oocyte can be used to enhance human ntESC derivation efficiency and their use for human therapeutic cloning.

REFERENCES

The references disclosed herein are incorporated in their entirety by reference.

Apostolou, E., & Hochedlinger, K. (2013). Chromatin dynamics during cellular reprogramming. *Nature*, 502 (7472), 462-71. doi:10.1038/nature12749

Chang, G., Gao, S., Hou, X., Xu, Z., Liu, Y., Kang, L., . . . Tian, J. (2014). High-throughput sequencing reveals the disruption of methylation of imprinted gene in induced pluripotent stem cells. *Cell Research*, 24(3), 293-306. doi:10.1038/cr.2013.173

Inoue, A., & Zhang, Y. (2014). Nucleosome assembly is required for nuclear pore complex assembly in mouse zygotes. *Nature Structural & Molecular Biology*, (June), 2-11. doi:10.1038/nsmb.2839

Jullien, J., Pasque, V., Halley-Stott, R. P., Miyamoto, K., & Gurdon, J. B. (2011). Mechanisms of nuclear reprogramming by eggs and oocytes: a deterministic process? *Nature Reviews. Molecular Cell Biology*, 12(7), 453-9. doi:10.1038/nrm3140

Ma, H., Morey, R., O'Neil, R. C., He, Y., Daughtry, B., Schultz, M. D., . . . Mitalipov, S. (2014). Abnormalities in human pluripotent cells due to reprogramming mechanisms. *Nature,* 511(7508), 177-183. doi:10.1038/nature13551

Matoba, S., Inoue, K., Kohda, T., Sugimoto, M., Mizutani, E., Ogonuki, N., . . . Ogura, A. (2011). RNAi-mediated knockdown of Xist can rescue the impaired postimplantation development of cloned mouse embryos. *Proceedings of the National Academy of Sciences of the United States of America,* 108(51), 20621-6. doi:10.1073/pnas.1112664108

Mitalipov, S., & Don Wolf. (2009). Totipotency, pluripotency and nuclear reprogramming. In *Advances in Biochemical Engineering/Biotechnology* (pp. 185-199).

Pasque, V., Miyamoto, K., & Gurdon, J. B. (2010). Efficiencies and mechanisms of nuclear reprogramming. *Cold Spring Harbor Symposia on Quantitative Biology,* 75, 189-200. doi:10.1101/sqb.2010.75.002

Pedersen, M. T., Agger, K., Laugesen, A., Johansen, J. V, Cloos, P. a C., Christensen, J., & Helin, K. (2014). The demethylase JMJD2C localizes to H3K4me3-positive transcription start sites and is dispensable for embryonic development. *Molecular and Cellular Biology,* 34(6), 1031-45. doi:10.1128/MCB.00864-13

Rideout, W. M., Wakayama, T., Wutz, a, Eggan, K., Jackson-Grusby, L., Dausman, J., . . . Jaenisch, R. (2000). Generation of mice from wild-type and targeted ES cells by nuclear cloning. *Nature Genetics,* 24(2), 109-10. doi:10.1038/72753

Sridharan, R., Gonzales-Cope, M., Chronis, C., Bonora, G., McKee, R., Huang, C., . . . Plath, K. (2013). Proteomic and genomic approaches reveal critical functions of H3K9 methylation and heterochromatin protein-1γ in reprogramming to pluripotency. *Nature Cell Biology,* 15(7), 872-82. doi:10.1038/ncb2768

Tachibana, M., Amato, P., Sparman, M., Gutierrez, N. M., Tippner-Hedges, R., Ma, H., . . . Mitalipov, S. (2013). Human embryonic stem cells derived by somatic cell nuclear transfer. *Cell,* 153(6), 1228-38. doi:10.1016/j.cell.2013.05.006

Yamada, M., Johannesson, B., Sagi, I., Burnett, L. C., Kort, D. H., Prosser, R. W., . . . Egli, D. (2014). Human oocytes reprogram adult somatic nuclei of a type 1 diabetic to diploid pluripotent stem cells. *Nature,* 510(7506), 533-6. doi:10.1038/nature13287

Yamanaka, S., & Blau, H. M. (2010). Nuclear reprogramming to a pluripotent state by three approaches. *Nature,* 465(7299), 704-12. doi:10.1038/nature09229

Akagi, S., Matsukawa, K., Mizutani, E., Fukunari, K., Kaneda, M., Watanabe, S., and Takahashi, S. (2011). Treatment with a histone deacetylase inhibitor after nuclear transfer improves the preimplantation development of cloned bovine embryos. J. Reprod. Dev. 57, 120-126.

Bannister, a J., Zegerman, P., Partridge, J. F., Miska, E. a, Thomas, J. O., Allshire, R. C., and Kouzarides, T. (2001). Selective recognition of methylated lysine 9 on histone H3 by the HP1 chromo domain. Nature 410, 120-124.

Bernstein, B. E., Birney, E., Dunham, I., Green, E. D., Gunter, C., and Snyder, M. (2012). An integrated encyclopedia of DNA elements in the human genome. Nature 489, 57-74.

Canzio, D., Liao, M., Naber, N., Pate, E., Larson, A., Wu, S., Marina, D. B., Garcia, J. F., Madhani, H. D., Cooke, R., et al. (2013). A conformational switch in HP1 releases auto-inhibition to drive heterochromatin assembly. Nature 496, 377-381.

Chen, J., Liu, H., Liu, J., Qi, J., Wei, B., Yang, J., Liang, H., Chen, Y., Chen, J., Wu, Y., et al. (2013). H3K9 methylation is a barrier during somatic cell reprogramming into iPSCs. Nat. Genet. 45, 34-42.

Chung, Y. G., Eum, J. H., Lee, J. E., Shim, S. H., Sepilian, V., Hong, S. W., Lee, Y., Treff, N. R., Choi, Y. H., Kimbrel, E. a, et al. (2014). Human Somatic Cell Nuclear Transfer Using Adult Cells. Cell Stem Cell 1-4.

Evsikov, a V, de Vries, W. N., Peaston, a E., Radford, E. E., Fancher, K. S., Chen, F. H., Blake, J. a, Bult, C. J., Latham, K. E., Solter, D., et al. (2004). Systems biology of the 2-cell mouse embryo. Cytogenet. Genome Res. 105, 240-250.

Falco, G., Lee, S.-L., Stanghellini, I., Bassey, U. C., Hamatani, T., and Ko, M. S. H. (2007). Zscan4: a novel gene expressed exclusively in late 2-cell embryos and embryonic stem cells. Dev. Biol. 307, 539-550.

Gurdon, J. B. (1962). The developmental capacity of nuclei taken from intestinal epithelium cells of feeding tadpoles. J. Embryol. Exp. Morphol. 10, 622-640.

Hochedlinger, K., and Jaenisch, R. (2003). Nuclear transplantation, embryonic stem cells, and the potential for cell therapy. N. Engl. J. Med. 349, 275-286.

Inoue, K., Ogonuki, N., Miki, H., Hirose, M., Noda, S., Kim, J.-M., Aoki, F., Miyoshi, H., and Ogura, A. (2006). Inefficient reprogramming of the hematopoietic stem cell genome following nuclear transfer. J. Cell Sci. 119, 1985-1991.

Inoue, K., Kohda, T., Sugimoto, M., Sado, T., Ogonuki, N., Matoba, S., Shiura, H., Ikeda, R., Mochida, K., Fujii, T., et al. (2010). Impeding Xist expression from the active X chromosome improves mouse somatic cell nuclear transfer. Science 330, 496-499.

Kigami, D. (2003). MuERV-L Is One of the Earliest Transcribed Genes in Mouse One-Cell Embryos. Biol. Reprod. 68, 651-654.

Kishigami, S., Mizutani, E., Ohta, H., Hikichi, T., Thuan, N. Van, Wakayama, S., Bui, H.-T., and Wakayama, T. (2006). Significant improvement of mouse cloning technique by treatment with trichostatin A after somatic nuclear transfer. Biochem. Biophys. Res. Commun. 340, 183-189.

Krishnan, S., and Trievel, R. C. (2013). Structural and functional analysis of JMJD2D reveals molecular basis for site-specific demethylation among JMJD2 demethylases. Structure 21, 98-108.

Lachner, M., O'Carroll, D., Rea, S., Mechtler, K., and Jenuwein, T. (2001). Methylation of histone H3 lysine 9 creates a binding site for HP1 proteins. Nature 410, 116-120.

Li, S., Chen, X., Fang, Z., Shi, J., and Sheng, H. Z. (2006). Rabbits generated from fibroblasts through nuclear transfer. Reproduction 131, 1085-1090.

Matsui, T., Leung, D., Miyashita, H., Maksakova, I. a, Miyachi, H., Kimura, H., Tachibana, M., Lorincz, M. C., and Shinkai, Y. (2010). Proviral silencing in embryonic stem cells requires the histone methyltransferase ESET. Nature 464, 927-931.

Noggle, S., Fung, H.-L., Gore, A., Martinez, H., Satriani, K. C., Prosser, R., Oum, K., Paull, D., Druckenmiller, S., Freeby, M., et al. (2011). Human oocytes reprogram somatic cells to a pluripotent state. Nature 478, 70-75.

Ogura, A., Inoue, K., and Wakayama, T. (2013). Recent advancements in cloning by somatic cell nuclear Recent advancements in cloning by somatic cell nuclear transfer. Phil. Trans. R. Soc. B 368, 20110329.

Ono, Y., Shimozawa, N., Ito, M., and Kono, T. (2001). Cloned Mice from Fetal Fibroblast Cells Arrested at Metaphase by a Serial Nuclear Transfer. Biol. Reprod. 64, 44-50.

Peaston, A. E., Evsikov, A. V, Graber, J. H., de Vries, W. N., Holbrook, A. E., Solter, D., and Knowles, B. B. (2004). Retrotransposons regulate host genes in mouse oocytes and preimplantation embryos. Dev. Cell 7, 597-606.

Peters, A., O'Carroll, D., Scherthan, H., Mechtler, K., Sauer, S., Schofer, C., Weipoltshammer, K., Pagani, M., Lachner, M., Kohlmaier, A., et al. (2001). Loss of the Suv39h histone methyltransferases impairs mammalian heterochromatin and genome stability. Cell 107, 323-337.

Pichugin, A., Le Bourhis, D., Adenot, P., Lehmann, G., Audouard, C., Renard, J.-P., Vignon, X., and Beaujean, N. (2010). Dynamics of constitutive heterochromatin: two contrasted kinetics of genome restructuring in early cloned bovine embryos. Reproduction 139, 129-137.

Poleshko, A., and Katz, R. A. (2014). Specifying peripheral heterochromatin during nuclear lamina reassembly. Nucleus 5, 32-39.

Probst, A. V, Okamoto, I., Casanova, M., El Marjou, F., Le Baccon, P., and Almouzni, G. (2010). A strand-specific burst in transcription of pericentric satellites is required for chromocenter formation and early mouse development. Dev. Cell 19, 625-638.

Rodriguez-Osorio, N., Urrego, R., Cibelli, J. B., Eilertsen, K., and Memili, E. (2012). Reprogramming mammalian somatic cells. Theriogenology 78, 1869-1886.

Santos, F., Zakhartchenko, V., Stojkovic, M., Peters, A., Jenuwein, T., Wolf, E., Reik, W., and Dean, W. (2003). Epigenetic Marking Correlates with Developmental Potential in Cloned Bovine Preimplantation Embryos. Curr. Biol. 13, 1116-1121.

Schultz, R. M. (2002). The molecular foundations of the maternal to zygotic transition in the preimplantation embryo. Hum. Reprod. Update 8, 323-331.

Soufi, A., Donahue, G., and Zaret, K. S. (2012). Facilitators and impediments of the pluripotency reprogramming factors' initial engagement with the genome. Cell 151, 994-1004.

Suzuki, T., Minami, N., Kono, T., and Imai, H. (2006). Zygotically activated genes are suppressed in mouse nuclear transferred embryos. Cloning Stem Cells 8, 295-304.

Van Thuan, N., Bui, H.-T., Kim, J.-H., Hikichi, T., Wakayama, S., Kishigami, S., Mizutani, E., and Wakayama, T. (2009). The histone deacetylase inhibitor scriptaid enhances nascent mRNA production and rescues full-term development in cloned inbred mice. Reproduction 138, 309-317.

Vassena, R., Han, Z., Gao, S., Baldwin, D. a, Schultz, R. M., and Latham, K. E. (2007). Tough beginnings: alterations in the transcriptome of cloned embryos during the first two cell cycles. Dev. Biol. 304, 75-89.

Wakayama, T., Tabar, V., Rodriguez, I., Perry, a C., Studer, L., and Mombaerts, P. (2001). Differentiation of embryonic stem cell lines generated from adult somatic cells by nuclear transfer. Science 292, 740-743.

Wang, H., Cao, R., Xia, L., Erdjument-bromage, H., Borchers, C., Tempst, P., and Zhang, Y. (2001). Purification and Functional Characterization of a Histone H3-Lysine 4-Specific Methyltransferase. Mol. Cell 8, 1207-1217.

Wilmut, I., Schnieke, A., McWhir, J., Kind, A., and Campbell, K. (1997). Viable offspring derived from fetal and adult mammalian cells. Nature 385, 810-813.

Yang, C., Liu, Z., Fleurot, R., Adenot, P., Vignon, X., Zhou, Q., Renard, J., and Beaujean, N. (2009). Heterochromatin reprogramming in rabbit embryos after fertilization, intra-, and inter-species SCNT correlates with preimplantation development. Reproduction 145, 149-159.

Yang, X., Smith, S. L., Tian, X. C., Lewin, H. A., Renard, J., and Wakayama, T. (2007). Nuclear reprogramming of cloned embryos and its implications for therapeutic cloning. Nat. Genet. 39, 295-302.

Zhao, J., Ross, J. W., Hao, Y., Spate, L. D., Walters, E. M., Samuel, M. S., Rieke, A., Murphy, C. N., and Prather, R. S. (2009). Significant Improvement in Cloning Efficiency of an Inbred Miniature Pig by Histone Deacetylase Inhibitor Treatment after Somatic Cell Nuclear Transfer. Biol. Reprod. 81, 525-530.

Bernstein, B. E., Birney, E., Dunham, I., Green, E. D., Gunter, C., and Snyder, M. (2012). An integrated encyclopedia of DNA elements in the human genome. Nature 489, 57-74

Chang, G., Gao, S., Hou, X., Xu, Z., Liu, Y., Kang, L., Tao, Y., Liu, W., Huang, B., Kou, X., et al. (2014). High-throughput sequencing reveals the disruption of methylation of imprinted gene in induced pluripotent stem cells. Cell Res. 24, 293-306.

Inoue, A., and Zhang, Y. (2014). Nucleosome assembly is required for nuclear pore complex assembly in mouse zygotes. Nat. Struct. Mol. Biol. 2-11.

Matoba, S., Inoue, K., Kohda, T., Sugimoto, M., Mizutani, E., Ogonuki, N., Nakamura, T., Abe, K., Nakano, T., Ishino, F., et al. (2011). RNAi-mediated knockdown of Xist can rescue the impaired postimplantation development of cloned mouse embryos. Proc. Natl. Acad. Sci. U.S.A 108, 20621-20626.

The Encode Consortium Project (2011). A user's guide to the encyclopedia of DNA elements (ENCODE). PLoS Biol. 9, e1001046.

| species | gene | SEQ ID NO: | CDS sequence (coding sequence) |
|---|---|---|---|
| human | KDM4D | SEQ ID NO: 1 | ATGGAAACTATGAAGTCTAAGGCCAACTGTGCCCAGAATCCAAATTGTAACATAATGATATTTCATCCAA CCAAAGAAGAGTTTAATGATTTTGATAAATATATTGCTTACATGGAATCCCAAGGTGCACACAGAGCTGG CTTGGCTAAGATAATTCCACCCAAAGAATGGAAAGCCAGAGAGACCTATGATAATATCAGTGAAATCTTA ATAGCCACTCCCCTCCAGCAGGTGGCCTCTGGGCGGGCAGGGGTGTTTACTCAATACCATAAAAAAAAGA AAGCCATGACTGTGGGGAGTATCGCCATTTGGCAAACAGTAAAAAATATCAGACTCCACCACACCAGAA TTTCGAAGATTTGGAGCGAAAATACTGGAAGAACCGCATCTATAATTCACCGATTTATGGTGCTGACATC AGTGGCTCCTTGTTTGATGAAAACACTAAACAATGGAATCTTGGGCACCTGGGAACAATTCAGGACCTGC TGGAAAAGGAATGTGGGGTTGTCATAGAAGGCGTCAATACACCCTACTTGTACTTTGGCATGTGGAAAAC CACGTTTGCTTGGCATACAGAGGACATGGACCTTTACAGCATCAACTACCTGCACCTTGGGGAGCCCAAA ACTTGGTATGTGGTGCCCCCAGAACATGGCCAGCGCCTGGAACGCCTGGCCAGGGAGCTCTTCCCAGGCA GTTCCCGGGGTTGTGGGGCCTTCCTGCGGCACAAGGTGGCCCTCATCTCGCCTACAGTTCTCAAGGAAAA |

| species | gene | SEQ ID NO: | CDS sequence (coding sequence) |
|---|---|---|---|
| | | | TGGGATTCCCTTCAATCGCATAACTCAGGAGGCTGGAGAGTTCATGGTGACCTTTCCCTATGGCTACCAT<br>GCTGGCTTCAACCATGGTTTCAACTGCGCAGAGGCCATCAATTTTGCCACTCCGCGATGGATTGATTATG<br>GCAAAATGGCCTCCCAGTGTAGCTGTGGGGAGGCAAGGGTGACCTTTTCCATGGATGCCTTCGTGCGCAT<br>CCTGCAACCTGAACGCTATGACCTGTGAAACGTGGGCAAGACCGGGCAGTTGTGGACCACATGGAGCCC<br>AGGGTACCAGCCAGCCAAGAGCTGAGCACCCAGAAGGAAGTCCAGTTACCCAGGAGAGCAGCGCTGGGCC<br>TGAGACAACTCCCTTCCCACTGGGCCCGGCATTCCCCTTGGCCTATGGCTGCCCGCAGTGGGACACGGTG<br>CCACACCCTTGTGTGCTCTTCACTCCCACGCCGATCTGCAGTTAGTGGCACTGCTACGCAGCCCCGGGCT<br>GCTGCTGTCCACAGCTCTAAGAAGCCCAGCTCAACTCCATCATCCACCCCTGGTCCATCTGCACAGATTA<br>TCCACCCGTCAAATGGCAGACGTGGTCGTGGTCGCCCTCCTCAGAAACTGAGAGCTCAGGAGCTGACCCT<br>CCAGACTCCAGCCAAGAGGCCCCTCTTGGCGGGCACAACATGCACAGCTTCGGGCCCAGAACCTGAGCCC<br>CTACCTGAGGATGGGGCTTTGATGGACAAGCCTGTACCACTGAGCCCAGGGCTCCAGCATCCTGTCAAGG<br>CTTCTGGGTGCAGCTGGGCCCCTGTGCCCTAA |
| mouse | Kdm4d | SEQ ID NO: 2 | ATGAAGACGAAGTCCACATGTGCTCAGAATCCAAATTGCAGCATAATGATATTTCGTCCAACCAAAGAAG<br>AGTTTAATGATTTTGACAAATACATTGCTTACATGGAGTCCCAAGGGGCACACCGAGCTGGACTGGCCAA<br>GGTCATCCCACCAAAAGAATGGAGGGCCAGGCAGTCTTATGACAATATCAGCAACATCTTAATAGCAACT<br>CCCCTGCAGCAAGTGGTCTCTGGGCAGGCAGGCGTGTTCACCCAATACCATAAGAAGAAGAAAGGCATGA<br>CAGTGGGGGAGTACCGTGAGCTGGCCAACAGCAAAAAGTACCAGACCCCGCCACACCTGGATTTTGAAGA<br>TTTGGAGCGAAAATACTGGAAGAATCGCCTATATGAGTCACCGATTTATGGTGCTGACGTCAGCGGCTCC<br>CTGTTTGATGGGAAGACTCAACAGTGGAATGTGGGCACCTGGGAACAATTCAAGACCTATTGGAACAGG<br>AATGTGGCATAGTGATTGAGGGCGTCAACACGCCCTACCTGTACTTTGGCATGTGGAAGACCACCTTTGC<br>GTGGCACACGGAGGACATGGACCTGTACAGTATCAACTACCTACACTTTGGGCAGCCCAAGACCTGGTAT<br>GCTGTGCCCCCTGAGCATGGCAGGCGCCTGGACGGAACTCTTCCCTGGCAGCTCCCAGG<br>GCTGCCAGGCCTTCCTGAGGCACAAGGTGGCGCTCATCTCGCCCACTGTGCTTAAGGAGAATGGCATCCC<br>CTTTGGTCGCATCACCCAGGAGGCTGGGGAGTTCATGGTCACCTTTCCCTATGGCTACCACGGGGCTTC<br>AACCATGGCTTCAACTGCGCAGAGGCCATCAATTTTGCCACCCCAAGGTGGATTGACTATGGCAAGGTGG<br>CATCTCAGTGCAGCTGTGGGAGGCCAGGGTGAGCTTCTCCATGGACGCCTTTGTGAGGATCTTGCAGCGC<br>TGAGCGATATGAACTGTGGAAACGTGGCCAAGATCAGGCAGTTGTGGACCACACAGAGACTATGGTGTCT<br>ACCAGTCAGGAGCTCACCACCCGGCGGGTGACCAAAGCACCAAGAAAACTTGGGGCTTGAAGCGTCTCC<br>GGCTTCGCCAGGTCTCACGATCTCTTCTGCCTATAGCCACGGTAAGTAACGTTCCTTGCAACATGCAGGT<br>GTGCCACATCCAGGCAACCATCAGATGTGAAAGGTGATGATGTCCAGAAGTCTGACTCAGCCAGAGCC<br>TCACCACATCCTCTGAGTCTGCCTTCTTCGGTCACATGTCAACTAGAAGATGTAGTCTTGGTCGTCGTC<br>CTTGTGAACTAGGAGCTCAGGAGTCCTCCAATGGAGCTCCAGTCAAGAGGCAACTTCCAGCAGGCAGAGA<br>TGACACAAGCCCCAGTCCAGAGCTTCAGCCCCAGGCTGTGAGTGGAGACTTAATAGTCGACTCAGGACTT<br>GTGAACCCTGGCCCACAGCATCTTATGACAGCTTCTGAAGGGGATTGACCTCCGACCCCTAA |
| rat | Kdm4d | SEQ ID NO: 3 | ATGAAGACTAAGTCCACCTGTGCTCAGAATCCAAATTGCAGCATAATGATATTTCGTCCA<br>ACCAAAGAAGAGTTTAACGACTTTGACAAATACATCGCCTACATGGAGTCCCAAGGGGCA<br>CACAGAGCTGGACTGGCCAAGGTCATCCCGCCAAAAGAATGGAGGGCCAGGCAGTCTTAT<br>GACAATATCAGTAACATCTTAATAGCAACTCCCTGCAGCAAGTAGTCTCCGGGCAGGCA<br>GGTGTGTTCACTCAATACCATAAGAAGAAGAAAGCCATGACAGTTGGGCAGTACCGGCAC<br>CTGGCCAACAGTAAAAAATACCAAACCCCACCACACCTGGATTTTGAAGATTTGGAGAGA<br>AAATACTGGAAGAATCGCCTATATGAGTCACCAATTTATGGTGCTGACGTCAGTGGCTCC<br>CTGTTTGATGGGAAGACTCAACAGTGGAATGTGGGCACCTGGGAACAATTCAAGACCTA<br>TTGGAACAGGAATGCGGCATAGTGATTGAGGGCGTCAACACGCCCTACCTGTACTTTGGC<br>ATGTGGAAGACCTCCTTTGCGTGGCACACGGAGGACATGGACCTGTACAGTATCAACTAC<br>CTGCACTTTGGACAGCCCAAGACCTGGTATGCTGTACCCCCTGAGCATGGCAGGCGCCTG<br>GAGCTCCTAGCCAAGGAACTCTTCCCAGGCAGCTCCCAGGGCTGCCAGGCCTTCCTGAGG<br>CACAAGGTGGCGCTCATCTCACCCACTGTGCTCAAGGAGAATGGCATCCCCTTTGGTCGA<br>ATCACCCAGGAGGCTGGGGAGTTCATGGTCACCTTTCCCTATGGCTACCACGGGGCTTC<br>AACCATGGCTTCAACTGTGCAGAAGCCATCAATTTCGCCACGCCGAGGTGGATTGACTAT<br>GGCAAGGTGGCATCTCAGTGCAGCTGTGGGGAGGCCAGGGTGAGCTTCTCCATGGATGCC<br>TTTGTGAGGATCCTGCAGCCTGAGCGATATGAGATGTGGAAACGAGGTCAAGATCAGGCA<br>GTTGTGGACCACACAGAGGCTATGGGCCTACCAGTCAGGAGCTCACCACCTGGCGGGTG<br>ATCCAGGCACCAAGAAAACTTGGGGCCTGAAGCATCTCCGGCTTCGCCAGGTTTCACGC<br>TGTCTTCGCCTGTAGCCACTGACAGTAACATTGCCAACAACACCCAGATGTGCCACACC<br>TCCAGGCAAGCAGCAGATTCGAAAGGTGATGAGGTCCAGGAGTCTGACCCAGCCATAGCC<br>CCACCATATCCTCTGGGTCTATCTTCTCCTGGCCACATGTCAACTGGAAAACGTGGTCTT<br>GGTCGTCGCCCTTGTGAACTAGGAGTTCAGGAGTCCACCAATGGAGCTCCAGTCAAGAGG<br>CGACTTCCAGAAGGCAGAGATGACAGAAGTCCAGCCCAGAGCTTCAGTCCCAGTCCGTG<br>ACTGGAGACTTAATAGTCAACTCAGACCTTGTAAATCCTGGGCCACAGCATCCTGTGACA<br>GCTTCTGAAGGGGATTGACCTCTGACCCCTAA |
| rabbit | Kdm4d | SEQ ID NO: 4 | ATGAAGTCTAAGGCCCATCGTGCTCAGAATCCAAATTGCAGCATAATGGTATTTCATCCA<br>ACCAAAGAAGAGTTTAGTGATTTTGATAACTATATTGCTTACATGGAATCTCAGGGTGCA<br>CACCGGGGAGGCCTGGCCAAGGTCATCCCACCCAAGGAGTGGAGGGCCAGACAGACCTAT<br>GATGACATCGATGACATCTTAATAACTCGCCCCCTCCAGCAGGTGGCCTATGGCGGGGCA<br>GGTGTCTTTACTCAATTCCATAAAAAGAGGAGAGCCATGACCCTGAGACAGTATCGCAG<br>CTGGCCACCAGCACAAAATACCAGACCCAGCGCACCTGACTTTGAAGAGTTGGAGCAA<br>AAATACTGGAAAAACCGTCTCTACGATGCCCCAATCTATGGTGCTGATATCAGCGGCTCT<br>CTGTTTGATGAAAACACGGCACACTGGAACCTCAGGCGCCTGGGCACCATTCAGGACCTG<br>TTGGAGCAGGAATGTGGTGTCGTCATCGAGGGCGTCAACACGCCCTACCTGTACTTTGGC<br>ATGTGGAAGACCACGTTCGCCTGGCACACGGAGGACATGGACCTGTACAGCATCAACTAC<br>CTGCACTTCGGGGAGCCCAAGACGTGGTACGCGGTGCCCCGGAGCACGGGCGGCGCCTG<br>GAGCGCCTGGCCGGGCAGCTGTTCCCGGGCAGTTCCCGCAGCTGCCAGGCCTTCCTGCGG<br>CACAAGGTGGCCCTCATCTCGCCCAGCGTCCTGCGGCAGAACGGCATCCCCTTCCGCCGC |

| species | gene | SEQ ID NO: | CDS sequence (coding sequence) |
|---|---|---|---|
| | | | ATCACTCAGCAGGCTGGCGAGTTCATGGTGACCTTTCCTTACGGCTACCACGCGGGGTTC<br>AACCCACGGCTTCAACTGCGCCGAAGCCATCAATTTCGCCACCCCGCGCTGGATCGAGTAT<br>GGCAAAGTGGCCTCCCAGTGCAGCTGCGGGAGGCCAGGGTCACCTTTTCCATGGATGCC<br>TTCGTTCGTATCCTGCAACCCGAGCGCTACGAACTGTGGAAGTGCGGCCAAGACCGGAAG<br>GCCGTGGACCACACGGAGCCTACGGCACGCACCAGCCCAGAGCTGACCAGGTGGAAGCAG<br>GATCGCAGGCTCTGGAGGGCAGCCGAGGCTTGGCCCCCAAACTCGCTAGGTCCCTGGCT<br>GCAGGTGATGGTACTAGCTGCAAGGCTCCCAAGCGCCTACGGGCTGCCAGGGAATCTACA<br>GCACAGCCAGGGGGCGTTGCCCACAGTTCCCGGAAACCTCACGCAGCCCCGCGGACTTCC<br>CTGGGTCCCTGTGCCCCAGAGGTCCTCTCAACTGTCACACGTGGCTGTCGGCGTCGCTCT<br>AGGGAACTGGGGGTGCAGGAGCCAAGCCTCCAATCTCCAGCAAAGAGGCGCCTCTCAGTC<br>AGAACAGGGCGCACAGCTGCGCGCTCCAAGCCTCAGTCCTCACCTGAGCGTGGTATCTTG<br>ATGGTCAATCCTGCACCAAGCCTGGGGCCGCAGCTCCCCGCTTAG |
| pig | Kdm4d | SEQ ID NO: 5 | ATGACGTCCAGGCCCTGTGGGGTCCAGAACCCAGGCTGTGCCATTATGACCTTCTACCCA<br>ACCCTGGAAGAATTTGAAGACTTCAGCCAATATATCGCTTACATGGAATCGCAAGGGGCA<br>CACCACGCTGGCCTGGCCAAGGTAATTCCCCCCAAAGGATGGAAAGCCAGACAGACTTAT<br>GAGGATATCAGTGACATCGTAATAGCTGCCCCTCTCCAGCAGGTAGCCTTTGGGGAGGCA<br>GGTGTGTTTACTCAGTACCACAGAAAGAAGAGAGCCATGACTGTGAGCCAGTATCACCAC<br>CTCGCACATACTGTAAAATATCAAGCTCCACCACACTTGGATTTTGAGGACCTGGAGCAA<br>ACATACTGGAAAACGCGCCTGTACGGTTCCCCCATCTACGGCGCGGATGTCAGTGGCTCG<br>TTGTTCGATGAGAACACGAAGCAGTGGAACCTGGGCCACCTGGGCACCATCCAGGACCTG<br>CTGGAGCAGGAGTGCGGAGTGGCCATCGACGGCGTCAACAGCCCGTACCTGTACTTCGGC<br>ATGTGGAAGACCGGCTTCGCCTGGCACACGGAGGACATGGACCTTTACAGCCTCAACTTC<br>CTGCACTTCGGGGAGCCCAAGACTGGTACGCGGTGCCCCCTGCGCATGGCCGGCGCCTG<br>GAACGCCTGGCCAGGGAGCTGTTCCCTGGCCCCGCGCGGGGCTGCGAGGCCTTCCTGAGA<br>CACAAGGTGGCGCTCATCTCGCCCACGGTCCTCAAGGCCCAGGGCATCCCCTTTGGCCGC<br>GTCACGCAGGAGGCGGGCGAGTTCATGGTGACGTTTCCCTATGGCTACCACTCGGGCTTC<br>AACCACGGCTTCAACTGCGCCGAAGCCATCAATTTCGCCACCCCGCGCTGGGTCGATTAT<br>GGCAAAGTGGCGTCGCAGTGCAGCTGCGGGGAGGCGCGGGTGGTGTTCTCCATGGACGCG<br>TTCGTGCGCATCCTGCAACCCGAGCGCTATGAGCTGTGGAAACGGGGCCAGGATCGGGTG<br>GCGCTGGAACACACGGAGCACCTGTCCTCGCCTGGCAGCCTGGAGTTGAGTGCCTGGAGG<br>GAGGTCCGCGAGCCTGCGGGGCTGAACTTGGCCTGGGGCACAGCCCACCCCACACTGCC<br>CGGGGTCGGCTCTGGGTGGCAGGCCGTGGGATCGCCGCCGAAACTCTGTGTGTTCGGTG<br>TCTCGGTGCCCCTCGCCTACCTGGGGTTCTTCCTCCGCTGCCCAGTTCCAGGTTGCAACT<br>CTCTGCAGCTCCCATGAGCCAGGACCCACCCCGCGCTGTCACCAGGCTCCTCTGCTCTG<br>GGTCTCCAATCAACTGGCAGACGTGGTCCTGTTCGATGTCGTAGGTCTCGACCCCATCGT<br>CGTCCTCGGGTACAGGAGACTTTGGAGCCAACAGTCCAGGCTCCAGCTAAGAGGCTCCTC<br>TCAGTAGGTACAGTGGGCACAGCTGCAGACTTGGAAGCTCATGTCCTTTTGGCCAAGGAA<br>CCCTTGATAGACAGCCCTGCC |
| cattle | Kdm4d | SEQ ID NO: 6 | ATGGAAGCTATGAAGCCCAGTTGTGCTCAGAACCCAAGTTGTAGCATAATGATATTTCAT<br>CCAACCAAAGAAGAGTTTACTGATTTTGATAAATACATTGCTTACATAGAATCGCAAGGG<br>GCCCACCGAGCAGGCTTGGCTAAGATAGTTCCACCCAAGGAATGGAAAGCCAGACAGACC<br>TACGACGATATCAATGACATCTTAATAACCGCTCCGCTCCAGCAGGTGGTCTCTGGGCGG<br>GCAGGTGTGTTTACTCAATACCACAAAAAGAAGAAAGCCATGACCGTGGCAGAGTACCGC<br>CACTTAGCAAATACTGAAAAATACCAGACTCCATTCTACTCCGATTTTGAGGAATTGGAG<br>CGAAAATATTGGAAAACCCGCCTCTTTGAGTCCCCAATATACGGCGCGGACATCAGTGGC<br>TCTTTATTTGATGAAAACACGAAGCAGTGGAACCTGGGACGCCTGGGGACCATCCAGGAC<br>CTGCTGGAGCAGGAGTGCGGGGTGGTCATCGAGGCGTCAACACCCCCTACCTGTACTTC<br>GGCATGTGGAAGACCGCCTTCGCCTGGCACACGGAGGACATGGACCTTTATAGCATCAAC<br>TTCCTGCACTTCGGGGAGCCCAAGACCTGGTACGCGGTGCCGCCCGAGCACGGCCGGCGC<br>CTGGAACGCCTGGCCGGCGCGCTCTTCCCGGGCAGCTCGCGGAGCTGCGAGGCCTTCCTG<br>CGCCACAAGGCGGCGCTCATCTCGCCCACGGTGCTCCGGGACAACGGCATCCCCTTCGGT<br>CGGGTCACGCAGGAGGCGGGCGAGTTCATGGTGACCTTCCCCTACGGCTACCACTCGGGC<br>TTCAACCACGGCTTCAACTGCGCCGAGGCCATCAATTTCGCCACCCCGCGCTGGATCGAT<br>TATGGCAAAGTGGCCTCGCAGTGCAGCTGCGGCGAGGCGCAGGTGGCCTTCTCCATGGAC<br>GCCTTCGTGCGCATCCTGCAGCCCGAGCGCTATGAGCTGTGGAAGCGCGGGCAGGACCGG<br>GCGGTGGTGAACCACGCCGAGCCCGCGGCGCCGGGCGGCCAGGAGCTGAGAGCCTGGAAG<br>GAGGTGCAGACGCTGGGCCCCAAGTACTTCCCGCCTCGCCGCTCCGCCCGCCTGCGTCAG<br>CCCGTGTCCTCAAGCGAGGGCACTGACCCCAGAGCCCCTGTGCGGGCCGTGTCCCTGCGA<br>CCCTTGCCTGCCCGGGGTTCCTGCTCGGCTTCCCAGTTTGACGCTGTCGCCGGCAGCAGC<br>TCACGGAAGCCCAGCCAGACCCCTCCGCTGTTGCCAGGTCCGTCGGTGGCGTCGTGCCTC<br>CACCCAGTTGGCAGATGTGGTTCTCGTCGTCGCCCTCAGGAAAAAGGCACTCAAGAGCTG<br>ACTGCCCCATCGGAGCTAAGAGGGCCTTGCCTTAGACCGCAAGGCTCAGGACCCCAAG<br>GCTCAACCCCTGTCTGCAGAGGGACGGATGGACAATCCTGCCCAACGAGCCCTGGACTC<br>TAG |
| macaque | Kdm4d | SEQ ID NO: 7 | ATGGAAACTATGAAGTCTAAGGCCAACTATGGCCAGAATCCAAATTGTAACATAATGATA<br>TTTCATCCAACCAAAGAAGAGTTTAATGATTTTGATAAATATATTGCTTACATGGAATCC<br>CAAGGTGCACACAGAGCTGGCTTGGCTAAGATAGTTCCACCCAAAGAATGGAAAGCCAGA<br>GAGACCTATGATAACATCAGTGAAATCTTAATAGCCACTCCCCTCCAACAGGTGGCCTCT<br>GGGCGGGCAGGGGTGTTTACTCAATACCATAAAAAAAGAAAGCCATGACCGTGGGGGAG<br>TATCGCCACTTGGCAAACAGTAAAAAATATCAAACTCCACCACACCAGAATTTCGAAGAT<br>TTGGAGCGAAAATACTGGAAGAACCGCATCTATAATTCACCAATTTATGGTGCTGACATC<br>AGTGGCTCCTTGTTTGATGAAAACACTAAACAGTGGAATCTTGGGCACCTGGGAACAATT<br>CAGGACCTGTTGGAAAAGGAATGTGGGGTTGTCATAGAAGGCGTTAACACACCCTACTTG |

| species | gene | SEQ ID NO: | CDS sequence (coding sequence) |
|---|---|---|---|
| | | | TACTTTGGCATGTGGAAGACCACATTTGCTTGGCACACGGAGGACATGGACCTTTACAGC<br>ATCAACTACCTGCACCTCGGGGAGCCCAAAACTTGGTATGTGGTGCCCCCAGAGCATGGC<br>CAGCGCCTGGAACGCCTGGCCAGGGAGCTCTTCCCAGGCAGTTCCCGGGGCTGTGGGGCC<br>TTCCTGCGGCACAAGGTGGCCCTCATCTCGCCTACAGTTCTCAAGGAAATGGGATCCCC<br>TTCAATCGCATAACTCAGGAGGCTGGAGAGTTCATGGTGACCTTTCCCTATGGCTACCAT<br>GCTGGCTTCAACCATGGTTTCAACTGTGCAGAGGCCATCAATTTTGCCACTCCACGATGG<br>ATTGATTATGGCAAAATGGCCTCCCAGTGTAGCTGTGGGGAGGCCAGGGTGACCTTTTCC<br>ATGGACGCCTTCGTGCGCATCCTGCAACCTGAGCGCTATGAGCTGTGAAACGTGGGCAA<br>GACCGGGCAGTTGTGGACCACATGGAGCCCAGGGTACCAGCCAGCCAAGAGCTGAGCACC<br>CAGAAGGAGGTCCAGTTGCCCAGGAGAGCAGCGCTGGGCCTGAGACAACTCCCTCCTCAC<br>TGGGCCCGGCATTCCCCTTGGCCTCTGGCTGCCCGCAGTGGGACGCGCTGCCACACCCTT<br>GTGTGCTCTTCACTCCCACGCCGATCTGCAGTTAGTGGCACTGCTACGCAGCCCCGGGCT<br>GCTGCCGTCCACAGCTCTAGGAAGCCCAGCTCAACTCCATCATCCACCCCTGGTCCATCT<br>GCACAGATTATCCACCCGTCAAATGGCAGAGTGGACGTGGTCGCCGTCCTCAGAAACTG<br>AGAGCTCAGGAGCTGACCCTCCAGACTCCAGCCAAGAGGCTCCTCTTAGCGGGCACAACA<br>TGCACAGTTTCAGGCCCAGAACCTGAGCCCCTACCTGAGGGTGGGGCTTTGATGGACAAG<br>CCTGTACCACTGAATCCAGGGCTCCAGCATCCTGTAAAGGCTTCTAGGTGCAGCTGGGCC<br>CCTGTGCCCTAA |
| chimpanzee | Kdm4d | SEQ ID NO: 8 | ATGGAAACTATGAAGTCTAAGGCCAACTGTGCCCAGAATCCAAATTGTAACATAATGATA<br>TTTCATCCAACCAAAGAAGAGTTTAATGATTTTGATAAATATATTGCTTACATGGAATCC<br>CAAGGTGCACACAGAGCTGGCTTGGCTAAGATAATTCCACCCAAAGAATGGAAAGCCAGA<br>GAGACCTATGATAATATCAGTGAAATCTTAATAGCCACTCCCCTCCAGCAGGTGGCCTCT<br>GGGCGGGCAGGGGTGTTTACTCAATACCATAAAAAAAAGAAAGCCATGACCGTGGGGGAG<br>TATCGCCATTTGGCAAACAGTAAAAAATATCAGACTCCACCACACCAGAATTTCGAAGAT<br>TTGGAGCGAAAATACTGGAAGAACCGCATCTATAATTCACCGATTTATGGTGCTGACATC<br>AGTGGCTCCTTGTTTGATGAAAAACACTAAACAATGGAATCTTGGGCACCTGGGAACAATT<br>CAGGACCTGCTGGAAAAGGAATGTGGGGTTGTCATAGAAGGCGTCAATACACCCTACTTG<br>TACTTTGGCATGTGGAAACCACGTTTGCTTGGCATACAGAGGACATGGACCTTTACAGC<br>ATCAACTACCTGCACCTTGGGGAGCCCAAAACTTGGTATGTGGTGCCCCCAGAACATGGC<br>CAGCGCCTGGAACGCCTGGCCAGGGAGCTCTTCCCAGGCAGTTCCCGGGGTTGTGGGGCC<br>TTCCTGCGGCACAAGGTGGCCCTCATCTCGCCTACAGTTCTCAAGGAAATGGGATTCCC<br>TTCAATCGCATAACTCAGGAGGCTGGAGAGTTCATGGTGACCTTTCCCTATGGCTACCAT<br>GCTGGCTTCAACCATGGTTTCAACTGCGCAGAGGCCATCAATTTTGCCACTCCACGATGG<br>ATTGATTATGGCAAAATGGCCTCCCAGTGTAGCTGTGGGGAGGCAAGGGTGACCTTTTCC<br>ATGGATGCCTTCGTGCGCATCCTGCAACCTGAACGCTATGACCTGTGGAAACGTGGGCAA<br>GACCGGGCAGTTGTGGACCACATGGAGCCCAGAGTACCAGCCAGCCAAGAGCTGAGCACC<br>CAGAAGGAAGTCCAGTTACCCAGGAGAGCAGCGCTGGGCCTGAGACAACTCCCTTCCCAC<br>TGGGCCCGGCATTCCCCTTGGCCTATGGCTGCCCGCAGTGGGACACGGTGCCACACCCTT<br>GTGTGCTCTTCACTCCCACGCCGATCTGCAGTTAGTGGCACTGCTACGCAGCCCCGGGCT<br>GCTGCTGTCCACAGCTCTAAGAAGCCCAGCTCAACTCCATCATCCACCCCTGGTCCATCT<br>GCACAGATTATCCACCCGTCAAATGTTAGACGTGGTCGTGGTCGCCCTCCTCAGAAACTG<br>AGAGCTCAGGAGCTGACCCTCCAGACTCCAGCCAAGAGGCCCCTCTTGGCGGGCACAACA<br>TGCACAGCTTCGGGTCCAGAACCTGAGCCCCTACCTGAGAATGGGGCTTTGATGGACAAG<br>CCTGTACCACTGAGCCCAGGGCTCCAGCAGCCTGTCAAGGCTTCTGGGTGCAGCTGGGCC<br>CCTGTGCCCTAA |
| human | SUV39H1 | SEQ ID NO: 9 | CGCGAGGCCGGCTAGGCCCGAATGTCGTTAGCCGTGGGGAAAGATGGCGGAAAATTTAAAAGGCTGCAGC<br>GTGTGTTGCAAGTCTTCTTGGAATCAGCTGCAGGACCTGTGCCGCCTGGCCAAGCTCTCCTGCCCTGCCC<br>TCGGTATCTCTAAGAGGAACCTCTATGACTTTGAAGTCGAGTACCTGTGCGATTACAAGAAGATCCGCGA<br>ACAGGAATATTACCTGGTGAAATGGCGTGGATATCCAGACTCAGAGAGCACCTGGGAGCCACGGCAGAAT<br>CTCAAGTGTGTGCGTATCCTCAAGCAGTTCCACAAGGACTTAGAAAGGGAGCTGCTCCGGCGGCACCACC<br>GGTCAAAGACCCCCGGCACCTGGACCCAAGCTTGGCCAACTACCTGGTGCAGAAGGCCAAGCAGAGGCG<br>GGCGCTCCGTCGCTGGGAGCAGGAGCTCAATGCCAAGCGCAGCCATCTGGACGCATCACTGTAGAGAAT<br>GAGGTGGACCTGGACGGGCCTCCGCGGGCCTTCGTGTACATCAATGAGTACCGTGTTGGTGAGGGCATCA<br>CCCTCAACCAGGTGGCTGTGGGCTGCGAGTGCCAAGACTGTCTGTGGGCACCCACTGGAGCTGCTGCCC<br>GGGGGCGTCACTGCACAAGTTTGCCTACAATGACCAGGGCCAGGTGCGGCTTCGAGCCGGGCTGCCCATC<br>TACGAGTGCAACTCCCGCTGCCGCTGCGGCTATGACTGCCCAAATCGTGTGGTACAGAAGGGTATCCGAT<br>ATGACCTCTGCATCTTCCGCACGGATGATGGGCGTGGCTGGGGCGTCCGCACCCTGGAGAAGATTCGCAA<br>GAACAGCTTCGTCATGGAGTACGTGGGAGAGATCATTACCTCAGAGGAGGCAGAGCGGCGGGGCCAGATC<br>TACGACCGTCAGGGCGCCACCTACCTCTTTGACCTGGACTACGTGGAGGACGTGTACACCGTGGATGCCG<br>CCTACTATGGCAACATCTCCCACTTTGTCAACCACAGTTGTGACCCCAACCTGCAGGTGTACAACGTCTT<br>CATAGACAACCTTGACGAGCGGCTGCCCCGCATCGCTTTCTTTGCCACAAGAACCATCCGGGCAGGCGAG<br>GAGCTCACCTTTGATTACAACATGCAAGTGGACCCCGTGGACATGGAGAGCACCCGCATGGACTCCAACT<br>TTGGCCTGGCTGGGCTCCCTGGCTCCCCTAAGAAGCGGGTCCGTATTGAATGCAAGTGTGGGACTGAGTC<br>CTGCCGCAAATACCTCTTCTAGCCCTTAGAAGTCTGAGGCCAGACTGACTGAGGGGGCCTGAAGCTACAT<br>GCACCTCCCCCACTGCTGCCCTCCTGTCGAGAATGACTGCCAGGGCCTCGCCTGCCTCCACCTGCCCCCA<br>CCTGCTCCTACCTGCTCTACGTTCAGGGCTGTGGCCGTGGTGAGGACCGACTCCAGGAGTCCCCTTTCCC<br>TGTCCCAGCCCCATCTGTGGGTTGCACTTACAAACCCCCACCCACCTTCAGAAATAGTTTTTCAACATCA<br>AGACTCTCTGTCGTTGGGATTCATGGCCTATTAAGGAGGTCCAAGGGGTGAGTCCCAACCAGCCCCAGA<br>ATATATTTGTTTTTGCACCTGCTTCTGCCTGGAGATTGAGGGGTCTGCTGCAGGCCTCCTCCCTGCTGCC<br>CCAAAGGTATGGGGAAGCAACCCCAGAGCAGGCAGACATCAGAGGCCAGAGTGCCTAGCCCGACATGAAG<br>CTGGTTCCCAACCACAGAAACTTTGTACTAGTGAAAGAAAGGGGGTCCCTGGGCTACGGGCTGAGGCTG<br>GTTTCTGCTCGTGCTTACAGTGCTGGGTAGTGTTGGCCCTAAGAGCTGTAGGGTCTCTTCTTCAGGGCTG<br>CATATCTGAGAAGTGGATGCCCACATGCCACTGGAAGGGAAGTGGGTGTCCATGGGCCACTGAGCAGTGA<br>GAGGAAGGCAGTGCAGAGCTGGCCAGCCCTGGAGGTAGGCTGGGACCAAGCTCTGCCTTCACAGTGCAGT |

| species | gene | SEQ ID NO: | CDS sequence (coding sequence) |
|---|---|---|---|
| | | | GAAGGTACCTAGGGCTCTTGGGAGCTCTGCGGTTGCTAGGGGCCCTGACCTGGGGTGTCATGACCGCTGA<br>CACCACTCAGAGCTGGAACCAAGATCTAGATAGTCCGTAGATAGCACTTAGGACAAGAATGTGCATTGAT<br>GGGGTGGTGATGAGGTGCCAGGCACTGGGTAGAGCACCTGGTCCACGTGGATTGTCTCAGGGAAGCCTTG<br>AAAACCACGGAGGTGGATGCCAGGAAAGGGCCCATGTGGCAGAAGGCAAAGTACAGGCCAAGAATTGGGG<br>GTGGGGGAGATGGCTTCCCCACTATGGGATGACGAGGCGAGAGGGAAGCCCTTGCTGCCTGCCATTCCCA<br>GACCCCAGCCCTTTGTGCTCACCCTGGTTCCACTGGTCTCAAAAGTCACCTGCCTACAAATGTACAAAAG<br>GCGAAGGTTCTGATGGCTGCCTTGCTCCTTGCTCCCCCACCCCCTGTGAGGACTTCTCTAGGAAGTCCTT<br>CCTGACTACCTGTGCCCAGAGTGCCCCTACATGAGACTGTATGCCCTGCTATCAGATGCCAGATCTATGT<br>GTCTGTCTGTGTGTCCATCCCGCCGACCCCCAGACTAACCTCCAGGCATGGACTGAATCTGGTTCTCCT<br>CTTGTACACCCCTCAACCCTATGCAGCCTGGAGTGGGCATCAATAAAATGAACTGTCGACTGAAAAAAAA<br>AAAAAAAAAAAAAA |
| human | SUV39H2 | SEQ ID NO: 10 | CGGGGCCGAGGCGCGAGGAGGTGAGGCTGGAGCGCGGCCCCCTCGCCTTCCCTGTTCCCAGGCAAGCTCC<br>CAAGGCCCGGGCGGCGGGGCCGTCCGCGGGCCAGCCAGATGGCGACGTGGCGGTTCCCCGCCGCCGCG<br>ACCCCAACTCCGGGACGCACGCTGCCGACGCCTATCCTCCCCCAGGCCGCTGACCCGCCTCCCTGCCCGG<br>CCGGCTCCCGCCGCGGAGGATATGGAATATTATCTTGTAAAATGGAAAGGATGGCCAGATTCTACAAATA<br>CTTGGGAACCTTTGCAAAATCTGAAGTGCCCGTTACTGCTTCAGCAATTCTCTAATGACAAGCATAATTA<br>TTTATCTCAGGTAAAGAAAGGCAAAGCAATAACTCCAAAAGACAATAACAAAACTTTGAAACCTGCCATT<br>GCTGAGTACATTGTGAAGAAGGCTAAACAAAGGATAGCTCTGCAGAGATGGCAAGATGAACTCAACAGAA<br>GAAAGAATCATAAAGGAATGATATTTGTTGAAAATACTGTTGATTTAGAGGGCCCACCTTCAGACTTCTA<br>TTACATTAACGAATACAAACCAGCTCCTGGAATCAGCTTAGTCAATGAAGCTACCTTTGGTTGTTCATGC<br>ACAGATTGCTTCTTTCAAAAATGTTGTCCTGCTGAAGCTGGAGTTCTTTTGGCTTATAATAAAACCAAC<br>AAATTAAAATCCCACCTGGTACTCCCATCTATGAATGCAACTCAAGGTGTCAGTGTGGTCCTGATTGTCC<br>AATAGGATTGTACAAAAAGGCACACAGTATTCGCTTTGCATCTTTCGAACTAGCAATGGACGTGGCTGG<br>GGTGTAAAGACCCTTGTGAAGATTAAAAGAATGAGTTTTGTCATGGAATATGTTGGAGAGGTAATCACAA<br>GTGAAGAAGCTGAAAGACGAGGACAGTTCTATGACAACAAGGGAATCACGTATCTCTTTGATCTGGACTA<br>TGAGTCTGATGAATTCACAGTGGATGCGGCTCGATACGGCAATGTGTCTCATTTTGTGAATCACAGCTGT<br>GACCCAAATCTTCAGGTGTTCAATGTTTTCATTGATAACCTCGATACTCGTCTTCCCCGAATAGCATTGT<br>TTTCCACAAGAACCATAAATGCTGGAGAAGAGCTGACTTTTGATTATCAAATGAAGGTTCTGGAGATAT<br>ATCTTCAGATTCTATTGACCACAGCCCAGCCAAAAGAGGGTCAGAACAGTATGTAAATGTGGAGCTGTG<br>ACTTGCAGAGGTTACCTCAACTGAACTTTTTCAGGAAATAGAGCTGATGATTATAATATTTTTTCCTAA<br>TGTTAACATTTTTAAAAATACATATTTGGGACTCTTATTATCAAGGTTCTACCTATGTTAATTTACAATT<br>CATGTTTCAAGCATTTGCCAAATGTATTACCGATGCCTCTGAAAAGGGGTCACTGGGTCTCATAGACT<br>GATATGAAGTCGACATATTTATAGTGCTTAGAGACCAAACTAATGGAAGGCAGACTATTTACAGCTTAGT<br>ATATGTGTACTTAAGTCTATGTGAACAGAGAAATGCCTCCCGTAGTGTTTGAAAGCGTTAAGCTGATAAT<br>GTAATTAACAACTGCTGAGAGATCAAAGATTCAACTTGCCATACACCTCAAATTCGGAGAAACAGTTAAT<br>TTGGGCAAATCTACAGTTCTGTTTTTGCTACTCTATTGTCATTCCTGTTTAATACTCACTGTACTTGTAT<br>TTGAGACAAATAGGTGATACTGAATTTTATACTGTTTTCTACTTTTCCATTAAAACATTGGCACCTCAAT<br>GATAAAGAAATTTAAGGTATAAAATTAAATGTAAAAATTAATTTCAGCTTCATTTCGTATTTCGAAGCAA<br>TCTAGACTGTTGTGATGAGTGTATGTCTGAACCTGTAATTCTTAAAAGACTTCTTAATCTTCTAGAAGAA<br>AAATCTCCGAAGAGCTCTCTCTAGAAGTCCAAAATGGCTAGCCATTATGCTTCTTTGAAAGGACATGATA<br>ATGGGACCAGGATGGTTTTTGGAGTACCAAGCAAGGGGAATGGAGCACTTTAAGGGCGCCTGTTAGTAA<br>CATGAATTGGAAATCTGTGTCGAGTACCTCTGATCTAAACGGTAAAACAAGCTGCCTGGAGAGCAGCTGT<br>ACCTAACAATACTGTAATGTACATTAACATTACAGCCTCTCAATTTCAGGCAGGTGTAACAGTTCCTTTC<br>CACCAGATTTAATATTTTTATACTTCCTGCAGGTTCTTCTTAAAAAGTAATTCTATATTTTTGAACTGATA<br>CTTGTTTTATACATAAATTTTTTTTAGATGTGATAAAGCTAAACTTGGCCAAAGTGTGTGCCTGAATTAT<br>TAGACCTTTTTATTAGTCAACCTACGAAGACTAAAATAGAATATATTAGTTTTCAAGGGAGTGGGAGGCT<br>TCCAACATGATTATTGAATCTCAGGAAAAACTATTCTTTCATGTCTGATTCTGAGATTTCTAATTGTGTTG<br>TGAAAATGATAAATGCAGCAAATCTAGCTTTCAGTATTCCTAATTTTTACCTAAGCTCATTGCTCCAGGC<br>TTTGATTACCTAAAATAAGCTTGGATAAAATTGAACCAACTTCAAGAATGCAGCACTTCTTAATCTTTAG<br>CTCTTTCTTGGGAGAAGCTAGACTTTATTCATTATATTGCTATGACAACTTCACTCTTTCATAATATATA<br>GGATAAATTGTTTACATGATTGGACCCTCAGATTCTGTTAACCAAAATTCTGAAAAATTGCTGGGCCAGGCCT<br>GTGTGGTGGCTCACACCTGTGATCCCAGCACTTTGGGAGGCTGAGGTAGGAGGATCACGTGGAGGTCGGGA<br>GTTCAAGACCAGCCTGGCCATCATGGTGAAACCCTGTCTCTACTGAAAATACAAAAATTAGCCGGGCGTG<br>GTGGCACACGCCTGTAGTCCCAGCTACTCAGGAGGCTGAGGCAGGAGAATCACTTGAATTCAGGAGGCGG<br>AGGTTGCAGTGAGCCAAGATCATACCACTGCACTGCAGCCTGAGTGACACAGTAAGACTGTCTCCAAAAA<br>AAAAAAAAAAAAA |
| mouse | Suv39h1 | SEQ ID NO: 11 | GTTGTTAGCTGTGGAGAAAGATGGCGGAAAATTTAAAAGGTTGCAGTGTGTGCTGTAAATCTTCTTGGAA<br>TCAACTGCAGGACCTGTGCCGACTAGCCAAGCTTTCTTGTCGTGCCCTTGGTGTTTCTAAGAAGAATCTG<br>TATGACTTTGAAGTTGAATACCTGTGTGATTATAAGAAGATCCGTGAGCAGGAGTATTACCTGGTTAAGT<br>GGCGTGGGTATCCCGACTCAGAAAACACCTGGGAGCCACGGCAGAATCTAAAATGTATACGAGTTCTTAA<br>GCAGTTCCACAAGGACTTAGAAAGAGAGCTTGTCCGACGACACCGCCGGTCAAAGCCACCCAGGCATCTG<br>GACCCAAACCTAGCCAATTACCTGGTGCAGAAGGCCAAGCAGAGGCGGGCACTTCAGCGTTGGGAACAAG<br>AGCTCAATGCCAAGCGCAGCCACCTGGGGCGGATCACCGTGGAGAATGAGGTAGCATGGATGGCCCTCC<br>AAGGTCCTTTGTCTATATCAATGAGTATCGAGTTGGTGAGGGCATCACCCTCAACCAGGTAGCTGTTGGC<br>TGTGAGTGCCAGGACTGTCTGTTGGCACCCACTGGAGGCTGTTGCCCTGGAGCATCCCTGACAAGTTTG<br>CCTACAATGACCAAGGCCAGGTGCGACTGAAAGCTGGGCAGCCCATCTACGAGTGCAACTCCCGCTGTTG<br>CTGTGGCTATGACTGCCCAAACCGTGTAGTCCAGAAAGGCATCCGCTACGATCTCTGCATCTTCCGCACT<br>AATGATGGCCGAGGCTGGGGTGTCCGCACGCTGGAAAAGATCCGCAAAAATAGCTTTGTTATGGAGTATG<br>TGGGAGAGATTATTACCTCAGAGGAGGCAGAGCGGAGGGGCCAGATCTACGACGCCAGGGCGCCACCTA<br>CCTCTTTGACCTGGACTACGTGGAAGACGTATATACCGTGGATGCCGCTTATTATGGCAACATCTCTCAT<br>TTTGTCAACCATAGTTGTGATCCCAACCTGCAGGTGTACAACGTATTCATAGACAACCTTGATGAGCGAC<br>TACCCCGCATCGCATTCTTTGCCACAAGAACCATCTGGGCGGCGAGGAGCTCACCTTTGATTACAACAT<br>GCAAGTGGACCCCGTGGACATGGAGAGTACCCGAATGGACTCCAACTTTGGCCTGGCTGGGCTCCCCGGC<br>TCCCCCAAGAAACGAGTCCGTATTGAATGCAAATGTGGGACAACGGCTTGCCGAAAATACCCTCTTCTAGC |

| species | gene | SEQ ID NO: | CDS sequence (coding sequence) |
|---|---|---|---|
| | | | CTTGAGAAGTCTGAGGCCAGACTAACTGAAGGGGCCTGAAGCCACCTTCCTCTCCTACAGCTACCCTCTT<br>GTCAAGGATGACCATCAATCAGAGCCTTGTCTGCCTCCACTTGTCCTCACCTACCCTAACCTGCTCTAGG<br>GTCAGGGCTGTTGTGAGGACTAACTCCGGGTACCCTTTTCCTGTTCCTTTCCCCCTGTTCCAGGCCCATC<br>AGGCATTGCACTTAAAACTCCCAGCCCCATTTTCAGAAACATATTTTTCACATCATGATTCCCCTAGAGT<br>TGGAATTCATGTCATATAATGGAGGTCCAGATTGAGGAACTCGGCTGTAAAACAGATTCTTTGTTTTGAC<br>AGCATCTCTGCAGCTCTATGTAGTAAGTCTGGTGTTTGGACCGTTAATCTTCCTGTCTCAGCCTTCCTCA<br>TGATGAGATTGTAGGTGTAAACCCAGCTAAGATTTTTGTTCTAATTGCATCTGCTTCTGCTTGGAGCTTG<br>TGTGTGAACCTGTTGCAGGTCCTCTTCATTACTCTAATGGTATGAGGAAGCAACCCCCTGGCAGACAGAC<br>TTCAGAGCTGAGATACCAGCCTAACATCAAGCTGGATCAGCAACCCCAGAGCCTTTGTACTCAGGAAAGA<br>AAAGGCAATCTTCAGAGCTGGGAGATAAGGCTGGTTCCGCTCTTTGTGCTTTTGATGCTGGCTGGTATTA<br>ACCTTAAGACCTATAGGGTCTCAACAGTTGCAAGTCTGAAAAGTAGTTGCCCAAATGCCATCAGAATGGG<br>GATGGAGTAAATACCTCTTTGAAAGCCCCACAGAAAGGTTAGAACTAAGTTTTACCATCAGGAAGTACAG<br>TGCTGGACTTGCTGGAAACCCAGCCTTGGCATTTGATGGCCACTAGAACTACTAGAAGCTGGAACCAAGA<br>TCTAGGTATTCTTTAGATAGCACTTAAGACAGTAATGTGCATCGACTAGAAGGCGATGTGATGCCAGGCA<br>CTTGGTAGAGCACCTGGTCCATACAGATTGTCTCAGGGAAGCCTTGAAAACCACAAAGGTGGAGCCCAGA<br>AAAAAGCCCATGTGACGAAGGCAATGTCTAGGCCAAAATACTTGTCAGCTCAAGTATTCACCTGGGTC<br>ACTTGTCTCAGTTAACTGCCTAGAAATGTACAAAAGGCAAAGATTCTGATGGCTGCCTTGCCCCCTGCTT<br>CCCCACCTCCAGGAAGCCTTTCCTGACTTCCTGTGCCCAGAGTGCCCTATGTGAAACTCTGTACCCTGCT<br>ACCAGATGCCAGGTCTGTGTGTGTATTTTGTATATATGTTTCCTGCCCATACTTCCCATACTTCCCAGGC<br>TGACCTTCAGGCATGGACTGAATCTGGTTCTCTGTACCCCTCAGCCCTCCCTAGCCTGGAGTGCACACCA<br>ATAAACTGTGTTGTTGAGTTA |
| mouse | Suv39h2 | SEQ ID NO: 12 | GAATGAAAGCTCCGCAAGATGGCGACGGCCAGGGCCAAGGCACGGGGCAGTGAGGCAGGAGCGCGGTGTC<br>ACCGGGCTCCAGGTCCGCCCCCGAGGGCCCAAGGCCAGGCGAACGGCGAGACGCCGCCGCGCGGAGACCCT<br>GACGGCGCGACGCTCGCGGCCGTCTGCGGGCGAGAGGCGCGCCGGCTCCCAGCGAGCGTGGTCCGGAGCT<br>CCGCGGGCCGCGGTCTTTGGCGACGAGTGTGCACGAGGTGCCTTATTCAAGGCCTGGTGTGTGCCTTGCC<br>TAGTTTCACTTGATACTCTCCAGGAATTATGTAGAAAAGAAAAGCTCACATGTAAATCGATTGGAATCAC<br>CAAAAGGAATCTAAACAATTATGAGGTGGAGTACTTGTGTGACTACAAGGTAGCAAAGGGTGTGGAATAT<br>TATCTTGTAAAATGGAAAGGATGGCCAGATTCTACAAACACCTGGGAGCCCTTGAGAAACCTCAGGTGTC<br>CACAGCTCCTGCGGCAGTTCTCTGATGACAAGAAGACTTACTTAGCTCAGGAAAGGAAATGCAAGGCTGT<br>CAATTCAAAATCCTTGCAACCTGCAATTGCTGAGTATATTGTACAGAAAGCTAAGCAAAGAATAGCTCTG<br>CAGAGATGGCAAGATTACCTCAACAGAAGAAAGAACCATAAGGGGATGATATTTGTTGAAAACACTGTTG<br>ACTTGGAGGGCCCACCTTTAGCTTCTACTACATTAACGAGTACAGGCCAGCTCCCGGGATCAGCATAAA<br>CAGTGAAGCCACCTTTGGATGTTCATGTACAGACTGCTTCTTTGCAAGTGTTGTCCTGCTGAAGCTGGA<br>GTTGTGTTGGCTTATAATAAGAAGCAACAAATTAAAATCCAACCAGGCACTCCCATCTACGAATGCAACT<br>CAAGGTGTCGATGTGGACCTGAATGTCCCAATAGGATTGTACAAAAAGGCACACAATATTCACTGTGCAT<br>CTTTTAAAACTAGCAATGGCTGTGGTTGGGGTGTAAAAACCCTTGTGAAGATTAAAAGAATGAGTTTTGTC<br>ATGGAATATGTTGGAGAGGTGATCACAAGTGAAGAGGCCGAGAGACGGGGACAGTTCTATGACAACAAAG<br>GGATCACCTACCTCTTTGACCTGGACTACAGTCTGATGAGTTCACAGTGGATGCAGCTCGATATGGAAA<br>CGTATCCCATTTTGTGAATCATAGTTGTGACCCAAATCTTCAGGTGTTTAGTGTTTTCATCGATAACCTT<br>GATACTCGGCTGCCCAGGATAGCATTGTTCTCTACAAGAACCATAAACGCTGGAGAAGAGTCGACTTTTG<br>ACTATCAAATGAAAGGTTCTGGAGAAGCATCTTCGACTCCATTGACCACAGCCCTGCCAAAAAAGGGT<br>CAGAACCCAATGTAAATGTGGAGCCGAGACTTGCAGAGGTTACCTCAACTGA |
| rat | Suv39h1 | SEQ ID NO: 13 | GTCGTTAGCTGTGGAGAAAGATGGCGGAAAATTTAAAAGGTTGCAGTGTGTGCTGTAAATCTTCCTGGAA<br>TCAGCTGCAGGATCTGTGCCGACTAGCCAAGCTTTCTTGTCCTGCCCTTGGTGTTTCTAAGAAGAATCTG<br>TATGACTTTGAAGTTGAATACCTGTGTGATTATAAGAAGATCCGTGAGCAGGAGTATTACCTGGTTAAAT<br>GGCGTGGGTATCCTGACTCAGAGAACCATCTGGGAGCCACGGCAGAATCTCAAATGTGTGCGCATTCTTAA<br>GCAGTTCCACAAGGACTTAGAAAGAGAGCTTGCCGGCGACACCGCCGGTCAAAGCCACCCAGGCATCTG<br>GACCCAAACTTAGCCAATTACCTGGTGCAGAAGGCCAAGCAGAGGCGGGCACTGCAGCGTGGGAACAAG<br>AGCTCAATGCCAAGCGCAGCCATCTGGGCGGATCACTGTGGAGAATGAGGTAGACCTGGATGGCCCTCC<br>AAGGTCCTTTGTCTATATCAATGAGTATCGAGTTGGTGAGGGCATCACCCTCAACCAGGTAGCTGTTGGC<br>TGTGAGTGCCAGGACTGTCTGTTGGCACCCACTGGAGGCTGTTGCCCTGGAGCATCCCTGCACAAGTTTG<br>CCTACAATGACCAAGGCCAGGTGCGACTGAAAGCTGGGCAGCCCATCTACGAGTGCAACTCTCGCTGTTG<br>CTGTGGCTATGACTGCCCAAACCGTGTAGTCCAGAAAGGCATCCGCTACAACCTCTGCATCTTCCGCACT<br>GATGATGGCCGAGGCTGGGGTGTCCGCACGCTGGAAAAGATCCGCAAAAATAGCTTTGTTATGGAGTATG<br>TGGGAGAGATTATTACCTCAGAGGAGGCAGAGCGGAGGGGCCAGATCTACGACCGCCAGGGCGCCACCTA<br>CCTCTTTGACCTGGACTACGTGGAGGACGTATATACCGTGGATGCCGCTATTATGGCAACATCTCTCAC<br>TTTGTCAACCATAGTTGTGATCCCAACCTGCAGGTGTACAACGTATTCATAGACAACCTTGATGAGCGAC<br>TACCCCGCATCGCATTCTTTGCCACAAGAACCATCTGGGCGGGCAGGAGCTCACCTTTGATTACAACAT<br>GCAAGTGGACCCCGTGCAACATGGAGAGTACCCGAATGGACTCCAACTTTGGCCTGGCAGGGCTCCCGGC<br>TCCCCCAAGAAACGGGTCCGTATTGAATGCAAATGTGGGCAACAGCTTGCCGAAAATACCTCTTCTAGC<br>CCTGAGAAGTCTGAGGCCAGACTAACTGAAGGGGCCTGAAGCCACCTTCCTCTTCTACTGCTACCCTC<br>TTGTCAAGAATGACCATCAATCAGAGCCTTGTCTGCCTCCACTTGTCCTCACCTGCCCCAACCTGCTCCA<br>GGGTCAGGGCTGTTGTGAGGACTAACTCCGGGTACCCTTTTCCCTGTTCCTTTCCCCTATCCAGGCCCATC<br>AGGCATTGCACTTAAAACTCCCAGCCCCATTTTCAGAAGCATATTTTTCACATCAGGATTCCCTAGATTT<br>GGAATTCATGTCAATGGAGGTCCAAAGACTGAAAAGACTGAGCAACTCAGCCCCAAAGCAGATTTTTTTC<br>TCTGCAGCTCTATGTAGTTAGTTCAGGCTGGCGTTGGACCTTTAATCCTCCTGTCTCAGCTTTCCTCATG<br>ATGAAATTATAGGTGTAAACCCAGCTAATTGTATCTGCTAATTTTCTAATTGTATCTGCTTCAGCTCTGA<br>GCCCGAGTGACCTGTTGCAGGCCTCTTCACTGCTCTATGAGGAAGCAACCCCTAGGCAGACAGACATCAG<br>AGCTGAGATACCAGCCCAACATCAAACTGGATCAGCAACCACGGGGCCTTTGTACTCATGAAAGAAAAGG<br>CAATCTCCAGAAAGGCTGATTCTGCTCATTGTGCTTTTAATGCTGGCTAATACTAACCTTAAGACGCATA<br>GGGTTGCAAAGAGAGTTGCAGGTCTGAAAAGTAGTTGCCCAAATCCCATCAGAATGGGAATGAAGTAAAT<br>ACCTCTTTGAAAGCCCCTCAGAAGGGTTAGAACTAAGTTTTACCATCAGGAAGTAGAGTGCTGGGCTTAC<br>TGGAAACCCAGCCATGGCATTTGATGGCCACTAGAATTAGAAGCTGGAACCAAGATCTAGGTATTCTGTA<br>GAAAGCACTTAAAAGACAATAACGTGCATCGATTAGAAGGTGATGTGATGCCAGGCACTTGGTAGAGCA |

| species | gene | SEQ ID NO: | CDS sequence (coding sequence) |
|---|---|---|---|
| | | | CCTGGTCCATATGGATTGTCTCAGGGAAGCCTTGAAAACCACAGAGGTGGAGCCCAGGAAAAAGCCCATG<br>TGACAGAAGGCAATGTCTAGGCCTAAAATACTTGTCAGCTCCAAGTATTCACCTGGGTCCACTTGTCTCA<br>AAGTTAACTGCCTAGAGTTGTACAAAAGGCAAAGATTCTGATGGCTGCCTTGTCCCCTGCTTCCCCACCT<br>CCAGGAAGCTTTTCCTGAGTTCCTATACCCAGAGTACCCCTTTGTGAAACTCTGTACCCTGCTACCAGAT<br>GCCAGGTCTGTGTGTGTATTTTGTATATATGTGTCCTGCCCACACTCCCCAGGCTGACCTTCAGGCATGG<br>ACTGAATCTGGTTTTCTGTGTACCCTCCTCAGCCCTCTCTAGCCTGGAGTGCACACCAATAAACTTTGTT<br>GTTGAATTAATAAGCTGGAGAAAAAAAAAAAAAAAAAAAAAAAAAAAAAAAA |
| rat | Suv39h2 | SEQ ID NO: 14 | TGAATGAAAGCTCCGCAAGATGGCGGCGGCCAGGGCCAAGGCACGGAGCGGTGAGGCCAGAGCGCGGTGT<br>CACCGGGCTCCAGGTCCGCCCCAGAGGCCCAAACCCAGGCGAACGACGAGACGCTGCCGCGCGGACACCG<br>TGACGGCGCGACGCTCGCGGTCGTCTGCGGGCGGGAGACGCGCCGGCTCCAACCGAGCGAGGTCCAGAGC<br>TCCGCGGGCCGCGGTCTTTGGCGGCGAGTGTGCACGAGGTGCCTCATTCAAGGCCTGGTGTGTGCCTTGC<br>CTAGTTTCACTTGATACTCTCCAGGAATTATGTAGAAAAGAAAAGCTCACATGTAAATCGATTGGAATCA<br>CCAAAAGGAATCTAAACAATTATGAGGTGGAGTACTTGTGTGACTACAAGGTAGTAAAGGGTGTGGAATA<br>TTATCTTGTAAAGTGGAAAGGATGGCCAGACTCTACAAACACCTGGGAGCCCTTGTGGAACCTCAGGTGC<br>CCACAGCTCCTGCAGCAGTTCTCTGACGACAAGAATACTTACTTATCCCAGGGAAGGAAACGAAGGCCA<br>TCACTTCAAAAGACAATAACAAATCCTTGCAACCTGCAGTTGCTGAGTATATTGTACAGAAAGCTAGGCA<br>AAGAATAGCTCTGCAGAGATGGCAAGATTACCTCAACAGAAGAAAGAACCACAAAGGGATGATATTTGTT<br>GAAAATACTGTTGACTTAGAGGGCCCACCTTCAGACTTCTACTACATCAATGAATACAGGCCAGCTCCTG<br>GGATCACCTTAAACAGTGAAGCTACCTTTGGGTGTTCGTGTACAAACTGCTTCTTTGAAAAGTGTTGTCC<br>TGCTGAAGCTGGAGTTGTTTTGGCTTATAATAAGAACCGACAAATTAAAATCCAACCAGGCACTCCCATC<br>TATGAATGCAACTCAAGGTGCCGATGTGGACCTGATTGTCCCAATAGGATTGTACAGAAAGGCACACAGT<br>ATTCCCTGTGCATCTTTAGAACTAGCAATGGCTGTGGCTGGGGTGTAAAAACCCTTGTGAAGATTAAAAG<br>GATGAGTTTTGTCATGGAATATGTTGGAGAGGTGATCACCAGTGAAGAGGCTGAGAGACGGGGACAGCTC<br>TATGACAACAAAGGGATCACCTACCTTTTTGATCTGGACTATGAGTCTGATGAGTTCACAGTGGATGCAG<br>CTCGATATGGAAATGTGTCTCATTTTGTGAATCATAGTTGTGACCCAAATCTTCAGGTGTTTAGTGTTTT<br>CATCGATAACCTTGATACTCGGCTTCCCAGGATAGCATTGTTCTCCACAAGAACCATAAAGGCTGGAGAA<br>GAGCTGACTTTTGACTATCAAATGAAAGGTTCTGGAGAACTGTCTTCAGACTCTATTGACTACAGCCCTG<br>CCAGAAAAAGGGTCAGAACCCAATGCAAATGTGGAGCTGAGACGTGCAGAGGTTACCTCAACTGAAATTT<br>CAGGAAGTGGAGCTCACGTTGTTTGTTTTTTGTTTGTTTGTCTTCTAACAACTGAAAAAAGTATTTGG<br>GACTCCTTTCTATTACCTATGTATTGTATTATATGATGTTAATGTACAATTCATGGCTCAAGATATATGC<br>CAAGTATATTACTATTGATTCTAAAAAGGACTGCAAGGCCATGTAAACAAGATGGTGGTTACATGGGAAG<br>TGAACTGTATAAATCACTTGCTTACTCGAGAGTCGAAGTAGACAGTCGTCCCTTTAGTTTTGGAAGTGAG<br>TCGACCACAGCTATTATTGAGCCTTTTATCCTGCCTCAAACAGAGAACTCACTTTAGGCAAATGTATAAA<br>TTTTATTTTTTTTACTATATTGTTTCTGTTTAATACTCACTGATCTTGTATCAGAGACAAATAAGTGACAC<br>TGAATTTTTTACTGTATTTTCTACTTTTACATTAAAACATTGGCATCTTAATGATATATTTCAGGTGTA<br>AAAAATGTGAAAGATTTACTTTTAGCTTGATCTTACTTTGAGGCAATAGATACCATTACAAAGGTATCTA<br>AACCTGAAATTCTTAAAAGATGTTTTTACTCCCACAGAAGAAAAGTCTCTGATCACCTTCTCGGAATTCT<br>GTAGTGCTGGCCACTGTGTTTCTGTGAACAGACAGACAGACAGAACAGTGACTGAGGACGCACTGGAGTG<br>TCAGGCAGGAAAGGAGTACAGCGTAAGCCACTCAGCATGTGTGAGCACGACAGCACCGTGTCTCTCTC<br>TCTCCGGAACAGGAGAGTGAGATCCCTGAGGGGCACAGGTCCCAATGGCAGTGTAATTCACATCACATA<br>CTGTCATCTCAAGGCAGTTTTAATTCCTACCCACTAAATTTCAATACTTTTGTATTTTGTGCATGCCCTT<br>GAAAAGCAAGCTCTATTTGCCCTGATGCTTGTTTTATACAAGAGTTTTTAGATAGGATGAAACTTAGCTT<br>GGCCAAAGTCGGCCTGATTGAACTTTTACACCTCTGGGGTTAGATGGGGCTTCCCCTGTGTAGTAAAA<br>CCCAATAAAGAAAAAAACTTTCATTTTTCTGGGTCTGGGAGTTCTAATCGTGGTGTCCAATGTGAAGACA<br>GAAACAAAATGCAGCAAATAAACAAAGCTTTTGGTATCCTAAGAGTTTCCTAAGCTCACTGCTCCAGGCT<br>TGAATAACTGTAATAAGCTTAAGTAAAATGAACTGAATTCAAGAACTCAGTACTTCCTTTAACTTTCTAA<br>CTCTTAACCTCTGTTTTGAGAGAAGCTACAATGTTATTCAGAATATTGCCTTCGGGGGCTACTTGTTCACAG<br>TCATGCCTGCTACCCAAAACTTTCAGAATGTGTCAAGAAAAAATATAATTTTAAATGGTATTTCTTTTGT<br>TTTTCTTTGAGAATCTTAAAAGCATCACAGGTCTGTTTTTCTCACACATACCTCCACCCCACTGCAACC<br>CTCCATGACCAAGCTCACTTTGAATTATTCTCAGGTTAAAAAATTAAAAAAAAAATGTTTGTCTAGATAT<br>TTGGTCTTATTTACTGTTTAGGTTAAAAGGAAACTTAGGAGGGCAAGAAGAAAATGACTTGTGTTTAGTA<br>AACGTGTGGCTTTGTTTTGTCTTACTAATAGAAATTTAATGGCCCTAAGGTTCTGTGGGAGTGGGTGGGC<br>CTTCAGACAGTATCTTGTAGCTCAGGTTGGCCTTGAATTTGCTGTGTACCTGAGTGCTTTCTTGAACTCT<br>TCAGTCCTCCTGCCTCTCCCTCCCAGTGCTGGGGTTGTGGGCCTGTGCCACCATGCCCTTTGACCTTTAA<br>ACGCACACCAATTTCACTCGTGTTCCACACATGACTGCATTACTCTCTCTCAGCATTCCCCCATTACTG<br>TCCTCCAGTTCCTCTTCTGCTTTCACCTCATGAGAGCTGTCCATACAGCGGTGTGTGTATTTCCTTGTTG<br>CTGTGATCAAAGCGATCAATTCAGCTCTGCCTTGATTCCTCAAATCACATGTTCTAAGTATGTCGTGTCT<br>TCATGACATACTCAGCTCTGGGAGGTGATCATGACAGGAACTTTCCAGCAGAGGCTAGAACTGTGGAGCA<br>CAGCTCACTGGCTGGCTCCCTGGCTCCCAGGCTCCCCTCAGCTAGGCGTTCCTACACAGCCCACCCGCCC<br>AGGAATGGTGTAATGGTACCTAATAAGCGAGACCCTGCCACATCAGTTAGCCATCAAGCAAATCCGGGCC<br>AATGGGACAGAGACAGTTCCTCAGAGGAGGTTGTTTCCCCAGGTAACCCCAGACTGTCAAGTATAAGGTA<br>CATGCAACCATTTTGCATTTGACTGACATCTCTTAAAGGCTGGCCCGCCCTTAGGATTCTGGGATGTATT<br>GTGACATTCCTAGACGTTTTTAACCTTTGCTAATCTGTAACTCTTGAATGAAGTAGCCACTATAGTTAGT<br>CCTGCCTGTTTTCCTGCTGTCTGTATGGAGCTTTCCCTCACACAGCCTAGATAACTCTGAAGCCCTGCTGC<br>TTGCACCTGGATCTGGCTGTGAGCTTACTAGCTGTGTGAACTAACCTGTGTGCCTTCCTGCCTACCTCA<br>AAGTGCGCTTTCACAGACTAAAGCTTTATGAAGTGTGTGTGTTTTTAAATCACAGAATAAACACATAT<br>GT |
| cattle | Suv39h1 | SEQ ID NO: 15 | GGAATGTCGTTAGCCGTGGGGAAAGATGGCGGAAAGTTTAAAAGGCTGCAGTGTGTGTTGCAAATCTTCT<br>TGGAATCAGCTACAGGACCTGTGCCGCCTGGCCAAGCTCTCCTGCCCTGCCCTTGGCATCTCCAAGAGGA<br>ACCTCTATGACTTTGAAGTCGAGTACCTGTGCGATTACAAAAAGATCCGCGAACAGGAGTATTACCTGGT<br>AAAAATGGCCGTGGGTACCCAGACTCCGAGAGCACTTGGGAACCACGGCAGAATCTCAAGTGTGCGCATT<br>CTCAAGCAGTTCCACAAGGACTTGGAAAGGGAGCTGCTCCGGCGGCACCACCGGTCAAAGCCACCCCGGC<br>ACCTGGACCCAAGCCTGCCAACTACCTGGTGCAGAAAGCCAAGCAGAGGCGGGCACTCCGGCGCTGGGA<br>GCAGGAGCTCAATGCCAAGCGCAGCCACCTGGGACGCATCACCGTGGAGAACGAAGTGGACCTGGATGGC |

| species | gene | SEQ ID NO: | CDS sequence (coding sequence) |
|---|---|---|---|
| | | | CCCCCACGGGCCTTCGTGTACATCAACGAGTACCGTGTTGGTGAGGGCATCACCCTCAACCAGGTGGCTG<br>TGGGCTGCGAGTGCCAGGACTGTCTGTGGGCACCGGCCGGAGGCTGCTGCCCTGGGGCGTCACTGCACAA<br>GTTTGCCTACAATGACCAGGGCCAGGTGCGCCTGCGAGCCGGGCTGCCCATCTATGAGTGCAACTCCGC<br>TGCCGCTGTGGCTATGACTGCCCCAACCGCGTGGTACAGAAGGGCATCCGCTACGACCTCTGCATCTTCC<br>GCACGGATGATGGACGCGGCTGGGGTGTCCGCACGCTGGAGAAGATCCGCAAGAACAGTTTCGTCATGGA<br>GTACGTGGGCGAGATCATTCCTCAGAGGAGGCAGAGCGGCGGGGCCAGATCTATGACCGCCAGGGTGCC<br>ACCTACCTCTTCGACCTGGACTACGTGGAGGATGTGTACACTGTGGACGCCGCCTATTACGGCAACATCT<br>CTCACTTTGTCAACCACAGTTGTGACCCCAACCTCCAGGTGTACAACGTCTTCATAGACAACCTTGATGA<br>GCGGCTGCCCCGCATTGCTTTCTTTGCCACCAGAACCATCCGGGCAGGCGAGGAGCTCACCTTTGATTAC<br>AACATGCAAGTGGACCCGGTGGACATGGAGAGCACACGCATGGACTCCAACTTTGGCCTGGCTGGGCTCC<br>CCGGCTCTCCCAAGAAGCGGGTCCGCATTGAATGCAAGTGTGGGACTGAATCCTGCCGCAAATACCTCTT<br>CTAGCCCCGTGAAGTCTGAGGCCAGACTGACCAAGGGAGGCTAAAAAGCTGCCCACCCCACCTACCCACT<br>GCTGCCCTCCTGTTGAAGAACAACTGCCAGGGCCTCCTGCCTGCCTCCGCCTGCCCCCTGCTCAGGGCTG<br>CATGGCCATGGGGAAGATGGACTCCAGGAGTCCCCTCTCCCTGTCCCAGCCCCATCCATGGGTTGCACTT<br>ACAAACCCCTGCCCACCTTCAGAAGTGATTTTTCAACACCAGGACTTTCTGCAGTTGGGATTCATGCCT<br>AGCAAGGCGGTCTGAGGGCTGAGCCTCAGCCCATACCCAAAGTAGAAACGTTTGTTTTTGCACCTGCTTC<br>TGGCCAGAGCTTGAAGGGTCTGCTGCAGGCCCTCTCCCTGCTGCCCCAAGGGTGTGAGGAAGCATTCCA<br>GGACAGGCTGACCCCAGAGCCCAGGATTCCCAGTCCATTCACCTCCCCTGCCACAGAAATGTGCTAGTGA<br>AGTGGGGGGGGGGCGGTCTTCAAGGGCTGCAGGCTGTGGCTGGGTCCTGCTCATGCTTGCATGCTGCT<br>GGTGTTGGCCTGACAGCTGTAGGGTCTCCTTTTCAAAGCTGTGCCTCTGAGAAGCAGACACCCACATGCC<br>ACTAGAGGAGAGTGGATGCCCACAGCCTGTTGGCCAGTGAGAGGCAGCCCAGACTTTGCCTGTCCTTAAG<br>GTGGGCAACCCACTCCAGTATTCTTGCCTGAAAAATCCCATGGACAGAGGAACCTGGTAGGCTACAGTCC<br>ATGGGGTCACAAAGAGTTGGACATGACTAAGCGACTTCACTTCACTAAGGTGGGCTGGGACTCAGCTCTG<br>CCTTTGCAACAGCTAGAAGGTGCCCAGGGCTCTTGAGCTCAAAGGATGCTGGGAGCCCTTAACCTGCAGC<br>GTGAGGACTGCTGATAGCACCCAGAGCTGGGCCCAAGACCTAGCTAGGCTGTAGACAGCACTTAGACAAA<br>ATGTGCATGGATGGGATACTGAGGAGGTGCCAGGCACTGGGCTGAGCACCTGGTCCACGTGGATCGTCTC<br>AGGGAAGCCTTGAAAACTATGGAGGTGGATCCCAGGAAAGGGCCCGTGTGGCAGAAGGCAAAGCACAGAC<br>CAAGAATGGGTGGGGCTGGCTTACCCACCAGGGTGTGGCGAGGTGAGGGGAAGCCCCTGTCGCCTCCTA<br>GCCCTCCAGCCCTTTGCACTCACCTTGGGTCCTCTGGTCTCAGTTCCCTGCCCACAAATGTATAAAAGGT<br>GAAGGCGCTGATGGCTGCCTCATCCCTTGCTTCCCCTGTGAGGTCTTCTCTAGGAAGCCTTCCATCCCTG<br>ACTACCTGTGCGCAGTGTCCCCACGTGAGACTGTGTGCCCTGCCAGCAGATGCCAGATCTGTGTGTCTGT<br>TTTTGTGTGTCTGTGCTCCCCACCCCCAGACTGACCTTCAGGCTTGTACTGAATCTGATTCTCCTCTTGT<br>ATATCCCCTTGGCCCTCCCAGTCTGGGAATGGGCGTCAATAAAACAGGTTATTGACTGAAAAAAAAAAAA<br>AAAAAAAAAAAAAAAAAAAAAAAAAAAAAAAAAAAAAAAAAAAAAAAAAAAAAAAAAAAAAAAAAAAAAAAA<br>AGAAAAAAAAAAAAAAAA |
| cattle | Suv39h2 | SEQ ID NO: 16 | GAGTTTGAATGAAAGCTTCCTCAAGATGGCGGCGGCCGGGGCCGAGGCGCCAGGAGCTTGGTGTGTGCCTT<br>GCCTAGTTTCACTTGATACTCTTCAGGAATTATGTAGAAAAGAAAAGCTCACATGTAAATCGATTGGAAT<br>CACCAAAAGGAATCTAAACAATTATGAGGTGGAATACTTGTGTGACTACAAGGTAGTAAAGGATATGGAA<br>TATTATCTTGTAAAATGGAAAGGATGGCCAGATTCTACAAATACTTTGGGAACCTTTGCAAAATCTCAAGT<br>GCCCATTACTACTTCAGCAGTTCTTTAATGACAAGCATAATTATTTATCTCAGGTAAAGAAAGGCAAAGC<br>AATAACTCTAAAAGAAAATCACAGAGCCTTGAAACCTGCTGTTGCTGAATACATTGTAAAGAAGGCTAAA<br>CAAAGGATAGCCCTGCAGAGATGGCAGGATGAACTCAACAGAAGGAAGACTCACAAAGGAATGATTTTTG<br>TTGAAAATACTGTGGACTTAGAGGGGCCCCCTTCAGCATTCTACATTAATGAATACAAACCAGCTCC<br>TGGAATCAGCTTAGTAAATGAAGCTACCTTTGGTTGTTCATGCACAGATTGCTTCTTTGAAAAATGTTGT<br>CCTGCTGAAGCTGGAGTTCTTTTGGCTTATAATAAAAATCAACAAATTAAAATCCCACCTGGTACCCCCA<br>TTTATGAGTGCAACTCAAGATGTCAATGTGGACCCGACTGTCCCAACAGGATCGTACAAAAAGGCACACA<br>GTATTCACTTTGCATCTTTCGAACTAGCAATGGCTGTGGCTGGGTGTAAAAACCCTTGTGAAGATTAAA<br>AGAATGAGTTTTGTCATGGAATATGTTGGAGAGGTGATCACCAGTGAGGAAGCTGAGACGTGGCCAGT<br>TATATGACAACAAAGGAATCACGTATCTCTTTGATCTGGACTATGAATCTGATGAATTCACAGTGGATGC<br>AGCTCGATATGGAAATGTGTCTCATTTTGTGAATCACAGTTGTGACCCAAACCTTCAGGTGTTCAATGTT<br>TTCATTGATAACCTCGATACCCGTCTTCCCCGATAGCATTATTTTCCACGAGAACTATCAATGCTGGAG<br>AAGAGCTCACTTTTGATTATCAAATGAAAGGTTCTGGAGATGTATCTTCAGATTCTATTGACCACAGCCC<br>AGCCAAAAGAGGGCCAGAACTGTGTGCAAATGTGGAGCTGTGACTTGCAGAGGTTACCTCAACTGAATT<br>TTCAGGAAATAGAACTTATGACGATTATAGTGTTTTTTCTAATGTTAACATTTTAAAAGTATTTTGGACT<br>CTTTTCATATTATCAAGATTATACACTACGTTGATTTACAAATTTACCTTTCAGACTATTGACCAAATGCG<br>TTACTGATCCTTTTGAAGAGAGGAACGTGGGGGTCACATAGACTAATTCTACATATACATATTCAGTGGT<br>TAGATACCAAACATGAAGGAAACTGTTTGCAAATCAACAACTATATACTTAACAGGAAGTCTATGTGAA<br>ATATAGAGAAATGCCTCCTTCAGTGTTTAAGTGTTAAACTGATGATGTAACAGTTGCTAAGATTGAACAT<br>TCAATTTGCCATATACCTTGAATTTAGAATTGGACAAATACACAAGTTCTATTTTTGTTATTGTCATTCC<br>TGTTTACCTACTTAACAACTCTTTGTACTTGTATTTGAGACAAATAGGTGATACTGAATTATACTCTATT<br>TTCTACTTTCATTAAAACATTGGTATCTTAAAAAAAAAAAAAAAAAAAAAAAAAAAAAAAAAAAAAAAAAAA<br>AAAAAAAAAAAAAAAAAAAAAAAAGAAAAAAAAAAAAAAAAAA |
| human | SETDB1 (cDNA) | SEQ ID NO: 45 | 1 ggcactaaag gtttgcttcc gggcgtttct tttgcttccc cttccctctt tcacgcttcc<br>61 tcccctcccc ctcctccctt atcccttcgc tttcgctctt ttccgtcgag gccgacccct<br>121 gagttgtgag tctgggtgtct ggttggtgaa aaagagccct tgaagctgga agacgggaga<br>181 ggacaaaagc atgtcttccc ttcctgggtg cattggtttg gatgcagcaa cagctacagt<br>241 ggagtctgaa gagattgcag agctgcaaca ggcagtggtt gaggaactgg gtatctctat<br>301 ggaggaactt cggcatttca tcgatgagga actggagaag atggattgtg tacagcaacg<br>361 caagaagcag ctagcagagt tagaacagtg ggtaatacag aaagaatctg aggtggctca<br>421 cgttgaccaa ctctctttgatg atgcatccag ggcagtgact aattgtgagt ctttggtgaa<br>481 ggacttctac tccaagctgg gactacaata ccgggacagt agctctgagg acgaatcttc<br>541 ccggcctaca gaaataattg agattcctga tgaagatgat gatgtcctca gtattgattc<br>601 aggtgatgct gggagcagaa ctccaaaaga ccagaagctc cgtgaagcta tggctgcctt<br>661 aagaaagtca gctcaagatg ttcagaagtt catggatgct gtcaacaaga agagcagttc |

| species | gene | SEQ ID NO: | CDS sequence (coding sequence) |
|---------|------|------------|-------------------------------|
| | | | 721 ccaggatctg cataaaggaa ccttgagtca gatgtctgga gaactaagca aagatggtga |
| | | | 781 cctgatagtc agcatgcgaa ttctgggcaa gaagagaact aagacttggc acaaaggcac |
| | | | 841 ccttattgcc atccagacag ttgggccagg gaagaaatac aaggtgaaat ttgacaacaa |
| | | | 901 aggaaagagt ctactgtcgg ggaaccatat tgcctatgat taccaccctc ctgctgacaa |
| | | | 961 gctgtatgtg ggcagtcggg tggtcgccaa atacaaagat gggaatcagg tctggctcta |
| | | | 1021 tgctggcatt gtagctgaga caccaaacgt caaaaacaag ctcaggtttc tcattttctt |
| | | | 1081 tgatgatggc tatgcttcct atgtcacaca gtcggaactg tatcccattt gccggccact |
| | | | 1141 gaaaaagact tgggaggaca tagaagacat ctcctgccgt gacttcatag aggagtatgt |
| | | | 1201 cactgcctac cccaaccgcc ccatggtact gctcaagagt ggccagctta tcaagactga |
| | | | 1261 gtgggaaggc acgtggtgga agtcccgagt tgaggaggtg gatggcagcc tagtcaggat |
| | | | 1321 cctcttcctg gatgacaaaa gatgtgagtg gatctatcga ggctctacac ggctggagcc |
| | | | 1381 catgttcagc atgaaaacat cctcagcctc tgcactggag aagaagcaag gacagctcag |
| | | | 1441 gacacgtcca aatatgggtg ctgtgaggca caaggccct gttgtccagt acacacagga |
| | | | 1501 tctgaccggt actggaaccc agttcaagcc agtggaaccc ccacagccta cagctccacc |
| | | | 1561 tgccccacct ttcccacctg ctccacctct atccccccaa gcaggtgaca gtgacttgga |
| | | | 1621 aagccagctt gcccagtcac ggaagcaggt agccaaaaag agcacgtcct ttcgaccagg |
| | | | 1681 atctgtgggc tctggtcatt cctcccctac atctcctgca ctcagtgaaa atgtctctgg |
| | | | 1741 tgggaaacct gggatcaacc agacatatag atcacctta ggctccacag cctctgcccc |
| | | | 1801 agcaccctca gcactcccgg ccctccagc accccagtc ttccatggca tgctggagcg |
| | | | 1861 ggcccagca gagccctcct accgtgctcc catggagaag cttttctact tacctcatgt |
| | | | 1921 ctgcagctat acctgtctgt ctcgagtcag acctatgagg aatgagcagt accggggcaa |
| | | | 1981 gaaccctctg ctggtccgt tactatatga cttccggcgg atgacagccc ggcgtcgagt |
| | | | 2041 taaccgcaag atgggctttc atgttatcta taagacacct tgtggtctct gccttcggac |
| | | | 2101 aatgcaggag atagaacgct accttttcga gactggctgt gacttcctct tcctggagat |
| | | | 2161 gttctgtttg gatccatatg ttcttgtgga ccgaaagttt cagcccctata agcttttta |
| | | | 2221 ctatatttg gacatcactt atgggaagga agatgttccc ctatcctgtg tcaatgagat |
| | | | 2281 tgacacaacc cctccacccc aggtggccta cagcaaggaa cgtatcccgg gcaagggtgt |
| | | | 2341 tttcattaac acaggccctg aatttctggt tggctgtgac tgcaaggatg ggtgtcggga |
| | | | 2401 caagtccaag tgtgcctgcc atcaactaac tatccaggct acagcctgta ccccaggagg |
| | | | 2461 ccaaatcaac cctaactctg ctaccagta caagagacta aagagtgtc tacccacagg |
| | | | 2521 ggtatatgag tgtaacaaac gctgcaaata tgacccaaac atgtgcacaa accggttggt |
| | | | 2581 gcaacatgga ctacaagttc ggctacagct attcaagaca cagaacaagg gctggggtat |
| | | | 2641 ccgctgcttg gatgacattg ccaaggctc ttttgtttgt atttatgcag gcaaaatcct |
| | | | 2701 gacagatgac tttgcagaca aggagggtct ggaaatgggt gatgagtact ttgcaaatct |
| | | | 2761 ggaccatatc gagagcgtgg agaacttcaa agaaggatat gagagtgatg cccctgttc |
| | | | 2821 ctctgacagc agtggtgtag acttgaagga ccaggaagat ggcaacagcg gtacagagga |
| | | | 2881 ccctgaagag tccaatgatg atagctcaga tgataacttc tgtaaggatg aggacttcag |
| | | | 2941 caccagttca gtgtggcgga gctatgctac ccggaggcag accccgggcc agaaagagaa |
| | | | 3001 cggactctct gagacaactt ccaaggactc ccacccccca gatcttggac ccccacatat |
| | | | 3061 tcctgttcct ccctcaatcc ctgtaggtcg ctgcaatcca ccttcctccg aagagacact |
| | | | 3121 caagaacaag gtggcctcat ggttgagctg caatagtgtc agtgaaggtg gttttgctga |
| | | | 3181 ctctgatagc cattcatcct tcaagactaa tgaaggtggg gagggccggg ctggggaaag |
| | | | 3241 ccgaatggag gctgagaagg cctccacctc aggactaggc atcaaggatg agggagacat |
| | | | 3301 caaacaggcc aagaaaggg acactgacga ccgaaacaat atgtcagtag ttactgaaag |
| | | | 3361 ctctcgaaat tacgttaca atccttctcc tgtgaagcct gaaggacttc gccgcccacc |
| | | | 3421 tagtaagact agtatgcatc aaagccgaag actcatggct tctgctcagt ccaaccctga |
| | | | 3481 tgatgtcctg acactgtcca gcagcacaga aagtgagggg gaaagtggga ccagccgaaa |
| | | | 3541 gcccactgct ggtcagactt cggctacgge ggttgacagt gatgatatcc agaccatatc |
| | | | 3601 ctctggctct gaaggggatg actttgagga caagaagaac atgactggtc caatgaagcg |
| | | | 3661 tcaagtggca gtaaaatcaa cccgaggctt tgctcttaaa tcaaccccatg ggattgcaat |
| | | | 3721 taaatcaacc aacatggcct ctgtggacaa gggggagagc gcacctgttc gtaagaacac |
| | | | 3781 acgccaattc tatgatgcg aggagtcttg ctacatcatt gatgccaagc ttgaaggcaa |
| | | | 3841 cctgggccgc tacctcaacc acagttgcag ccccaacctg tttgtccaga atgtcttcgt |
| | | | 3901 ggatacccat gatcttcgct tcccctgggt ggccttcttt gccagcaaaa gaatccgggc |
| | | | 3961 tgggacagaa cttacttggg actacaacta cgaggtggc agtgtggaag gcaaggagct |
| | | | 4021 actctgttgc tgtgggggcca ttgaatgcag aggacgtctt ctttagagga cagccttctt |
| | | | 4081 cccaacccctt cttgaactgt cgttttcctca ggaactgggt cttcctgatt gttgaaccct |
| | | | 4141 gacccgaagt ctctgggcta gctactcccc ccagctccta gttgataaa atggggttc |
| | | | 4201 tggaccagat gatcccttcc aatgtggtgc tagcaggcag gatccttct ccacctccaa |
| | | | 4261 aggccctaaa gggtggggag agatcaccac tctaacctcg gcctgacatc cctcccatcc |
| | | | 4321 catatttgtc caagtgttcc tgcttctaac agactttgtt cttagaatgg agcctgtgta |
| | | | 4381 tctactatct ccagtttgta ttatttcttg aaagtctttt aacaatatga taaaactaag |
| | | | 4441 attgtgaaa |
| human | euchromatic histone-lysine N-methyl transferase1 (EHMT1) (cDNA) | SEQ ID NO: 46 | 1 gcgcgggagg ggcggggcca cgctgcgggc ccgggccatg gccgccgccg atgccgaggc |
| | | | 61 agttccggcg aggggggagc ctcagcagga ttgctgtgtg aaaaccgagc tgctgggaga |
| | | | 121 agagacacct atggctgccg atgaaggctc agcagagaaa caggcaggag aggcccacat |
| | | | 181 ggctgcggac ggtgagacca atgggtcttg tgaaaacagc gatgccagca gtcatgcaaa |
| | | | 241 tgctgcaaag cacactcagg acagcgcaag ggtcaacccc caggatggca ccaacacact |
| | | | 301 aactcggata gcggaaaatg gggtttcaga aagagactcg gaagcggcga agcaaaacca |
| | | | 361 cgtcactgcc gacgactttg tgcagacttc tgtcatcggc agcaacggat acatcttaaa |
| | | | 421 taagccggcc ctacaggcac agccccttgag gactaccagc actctggcct cttcgctgcc |
| | | | 481 tggccatgct gcaaaaaccc ttcctgagg ggctggcaaa ggcaggactc caagcgcttt |
| | | | 541 tccccagacg ccagccgccc caccagccac ccttggggag gggagtgctg acacagagga |
| | | | 601 caggaagctc ccggcccctg gcgccgacgt caaggtccac agggcacgca agaccatgcc |
| | | | 661 gaagtccgtc gtgggcctgc atgcagccag taaagatccc agagaagttc gagaagctag |

| species | gene | SEQ ID NO: | CDS sequence (coding sequence) |
|---|---|---|---|
| | | 721 | agatcataag gaaccaaaag aggagatcaa caaaaacatt tctgactttg gacgacagca |
| | | 781 | gcttttaccc cccttcccat cccttcatca gtcgctacct cagaaccagt gctacatggc |
| | | 841 | caccacaaaa tcacagacag cttgcttgcc ttttgtttta gcagctgcag tatctcggaa |
| | | 901 | gaaaaaacga agaatgggaa cctatagcct ggttcctaag aaaaagacca aagtattaaa |
| | | 961 | acagaggacg gtgattgaga tgtttaagag cataactcat tccactgtgg gttccaaggg |
| | | 1021 | ggagaaggac ctgggcgcca gcagcctgca cgtgaatggg gagagcctgg agatggactc |
| | | 1081 | ggatgaggac gactcagagg agctcgagga ggacgacggc catggtgcag agcaggcggc |
| | | 1141 | cgcgttcccc acagaggaca gcaggacttc caaggagagc atgtcggagg ctgatcgcgc |
| | | 1201 | ccagaaagatg gacggggagt ccgaggagga gcaggagtcc gtggacaccg gggaggagga |
| | | 1261 | ggaaggcggt gacgagtctg acctgagttc ggaatccagc attaagaaga aatttctcaa |
| | | 1321 | gaggaaggaa aagaccgaca gtccctggat caagccagcc aggaaaagga ggcggagaag |
| | | 1381 | tagaaagaag cccagcggtg ccctcggttc tgagtcgtat aagtcatctg caggaagcgc |
| | | 1441 | tgagcagacg gcaccaggag acagcacagg gtacatggaa gtttctctgg actccctgga |
| | | 1501 | tctccgagtc aaaggaattc tgtcttcaca agcagaaggg ttggccaacg gtccagatgt |
| | | 1561 | gctggagaca gacggcctcc aggaagtgcc tctctgcagc tgccggatgg aaacaccgaa |
| | | 1621 | gagtcgagag atcaccacac tggccaacaa ccagtgcatg gctacagaga gcgtggacca |
| | | 1681 | tgaattgggc cggtgcacaa acagcgtggt caagtatgag ctgatgcgcc cctccaacaa |
| | | 1741 | ggccccgctc ctcgtgctgt gtgaagacca ccggggccgc atggtgaagc accagtgctg |
| | | 1801 | tcctggctgt ggctacttct gcacagcggg taattttatg gagtgtcagc ccgagagcag |
| | | 1861 | catctctcac cgtttccaca aagactgtgc ctctcgagtc aataacgcca gctattgtcc |
| | | 1921 | ccactgtggg gaggagagct ccaaggccaa agaggtgacg atagctaaag cagacaccac |
| | | 1981 | ctcgaccgtg acaccagtcc ccggcaggaa gaagggctcg gccctggagg cagggccga |
| | | 2041 | caccacaacg ggcagtgctg ccgggccacc actctcggag gacgacaagc tgcagggtgc |
| | | 2101 | agcctccac gtgcccgagg gctttgatcc aacgggacct gctgggcttg ggaggccaac |
| | | 2161 | tcccggcctt tcccaggac cagggaagga aaccttggag agcgctctca tcgccctcga |
| | | 2221 | ctcggaaaaa cccaagaagc ttcgcttcca cccaaagcag ctgtacttct ccgccaggca |
| | | 2281 | aggggagctt cagaaggtgc tcctcatgct ggtggacgga attgaccccca actttcaaaat |
| | | 2341 | ggagcaccag aataagcgct ctccactgca cgccgcggca gaggctggac acgtggacat |
| | | 2401 | ctgccacatg ctggttcagg cgggcgctaa tattgacacc tgctcagaag accagaggac |
| | | 2461 | cccgttgatg gaagcagccg aaaacaacca tctggaagca gtgaagtacc tcatcaaggc |
| | | 2521 | tggggccctg gtggatccca aggacgcaga gggctctacg tgtttgcacc tggctgccaa |
| | | 2581 | gaaaggccac tacgaagtgg tccagtacct gcttttcaaat ggacagatgg acgtcaactg |
| | | 2641 | tcaggatgac ggaggctgga cacccatgat ctgggccaca gagtacaagc acgtggacct |
| | | 2701 | cgtgaagctg ctgctgtcca agggctctga catcaacatc cgagacaacg aggagaacat |
| | | 2761 | ttgcctgcac tgggcggcgt tctccggctg cgtggacata gccgagatcc tgctggctgc |
| | | 2821 | caagtgcgac ctccacgccg tgaacatcca cggagactcg ccactgcaca ttgccgcccg |
| | | 2881 | ggagaaccgc tacgactgtg tcgtcctctt tctttctcgg gattcagatg tcaccttaaa |
| | | 2941 | gaacaaggaa ggagagacgc ccctgcagtg tgcgagcctc aactctcagg tgtggagcgc |
| | | 3001 | tctgcagatg agcaaggctc tgcaggactc ggccccccgac aggcccagcc ccgtggagag |
| | | 3061 | gatagtgagc agggacatcg ctcgaggcta cgagcgcatc cccatcccct gtgtcaacgc |
| | | 3121 | cgtggacagc gagccatgcc ccagcaacta caagtacgtc tctcagaact gcgtgacgtc |
| | | 3181 | ccccatgaac atcgacagaa atatcactca tctgcagtac tgcgtgtgca tcgacgactg |
| | | 3241 | ctcctccagc aactgcatgt gcggccagct cagcatgcgc tgctggtacg acaaggatgg |
| | | 3301 | ccggctcctg ccagagttca acatgcgga gcctcccttg atcttcgaat gcaaccacgc |
| | | 3361 | gtgctcctgc tggaggaact gccgaaatcg cgtcgtacag aatggtctca gggcaaggct |
| | | 3421 | gcagctctac cggacgcggg acatgggctg gggcgtgcgg tccctgcagg acatcccacc |
| | | 3481 | aggcaccttt gtctgcgagt atgttgggga gctgatttca gactcagaag ccgacgttcg |
| | | 3541 | agaggaagat tcttacctct ttgatctcga caataagagc ggggaggttt actgcatcga |
| | | 3601 | cgcgcggttc tacgggaacg tcagccggtt catcaaccac cactgcgagc caacctggt |
| | | 3661 | gcccgtgcgc gtgttcatgg cccaccagga cctgcggttc ccccggatcg ccttcttcag |
| | | 3721 | caccccgctg atcgaggccg gcgagcagct cgggtttgac tatgagagc gcttctggga |
| | | 3781 | catcaaaggc aagctcttca gctgccgctg cggctcccccc aagtgccggc actcgagcgc |
| | | 3841 | ggccctggcc cagcgtcagg ccagcgcggc caggaggacg cagggaggtt gcttgcccga |
| | | 3901 | caccagctcc gcggctgccg ccgaccccct atgagacgcc gccgccagc ggggcgctcg |
| | | 3961 | ggagcagggg accgccgcgt cgccgattag aggacgagga ggagagattc cgcacgcaac |
| | | 4021 | cgaaagggtc cttcggggct gcgccgccgg cttcctggag gggtcggagg tgaggctgca |
| | | 4081 | gcccctgcgg gcgggtgtgg atgcctccca gccaccttcc cagacctgcg gcctcaccgc |
| | | 4141 | gggccagtg cccaggctgg agcgcacact ttggtccgcg cgccagagac gctgggagtc |
| | | 4201 | cgcactggca tcaccttctg agtttctgat gctgatttgt cgttgcgaag tttctcgttt |
| | | 4261 | cttcctctga cctccgaggt ccccgctgca ccacgggtt gctctgttct cctgtccggc |
| | | 4321 | ccagactctt ctgtgtgcg ccgccgaagc caccgttagc gcgagctgct ccgttcgccc |
| | | 4381 | tgcccacggc ctgcgtggct ggggccgagt cccaggggcc gcacggaggg cacagtctcc |
| | | 4441 | tgtcaggctc ggagaggtca ggagaccgac cccaccacta actttggaga aaatgtgggt |
| | | 4501 | ttgcttttta aaggaatcct atatctagtc ctatatatca aacctctaac tgacgtttct |
| | | 4561 | tttcgaggaa gtggcttggt gggtgcagcc ccgccggtt ccgttgacgc tggcaccttc |
| | | 4621 | tgttgatttt ttaagccaca tgctatgatg aataaactga tttatttct accattactg |
| | | 4681 | aacattagga caaacacaaa ataaaaaaca aaacacagac aacggtgctg attctggtgt |
| | | 4741 | ggtttctact caccacgtga aataaactat caactgtata aagagaacaa agtgattta |
| | | 4801 | gaataaaaatg caggaaaaac tttttaaaag atgttagtct ttagcgctga ataaatttgc |
| | | 4861 | catcaccttt tgtgtggtgg cctggcaggt catatacttt ttttggcat atacctttt |
| | | 4921 | aaagactgta attagtgcag taacagtggg gttttttttg tgcaactctt ctaaaaacat |
| | | 4981 | tcataatgca gtcatgttta ttttttcttg ttaaaatgtt tttgacagtt ttaagagcag |
| | | 5041 | tcttttggct ctgaccattt cttgttctgt ttccaatgaa atcaataaaa aaaaagaagt |
| | | 5101 | acttttaaaaa aaaaaaaaaa aaa |

| species | gene | SEQ ID NO: | CDS sequence (coding sequence) |
|---|---|---|---|
| human | PR domain containing 2, with ZNF domain (PRDM2), (cDNA) | SEQ ID NO: 47 | 1 gtaaaagtga cattctaaat gttcctcact ctgcgaggct tattttttag ggactttgct<br>61 ataattctga aagacttagt tttacagtac atctgaaagt aggagttttc agaagtatgg<br>121 ctcttgggat aaatttagat tcttaattgt gaagctctgt taccacttgt tagaaggcag<br>181 gtcagctcac ctgcttgggg aggtaaaatat atgaatgcac tctcgagtaa tttaatggag<br>241 ccctacctca atgtacagaa tgacagtatc acagatcaag aatggagtac gagtgatttt<br>301 cggctatggt gggggtaggt aggtcacttg tcccctgttg tctcttacta tttgtaaagt<br>361 gaagactatg attagtcttt ttgatcggga tggtttgaga tgaataaaga ataggcaggc<br>421 aatttggata cttttaggct tcaagaacaa ttagtaacat ttttcttag atatttctcc<br>481 taatacaatg agtgttgtga ataacatgg cagttattgt tgagagaaaa gccttcccag<br>541 ttatgtattg agtccttagg cgttttgcc ttccctccac tcttacagaa cttggtggaa<br>601 ggggccacta tgttttctac ctccttccgt gccttcaca aagccacatc ctgcaccgtc<br>661 tacccttctc tgtggatatt ttccgcttg gcaatttcct ttcctgagc acccacttgg<br>721 gacatctgaa tctccatctc catgttgatg gcccgtttgt gcttggacgt gttcttccac<br>781 ttgagactga gggttcatgt aatcaaagaa gtttctttgt tgtgtgtatc tttacagaac<br>841 acaacaggaa ttgaaaatga atcagaacac tactgagcgt gtggcggcca ccgagaccct<br>901 ggctgaggta cccgaacatg tgctgcgagg acttccggag gaagtggagc ttttcccttc<br>961 tgctgttgac aagacccgga ttggtgtctg ggccactaaa ccaatttaa aaggcaaaaa<br>1021 atttgggcca tttgttggtg ataagaaaaa aagatctcag gttaagaata atgtatacat<br>1081 gtgggaggtg tattacccaa atttgggatg gatgtgcatt gatgccactg atccagagaa<br>1141 gggaaactgg ctgcgatatg tgaattgggc ttgctcagga gaagagcaaa atttattccc<br>1201 actggaaatc aacagagcca tttactataa aactttaaag ccaatcgcgc cgggcgagga<br>1261 gctcctggtc tggtacaatg gggaagacaa ccctgagata gcagctgcga ttgaggaaga<br>1321 gcgagccagc gcccggagca agcggaccgc ccccaagagc cggaaaggga agaaaaaatc<br>1381 ccaggaaaat aaaaaacaaag gaaacaaaat ccaagacata caactgaaga caagtgagcc<br>1441 agatttcacc tctgcaaata tgagagattc tgcagaaggt cctaaagaag acgaagagaa<br>1501 gccttcagcc tcagcacttg agcagccggc caccctccag gaggtggcca gtcaggaggt<br>1561 gcctccagaa ctagcaaccc ctgccctccc ctgggagcca cagccagaac cagacgagcg<br>1621 attagaagcg gcagcttgtg aggtgaatga tttggggaa gaggaggag aggaagagga<br>1681 ggaggatgaa gaagaagaag aagatgatga tgatgatgag ttggaagacg aggggggaaga<br>1741 agaagccagc atgccaaatg aaaattctgt gaaagagcca gaaatacggt gtgatgagaa<br>1801 gccagaaagat ttattagagg aaccaaaaac aacttcagaa gaaactcttg aagactgctc<br>1861 agaggtaaca cctgccatgc aaatccccag aactaaagaa gaggccaatg tgatgtatt<br>1921 tgaaacgttt atgtttccgt gtcaacattg tgaaggaag tttacaacca aacaggggct<br>1981 tgagcgtcac atgcatatcc atatatccac cgtcaatcat gctttcaaat gcaagtactg<br>2041 tgggaaagcc tttggcacac agattaaccg gcggcgacat gagcggcgcc atgaagcagg<br>2101 gttaaagcgg aaaccagcc aaacactaca gccgtcagag gatctggctg atggcaaagc<br>2161 atctggagaa aacgttgctt caaaagatga ttcgagtcct cccagtcttg ggccagactg<br>2221 tctgatcatg aattcagaga aggcttccca agacacaata aattcttctg tcgtagaaga<br>2281 gaatggggaa gttaagaac ttcatccgtg caaatattgt aaaaaggttt ttggaactca<br>2341 tactaatatg agacggcatc agcgtagagt tcacgaagct catctgattc ccaaaggtgt<br>2401 acggcgaaaa ggaggccttg aagagcccca gcctccagca aacaggccc aggccaccca<br>2461 gaacgtgtat gtaccaagca cagagccgga ggaggaaggg gaagcagatg atgtgtacat<br>2521 catggacatt tctagcaata tctctgaaaa cttaaattac tatattgatg gtaaaattca<br>2581 aactaataac aacactagta actgatgt gattgagatg gagtctgctt cggcagattt<br>2641 gtatggtata aattgtctgc tcactccagt tacagtggaa attactcaaa atataaagac<br>2701 cacacaggtc cctgtaacag aagatcttcc taaagagcct ttgggcagca caaatagtga<br>2761 ggccaagaag cggagaactg cgagcccacc tgcactgccc aaaattaagg ccgaaacaga<br>2821 ctctgacccc atggtccct cttgctcttcct cttagcatat caacaacaga<br>2881 ggcagtgtct ttccacaaag agaaaagtgt ttatttgtca tcaaagctca aacaacttct<br>2941 tcaaacccaa gataaactaa ctcctgcagg gatttcagca actgaaatag ctaaattagg<br>3001 tcctgtttgt gtgtctgctc ctgcatcaat gttgcctgtg acctcaagta ggtttaagag<br>3061 gcggaccagc tctcctccca gttctccaca gcacagtcct gccctttcag actttggaaa<br>3121 gccaagtgat gggaaagcag catggaccga tgccgggctg acttccaaaa aatccaaatt<br>3181 agaaagtcac agcgactcac cagcatggag tttgtctggg agagatgaga gagaaactgt<br>3241 gagccctcca tgctttgatg aatataaaat gtctaaagag tggacagcta gttctgcttt<br>3301 tagcagtgtg tgcaaccagc agccactgga tttatccagc ggtgtcaaac agaaggctga<br>3361 gggtacaggc aagactccag tccagtggga atctgtctta gatctcagtg tgcataaaaa<br>3421 gcattgtagt gactctgaag gcaaggaatt caaagaaagt cattcagtgc agcctacgtg<br>3481 tagtgctgta aagaaaagga accaaccac ctgcatgctg cagaaggttc ttctcaatga<br>3541 atataatggc atcgatttac ctgtagaaaa ccctgcagat gggaccagga gcccaagtcc<br>3601 ttgtaaatcc ctagaagctc agccagatctc tgacctcggt ccgggctctg gtttccctgc<br>3661 ccctactgtt gagtccacac ctgatgtttg tccttcatca cctgccctgc agacacccctc<br>3721 cctttcatcc ggtcagctgc ctcctctctt gatccccaca gatccctctt ccctccacc<br>3781 ctgtccccccg gtattaactg ttgccactcc gccccctccc ctccttccta ccgtacctct<br>3841 tccagccccc ccactccaca cccatgccct catctgccct ctccactct caaatgccac<br>3901 cgcacagtcc ccacttccaa ttctgtcccc aacagtgtcc ccctctccct ctcccattct<br>3961 tcccgtggag ccctgatgt ctgccgcctc accgggcct caacactttt cttcttcctc<br>4021 ctcttcatct tcctcctcct cttcgttttc ttcttcatct tcctcctctt ccttctcc<br>4081 acctcctctc tccgcaatat catctgttgt ttcctctggt gataatctgg aggcttctct<br>4141 ccccatgata tctttcaaac aggaggaatt agagaatgaa ggtctgaaac ccagggaaga<br>4201 gcccccgtct gtggccagac aggatgttgt tgttcaggaa acattcaaca aaaacttgt<br>4261 ttgcaacgtc tgtgaatcac cttttcttt cattaaagat ctaaccaaac atttatctat<br>4321 tcatgctgaa gaatggcccct tcaaatgtga attttgtgtg cagctttta aggataaaac<br>4381 ggacttgtca gaacatcgct ttttgcttca tggagttggg aatatctttg tgtgttctgt<br>4441 ttgtaaaaaa gaatttgctt ttttgtgcaa tttgcagcag caccagcgag atctccaccc<br>4501 agataaggtg tgcacacatc acgagtttga aagcgggact ctgaggcccc agaactttac |

| species | gene | SEQ ID NO: | CDS sequence (coding sequence) |
|---|---|---|---|
| | | | 4561 agatcccagc aaggcccatg tagagcatat gcagagcttg ccagaagatc ctttagaaac |
| | | | 4621 ttctaaagaa gaagaggagt taaatgaaat ctctgaagag ctttacacga ctataaaaat |
| | | | 4681 aatggcttct ggaataaaga caaaagatcc agatgttcga ttgggcctca atcagcatta |
| | | | 4741 cccaagcttt aaaccacctc catttcagta ccatcaccgt aaccccatgg ggattggtgt |
| | | | 4801 gacagccaca aatttcacta cacacaatat tccacagact ttcactaccg ccattcgctg |
| | | | 4861 cacaaagtgt ggaaaaggtg tcgacaatat gccggagttg cacaaacata tcctggcttg |
| | | | 4921 tgcttctgca agtgacaaga agaggtacac gcctaagaaa aacccagtac cattaaaaca |
| | | | 4981 aactgtgcaa cccaaaaatg gcgtggtggt tttagataac tctgggaaaa atgccttccg |
| | | | 5041 acgaatggga cagcccaaaa ggcttaactt tagtgttgag ctcagcaaaa tgtcgtcgaa |
| | | | 5101 taagctcaaa ttaaatgcat tgaagaaaaa aaatcagcta gtacagaaag caattcttca |
| | | | 5161 gaaaaacaaa tctgcaaagc agaaggccga cttgaaaaat gcttgtgagt catcctctca |
| | | | 5221 catctgccct tactgtaatc gagagttcac ttacattgga agcctgaata aacacgccgc |
| | | | 5281 cttcagctgt cccaaaaaac cccttttctcc tcccaaaaaa aaagtttctc attcatctaa |
| | | | 5341 gaaaggtgga cactcatcac ctgcaagtag tgacaaaaac agtaacagca accaccgcag |
| | | | 5401 acggacagcg gatgcggaga ttaaaatgca aagcatgcag actccgttgg gcaagaccag |
| | | | 5461 agcccgcagc tcaggcccca cccaagtccc acttccctcc tcatccttca ggtccaagca |
| | | | 5521 gaacgtcaag tttgcagctt cggtgaaatc caaaaaacca agctcctcct ctttaaggaa |
| | | | 5581 ctccagcccg ataagaatgg ccaaaataac tcatgttgag gggaaaaaac ctaaagctgt |
| | | | 5641 ggccaagaat cattctgctc agctttccag caaaacatca cggagcctgc acgtgagggt |
| | | | 5701 acagaaaagc aaagctgttt tacaaagcaa atccaccttg gcgagtaaga aaagaacaga |
| | | | 5761 ccggttcaat ataaaatcta gagagcggag tggggggcca gtcacccgga gccttcagct |
| | | | 5821 ggcagctgct gctgacttga gtgagaacaa gagagaggac ggcagcgcca agcaggagct |
| | | | 5881 gaaggacttc agctacagcc tccgcttggc gtcccgatgc tctccaccag cggcccgta |
| | | | 5941 catcaccagg cagtatagga aggtcaaagc tccagctgca gcccagttcc agggaccatt |
| | | | 6001 cttcaaagag tagacactct ggctgctccc tgacagcacc tgaagtgacc tggaatcagt |
| | | | 6061 gaagccaaag ggactggcag tctgccctgc agggagtacc gacctatccc agttgtgtga |
| | | | 6121 ggctgcgaga gaaaggagt gcatgtgccg gcgtgcatgt gtgcgtgcgt gtgtgttcac |
| | | | 6181 gtgttctcgt gcgggcgcgt gagtggtctt caaacgaggg tcccgatccc cggggcggca |
| | | | 6241 ggaaggggggc cgactccacg ctgtcctttg gatgatact tggatgcagc tcttgggacc |
| | | | 6301 gtgttctgca gcccagcctt cctgttgggg tggggcctct cctactatgc aattttttcaa |
| | | | 6361 gagctccttg accctgcttt ttgcttcttg agttgtcttt tgccattatg gggactttgg |
| | | | 6421 tttgacccag gggtcagcct ttgaaggcc ttcaggagga ggccgagttc cccttcagta |
| | | | 6481 ccacccctct ctccccacct tccctctccc ggcaacatct ctgggaatca acagcatatt |
| | | | 6541 gacacgttgg agccgagcct gaacatgccc ctcggcccca gcacatggaa accccccttc |
| | | | 6601 cttgcctaag gtgtctgagt ttctggctct tgaggcattt ccagacttga aattctcatc |
| | | | 6661 agtccattgc tcttgagtct ttgcagagaa cctcagatca ggtgcacctg ggagaaagac |
| | | | 6721 tttgtcccca cttacagatc tatctcctcc cttgggaagg gcagggaatg gggacggtgt |
| | | | 6781 atggagggga gggatctcct gcgcccttca ttgccacact tggtgggacc atgaacatct |
| | | | 6841 ttagtgtctg agcttctcaa attagctgca ataggaaaaa aacaaattgg gaaatgaaaa |
| | | | 6901 aaaaatggga agattaaaaa gcacaggggg aagaagaaga gattttcggag gccatcctgc |
| | | | 6961 caggggcgga cggggctgac tcctgctctc tggaggacgg tcagtccatg tctcggagaa |
| | | | 7021 acgggtgagc tgagcttggc gtttggaccc agttcagtga ggttcttggg ttttgtgcct |
| | | | 7081 ttggggcaga ccccaggcaa ggatgtctga gaccacttgg gcgctgtttt ctcagctcca |
| | | | 7141 atttcaagag tgagctatca aacccagagc ggaaggaggg agctctgatg agcacggtt |
| | | | 7201 gtcacacgat aaagggattt ttttttttcag ggctactacg gttgatcttg caactctgta |
| | | | 7261 aatatgtatg tagacacttt taaaagcacg tatttatgtc cctgactgta aatgctccat |
| | | | 7321 ttttaaagtt ttataacttg tgttatttaa tgagtcagtc aatcggctgc agtatgggat |
| | | | 7381 ctgataagga tctaggagaa gggtctcatg cggaccctca catgggcaga aaatggttg |
| | | | 7441 tcattggccg acatcacagt tttcctgttt cccacccagc taaaaaccgt tgtttgcttt |
| | | | 7501 aaattttcat aaactggaat cctttcaccc gctcctacag ctaaccctca caagcatgaa |
| | | | 7561 gtgctgtggc tgttccttat cctaatgatg cgcttttgtc ccgtaaatgt taacactcat |
| | | | 7621 gaagcatacc ccggcctctc agttcttgag ggctccccca ccgcagcagc aaggaaagct |
| | | | 7681 cacgaaccccc aaacctggca agtcacctgc agcccatggt gagctctggg aagtgtggtt |
| | | | 7741 gaggccttgg ggtcactcct tttttgcatg tgcaaatgtg ctggtcaccc ttcaacgctc |
| | | | 7801 ccagacggtc aggaaaactg ttccaatcat gaaaaggggg gatgattttg taaaagtggc |
| | | | 7861 atttcctggt cagtggtggt cttcaagacg acagctctgt atctgccatg tgaagagaat |
| | | | 7921 taacaataaa agtgtgaaga gcgattgtga ggaacaaaaa aaaaaaaaa |
| human | KDM4A), mRNA | SEQ ID NO: 49 | 1 acggctgcgc agatgccgac tttagaggag gcggagtttc ggccttcgc tgctggaaaa |
| | | | 61 gcagtaggat cggccagtgg cgacagcagg agctgagcct aagccctggc ggggctttgg |
| | | | 121 gctgtagatt cctgtctgac taaaggaacc tcaaaaagga gggaaaatgg cttctgagtc |
| | | | 181 tgaaactctg aatcccagtc ctaggataat gaccttttat ccaactatgg aagagttccg |
| | | | 241 aaacttcagt agatacattg cctacattga atcccaagga gctcatcggg cagggctagc |
| | | | 301 caaggttgtt cctccaaaag agtggaagcc acgagcatcc tatgatgaca ttgatgattt |
| | | | 361 ggtcattcct gccccattc aacagctggt gacggggcag tctggcctct ttactcagta |
| | | | 421 caacatacag aagaaagcca tgactgttga agagttccgc aagatagcca atagcgataa |
| | | | 481 gtactgtacc ccacgctata tgagttttga agagctcgag cggaaaatact ggaaaaatct |
| | | | 541 tacattcaat cctccaatct atggtcagat tgtgaatggt acccctctatg aaaagcatgt |
| | | | 601 tgatgagtgg aatattggcc ggctgagaac aatcctggac ttggtggaaa aggagagtgg |
| | | | 661 gatcaccatt gagggtgtga cacccccata cctgtacttt ggcatgtgga gacatccctt |
| | | | 721 tgcttggcac actgaagaca tggacttcta cagcatcaac tacctgcact ttggagaacc |
| | | | 781 aaagtcctgg tactctgttc cacctgagca tggaaagcgg ttgaacgcc tcgccaaagg |
| | | | 841 ctttttttcca ggaagtgtct aaagctgtga gcatttctc cgccacaaga tgaccctgat |
| | | | 901 ttccccgtta atgctgaaga aatatgggaat tcccttttgac aaggtgactc aagaggctgg |
| | | | 961 agagtttatg atcactttcc cttatggttta ccatgccggc tttaaccatg gttttaactg |
| | | | 1021 tgcggagtct accaatttttg ctacccgtcg gtggattgag tacggcaagc aagctgtgct |

| species | gene | SEQ ID NO: | CDS sequence (coding sequence) |
|---|---|---|---|
| | | | 1081 gtgctcctgt agaaaggaca tggtgaagat ctccatggat gtgtttgtga gaaagttcca |
| | | | 1141 gccagaaagg tacaaacttt ggaaagtcgg gaaggacaac acagttattg accatactct |
| | | | 1201 gcccacgcca gaagcagctg agtttcttaa ggagagtgaa ctgcctccaa gagctggcaa |
| | | | 1261 cgaggaggag tgcccagagg aggacatgga aggggtggag gatggagagg aaggagacct |
| | | | 1321 gaagacaagc ctggccaagc accgaatagg gacaaagagg caccgagttt gtcttgaaat |
| | | | 1381 accacaggag gtgagtcaga gtgagctctt ccccaaggag gatctgagtt ctgagcagta |
| | | | 1441 tgagatgacg gagtgccccga cagccctcgc ccctgtgagg cccacccata gctctgtgcg |
| | | | 1501 gcaagttgag gatggtctta ccttcccaga ttattctgac tccactgaag tcaaatttga |
| | | | 1561 agagcttaaa aatgtcaaac tagaagagga ggatgaggag gaagaacaag cagcagctgc |
| | | | 1621 cttggatctt tctgtgaatc ctgcgtctgt aggggggacgc cttgtcttct caggctccaa |
| | | | 1681 aaagaaatca tcttcagcc tgggctctgg ctcctcacgg gattctatct cttctgattc |
| | | | 1741 agaaactagt gagcctctct cctgccgagc ccaagggcaa acgggagttc tcactgtgca |
| | | | 1801 cagttatgcc aaaggggatg gcagggtcac tgtgggagag ccatgcacga ggaagaaagg |
| | | | 1861 aagcgccgct agaagtttca gtgagcggga gctggcagag gttgcagatg aatacatgtt |
| | | | 1921 ttccctagaa gagaataaga agtccaaggg acgccgtcac ccttttaagca agctccccccg |
| | | | 1981 ccatcaccca cttgctctgc aggagtgtgt cagtgatgat gagacatctg aacagctgac |
| | | | 2041 ccctgaggaa gaggctgagg agacagaggc ctgggccaag cctctgagcc aactgtggca |
| | | | 2101 gaaccgacct ccaaactttg aggctgagaa ggaattcaat gagaccatgg cccaacaggc |
| | | | 2161 ccctcactgc gctgtctgta tgatcttcca gacttatcat caggttgaat ttggaggctt |
| | | | 2221 taatcagaac tgtggaaatg cttcagattt agccccccag aagcagagga ccaagccatt |
| | | | 2281 gattccagaa atgtgcttca cttcgactgg ctgcagcacg gacatcaacc tttctactcc |
| | | | 2341 ttatcttgag gaggatggca ccagcatact cgtttcctgc aagaagtgca gcgtccgggt |
| | | | 2401 ccatgccagt tgctatgggg tccccccgtc aaaggcttct gaagactgga tgtgttctcg |
| | | | 2461 gtgttcagcc aatgccctag aggaggactg ctgtttatgc tcattacgag gaggggccct |
| | | | 2521 gcagagagca aatgatgaca ggtgggtcca cgtttcatgt gctgtggcaa ttctggaagc |
| | | | 2581 aaggtttgtc aacattgcag aaagaagtcc ggtggatgtg agcaaaatcc ccctgccccg |
| | | | 2641 cttcaaactg aaatgtatct tctgtaagaa gcggaggaaa agaactgctg gctgctgtgt |
| | | | 2701 gcagtgttct cacggccgct gcccaactgc cttccatgtc agctgcgccc aggctgccgg |
| | | | 2761 tgtgatgatg cagcctgacg actggccttt tgtggtcttc attacctgct ttcggcacaa |
| | | | 2821 gattcctaat ttggagcgtg ccaaggggga cttgcaaagc atcactgcag gccagaaagt |
| | | | 2881 cattagcaag cataagaacg ggcgcttcta ccagtgtgaa gtggtcaggc tcaccaccga |
| | | | 2941 gaccttctat gaagtcaact ttgatgatgc ctccttcagc gacaatcttt atcctgagga |
| | | | 3001 catagtgagc caggactgtc tccagtttgg tcctcctgct gaagggggaag tggtccaagt |
| | | | 3061 gagatggaca gacggccaag tctatggagc caagtttgtg gcctccaccc tatccaaat |
| | | | 3121 gtaccaggtg gagtttgagg atggctcaca acttgtggtt aagagagatg atgtatacac |
| | | | 3181 actgatgaa gagctccca agagagtcaa atctagactg tcagtagcct cagacatgcg |
| | | | 3241 cttcaatgag atttcacag agaagagggt taagcaagaa agaaacggc aacgagttat |
| | | | 3301 caactcaaga taccgggaag attatattga gcctgcacta taccgggcca tcatggagta |
| | | | 3361 ggtgcttcca gggtccaagg gattctcagc catccaggca agagcactct gggttccaca |
| | | | 3421 gcacagcaga catggaacgc tgaagtctct gaaagtgaag ttgtaaaaag aaaaggaatg |
| | | | 3481 aaataaccga cccatcatct tctcacccac cctcattgca ttccgctgta gtgaaaggac |
| | | | 3541 gagccatttc tgggcacgtg gcagcagtcg ctgatctccc agctgagggg ctgagcactg |
| | | | 3601 gaatgctgtg gctgcactgg ccccagtcca tagaggggtc aactatgctg gctggactgg |
| | | | 3661 ctgccttgtt cctggcctag gacttagctt cataactatc acctgcaccg actaggctga |
| | | | 3721 ggtgctggta cttgccccaa cccctacttt tgtatttata tgtgtgtgtg tgtgtgcgtg |
| | | | 3781 cgtgcgtgcg tgcgtgtatg tttggtctgg accagcttct gccagcccct ggcctttact |
| | | | 3841 ttcttccttg cctatgcagg gcaaacaaaa tgtgaaattc tgccctcagc tgagctgagt |
| | | | 3901 aagggctcct gggggttggc tggagatggg tgtgcatct gtccaggcct ggaaccgtcc |
| | | | 3961 caagacagtg ctggcaaagc tgcagtattg agatgctaag gagctgatgc cacctctttg |
| | | | 4021 tcttcccta aaggagaaca tggggataac atgggtgtgt gcccacaaca ctctaggtgc |
| | | | 4081 agagccctg tggcaaagta ttacagggtg tgggtgggga ttaccctgaa tcgggggattt |
| | | | 4141 taatgatgga gacaggcaga gcctggtggg tgattcgtc aacagaaaat tgcaatcatg |
| | | | 4201 caggggctgg gaggggttagg atgaaaaaac tggggccatt ggaggcccac tgtaggtggg |
| | | | 4261 agggagctga ttttgggtgt ggggtggga ctagagggca atactcaagg ggttaaacag |
| | | | 4321 gttttgctc tcaagaatt tgtttgcctg gcccaggat tggagggctt cacaccaata |
| | | | 4381 ccctgtgtat acaagaatca gatttataat acttccccctt ttttgttacg tatgaacact |
| | | | 4441 ataaaccaaa ttattttgaa aactggtgca tcaccttgtc cttagcaata aaatgtgttg |
| | | | 4501 agcagaggaa aaaaaaaaaa aaaaaa |
| human | lysine (K)-specific demethylase 4B (KDM4B), (mRNA) | SEQ ID NO: 51 | 1 agggctcggt cgccagcaac cgagcggggc ccggcccgag cggggcctgg gggtgcgacg |
| | | | 61 ccgggggcgg gggagagcgg gccgctgctc ccggccccgg cgcgcacgc cgcctcagga |
| | | | 121 accatcactg ttgctggagg cacctgacaa atcctagcga atttttggag catctccacc |
| | | | 181 caggaacctc gccatccaga agtgtgcttc ccgcacagct gcagccatgg gtctgaggga |
| | | | 241 ccacgcgcc cagaacccca gctgtaaaat catgacgttt cgcccaacca tggaagaatt |
| | | | 301 taaagacttc aacaaatacg tggctctacat agagtcgcag ggagcccacc gggcggcct |
| | | | 361 ggccaagatc atcccccaca aggagtggga gccgcggcag acgtatgatg acatcgacga |
| | | | 421 cgtggtgatc ccggcgccca tccagcaggt ggtgacgggc cagtcgggcc tcttcacgca |
| | | | 481 gtacaatatc cagaagaagg ccatgacagt gggcgagtac cgccgcctgg ccaacagcga |
| | | | 541 gaagtactgt accccgcggc caccaggactt tgatgacctt gaacgcaaat actggaagaa |
| | | | 601 cctcaccttt gtctccccga tctacgggc tgacatcagc ggctctttgt atgatgacga |
| | | | 661 cgtggcccag tggaacaggc ggagcctgcg gaccatcctg gacatggtgg agcgcgagttg |
| | | | 721 cggcaccatc atcgaggcg tgaacacgcc ctaccgtgtac ttcggcatgt ggaagaccac |
| | | | 781 cttcgcctgg cacaccgagg acatggacct gtacagcatc aactacctgc acttgggga |
| | | | 841 gcctaagtcc tggtacgcca tcccaccaga gcacgcaag cgcctggagc ggctggccat |
| | | | 901 cggcttcttc ccccggagct cgcagggctg cgacgccttc ctgcggcata agatgaccct |
| | | | 961 catcctcgcc atcatcctga agaagtacgg gatcccttc agccggatca cgcaggaggc |

| species | gene | SEQ ID NO: | CDS sequence (coding sequence) |
|---|---|---|---|
| | | 1021 | cggggaattc atgatcacat ttccctacgg ctaccacgcc ggcttcaatc acgggttcaa |
| | | 1081 | ctgcgcagaa tctaccaact tcgccaccct gcggtggatt gactacggca aagtggccac |
| | | 1141 | tcagtgcacg tgccggaagg acatggtcaa gatctccatg gacgtgttcg tgcgcatcct |
| | | 1201 | gcagcccgag cgctacgagc tgtggaagca gggcaaggac ctcacggtgc tggaccacac |
| | | 1261 | gcggcccacg cgcgctcacca gccccgagct gagctcctgg agtgcatccc gggcctcgct |
| | | 1321 | gaaggccaag ctcctccgca ggtctcaccg gaaacggagc cagcccaaga gcccgaagcc |
| | | 1381 | cgaagacccc aagttccctg gggagggtac ggctggggca gcgctcctag aggaggctgg |
| | | 1441 | gggcagcgtg aaggaggagg ctgggccgga ggttgacccc gaggaggagg aggaggagcc |
| | | 1501 | gcagccactg ccacacgccc gggaggccga gggcgcagaa gaggacggga ggggcaagct |
| | | 1561 | gcggccaacc aaggccaaga gcgagcggaa gaagaagagc ttcggcctgc tgccccccaca |
| | | 1621 | gctgcgcgcc ccgcctgctc acttcccctc agaggaggcg ctgtggctgc catcccccact |
| | | 1681 | ggagccccg tgctgggcc caggccctgc agccatggag gagagccccc tgccggcacc |
| | | 1741 | ccttaatgtc gtgcccctg aggtgcccga tgaggagcta gaggccaagc ctcggcccat |
| | | 1801 | catccccatg ctgtacgtgg tgccgcggcc gggcaaggca gccttcaacc aggagcacgt |
| | | 1861 | gtcctgccag caggccttg agcactttgc ccagaaggt ccgacctgga aggaaccagt |
| | | 1921 | ttcccccatg gagctgacgg gccagagga cggtgcagcc agcagtgggg caggtcgcat |
| | | 1981 | ggagaccaaa gcccgggccg gagagggca ggcaccgtcc acatttccca aattgaagat |
| | | 2041 | ggagatcaag aagagccggc gccatccct gggccggccg cccacccggt ccccactgtc |
| | | 2101 | ggtggtgaaa caggaggcct caagtgacga ggaggcatcc cctttctccg gggaggaaga |
| | | 2161 | tgtgagtgac ccggacgcct tgaggccgc gctgtctctg cagtggaaga caggcgggc |
| | | 2221 | cagcttccag gccgagagga gttcaacgc agcggctgcg cgcacggagc cctactgcgc |
| | | 2281 | catctgcacg ctcttctacc cctactgcca ggcctacag actgagaagg aggcacccat |
| | | 2341 | agcctccctc ggagagggct gcccggccac attaccctcc aaaagccgtc agaagacccg |
| | | 2401 | accgctcatc cctgagatgt gcttccacct tggcggtgag aacacggagc cgctgcctgc |
| | | 2461 | caactcctac atcggcgacg acgggaccag ccccctgatc gcctgcggca agtgctgcct |
| | | 2521 | gcaggtccat gccagttgct atggcatccg tcccgagctg gtcaatgaag gctggacgtg |
| | | 2581 | ttcccggtgc gcggcccacg cctggactgc ggagtgctgc ctgtgcaacc tgcgaggagg |
| | | 2641 | tgcgctgcag atgaccaccg ataggaggtg gatccacgta atctgtgcca tcgcagtccc |
| | | 2701 | cgaggcgcgc ttcctgaacg tgattgagcg ccaccctgtg gacatcagcg ccatccccga |
| | | 2761 | gcagcggtgg aagctgaaat gcgtgtactg ccggaagcgg atgaagaagg tgtcaggtgc |
| | | 2821 | ctgtatccag tgctcctacg agcactgcc cacgtcctc cacgtgacct gcgcccacgc |
| | | 2881 | cgcaggcgtg ctcatggagc cggacgactg gccctatgtg gtctccatca cctgcctcaa |
| | | 2941 | gcacaagtcg gggggtcacg ctgtccaact cctgagggcc gtgtccctag gccaggtggt |
| | | 3001 | catcaccaag aaccgcaacg ggctgtacta ccgctgtcgc gtcatcggtc ccgcctcgca |
| | | 3061 | gacctgctac gaagtgaact tcgacgatgg ctcctacagc gacaacctgt accctgagag |
| | | 3121 | catcacgagt agggactgtg accccccttcc gagggggagc tggtggagct |
| | | 3181 | ccggtggact gacggcaacc tctacaaggc caagttcatc tcctccgtca ccagccacat |
| | | 3241 | ctaccaggtg gagtttgagg acggtgtcca gctgacggtg aagcgtgggg acatcttcac |
| | | 3301 | cctggaggag gagctgccca gagggtccg ctctcggctg tcactgagca cgggggcacc |
| | | 3361 | gcaggagccc gccttctcgg gggaggaggc caaggccgcc aagcgcccgc gtgtgggcac |
| | | 3421 | cccgcttgcc acggaggact ccgggcggag ccaggactac gtgggcttcg tggagagcct |
| | | 3481 | cctgcaggtg cagggccggc ccggagcccc cttctaggac agctggccgc tcaggcgacc |
| | | 3541 | ctcagcccgg cggggaggcc atggcatgcc ccgggcgttc gcttgctgtg aattcctgtc |
| | | 3601 | ctcgtgtccc cgaccccga gaggccacc ccaagccgcg ggtgccccct agggcgacag |
| | | 3661 | gagccagcgg gacgccgcac gcggccccag actcagggag caggccagg cgggctcggg |
| | | 3721 | ggccggccag gggagcaccc cactcaacta tcagaatttt aaaccatgt aagctctctt |
| | | 3781 | ctttctcgaaa aggtgctact gcaatgccct actgagcaac ctttgagatt gtcacttctg |
| | | 3841 | tacataaacc acctttgtga ggctcttttct ataaatacat attgtttaaa aaaaagcaag |
| | | 3901 | aaaaaaagga aaacaaagga aaatatcccc aaagttgttt tctagattg tggctttaag |
| | | 3961 | aaaaacaaaa caaaacaaac acattgtttt tctcagaacc aggattctct gagaggtcag |
| | | 4021 | agcatctcgc tgtttttttg ttgttgtttt aaaatattat gatttggcta cagaccaggc |
| | | 4081 | agggaaagag acccggtaat tggaggtga gcctcgggga ggggcagga cgccccggtt |
| | | 4141 | tcggcacagc ccggtcactc acggcctcgc tctcgcctca ccccggctca tgggctttga |
| | | 4201 | tggtctggtg ccagtgctg tgcccactct gtgcctgctg ggaggaggcc caggctctct |
| | | 4261 | ggtggccgcc cctgtgcacc tggcaggga agcccgggg tctgggcc tccctccgtc |
| | | 4321 | tgcgcccacc tttgcagaat aaactctctc ctgggttttg tctatctttg tttctctcac |
| | | 4381 | ctgagagaaa cgcaggtgtt ccagagggctt ccttgcagac aaagcacccc tgcaccctcct |
| | | 4441 | atggctcagg atgagggagg ccccaggcc cttctggttg gtagtgagtg tggacagctt |
| | | 4501 | cccagctctt cggtacaac cctgagcagg tcggggaca cagggcgag gcaggccttc |
| | | 4561 | ggggcccctt tcgcctgctt ccgggcaggg acgaggcctg gtgtcctcgc tccacccacc |
| | | 4621 | cacgctgctg tcacctgagg ggaatctgct tcttaggagt gggttgagct gatagagaaa |
| | | 4681 | aaacggcctt cagcccaggc tgggaagcgc cttctccagg tgcctctccc tcaccagctc |
| | | 4741 | tgcaccctc tggggagcct tccccacctt agctgtctcc tgccccaggg agggatggag |
| | | 4801 | gagataattt gcttatatta aaaacaaaaa atggctgagg caggagtttg gaccagcct |
| | | 4861 | gggctatata gcaagacccc atcactacaa attttttaca aattagctag gtgtggtggt |
| | | 4921 | gcgcacctgt ggtcccagct actcgggagg ctgtggtggg aggattgctt gagtccagga |
| | | 4981 | ggttgaggct gcagtcagct cagattgcac cactgcactc cagcctgggc aacagagcga |
| | | 5041 | gaccctgtct ccaaaaaaa aaaaaagcaa tgtttatatt ataaaagagt gtcctaacag |
| | | 5101 | tccccgggct agagaggact aaggaaaaca gagagagtgt tacgcaggag caagcctttc |
| | | 5161 | atttccttgg tggggaggg ggcggttgc cctggagagg gccggggtcg ggaggttgg |
| | | 5221 | gggtgtcag ccaaaacgtg gaggtgtcc tctgcacgca gccctcgccc gccgtgcgc |
| | | 5281 | tgacactgta ttcttatgtt gtttgaaaat gctatttata ttgtaaagaa gcgggcggt |
| | | 5341 | gccctgctg cccttgtccc ttggggtca cacccatccc ctggtgggct cctgggcggc |
| | | 5401 | ctgcgcagat gggccacaga agggcaggcc ggagctgcac actctcccca cgaaggtatc |
| | | 5461 | tctgtgtctt actctgtgca aagacgcggc aaaacccagt gcctggtttt ttccccaccc |
| | | 5521 | gagatgaagg atacgctgta tttttgcct aatgtccctg cctctaggtt cataatgaat |

| species | gene | SEQ ID NO: | CDS sequence (coding sequence) |
|---|---|---|---|
| | | | 5581 taaaggttca tgaacgctgc gaaaaaaaaa aaaaaaaaaa aaaaaaaaaa aaaaaaaaaa |
| | | | 5641 aaaaaaaaaa aaaaaaaaaa aaaaaaaaaa aaaaa |
| human | lysine (K)-specific demethylase 4C (KDM4C), transcript variant 1, mRNA | SEQ ID NO: 53 | 1 gccataggtg cgcgtcggcg cccaggagga cgtgtggcgc gtggactaca tcaggtccag |
| | | | 61 ccctgcggga ccccagccag cgcttccggg caaggttctg tgcacctgtt ttctccttct |
| | | | 121 acgcgagtat cttccccctc cggaaagaat gggatatgcc tgagcccaaa ggacaagaag |
| | | | 181 atgcgcgcca gcaagcctaa gttaaccaca gcgcggaagt tgagcccaaa gcaagagcgt |
| | | | 241 gccgggcacc tttaagctgt tgtaagccc acgtgactca ccaagtgcgg gccccagcgg |
| | | | 301 tcacgtgacg gcgcgcgcgc cctcgcgcag ggagagccgg cggtgcgcgc gccttcgccg |
| | | | 361 ctgcctccca cccacccct cgacgggagg gtgaggcgcg gcgcagtgat cgggcggccg |
| | | | 421 gggtcctgtg cgcgtgcgca gcgaacagct gtcacctagt gcggaacaag tctcccaaat |
| | | | 481 ttcccaaatc tccctggcc ggaggccact gtcttctctt cctcctccac cgagtcgtgc |
| | | | 541 tctcgcccca acccgcgcgc cagacactgc cctaaccatc atggaggtgg ccgaggtgga |
| | | | 601 aagtcctctg aacccagct gtaagataat gaccttcaga ccctccatgg aggagttccg |
| | | | 661 ggagttcaac aaataccttg catcatgga gtctaaagga gcccatcgtg cgggtcttgc |
| | | | 721 aaaggtgatt cctcctaagg agtggaagcc aagacagtgc tatgatgaca ttgataattt |
| | | | 781 gctcattcca gcaccaattc agcagatggt cacagggcag tcaggactgt tcactcagta |
| | | | 841 caacatccag aaaaaagcga tgactgtgaa ggagttcagg cagctggcca acagtggcaa |
| | | | 901 atattgtact ccaagatact tggattacga agatttggag cgcaagtact ggaagaactt |
| | | | 961 aactttgtg gcacctatct atggtcagaa tattaatggg agcatatatg atgagggtgt |
| | | | 1021 ggatgaatgg aacatagctc gcctcaatac agtcttggat gtggttgaag aagagtgtgg |
| | | | 1081 catttctatt gagggtgtaa ataccccata tctctatttt ggcatgtgga agaccacgtt |
| | | | 1141 tgcatggcac accgaagaca tggacctcta tagcattaat tatctccact ttggagagcc |
| | | | 1201 caagtcttgg tatgctatac ctccggagca tggaaaacga cttgaaagac tagctcaagg |
| | | | 1261 ttttttccca agcagctccc aagggtgtga tgcattcttt cgccacaaga tgacattgat |
| | | | 1321 ttctccatca gtattgaaga aatatgtgat tcccttgac aagataaccc aggaggctgg |
| | | | 1381 agaattcatg atcacttcc catatgccta ccatgctggt tttaatcatg gtttcaactg |
| | | | 1441 tgcagaatct acaaattttg ctactgtcag atggattgac tatggaaag ttgccaaatt |
| | | | 1501 gtgcacttgc aggaaagaca tggtgaagat ttcaatggat atcttgtga ggaaatttca |
| | | | 1561 gccagacaga tatcagcttt ggaaacaagg aaaggatata tacaccattg atcacacgaa |
| | | | 1621 gcctactcca gcatccaccc ctgaagtaaa agcatggctg cagaggagga ggaaagtaag |
| | | | 1681 aaaagcatcc cgaagcttcc agtgtgctag gtctacctct aaaaggccta aggctgatga |
| | | | 1741 ggaagaggaa gtgtcagatg aagtcgatgg ggcagaggtc cctaaccccg actcagtcac |
| | | | 1801 agatgacctc aaggtcagtg aaaagtcaga agcagcagtg aagctgagga cacagaagc |
| | | | 1861 atcttcagaa gaagagtcat ctgctagcag gatgcaggtg gagcagaatt tatcagatca |
| | | | 1921 tatcaaactc tcaggaaaca gctgcttaag tacatctgta acagaagaca taaaaactga |
| | | | 1981 ggatgacaaa gcttatgcat atagaagtgt accttctata tccagtgagg ctgatgattc |
| | | | 2041 cattccattg tctagtggct atgagaagcc cgagaaatca gacccatccg agctttcatg |
| | | | 2101 gccaaagtca cctgagtcat gctcatcagt ggcagagagt aatggtgtgt taacagaggg |
| | | | 2161 agaagagagt gatgtggaga gccatggaaa tggccttgaa cctggggaaa tcccagcggt |
| | | | 2221 ccccagtgga gagagaaata gcttcaaagt cccagtata gcagaggag agaacaaaac |
| | | | 2281 ctctaagagt tggcgccatc cacttagcag gcctccagca agatctccga tgactcttgt |
| | | | 2341 gaagcagcag gcgccaagtg atgaagaatt gcctgaggtt ctgtccattg aggaggaagt |
| | | | 2401 ggaagaaaca gagtcttggg cgaaacctct catccacctt tggcagacga agtcccctaa |
| | | | 2461 cttcgcagct gagcaagagt ataatgcaac agtggccagg atgaagccac actgtgccat |
| | | | 2521 ctgcactctg ctcatgccgt accacaagcc agatagcagc aatgaagaaa atgatgctag |
| | | | 2581 atgggagaca aaattagatg aagtcgttac atcggaggga aagactaagc ccctcatacc |
| | | | 2641 agagatgtgt tttatttata gtgaagaaaa tctccaccca atgccttcct |
| | | | 2701 tgaagaggat ggaacaagtc tccttatttc ctgtgcaaag tgctgcgtac gggttcatgc |
| | | | 2761 aagttgttat ggtattcctt ctcatgagat ctgtgatgga tggctgtgtg cccggtgcaa |
| | | | 2821 aagaaatgcg tggacagcag aatgctgtct ctgcaatttg agaggaggtg ctcttaagca |
| | | | 2881 aacgaagaac aataagtggg gccatgtcat gtgcgccgtt gcggtcccaa aagttcgatt |
| | | | 2941 cactaatgtc ccagaaagga cacaaataga tgtaggcaga atacctttac agaggttaaa |
| | | | 3001 attgaaatgc atcttctgca gacaccgggt taagagggtc tctggagcct gcatccagtg |
| | | | 3061 ttcctacggt cgctgccgg cctccttcca tgtcacttgt gcccatgctg ctggggtact |
| | | | 3121 gatggagcct gatgactggc cttatgtggt gaacattaca tgcttccgac ataaggtcaa |
| | | | 3181 ccccaacgtg aagtccaaga cttgcgagaa ggtcattcc gtgggtcaaa cggtcatcac |
| | | | 3241 gaagcatcgg aacacccggt attacagttg cagagtgatg gctgtgacat cgcagaccat |
| | | | 3301 ctatgaggtc atgtttgatg atggctcctt tagcagagac acatttcctg aggatatcgt |
| | | | 3361 gagccgagac tgtctgaagc tgggcccacc tgctgaggga gaagtcgtcc aagtcaagtg |
| | | | 3421 gcccgatggc aaactctatg gagcaaaata ttttgatca aatattgctc acatgtacca |
| | | | 3481 ggttgagttt gaagatggat cccagatagc aatgaagaga ggggacatct cactttaga |
| | | | 3541 tgaagagtta cccaagagag tgaaagctcg attttccaca gcctctgaca tgcgatttga |
| | | | 3601 agacacgttt tatggagcag acattatcca aggggagaga aagagacaaa gagtgctgag |
| | | | 3661 ctccaggttt aagaatgaat atgtggccga ccctgtatac cgcacttttt tgaagagctc |
| | | | 3721 tttccagaag aagtgcagta gagacagta gtctgcatac atcgctgcag gccacagagc |
| | | | 3781 agcttgggtt ggaagagaga agatgaaggg acatccttgg ggctgtgccg tgagtttgc |
| | | | 3841 tggcataggt gacagggtgt gtctctgaca gtggtaaatc gggtttccag agtttggtca |
| | | | 3901 ccaaaaatac aaaatacacc caatgaattg gacgcagcaa tctgaaatca tctctagtct |
| | | | 3961 tgctttcact tgtgagcagt tgtcttctat gatcccaaag aagttttcta agtgaaagga |
| | | | 4021 aaatactagtg aatcacccac aaggaaaagc cactgccaga gtcccatgga gtcctctgga |
| | | | 4081 gcggcttagg gcctgtcag gaaacacactg ggaccctctc tctagctc cagcaggtgg |
| | | | 4141 cacctcggta cccagcgggt agggcgataa tttatatatt tccacagtc agggaaggac |
| | | | 4201 tctcacttat ttgtttcaaa ttgcagtttt tataaacat ttttaaaaca caaatggcat |
| | | | 4261 gtatgctaat gagatttacc cgtgtgctat ctgtatttcc cttgtacaga acttttacat |
| | | | 4321 ttttgaatat tccattact tttgattgtg tctgatggga actgagttgt tggcctttgt |

| species | gene | SEQ ID NO: | CDS sequence (coding sequence) |
|---|---|---|---|
| | | | 4381 gaaatgaaat ttttggctct tgagaaagaa ttcttatgaa ttgttatgcg aattttatat |
| | | | 4441 atttaaagag ggagatctgg ggctgttatt tttaaacact ttttttcata atacatattc |
| | | | 4501 cgagtagata tttataaaat atatgtttct ttcattatgt gtttgtaaaa ttagagttta |
| | | | 4561 aataaatatg ctttgatgca tagttttgaa ctaatgtaac atgatttttc ttttttaaaa |
| | | | 4621 cagcctgaaa atgtactagt gtttaaaaat aaagatttcc attttctcca aaaaaaaaaa |
| | | | 4681 aaaaaaa |

The invention claimed is:

1. A method of increasing the efficiency of mammalian somatic cell nuclear transfer (SCNT), the method comprising:

injecting a SCNT embryo comprising an enucleated mammalian oocyte comprising a mammalian somatic cell donor nucleus of the same species with a Kdm4 histone demethylase or an mRNA encoding a Kdm4 histone demethylase, thereby increasing the efficiency of SCNT when compared to a control embryo.

2. The method of claim 1, further comprising culturing the injected SCNT embryo of claim 1 to form a blastocyst comprising one or more inner cell mass cells.

3. The method of claim 2, further comprising isolating one or more inner cell mass cells and culturing said cells to produce embryonic stem cells.

4. The method of claim 2, further comprising implanting said injected SCNT embryo into an oviduct of a mammalian female subject of the same species.

5. The method of claim 2, wherein the Kdm4 histone demethylase or an mRNA encoding a Kdm4 histone demethylase contacts any one or more of:
   i) the SCNT embryo comprising an enucleated mammalian oocyte comprising a mammalian somatic donor cell nucleus of the same species, or a cell descended from said embryo, prior to or at 5 hours post activation;
   ii) the SCNT embryo at the 1-cell stage;
   iii) the SCNT embryo after 5 hours post-activation (5 hpa), after 12 hours post-activation (12 hpa), or after 20 hours post-activation (20 hpa);
   iv) the SCNT embryo between 5-28 hours post-activation (5-28 hpa), between 10-12 hours post-activation (10-12 hpa), or between 20-28 hours post-activation (20-28 hpa) or
   v) the SCNT embryo at the 2 cell stage.

6. The method of claim 1, wherein the injecting is into the somatic cell donor nucleus or into the cytoplasm of the enucleated mammalian oocyte.

7. The method of claim 1, wherein the somatic cell donor nucleus and the enucleated mammalian oocyte are both from the same mammalian species selected from the group consisting of a human, a domestic commercial mammal, a companion mammal or pet mammal, a mammalian species that is near extinction, or any other non-human mammal.

8. The method of claim 1, wherein the method increases the efficiency of somatic cell nuclear transfer (SCNT) at least 50% compared to SCNT performed in the absence of the Kdm4 histone demethylase or the polynucleotide encoding the Kdm4 histone demethylase.

* * * * *

SEQUENCE LISTING

<160> NUMBER OF SEQ ID NOS: 65

<210> SEQ ID NO 1
<211> LENGTH: 1572
<212> TYPE: DNA
<213> ORGANISM: Homo sapiens

<400> SEQUENCE: 1

```
atggaaacta tgaagtctaa ggccaactgt gcccagaatc caaattgtaa cataatgata      60
tttcatccaa ccaaagaaga gtttaatgat tttgataaat atattgctta catggaatcc     120
caaggtgcac acagagctgg cttggctaag ataattccac ccaaagaatg aaagccaga      180
gagacctatg ataatatcag tgaaatctta atagccactc ccctccagca ggtggcctct     240
gggcgggcag gggtgtttac tcaataccat aaaaaaaaga agccatgac tgtgggggag      300
tatcgccatt tggcaaacag taaaaaatat cagactccac cacaccagaa tttcgaagat     360
ttggagcgaa aatactggaa gaaccgcatc tataattcac cgatttatgg tgctgacatc     420
agtggctcct tgtttgatga aaacactaaa caatggaatc ttgggcacct gggaacaatt     480
caggacctgc tggaaaagga atgtgggggtt gtcatagaag cgtcaatac accctacttg     540
tactttggca tgtggaaaac cacgtttgct tggcatacag aggacatgga cctttacagc     600
atcaactacc tgcaccttgg ggagcccaaa acttggtatg tggtgccccc agaacatggc     660
cagcgcctgg aacgcctggc cagggagctc ttcccaggca gttcccgggg ttgtggggcc     720
ttcctgcggc acaaggtggc cctcatctcg cctacagttc tcaaggaaaa tgggattccc     780
ttcaatcgca taactcagga ggctggagag ttcatggtga cctttcccta tggctaccat     840
gctggcttca accatggttt caactgcgca gaggccatca ttttgccac tccgcgatgg     900
attgattatg gcaaaatggc ctcccagtgt agctgtgggg aggcaagggt gacctttttcc     960
atggatgcct tcgtgcgcat cctgcaacct gaacgctatg acctgtggaa acgtgggcaa    1020
gacccgggcag ttgtggacca catggagccc agggtaccag ccagccaaga gctgagcacc    1080
cagaaggaag tccagttacc caggagagca gcgctgggcc tgagacaact cccttcccac    1140
tgggcccggc attcccttg gcctatggct gcccgcagtg ggacacggtg ccacaccctt    1200
gtgtgctctt cactcccacg ccgatctgca gttagtggca ctgctacgca gccccgggct    1260
gctgctgtcc acagctctaa gaagcccagc tcaactccat catccacccc tggtccatct    1320
gcacagatta tccacccgtc aaatggcaga cgtggtcgtg gtcgccctcc tcagaaactg    1380
agagctcagg agctgaccct ccagactcca gccaagaggc ccctcttggc gggcacaaca    1440
tgcacagctt cgggcccaga acctgagccc ctacctgagg atggggcttt gatggacaag    1500
cctgtaccac tgagcccagg gctccagcat cctgtcaagg cttctgggtg cagctgggcc    1560
cctgtgccct aa                                                       1572
```

<210> SEQ ID NO 2
<211> LENGTH: 1533
<212> TYPE: DNA
<213> ORGANISM: Mus sp.

<400> SEQUENCE: 2

```
atgaagacga agtccacatg tgctcagaat ccaaattgca gcataatgat atttcgtcca     60
accaaagaag agtttaatga ttttgacaaa tacattgctt acatggagtc ccaaggggca    120
caccgagctg gactggccaa ggtcatccca ccaaaagaat ggagggccag gcagtcttat    180
gacaatatca gcaacatctt aatagcaact cccctgcagc aagtggtctc tgggcaggca    240
ggcgtgttca cccaatacca taagaagaag aaaggcatga cagtggggga gtaccgtgag    300
ctggccaaca gcaaaaagta ccagaccccg ccacacctgg attttgaaga tttggagcga    360
aaatactgga agaatcgcct gtatgagtca ccgatttatg gtgctgacgt cagcggctcc    420
ctgtttgatg gaagactca acagtggaat gtgggtcacc tgggaacaat tcaagaccta    480
ttggaacagg aatgtggcat agtgattgag gcgtcaacag cgccctacct gtactttggc    540
atgtggaaga ccacctttgc gtggcacacg gaggacatgg acctgtacag tatcaactac    600
ctacactttg gcagcccaa gacctggtat gctgtgcccc tgagcatgg caggcgcctg    660
gagcgcctgg ccagggaact cttccctggc agctcccagg gctgccaggc cttcctgagg    720
cacaaggtgg cgctcatctc gcccactgtg cttaaggaga atggcatccc ctttggtcgc    780
atcacccagg aggctgggga gttcatggtc acctttcct atggctacca cgcgggcttc    840
aaccatggct tcaactgcgc agaggccatc aattttgcca ccccaaggtg gattgactat    900
ggcaaggtgg catctcagtg cagctgtggg gaggccaggg tgagcttctc catggacgcc    960
tttgtgagga tcttgcagcc tgagcgatat gaactgtgga acgtggcca agatcaggca   1020
gttgtggacc acacagagac tatggtgtct accagtcagg agctcaccac ccggcgggtg   1080
accaaagcac aagaaaaac ttggggcttg aagcgtctcc ggcttcgcca ggtctcacga   1140
tctcttctgc ctatagccac ggtaagtaac gttccttgca acatgcaggt gtgccacacc   1200
tccaggcaac catcagatgt gaaaggtgat gatgtccaga agtctgactc agccagagcc   1260
tcaccacatc ctctgagtct gccttcttct ggtcacatgt caactagaag atgtagtctt   1320
ggtcgtcgtc cttgtgaact aggagctcag gagtcctcca atggagctcc agtcaagagg   1380
caacttccag caggcagaga tgacacaagc cccagtccag agcttcagcc caggctgtg   1440
agtggagact aatagtcga ctcaggactt gtgaaccctg cccacagca tcttatgaca   1500
gcttctgaag ggggattgac ctccgacccc taa                               1533
```

<210> SEQ ID NO 3
<211> LENGTH: 1533
<212> TYPE: DNA
<213> ORGANISM: Rattus sp.

<400> SEQUENCE: 3

```
atgaagacta agtccacctg tgctcagaat ccaaattgca gcataatgat atttcgtcca     60
accaaagaag agtttaacga cttttgacaaa tacatcgcct acatggagtc ccaaggggca   120
cacagagctg gactggccaa ggtcatcccg ccaaaagaat ggagggccag gcagtcttat    180
gacaatatca gtaacatctt aatagcaact cccctgcagc aagtagtctc cgggcaggca    240
ggtgtgttca ctcaatacca taagaagaag aaagccatga cagttgggca gtaccggcac    300
ctggccaaca gtaaaaata ccaaaccccca ccacacctgg attttgaaga tttggagaga   360
```

```
aaatactgga agaatcgcct gtatgagtca ccaatttatg gtgctgacgt cagtggctcc    420
ctgtttgatg ggaagactca acagtggaat gtgggccacc tgggaacaat tcaagaccta    480
ttggaacagg aatgcggcat agtgattgag ggcgtcaaca cgccctacct gtactttggc    540
atgtggaaga cctcctttgc gtggcacacg gaggacatgg acctgtacag tatcaactac    600
ctgcactttg gacagcccaa gacctggtat gctgtacccc ctgagcatgg caggcgcctg    660
gagctcctag ccaaggaact cttcccaggc agctcccagg gctgccaggc cttcctgagg    720
cacaaggtgg cgctcatctc acccactgtg ctcaaggaga atggcatccc ctttggtcga    780
atcacccagg aggctgggga gttcatggtc acctttccct atggctacca cgcgggcttc    840
aaccatggct tcaactgtgc agaagccatc aatttcgcca cgccgaggtg gattgactat    900
ggcaaggtgg catctcagtg cagctgtggg gaggccaggg tgagcttctc catggatgcc    960
tttgtgagga tcctgcagcc tgagcgatat gagatgtgga aacgaggtca agatcaggca   1020
gttgtggacc acacagaggc tatggggcct accagtcagg agctcaccac ctggcgggtg   1080
atccaggcac caagaaaaac ttggggcctg aagcatctcc ggcttcgcca ggtttcacgc   1140
tgtcttctgc ctgtagccac tgacagtaac attgccaaca cacccagat gtgccacacc   1200
tccaggcaag cagcagattc gaaaggtgat gaggtccagg agtctgaccc agccatagcc   1260
ccaccatatc ctctgggtct atcttctcct ggccacatgt caactggaaa acgtggtctt   1320
ggtcgtcgcc cttgtgaact aggagttcag gagtccacca tggagctcc agtcaagagg   1380
cgacttccag aaggcagaga tgacagaagt cccagcccag agcttcagtc ccagtccgtg   1440
actggagact aatagtcaa ctcagacctt gtaaatcctg gccacagca tcctgtgaca   1500
gcttctgaag ggggattgac ctctgacccc taa                                 1533

<210> SEQ ID NO 4
<211> LENGTH: 1485
<212> TYPE: DNA
<213> ORGANISM: Oryctolagus cuniculus

<400> SEQUENCE: 4
atgaagtcta aggcccatcg tgctcagaat ccaaattgca gcataatggt atttcatcca     60
accaaagaag agtttagtga ttttgataac tatattgctt acatggaatc tcagggtgca    120
caccggggag gcctggccaa ggtcatccca cccaaggagt ggagggccag acagacctat    180
gatgacatcg atgacatctt aataactcgc cccctccagc aggtggccta tggcggggca    240
ggtgtcttta ctcaattcca taaaagagg agagccatga ccctgagaca gtatcgccag    300
ctggccacca gcacaaaata ccagacccca gcgcacctga cttcgaaga gttggagcaa    360
aaatactgga aaaccgtct ctacgatgcc ccaatctatg gtgctgatat cagcggctct    420
ctgtttgatg aaaacacggc acactggaac ctcaggcgcc tgggcaccat tcaggacctg    480
ttggagcagg aatgtggtgt cgtcatcgag ggcgtcaaca cgccctacct gtactttggc    540
atgtggaaga ccacgttcgc ctggcacacg gaggacatgg acctgtacag catcaactac    600
ctgcacttcg gggagcccaa gacgtggtac gcggtgcccc cggagcacgg cggcgcctg    660
gagcgcctgg ccgggcagct gttcccgggc agttcccgca gctgccaggc cttcctgcgg    720
cacaaggtgg ccctcatctc gcccagcgtc ctgcggcaga acggcatccc cttccgccgc    780
atcactcagc aggctggcga gttcatggtc acctttcctt acggctacca cgcgggggtc    840
aaccacggct tcaactgcgc cgaagccatc aatttcgcca cccgcgctg gatcgagtat    900
ggcaaagtgg cctcccagtg cagctgcggg gaggccaggg tcaccttttc catggatgcc    960
```

```
ttcgttcgta tcctgcaacc cgagcgctac gaactgtgga agtgcggcca agaccggaag    1020
gccgtggacc acacggagcc tacggcacgc accagcccag agctgaccag gtggaagcag    1080
gatcgcaggc tctggagggc agcccgaggc ttggccccca aactcgctag gtccctggct    1140
gcaggtgatg gtactagctg caaggctccc aagcgcctac gggctgccag ggaatctaca    1200
gcacagccag ggggcgttgc ccacagttcc cggaaacctc acgcagcccc gcggacttcc    1260
ctgggtccct gtgccccaga ggtcctctca actgtcacac gtggctgtcg gcgtcgctct    1320
agggaactgg gggtgcagga gccaagcctc caatctccag caaagaggcg cctctcagtc    1380
agaacagggc gcacagctgc gcgctccaag cctcagtcct cacctgagcg tggtatcttg    1440
atggtcaatc ctgcaccaag cctggggccg cagctccccg cttag                   1485
```

<210> SEQ ID NO 5
<211> LENGTH: 1521
<212> TYPE: DNA
<213> ORGANISM: Sus scrofa

<400> SEQUENCE: 5

```
atgacgtcca ggccctgtgg ggtccagaac ccaggctgtg ccattatgac cttctaccca      60
accctggaag aatttgaaga cttcagccaa tatatcgctt acatggaatc gcaaggggca     120
caccacgctg gcctggccaa ggtaattccc cccaaaggat ggaaagccag acagacttat     180
gaggatatca gtgacatcgt aatagctgcc cctctccagc aggtagcctt tggggaggca     240
ggtgtgttta ctcagtacca cagaaagaag agagccatga ctgtgagcca gtatcaccac     300
ctcgcacata ctgtaaaata tcaagctcca ccacacttgg attttgagga cctggagcaa     360
acatactgga aaacgcgcct gtacggttcc cccatctacg gcgcggatgt cagtggctcg     420
ttgttcgatg agaacacgaa gcagtggaac ctgggccacc tgggcaccat ccaggacctg     480
ctggagcagg agtgcggagt ggccatcgac ggcgtcaaca gcccgtacct gtacttcggc     540
atgtggaaga ccggcttcgc ctggcacacg gaggacatgg acctttacag cctcaacttc     600
ctgcacttcg gggagcccaa gacgtggtac gcggtgcccc tgcgcatggc cggcgcctg      660 gaacgcctgg ccagggagct gttccctggc cccgcgcggg gctgcgaggc cttcctgaga     720
cacaaggtgg cgctcatctc gcccacggtc ctcaaggccc agggcatccc ctttggccgc     780
gtcacgcagg aggcgggcga gttcatggtg acgtttccct atggctacca ctcgggcttc     840
aaccacggct tcaactgcgc cgaagccatc aatttcgcca cccgcgctg gtcgattat      900 ggcaaagtgc cgtcgcagtg cagctgcggg gaggcgcggg tggtgttctc catgacgcg     960 ttcgtgcgca tcctgcaacc cgagcgctat gagctgtgga acggggcca ggatcgggtg    1020 gcgctggaac acacggagca cctgtcctcg cctggcagcc tggagttgag tgcctggagg    1080
gaggtccgcg agcctgcggg ggctgaactt ggcctggggc acagcccacc ccacactgcc    1140
cggggtcggc tctgggtggc aggccgtggg atccgccgcc gaaactctgt gtgttcggtg    1200
tctcggtgcc cctcgcctac ctggggttct tcctccgctg cccagttcca ggttgcaact    1260
ctctgcagct cccatgagcc aggacccacc ccgccgctgt caccaggctc ctctgctctg    1320
ggtctccaat caactggcag acgtggtcct gttcgatgtc gtaggtctcg accccatcgt    1380
cgtcctcggg tacaggagac tttggagcca acagtccagg ctccagctaa gaggctcctc    1440
tcagtaggta cagtgggcac agctgcagac ttggaagctc atgtcctttt ggccaaggaa    1500
cccttgatag acagccctgc c                                              1521
```

<210> SEQ ID NO 6
<211> LENGTH: 1503
<212> TYPE: DNA
<213> ORGANISM: Bos taurus

<400> SEQUENCE: 6

```
atggaagcta tgaagcccag ttgtgctcag aacccaagtt gtagcataat gatatttcat      60
ccaaccaaag aagagtttac tgattttgat aaatacattg cttacataga atcgcaaggg     120
gcccaccgag caggcttggc taagatagtt ccacccaagg aatggaaagc cagacagacc     180
tacgacgata tcaatgacat cttaataacc gctccgctcc agcaggtggt ctctgggcgg     240
gcaggtgtgt ttactcaata ccacaaaaag aagaaagcca tgaccgtggc agagtaccgc     300
cacttagcaa atactgaaaa ataccagact ccattctact ccgattttga ggaattggag     360
cgaaaatatt ggaaaacccg cctctttgag tccccaatat acgcgcggga catcagtggc     420
tctttatttg atgaaaacac gaagcagtgg aacctgggac gcctgggac catccaggac     480
ctgctggagc aggagtgcgg ggtggtcatc gagggcgtca cacccccta cctgtacttc     540
ggcatgtgga agaccgcctt cgcctggcac acggaggaca tggacctta gcatcaac      600
ttcctgcact cggggagcc caagacctgg tacgcggtgc cgcccgagca cggccggcgc     660
ctggaacgcc tggccggcgc gctcttcccg ggcagctcgc ggagctgcga ggccttcctg     720
cgccacaagg cggcgctcat ctcgcccacg gtgctccggg acaacggcat ccccttcggt     780
cgggtcacgc aggaggcggg cgagttcatg gtgaccttcc cctacggcta ccactcgggc     840
ttcaaccacg gcttcaactg cgccgaggcc atcaatttcg ccaccccgcg ctggatcgat     900
tatggcaaag tggcctcgca gtgcagctgc ggcgaggcgc aggtggcctt ctccatggac     960
gccttcgtgc gcatcctgca gcccgagcgc tatgagctgt ggaagcgcgg gcaggaccgg    1020
gcggtggtga accacgccga gcccgcggcg ccgggcggcc aggagctgag agcctggaag    1080
gaggtgcaga cgctgggccc caagtacttc ccgcctcgcc gctccgcccg cctgcgtcag    1140
cccgtgtcct caagcgaggg cactgacccc agagcccctg tgcgggccgt gtccctgcga    1200
cccttgcctg cccgggggttc ctgctcggct tcccagtttg acgctgtcgc cggcagcagc    1260
tcacggaagc ccagccagac ccctccgctg ttgccaggtc cgtcggtggc gtcgtgcctc    1320
cacccagttg gcagatgtgg ttctcgtcgt cgccctcagg aaaaaggcac tcaagagctg    1380
actgccccca tcggagctaa gaggggcctt gccttagacc gcaaggctca ggaccccaag    1440
gctcaacccc tgtctgcaga gggacggatg gacaatcctg ccccaacgag ccctggactc    1500
tag                                                                  1503
```

<210> SEQ ID NO 7
<211> LENGTH: 1572
<212> TYPE: DNA
<213> ORGANISM: Macaca sp.

<400> SEQUENCE: 7

```
atggaaacta tgaagtctaa ggccaactat ggccagaatc caaattgtaa cataatgata      60
tttcatccaa ccaagaaga gtttaatgat tttgataaat atattgctta catggaatcc     120
caaggtgcac acagagctgg cttggctaag atagttccac ccaagaatg gaaagccaga     180
gagacctatg ataacatcag tgaaatctta atagccactc ccctccaaca ggtggcctct     240
gggcggggcag gggtgtttac tcaataccat aaaaaaaaga agccatgac cgtggggag     300
tatcgccact ggcaaacag taaaaaatat caaactccac cacaccagaa tttcgaagat     360
```

```
ttggagcgaa aatactggaa gaaccgcatc tataattcac caatttatgg tgctgacatc      420
agtggctcct tgtttgatga aaacactaaa cagtggaatc ttgggcacct gggaacaatt      480
caggacctgt tggaaaagga atgtgggtt gtcatagaag gcgttaacac accctacttg       540
tactttggca tgtggaagac cacatttgct tggcacacgg aggacatgga cctttacagc      600
atcaactacc tgcacctcgg ggagcccaaa acttggtatg tggtgccccc agagcatggc      660
cagcgcctgg aacgcctggc cagggagctc ttcccaggca gttccgggg ctgtggggcc       720 ttcctgcggc acaaggtggc cctcatctcg cctacagttc tcaaggaaaa tgggatcccc      780
ttcaatcgca taactcagga ggctggagag ttcatggtga cctttcccta tggctaccat      840
gctggcttca accatggttt caactgtgca gaggccatca attttgccac tccacgatgg      900
attgattatg gcaaaatggc ctcccagtgt agctgtgggg aggccagggt gaccttttcc      960
atggacgcct tcgtgcgcat cctgcaacct gagcgctatg agctgtggaa acgtgggcaa     1020
gaccgggcag ttgtggacca catggagccc agggtaccag ccagccaaga gctgagcacc     1080
cagaaggagg tccagttgcc caggagagca gcgctgggcc tgagacaact ccctcctcac     1140
tgggcccggc attcccttg gcctctggct gcccgcagtg ggacgcgctg ccacacccttt     1200 gtgtgctctt cactcccacg ccgatctgca gttagtggca ctgctacgca gccccgggct     1260
gctgccgtcc acagtctag gaagcccagc tcaactccat catccacccc tggtccatct     1320
gcacagatta tccacccgtc aaatggcaga cgtggacgtg gtcgccgtcc tcagaaactg     1380
agagctcagg agctgaccct ccagactcca gccaagaggc tcctcttagc gggcacaaca     1440
tgcacagttt caggcccaga acctgagccc ctacctgagg gtggggcttt gatggacaag     1500
cctgtaccac tgaatccagg gctccagcat cctgtaaagg cttctaggtg cagctgggcc     1560
cctgtgccct aa                                                          1572

<210> SEQ ID NO 8
<211> LENGTH: 1572
<212> TYPE: DNA
<213> ORGANISM: Pan troglodytes

<400> SEQUENCE: 8
atggaaacta tgaagtctaa ggccaactgt gcccagaatc caaattgtaa cataatgata       60
tttcatccaa ccaagaaga gtttaatgat tttgataaat atattgctta catggaatcc      120
caaggtgcac acagagctgg cttggctaag ataattccac ccaaagaatg gaaagccaga      180
gagacctatg ataatatcag tgaaatctta atagccactc ccctccagca ggtggcctct      240
gggcgggcag gggtgtttac tcaataccat aaaaaaaaga agccatgacc gtgggggag      300 tatcgccatt tggcaaacag taaaaaatat cagactccac cacaccagaa tttcgaagat      360
ttggagcgaa aatactggaa gaaccgcatc tataattcac cgatttatgg tgctgacatc      420
agtggctcct tgtttgatga aaacactaaa caatggaatc ttgggcacct gggaacaatt      480
caggacctgc tggaaaagga atgtgggtt gtcatagaag gcgtcaatac accctacttg      540
tactttggca tgtggaaaac cacgtttgct tggcatacag aggacatgga cctttacagc      600
atcaactacc tgcaccttgg ggagcccaaa acttggtatg tggtgccccc agaacatggc      660
cagcgcctgg aacgcctggc cagggagctc ttcccaggca gttccgggg ttgtggggcc       720 ttcctgcggc acaaggtggc cctcatctcg cctacagttc tcaaggaaaa tgggattccc      780
ttcaatcgca taactcagga ggctggagag ttcatggtga cctttcccta tggctaccat      840
```

-continued

| | |
|---|---|
| gctggcttca accatggttt caactgcgca gaggccatca attttgccac tccacgatgg | 900 |
| attgattatg gcaaaatggc ctcccagtgt agctgtgggg aggcaagggt gaccttttcc | 960 |
| atggatgcct tcgtgcgcat cctgcaacct gaacgctatg acctgtggaa acgtgggcaa | 1020 |
| gaccgggcag ttgtggacca catggagccc agagtaccag ccagccaaga gctgagcacc | 1080 |
| cagaaggaag tccagttacc caggagagca gcgctgggcc tgagacaact cccttcccac | 1140 |
| tgggcccggc attcccttg gcctatggct gcccgcagtg ggacacggtg ccacacccctt | 1200 |
| gtgtgctctt cactcccacg ccgatctgca gttagtggca ctgctacgca gccccgggct | 1260 |
| gctgctgtcc acagctctaa gaagcccagc tcaactccat catccacccc tggtccatct | 1320 |
| gcacagatta tccacccgtc aaatgttaga cgtggtcgtg gtcgccctcc tcagaaactg | 1380 |
| agagctcagg agctgacccct ccagactcca gccaagaggc ccctcttggc gggcacaaca | 1440 |
| tgcacagctt cgggtccaga acctgagccc ctacctgaga tggggctttt gatggacaag | 1500 |
| cctgtaccac tgagcccagg gctccagcag cctgtcaagg cttctgggtg cagctgggcc | 1560 |
| cctgtgccct aa | 1572 |

<210> SEQ ID NO 9
<211> LENGTH: 2745
<212> TYPE: DNA
<213> ORGANISM: Homo sapiens

<400> SEQUENCE: 9

| | |
|---|---|
| cgcgaggccg gctaggcccg aatgtcgtta gccgtgggga agatggcgg aaaatttaaa | 60 |
| aggctgcagc gtgtgttgca agtcttcttg gaatcagctg caggacctgt gccgcctggc | 120 |
| caagctctcc tgccctgccc tcggtatctc taagaggaac ctctatgact ttgaagtcga | 180 |
| gtacctgtgc gattacaaga agatccgcga acaggaatat acctggtga atggcgtgg | 240 |
| atatccagac tcagagagca cctgggagcc acggcagaat ctcaagtgtg tgcgtatcct | 300 |
| caagcagttc cacaaggact agaaaaggga gctgctccgg cggcaccacc ggtcaaagac | 360 |
| ccccccggcac ctggacccaa gcttggccaa ctacctggtg cagaaggcca agcagaggcg | 420 |
| ggcgctccgt cgctgggagc aggagctcaa tgccaagcgc agccatctgg gacgcatcac | 480 |
| tgtagagaat gaggtggacc tggacggccc tccgcgggcc ttcgtgtaca tcaatgagta | 540 |
| ccgtgttggt gagggcatca ccctcaacca ggtggctgtg ggctgcgagt gccaggactg | 600 |
| tctgtgggca cccactggag gctgctgccc ggggcgtca ctgcacaagt ttgcctacaa | 660 |
| tgaccagggc caggtgcggc ttcgagccgg gctgccatc tacgagtgca actcccgctg | 720 |
| ccgctgcggc tatgactgcc caaatcgtgt ggtacagaag ggtatccgat atgacctctg | 780 |
| catcttccgc acggatgatg ggcgtggctg gggcgtccgc accctggaga agattcgcaa | 840 |
| gaacagcttc gtcatggagt acgtgggaga gatcattacc tcagaggagg cagagcggcg | 900 |
| gggccagatc tacgaccgtc agggcgccac ctacctcttt gacctggact acgtggagga | 960 |
| cgtgtacacc gtggatgccg cctactatgg caacatctcc cactttgtca accacagttg | 1020 |
| tgaccccaac ctgcaggtgt acaacgtctt catagacaac cttgacgagc ggctgccccg | 1080 |
| catcgctttc tttgccacaa gaaccatccg ggcaggcgag gagctcacct tgattacaa | 1140 |
| catgcaagtg gaccccgtgg acatggagag cacccgcatg gactccaact ttggcctggc | 1200 |
| tgggctcccct ggctccccta gaagcgggt ccgtattgaa tgcaagtgtg ggactgagtc | 1260 |
| ctgccgcaaa tacctcttct agcccttaga agtctgaggc cagactgact gagggggcct | 1320 |
| gaagctacat gcacctcccc cactgctgcc ctcctgtcga gaatgactgc cagggcctcg | 1380 |

| | |
|---|---|
| cctgcctcca cctgccccca cctgctccta cctgctctac gttcagggct gtggccgtgg | 1440 |
| tgaggaccga ctccaggagt ccccttccc tgtcccagcc ccatctgtgg gttgcactta | 1500 |
| caaaccccca cccaccttca gaaatagttt ttcaacatca agactctctg tcgttgggat | 1560 |
| tcatggccta ttaaggaggt ccaaggggtg agtcccaacc cagccccaga atatatttgt | 1620 |
| ttttgcacct gcttctgcct ggagattgag gggtctgctg caggcctcct ccctgctgcc | 1680 |
| ccaaaggtat ggggaagcaa ccccagagca ggcagacatc agaggccaga gtgcctagcc | 1740 |
| cgacatgaag ctggttcccc aaccacagaa actttgtact agtgaaagaa aggggtccc | 1800 |
| tgggctacgg gctgaggctg gtttctgctc gtgcttacag tgctgggtag tgttggccct | 1860 |
| aagagctgta gggtctcttc ttcagggctg catatctgag aagtggatgc ccacatgcca | 1920 |
| ctggaaggga agtgggtgtc catgggccac tgagcagtga gaggaaggca gtgcagagct | 1980 |
| ggccagccct ggaggtaggc tgggaccaag ctctgccttc acagtgcagt gaaggtacct | 2040 |
| agggctcttg ggagctctgc ggttgctagg ggccctgacc tggggtgtca tgaccgctga | 2100 |
| caccactcag agctggaacc aagatctaga tagtccgtag atagcactta ggacaagaat | 2160 |
| gtgcattgat ggggtggtga tgaggtgcca ggcactgggt agagcacctg gtccacgtgg | 2220 |
| attgtctcag ggaagccttg aaaccacgg aggtggatgc caggaaaggg cccatgtggc | 2280 |
| agaaggcaaa gtacaggcca agaattgggg gtgggggaga tggcttcccc actatgggat | 2340 |
| gacgaggcga gagggaagcc cttgctgcct gccattccca gaccccagcc ctttgtgctc | 2400 |
| accctggttc cactggtctc aaaagtcacc tgcctacaaa tgtacaaaag gcgaaggttc | 2460 |
| tgatggctgc cttgctcctt gctcccccac ccctgtgag gacttctcta ggaagtcctt | 2520 |
| cctgactacc tgtgcccaga gtgcccctac atgagactgt atgccctgct atcagatgcc | 2580 |
| agatctatgt gtctgtctgt gtgtccatcc cgccgacccc ccagactaac ctccaggcat | 2640 |
| ggactgaatc tggttctcct cttgtacacc cctcaaccct atgcagcctg gagtgggcat | 2700 |
| caataaaatg aactgtcgac tgaaaaaaaa aaaaaaaaa aaaaa | 2745 |

<210> SEQ ID NO 10
<211> LENGTH: 3093
<212> TYPE: DNA
<213> ORGANISM: Homo sapiens

<400> SEQUENCE: 10

| | |
|---|---|
| cggggccgag gcgcgaggag gtgaggctgg agcgcggccc cctcgccttc cctgttccca | 60 |
| ggcaagctcc caaggcccgg gcggcggggc cgtcccgcgg gccagccaga tggcgacgtg | 120 |
| gcggttcccc gcccgccgcg accccaactc cgggacgcac gctgcggacg cctatcctcc | 180 |
| cccaggccgc tgacccgcct ccctgcccgg ccggctcccg ccgcgaggga tatggaatat | 240 |
| tatcttgtaa aatggaaagg atggccagat tctacaaata cttgggaacc tttgcaaaat | 300 |
| ctgaagtgcc cgttactgct tcagcaattc tctaatgaca agcataatta tttatctcag | 360 |
| gtaaagaaag gcaaagcaat aactccaaaa gacaataaca aaactttgaa acctgccatt | 420 |
| gctgagtaca ttgtgaagaa ggctaaacaa aggatagctc tgcagagatg gcaagatgaa | 480 |
| ctcaacagaa gaaagaatca taaggaatg atatttgttg aaaatactgt tgatttagag | 540 |
| ggcccacctt cagacttcta ttacattaac gaatacaaac cagctcctgg aatcagctta | 600 |
| gtcaatgaag ctacctttgg ttgttcatgc acagattgct tctttcaaaa atgttgtcct | 660 |
| gctgaagctg gagttctttt ggcttataat aaaaaccaac aaattaaaat cccacctggt | 720 |

```
actcccatct atgaatgcaa ctcaaggtgt cagtgtggtc ctgattgtcc caataggatt    780
gtacaaaaag gcacacagta ttcgctttgc atctttcgaa ctagcaatgg acgtggctgg    840
ggtgtaaaga cccttgtgaa gattaaaaga atgagttttg tcatggaata tgttggagag    900
gtaatcacaa gtgaagaagc tgaaagacga ggacagttct atgacaacaa gggaatcacg    960
tatctctttg atctggacta tgagtctgat gaattcacag tggatgcggc tcgatacggc   1020
aatgtgtctc attttgtgaa tcacagctgt gacccaaatc ttcaggtgtt caatgttttc   1080
attgataacc tcgatactcg tcttccccga atagcattgt tttccacaag aaccataaat   1140
gctggagaag agctgacttt tgattatcaa atgaaaggtt ctggagatat atcttcagat   1200
tctattgacc acagcccagc caaaagagg gtcagaacag tatgtaaatg tggagctgtg   1260
acttgcagag gttacctcaa ctgaacttttt tcaggaaata gagctgatga ttataatatt   1320
tttttcctaa tgttaacatt tttaaaaata catatttggg actcttatta tcaaggttct   1380
acctatgtta atttacaatt catgtttcaa gacatttgcc aaatgtatta ccgatgcctc   1440
tgaaaagggg gtcactgggt ctcatagact gatatgaagt cgacatattt atagtgctta   1500
gagaccaaac taatggaagg cagactattt acagcttagt atatgtgtac ttaagtctat   1560
gtgaacagag aaatgcctcc cgtagtgttt gaaagcgtta agctgataat gtaattaaca   1620
actgctgaga gatcaaagat tcaacttgcc atacacctca aattcggaga aacagttaat   1680
ttgggcaaat ctacagttct gttttttgcta ctctattgtc attcctgttt aatactcact   1740
gtacttgtat ttgagacaaa taggtgatac tgaattttat actgttttct acttttccat   1800
taaaacattg gcacctcaat gataaagaaa tttaaggtat aaaattaaat gtaaaaatta   1860
atttcagctt catttcgtat ttcgaagcaa tctagactgt tgtgatgagt gtatgtctga   1920
acctgtaatt cttaaaagac ttcttaatct tctagaagaa aaatctccga agagctctct   1980
ctagaagtcc aaaatggcta gccattatgc ttctttgaaa ggacatgata atgggaccag   2040
gatggttttt tggagtacca agcaaggga atggagcact ttaagggcgc ctgttagtaa   2100
catgaattgg aaatctgtgt cgagtacctc tgatctaaac ggtaaaacaa gctgcctgga   2160
gagcagctgt acctaacaat actgtaatgt acattaacat tacagcctct caatttcagg   2220
caggtgtaac agttccttc caccagattt aatatttta tacttcctgc aggttcttct   2280
taaaaagtaa tctatatttt tgaactgata cttgttttat acataaattt tttttagatg   2340
tgataaagct aaacttggcc aaagtgtgtg cctgaattat tagacctttt tattagtcaa   2400
cctacgaaga ctaaaataga atatattagt tttcaaggga gtgggaggct tccaacatag   2460
tattgaatct caggaaaaac tattctttca tgtctgattc tgagatttct aattgtgttg   2520
tgaaaatgat aaatgcagca aatctagctt tcagtattcc taattttac ctaagctcat   2580 tgctccaggc tttgattacc taaaataagc ttggataaaa ttgaaccaac ttcaagaatg   2640
cagcacttct taatctttag ctctttcttg ggagaagcta gactttattc attatattgc   2700
tatgacaact tcactctttc ataatatata ggataaattg tttacatgat tggaccctca   2760
gattctgtta accaaaattg cagaatgggg ggccaggcct gtgtggtggc tcacacctgt   2820
gatcccagca ctttgggagg ctgaggtagg aggatcacgt gaggtcggga gttcaagacc   2880
agcctggcca tcatggtgaa accctgtctc tactgaaaat acaaaaatta gccgggcgtg   2940
gtggcacacg cctgtagtcc cagctactca ggaggctgag gcaggagaat cacttgaatt   3000
caggaggcgg aggttgcagt gagccaagat cataccactg cactgcagcc tgagtgacac   3060
agtaagactg tctccaaaaa aaaaaaaaaa aaa                                3093
```

<210> SEQ ID NO 11
<211> LENGTH: 2681
<212> TYPE: DNA
<213> ORGANISM: Mus sp.

<400> SEQUENCE: 11

| | | | | | |
|---|---|---|---|---|---|
| gttgttagct | gtggagaaag | atggcggaaa | atttaaaagg | ttgcagtgtg | tgctgtaaat | 60 |
| cttcttggaa | tcaactgcag | gacctgtgcc | gactagccaa | gctttcttgt | cctgcccttg | 120 |
| gtgtttctaa | gaagaatctg | tatgactttg | aagttgaata | cctgtgtgat | tataagaaga | 180 |
| tccgtgagca | ggagtattac | ctggttaagt | ggcgtgggta | tcccgactca | gaaaacacct | 240 |
| gggagccacg | gcagaatcta | aatgtatac | gagttcttaa | gcagttccac | aaggacttag | 300 |
| aaagagagct | tgtccgacga | caccgccggt | caaagccacc | caggcatctg | gacccaaacc | 360 |
| tagccaatta | cctggtgcag | aaggccaagc | agaggcgggc | acttcagcgt | tgggaacaag | 420 |
| agctcaatgc | caagcgcagc | cacctggggc | ggatcaccgt | ggagaatgag | gtagacctgg | 480 |
| atggccctcc | aaggtccttt | gtctatatca | atgagtatcg | agttggtgag | ggcatcaccc | 540 |
| tcaaccaggt | agctgttggc | tgtgagtgcc | aggactgtct | gttggcaccc | actggaggct | 600 |
| gttgccctgg | agcatccctg | cacaagtttg | cctacaatga | ccaaggccag | gtgcgactga | 660 |
| aagctgggca | gcccatctac | gagtgcaact | cccgctgttg | ctgtggctat | gactgcccaa | 720 |
| accgtgtagt | ccagaaaggc | atccgctacg | atctctgcat | cttccgcact | aatgatggcc | 780 |
| gaggctgggg | tgtccgcacg | ctggaaaaga | tccgaaaaaa | tagctttgtt | atggagtatg | 840 |
| tgggagagat | tattacctca | gaggaggcag | agcggagggg | ccagatctac | gaccgccagg | 900 |
| gcgccaccta | cctctttgac | ctggactacg | tggaagacgt | ataccgtg | gatgccgctt | 960 |
| attatggcaa | catctctcat | tttgtcaacc | atagttgtga | tcccaacctg | caggtgtaca | 1020 |
| acgtattcat | agacaacctt | gatgagcgac | taccccgcat | cgcattcttt | gccacaagaa | 1080 |
| ccatctgggc | gggcgaggag | ctcacctttg | attacaacat | gcaagtggac | cccgtggaca | 1140 |
| tggagagtac | ccgaatggac | tccaactttg | gcctggctgg | gctccccggc | tcccccaaga | 1200 |
| aacgagtccg | tattgaatgc | aaatgtggga | caacggcttg | ccgaaaatac | ctcttctagc | 1260 |
| cttgagaagt | ctgaggccag | actaactgaa | ggggcctgaa | gccaccttcc | tctcctacag | 1320 |
| ctaccctctt | gtcaaggatg | accatcaatc | agagccttgt | ctgcctccac | ttgtcctcac | 1380 |
| ctaccctaac | ctgctctagg | gtcagggctg | ttgtgaggac | taactccggg | tacccttttc | 1440 |
| ctgttccttt | cccctgttc | caggcccatc | aggcattgca | cttaaaactc | ccagccccat | 1500 |
| tttcagaaac | atattttca | catcatgatt | cccctagagt | tggaattcat | gtcatataat | 1560 |
| ggaggtccag | attgaggaac | tcggctgtaa | aacagattct | ttgttttgac | agcatctctg | 1620 |
| cagctctatg | tagtaagtct | ggtgtttgga | ccgttaatct | tcctgtctca | gccttcctca | 1680 |
| tgatgagatt | gtaggtgtaa | acccagctaa | gattttgtt | ctaattgcat | ctgcttctgc | 1740 |
| ttggagcttg | tgtgtgaacc | tgttgcaggt | cctcttcatt | actctaatgg | tatgaggaag | 1800 |
| caaccccctg | gcagacagac | ttcagagctg | agataccagc | ctaacatcaa | gctggatcag | 1860 |
| caaccccaga | gcctttgtac | tcaggaaaga | aaaggcaatc | ttcagagctg | ggagataagg | 1920 |
| ctggttccgc | tctttgtgct | tttgatgctg | gctggtatta | accttaagac | ctatagggtc | 1980 |
| tcaacagttg | caagtctgaa | aagtagttgc | ccaaatgcca | tcagaatggg | gatggagtaa | 2040 |
| atacctcttt | gaaagccca | cagaaaggtt | agaactaagt | tttaccatca | ggaagtacag | 2100 |

| | |
|---|---:|
| tgctggactt gctggaaacc cagccttggc atttgatggc cactagaact actagaagct | 2160 |
| ggaaccaaga tctaggtatt ctttagatag cacttaagac agtaatgtgc atcgactaga | 2220 |
| aggcgatgtg atgccaggca cttggtagag cacctggtcc atacagattg tctcagggaa | 2280 |
| gccttgaaaa ccacaaaggt ggagcccaga aaaagcccca tgtgacagaa ggcaatgtct | 2340 |
| aggccaaaaa tacttgtcag ctcaagtatt cacctgggtc acttgtctca gttaactgcc | 2400 |
| tagaaatgta caaaggcaa agattctgat ggctgccttg cccctgctt ccccacctcc | 2460 |
| aggaagcctt tcctgacttc ctgtgcccag agtgccctat gtgaaactct gtaccctgct | 2520 |
| accagatgcc aggtctgtgt gtgtattttg tatatatgtt tcctgcccat acttcccata | 2580 |
| cttcccaggc tgaccttcag gcatggactg aatctggttc tctgtacccc tcagccctcc | 2640 |
| ctagcctgga gtgcacacca ataaactgtg ttgttgagtt a | 2681 |

<210> SEQ ID NO 12
<211> LENGTH: 1452
<212> TYPE: DNA
<213> ORGANISM: Mus sp.

<400> SEQUENCE: 12

| | |
|---|---:|
| gaatgaaagc tccgcaagat ggcgacggcc agggccaagg cacggggcag tgaggcagga | 60 |
| gcgcggtgtc accgggctcc aggtccgccc ccgaggccca aggccaggcg aacggcgaga | 120 |
| cgccgccgcg cggagaccct gacgcgcga cgctcgcggc cgtctgcggg cgagaggcgc | 180 |
| gccggctccc agcgagcgtg gtccggagct ccgcgggccg cggtctttgg cgacgagtgt | 240 |
| gcacgaggtg ccttattcaa ggcctggtgt gtgccttgcc tagtttcact tgatactctc | 300 |
| caggaattat gtagaaaaga aaagctcaca tgtaaatcga ttggaatcac caaaaggaat | 360 |
| ctaaacaatt atgaggtgga gtacttgtgt gactacaagg tagcaaaggg tgtggaatat | 420 |
| tatcttgtaa aatggaaagg atggccagat tctacaaaca cctgggagcc cttgagaaac | 480 |
| ctcaggtgtc cacagctcct gcggcagttc tctgatgaca agaagactta cttagctcag | 540 |
| gaaaggaaat gcaaggctgt caattcaaaa tccttgcaac ctgcaattgc tgagtatatt | 600 |
| gtacagaaag ctaagcaaag aatagctctg cagagatggc aagattacct caacagaaga | 660 |
| agaaccata aggggatgat atttgttgaa acactgttg acttggaggg cccacccttta | 720 |
| gacttctact acattaacga gtacaggcca gctcccggga tcagcataaa cagtgaagcc | 780 |
| acctttggat gttcatgtac agactgcttc tttgacaagt gttgtcctgc tgaagctgga | 840 |
| gttgtgttgg cttataataa gaagcaacaa attaaaatcc aaccaggcac tcccatctac | 900 |
| gaatgcaact caaggtgtcg atgtggacct gaatgtccca ataggattgt acaaaaaggc | 960 |
| acacaatatt cactgtgcat cttttaaaact agcaatggct gtggttgggg tgtaaaaacc | 1020 |
| cttgtgaaga ttaaaagaat gagttttgtc atggaatatg ttggagaggt gatcacaagt | 1080 |
| gaagaggccg agacgcgggg acagttctat gacaacaaag ggatcaccta cctctttgac | 1140 |
| ctggactacg agtctgatga gttcacagtg gatgcagctc gatatggaaa cgtatcccat | 1200 |
| tttgtgaatc atagttgtga cccaaatctt caggtgttta gtgttttcat cgataacctt | 1260 |
| gatactcggc tgcccaggat agcattgttc tctacaagaa ccataaacgc tggagaagag | 1320 |
| ctgacttttg actatcaaat gaaaggttct ggagaagcat cttcagactc cattgaccac | 1380 |
| agccctgcca aaaaaagggt cagaacccaa tgtaaatgtg gagccgagac ttgcagaggt | 1440 |
| tacctcaact ga | 1452 |

<210> SEQ ID NO 13
<211> LENGTH: 2711
<212> TYPE: DNA
<213> ORGANISM: Rattus sp.

<400> SEQUENCE: 13

| | | | | | |
|---|---|---|---|---|---|
| gtcgttagct | gtggagaaag | atggcggaaa | atttaaaagg | ttgcagtgtg | tgctgtaaat | 60 |
| cttcctggaa | tcagctgcag | gatctgtgcc | gactagccaa | gctttcttgt | cctgcccttg | 120 |
| gtgtttctaa | gaagaatctg | tatgactttg | aagttgaata | cctgtgtgat | tataagaaga | 180 |
| tccgtgagca | ggagtattac | ctggttaaat | ggcgtgggta | tcctgactca | gagaacacct | 240 |
| gggagccacg | gcagaatctc | aaatgtgtgc | gcattcttaa | gcagttccac | aaggacttag | 300 |
| aaagagagct | tgtccggcga | caccgccggt | caaagccacc | caggcatctg | acccaaaact | 360 |
| tagccaatta | cctggtgcag | aaggccaagc | agaggcgggc | actgcagcgt | tgggaacaag | 420 |
| agctcaatgc | caagcgcagc | catctggggc | ggatcactgt | ggagaatgag | gtagacctgg | 480 |
| atggccctcc | aaggtccttt | gtctatatca | atgagtatcg | agttggtgag | ggcatcaccc | 540 |
| tcaaccaggt | agctgttggc | tgtgagtgcc | aggactgtct | gttggcaccc | actggaggct | 600 |
| gttgccctgg | agcatccctg | cacaagtttg | cctacaatga | ccaaggccag | gtgcgactga | 660 |
| aagctgggca | gcccatctac | gagtgcaact | ctcgctgttg | ctgtggctat | gactgcccaa | 720 |
| accgtgtagt | ccagaaaggc | atccgctaca | acctctgcat | cttccgcact | gatgatggcc | 780 |
| gaggctgggg | tgtccgcacg | ctggaaaaga | tccgcaaaaa | tagctttgtt | atggagtatg | 840 |
| tgggagagat | tattacctca | gaggaggcag | agcggagggg | ccagatctac | gaccgccagg | 900 |
| gcgccaccta | cctctttgac | ctggactacg | tggaggacgt | atataccgtg | gatgccgcct | 960 |
| attatgcaa | catctctcac | tttgtcaacc | atagttgtga | tcccaacctg | caggtgtaca | 1020 |
| acgtattcat | agacaacctt | gatgagcgac | taccccgcat | cgcattcttt | gccacaagaa | 1080 |
| ccatctgggc | gggcgaggag | ctcacctttg | attacaacat | gcaagtggac | ccgtggaca | 1140 |
| tggagagtac | ccgaatggac | tccaactttg | gcctggcagg | gctccccggc | tcccccaaga | 1200 |
| aacgggtccg | tattgaatgc | aaatgtggga | caacagcttg | ccgaaaatac | ctcttctagc | 1260 |
| cctgagaagt | ctgaggccag | actaactgaa | ggggcctgaa | gccaccttcc | tcttctctac | 1320 |
| tgctacccte | ttgtcaagaa | tgaccatcaa | tcagagcctt | gtctgcctcc | acttgtcctc | 1380 |
| acctgccca | acctgctcca | gggtcagggc | tgttgtgagg | actaactccc | ggtacccttt | 1440 |
| ccctgttcct | ttccctatc | caggcccatc | aggcattgca | cttaaaactc | ccagccccat | 1500 |
| tttcagaagc | atatttttca | catcaggatt | ccctagattt | ggaattcatg | tcaatggagg | 1560 |
| tccaaagact | gaaaagactg | agcaactcag | ccccaaagca | gatttttttc | tctgcagctc | 1620 |
| tatgtagtta | gttcaggctg | gcgttggacc | tttaatcctc | ctgtctcagc | tttcctcatg | 1680 |
| atgaaattat | aggtgtaaac | ccagctaatt | gtatctgcta | attttctaat | tgtatctgct | 1740 |
| tcagctctga | gcccgagtga | cctgttgcag | gcctcttcac | tgctctatga | ggaagcaacc | 1800 |
| cctaggcaga | cagacatcag | agctgagata | ccagcccaac | atcaaactgg | atcagcaacc | 1860 |
| acggggcctt | tgtactcatg | aaagaaaagg | caatctccag | aaaggctgat | tctgctcatt | 1920 |
| gtgcttttaa | tgctggctaa | tactaacctt | aagacgcata | gggttgcaaa | gagagttgca | 1980 |
| ggtctgaaaa | gtagttgccc | aaatcccatc | agaatgggaa | tgaagtaaat | acctctttga | 2040 |
| aagcccctca | gaagggttag | aactaagttt | taccatcagg | aagtagagtg | ctgggcttac | 2100 |
| tggaaaccca | gccatggcat | ttgatggcca | ctagaattag | aagctggaac | caagatctag | 2160 |

-continued

```
gtattctgta gaaagcactt aaaaagacaa taacgtgcat cgattagaag gtgatgtgat    2220
gccaggcact tggtagagca cctggtccat atggattgtc tcagggaagc cttgaaaacc    2280
acagaggtgg agcccaggaa aaagcccatg tgacagaagg caatgtctag gcctaaaata    2340
cttgtcagct ccaagtattc acctgggtcc acttgtctca agttaactg cctagagttg     2400
tacaaaaggc aaagattctg atggctgcct tgtcccctgc ttccccacct ccaggaagct    2460
tttcctgagt tcctataccc agagtacccc tttgtgaaac tctgtaccct gctaccagat    2520
gccaggtctg tgtgtgtatt ttgtatatat gtgtcctgcc cacactcccc aggctgacct    2580
tcaggcatgg actgaatctg gttttctgtg taccctcctc agccctctct agcctggagt    2640
gcacaccaat aaactttgtt gttgaattaa taagctggag aaaaaaaaaa aaaaaaaaa     2700
aaaaaaaaaa a                                                         2711

<210> SEQ ID NO 14
<211> LENGTH: 4132
<212> TYPE: DNA
<213> ORGANISM: Rattus sp.

<400> SEQUENCE: 14
tgaatgaaag ctccgcaaga tggcggcggc cagggccaag gcacggagcg gtgaggccag      60
agcgcggtgt caccgggctc caggtccgcc ccagaggccc aaacccaggc gaacgacgag     120
acgctgccgc gcggacaccg tgacggcgcg acgctcgcgg tcgtctgcgg gcgggagacg     180
cgccggctcc aaccgagcga ggtccagagc tccgcgggcc gcggtctttg gcggcgagtg     240
tgcacgaggt gcctcattca aggcctggtg tgtgccttgc ctagtttcac ttgatactct     300
ccaggaatta tgtagaaaag aaaagctcac atgtaaatcg attggaatca ccaaaaggaa     360
tctaaacaat tatgaggtgg agtacttgtg tgactacaag gtagtaaagg gtgtggaata     420
ttatcttgta aagtggaaag gatggccaga ctctacaaac acctgggagc ccttgtggaa     480
cctcaggtgc ccacagctcc tgcagcagtt ctctgacgac aagaatactt acttatccca     540
gggaaggaaa cgcaaggcca tcacttcaaa agacaataac aaatccttgc aacctgcagt     600
tgctgagtat attgtacaga aagctaggca aagaatagct ctgcagagat ggcaagatta     660
cctcaacaga agaaagaacc acaaagggat gatatttgtt gaaaatactg ttgacttaga     720
gggcccacct tcagacttct actacatcaa tgaatacagg ccagctcctg ggatcacctt     780
aaacagtgaa gctaccttg ggtgttcgtg tacaaactgc ttctttgaaa agtgttgtcc      840
tgctgaagct ggagttgttt tggcttataa taagaaccga caaattaaaa tccaaccagg     900
cactcccatc tatgaatgca actcaaggtg ccgatgtgga cctgattgtc ccaataggat     960
tgtacagaaa ggcacacagt attccctgtg catctttaga actagcaatg gctgtggctg    1020
gggtgtaaaa acccttgtga agattaaaag gatgagtttt gtcatggaat atgttggaga    1080
ggtgatcacc agtgaagagg ctgagagacg gggacagctc tatgacaaca aagggatcac    1140
ctaccttttt gatctggact atgagtctga tgagttcaca gtggatgcag ctcgatatgg    1200
aaatgtgtct cattttgtga atcatagttg tgacccaaat cttcaggtgt ttagtgtttt    1260
catcgataac cttgatactc ggcttcccag gatagcattg ttctccacaa gaaccataaa    1320
ggctggagaa gagctgactt ttgactatca atgaaaggt tctggagaac tgtcttcaga     1380
ctctattgac tacagccctg ccagaaaaag ggtcagaacc caatgcaaat gtggagctga    1440
gacgtgcaga ggttacctca actgaaattt caggaagtgg agctcacgtt gtttgttttt    1500
ttgttttgtt tgtcttctaa caactgaaaa aagtatttgg gactcctttc tattacctat    1560
```

-continued

```
gtattgtatt atatgatgtt aatgtacaat tcatggctca agatatatgc caagtatatt    1620
actattgatt ctaaaaagga ctgcaaggcc atgtaaacaa gatggtggtt acatgggaag    1680
tgaactgtat aaatcacttg cttactcgag agtcgaagta gacagtcgtc cctttagttt    1740
tggaagtgag tcgaccacag ctattattga gccttttatc ctgcctcaaa cagagaactc    1800
actttaggca aatgtataaa ttttattttt ttactatatt gtttctgttt aatactcact    1860
gatcttgtat cagagacaaa taagtgacac tgaattttt tactgtattt tctactttta    1920
cattaaaaca ttggcatctt aatgatatat ttcaggtgta aaaaatgtga agatttact    1980 tttagcttga tcttactttg aggcaataga taccattaca aaggtatcta aacctgaaat    2040
tcttaaaaga tgtttttact cccacagaag aaaagtctct gatcaccttc tcggaattct    2100
gtagtgctgg ccactgtgtt tctgtgaaca gacagacaga cagaacagtg actgaggacg    2160
cactggagtg tcaggcagga aaggagtaca gcgtaagcca ctcagcatgt gtgagcacga    2220
cagcaccgtg tctctctctc tctccggaac aggagagtga gatccctgag ggcacaggt    2280 ccccaatggc agtgtaattc acatcacata ctgtcatctc aaggcagttt taattcctac    2340
ccactaaatt tcaatacttt tgtatttgt gcatgccctt gaaaagcaag ctctatttgc    2400
cctgatgctt gttttataca agagttttta gataggatga aacttagctt ggccaaaagt    2460
cggcctgatt gaacttttat cacctctggg gttagatggg gcttcccctg tgtagtaaaa    2520
cccaataaag aaaaaaactt tcattttct gggtctggga gttctaatcg tggtgtccaa    2580
tgtgaagaca gaaacaaaat gcagcaaata aacaaagctt ttggtatcct aagagtttcc    2640
taagctcact gctccaggct tgaataactg taataagctt aagtaaaatg aactgaattc    2700
aagaactcag tacttccttt aactttctaa ctcttaacct gttttgagag aagctacaat    2760
gttattcaga atattgcctt cgggggctac ttgttcacag tcatgcctgc tacccaaaac    2820
tttcagaatg tgtcaagaaa aaatataatt taaatggta tttcttttgt ttttctttga    2880
gaatcttaaa agcatcacag gtctgttttt ctcacacata cctccacccc cactgcaacc    2940
ctccatgacc aagctcactt tgaattattc tcaggttaaa aaattaaaaa aaaaatgttt    3000
gtctagatat ttggtcttat ttactgttta ggttaaaagg aaacttagga gggcaagaag    3060
aaaatgactt gtgtttagta aacgtgtggc tttgttttgt cttactaata gaaatttaat    3120
ggccctaagg ttctgtggga gtgggtgggc cttcagacag tatcttgtag ctcaggttgg    3180
ccttgaattt gctgtgtacc tgagtgcttt cttgaactct tcagtcctcc tgcctctccc    3240
tcccagtgct ggggttgtgg gcctgtgcca ccatgccctt tgacctttaa acgcacacca    3300
atttcactcg tgttccacac atggactgca ttactctctc tcagcattcc cccattactg    3360
tcctccagtt cctcttctgc tttcacctca tgagagctgt ccatacagcg gtgtgtgtat    3420
ttccttgttg ctgtgatcaa agcgatcaat tcagctctgc cttgattcct caaatcacat    3480
gttctaagta tgtcgtgtct tcatgacata ctcagctctg ggaggtgatc atgacaggaa    3540 cttttccagca gaggctagaa ctgtggagca cagctcactg gctggctccc tggctcccag    3600
gctcccctca gctaggcgtt cctacacagc ccacccgccc aggaatggtg taatggtacc    3660
taataagcga gaccctgcca catcagttag ccatcaagaa aatccgggcc aatgggacag    3720
agacagttcc tcagaggagg ttgtttcccc aggtaacccc agactgtcaa gtataaggta    3780
catgcaacca ttttgcattt gactgacatc tcttaaaggc tggcccgccc ttaggattct    3840
gggatgtatt gtgacattcc tagacgtttt taacctttgc taatctgtaa ctcttgaatg    3900
```

-continued

```
aagtagccac tatagttagt cctgcctgtt ttcctgctgt ctgtatggag cttccctcac    3960
acagcctaga taactctgaa gccctgctgc ttgcacctgg atgctggctg tgagcttact    4020
agctgtgtga actaacctgt gtgccttcct gcctacctca aagtgcgctt tcacagacta    4080
aagctttatg aagtgtgtgt gtgttttaa atcacagaat aaacacatat gt            4132
```

<210> SEQ ID NO 15
<211> LENGTH: 2888
<212> TYPE: DNA
<213> ORGANISM: Bos taurus

<400> SEQUENCE: 15

```
ggaatgtcgt tagccgtggg gaaagatggc ggaaagttta aaaggctgca gtgtgtgttg      60
caaatcttct tggaatcagc tacaggacct gtgccgcctg ccaagctct cctgccctgc     120 ccttggcatc tccaagagga acctctatga ctttgaagtc gagtacctgt gcgattacaa     180
aaagatccgc gaacaggagt attacctggt aaaatggcgt gggtacccag actccgagag     240
cacttgggaa ccacggcaga atctcaagtg tgtgcgcatt ctcaagcagt tccacaagga     300
cttggaaagg gagctgctcc ggcggcacca ccggtcaaag ccaccccggc acctggaccc     360
aagcctggcc aactacctgg tgcagaaggc caagcagagg cgggcactcc ggcgctggga     420
gcaggagctc aatgccaagc gcagccacct gggacgcatc accgtggaga acgaagtgga     480
cctggatggc cccccacggg ccttcgtgta catcaacgag taccgtgttg gtgagggcat     540
caccctcaac caggtggctg tgggctgcga gtgccaggac tgtctgtggg caccggccgg     600
aggctgctgc cctggggcgt cactgcacaa gtttgcctac aatgaccagg gccaggtgcg     660
cctgcgagcc gggctgccca tctatgagtg caactcccgc tgccgctgtg gctatgactg     720 cccccaaccgc gtggtacaga agggcatccg ctacgacctc tgcatcttcc gcacggatga     780
tggacgcggc tggggtgtcc gcacgctgga agagatccgc aagaacagtt tcgtcatgga     840
gtacgtgggc gagatcatta cctcagagga ggcagagcgg cggggccaga tctatgaccg     900
ccagggtgcc acctacctct tcgacctgga ctacgtggag gatgtgtaca ctgtggacgc     960
cgcctattac ggcaacatct tcacttttgt caaccacagt tgtgacccca acctccaggt    1020
gtacaacgtc ttcatagaca accttgatga gcggctgccc cgcattgctt tctttgccac    1080
cagaaccatc cggcaggcg aggagctcac ctttgattac aacatgcaag tggacccggt    1140
ggacatggag agcacacgca tggactccaa cttttggcctg gctgggctcc ccggctctcc    1200
caagaagcgg gtccgcattg aatgcaagtg tgggactgaa tcctgccgca aatacctctt    1260
ctagccccgt gaagtctgag gccagactga ccaagggagg ctaaaaagct gcccaccccca    1320 cctacccact gctgccctcc tgttgaagaa caactgccag ggcctcctgc ctgcctccgc    1380
ctgccccctg ctcagggctg catggccatg gggaagatgg actccaggag tcccctctcc    1440
ctgtcccagc cccatccatg ggttgcactt acaaacccct gcccaccttc agaagtgatt    1500
tttcaacacc aggactttct gcagttggga ttcatggcct agcaaggcgg tctgagggct    1560
gagcctcagc ccatacccaa agtagaaacg tttgtttttg cacctgcttc tggccagagc    1620
ttgaagggtc tgctgcaggc cctctccctg ctgcccaag ggtgtgagga agcattccca     1680
ggacaggctg accccagagc ccaggattcc cagtccattc acctcccctg ccacagaaat    1740
gtgctagtga agtgggggggg ggggcggtct tcaagggctg caggctgtgg ctgggtcctg    1800
ctcatgcttg catgctggct ggtgttggcc tgacagctgt agggtctcct tttcaaagct    1860
gtgcctctga gaagcagaca cccacatgcc actagaggag agtggatgcc cacagcctgt    1920
```

| | |
|---|---|
| tggccagtga gaggcagccc agactttgcc tgtccttaag gtgggcaacc cactccagta | 1980 |
| ttcttgcctg aaaaatccca tggacagagg aacctggtag gctacagtcc atggggtcac | 2040 |
| aaagagttgg acatgactaa gcgacttcac ttcactaagg tgggctggga ctcagctctg | 2100 |
| cctttgcaac agctagaagg tgcccagggc tcttgagctc aaaggatgct gggagccctt | 2160 |
| aacctgcagc gtgaggactg ctgatagcac ccagagctgg gcccaagacc tagctaggct | 2220 |
| gtagacagca cttagacaaa atgtgcatgg atgggatact gaggaggtgc caggcactgg | 2280 |
| gctgagcacc tggtccacgt ggatcgtctc agggaagcct tgaaaactat ggaggtggat | 2340 |
| cccaggaaag ggcccgtgtg gcagaaggca agcacagac caagaatggg gtggggctgg | 2400 |
| cttacccacc agggtgtggc gaggtgaggg gaagcccctg tcgcctccta gccctccagc | 2460 |
| cctttgcact caccttgggt cctctggtct cagttccctg cccacaaatg tataaaaggt | 2520 |
| gaaggcgctg atggctgcct catcccttgc ttcccctgtg aggtcttctc taggaagcct | 2580 |
| tccatccctg actacctgtg cgcagtgtcc ccacgtgaga ctgtgtgccc tgccagcaga | 2640 |
| tgccagatct gtgtgtctgt ttttgtgtgt ctgtgctccc cacccccaga ctgaccttca | 2700 |
| ggcttgtact gaatctgatt ctcctcttgt atatccccct ggccctccca gtctgggaat | 2760 |
| gggcgtcaat aaaacaggtt attgactgaa aaaaaaaaa aaaaaaaaa aaaaaaaaa | 2820 |
| aaaaaaaaa aaaaaaaaa aaaaaaaaa aaaaaaaaa aaaaaaaaa agaaaaaaaa | 2880 |
| aaaaaaaa | 2888 |

<210> SEQ ID NO 16
<211> LENGTH: 1863
<212> TYPE: DNA
<213> ORGANISM: Bos taurus

<400> SEQUENCE: 16

| | |
|---|---|
| gagtttgaat gaaagctcct caagatggcg gcggccgggg ccgaggcgcc aggagcttgg | 60 |
| tgtgtgcctt gcctagtttc acttgatact cttcaggaat tatgtagaaa agaaaagctc | 120 |
| acatgtaaat cgattggaat caccaaaagg aatctaaaca attatgaggt ggaatacttg | 180 |
| tgtgactaca aggtagtaaa ggatatggaa tattatcttg taaaatggaa aggatggcca | 240 |
| gattctacaa atacttggga accttttgcaa aatctcaagt gcccattact acttcagcag | 300 |
| ttctttaatg acaagcataa ttatttatct caggtaaaga aaggcaaagc aataactcta | 360 |
| aaagaaaatc acagagcctt gaaacctgct gttgctgaat acattgtaaa gaaggctaaa | 420 |
| caaaggatag ccctgcagag atggcaggat gaactcaaca gaaggaagac tcacaaagga | 480 |
| atgatttttg ttgaaaatac tgtggactta gagggcccc cttcagactt ctactacatt | 540 |
| aatgaataca aaccagctcc tggaatcagc ttagtaaatg aagctacctt tggttgttca | 600 |
| tgcacagatt gcttctttga aaatgttgt cctgctgaag ctggagttct tttggcttat | 660 |
| aataaaaatc aacaaattaa atcccacct ggtacccca tttatgagtg caactcaaga | 720 |
| tgtcaatgtg acccgactg tcccaacagg atcgtacaaa aaggcacaca gtattcactt | 780 |
| tgcatctttc gaactagcaa tggctgtggc tggggtgtaa aaaccccttgt gaagattaaa | 840 |
| agaatgagtt ttgtcatgga atatgttgga gaggtgatca ccagtgagga agctgagaga | 900 |
| cgtggccagt tatatgacaa caaaggaatc acgtatctct ttgatctgga ctatgaatct | 960 |
| gatgaattca cagtggatgc agctcgatat ggaaatgtgt ctcattttgt gaatcacagt | 1020 |
| tgtgacccaa accttcaggt gttcaatgtt ttcattgata acctcgatac ccgtcttccc | 1080 |

```
cgaatagcat tattttccac gagaactatc aatgctggag aagagctcac ttttgattat    1140
caaatgaaag gttctggaga tgtatcttca gattctattg accacagccc agccaaaaag    1200
agggccagaa ctgtgtgcaa atgtggagct gtgacttgca gaggttacct caactgaatt    1260
ttcaggaaat agaacttatg acgattatag tgttttttct aatgttaaca ttttaaaagt    1320
attttggact cttttcatat tatcaagatt atacactacg ttgatttaca atttaccttt    1380
cagactattg accaaatgcg ttactgatcc ttttgaagag aggaacgtgg gggtcacata    1440
gactaattct acatatacat attcagtggt tagataccaa acatgaaagg aaaactgttt    1500
gcaaatcaac aactatatac ttaacaggaa gtctatgtga atatagagaa atgcctcctt    1560
cagtgtttaa gtgttaaact gatgatgtaa cagttgctaa gattgaacat tcaatttgcc    1620
atataccttg aatttagaat tggacaaata cacaagttct attttttgtta ttgtcattcc    1680 tgtttaccta cttaacaact ctttgtactt gtatttgaga caaataggtg atactgaatt    1740
atactctatt ttctactttc attaaaacat tggtatctta aaaaaaaaa aaaaaaaaa     1800 aaaaaaaaa aaaaaaaaa aaaaaaaaa aaaaaaaaa aaaaagaaa aaaaaaaaa        1860 aaa                                                                 1863

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gaaacgaguc cguauugaat t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
uucaauacgg acucguuuct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
gcucacaugu aaaucgauut t                                              21

<210> SEQ ID NO 20
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
aaucgauuua caugugagct t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
gguguacaac guauucauat t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
uaugaauacg uuguacacct g                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
gguccuuugu cuauaucaat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
uugauauaga caaaggacct t                                              21

<210> SEQ ID NO 25
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
gcucacaugu aaaucgauut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
aaucgauuua caugugagct t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
gugucgaugu ggaccugaat t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
uucaggucca caucgacacc t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
ggacuacagu aucaugacat t                                              21
```

```
<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
ugucaugaua cuguaguccc a                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
ggacgaugca ggagauagat t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
ucuaucuccu gcaucguccg a                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
ggaugggugu cgggauaaat t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
uuuaucccga cacccauect t                                              21
```

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 35
gcaccuuugu cugcgaauat t          21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 36
uauucgcaga caaaggugcc c          21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 37
gaucaaaccu gcucggaaat t          21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 38
uuuccgagca gguuugaucc a          21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 39
gaauuugccu ucuuaugcat t          21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
ugcauaagaa ggcaaauuct t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gaggaauucu agucccguat t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
uacgggacua gaauuccuca a                                              21

<210> SEQ ID NO 43
<211> LENGTH: 2752
<212> TYPE: DNA
<213> ORGANISM: Homo sapiens

<400> SEQUENCE: 43
cgctcttctc gcgaggccgg ctaggcccga atgtcgttag ccgtggggaa agatggcgga      60
aaatttaaaa ggctgcagcg tgtgttgcaa gtcttcttgg aatcagctgc aggacctgtg     120
ccgcctggcc aagctctcct gccctgccct cggtatctct aagaggaacc tctatgactt     180
tgaagtcgag tacctgtgcg attacaagaa gatccgcgaa caggaatatt acctggtgaa     240
atggcgtgga tatccagact cagagagcac ctggagccaa cggcagaatc tcaagtgtgt     300
gcgtatcctc aagcagttcc acaaggactt agaaagggag ctgctccggc ggcaccaccg     360
gtcaaagacc ccccggcacc tggacccaag cttggccaac tacctggtgc agaaggccaa     420
gcagaggcgg gcgctccgtc gctgggagca ggagctcaat gccaagcgca gccatctggg     480
acgcatcact gtagagaatg aggtggacct ggacggccct ccgcgggcct tcgtgtacat     540
caatgagtac cgtgttggtg agggcatcac cctcaaccag gtggctgtgg gctgcgagtg     600
ccaggactgt ctgtgggcac ccactggagg ctgctgcccg ggggcgtcac tgcacaagtt     660

```
tgcctacaat gaccagggcc aggtgcggct tcgagccggg ctgcccatct acgagtgcaa      720
ctcccgctgc cgctgcggct atgactgccc aaatcgtgtg gtacagaagg gtatccgata     780
tgacctctgc atcttccgca cggatgatgg gcgtggctgg ggcgtccgca ccctggagaa     840
gattcgcaag aacagcttcg tcatggagta cgtgggagag atcattacct cagaggaggc     900
agagcggcgg ggccagatct acgaccgtca gggcgccacc tacctctttg acctggacta     960
cgtggaggac gtgtacaccg tggatgccgc ctactatggc aacatctccc actttgtcaa     1020
ccacagttgt gaccccaacc tgcaggtgta caacgtcttc atagacaacc ttgacgagcg     1080
gctgccccgc atcgctttct ttgccacaag aaccatccgg gcaggcgagg agctcacctt     1140
tgattacaac atgcaagtgg accccgtgga catggagagc acccgcatgg actccaactt     1200
tggcctggct gggctccctg ctcccctaa gaagcgggtc cgtattgaat gcaagtgtgg      1260
gactgagtcc tgccgcaaat acctcttcta gcccttagaa gtctgaggcc agactgactg     1320 aggggcctg aagctacatg cacctccccc actgctgccc tcctgtcgag aatgactgcc      1380
agggcctcgc ctgcctccac ctgccccac ctgctcctac ctgctctacg ttcagggctg      1440
tggccgtggt gaggaccgac tccaggagtc ccctttccct gtcccagccc catctgtggg     1500
ttgcacttac aaacccccac ccaccttcag aaatagtttt tcaacatcaa gactctctgt     1560
cgttgggatt catggcctat taaggaggtc caaggggtga gtcccaaccc agccccagaa     1620
tatatttgtt tttgcacctg cttctgcctg gagattgagg ggtctgctgc aggcctcctc     1680
cctgctgccc caaaggtatg ggaagcaac cccagagcag gcagacatca gaggccagag      1740
tgcctagccc gacatgaagc tggttcccca accacagaaa ctttgtacta gtgaaagaaa     1800 ggggtccct gggctacggg ctgaggctgg tttctgctcg tgcttacagt gctgggtagt      1860
gttggcccta agagctgtag ggtctcttct tcagggctgc atatctgaga agtggatgcc     1920
cacatgccac tggaagggaa gtgggtgtcc atgggccact gagcagtgag aggaaggcag     1980
tgcagagctg gccagccctg gaggtaggct gggaccaagc tctgccttca cagtgcagtg     2040
aaggtaccta gggctcttgg gagctctgcg gttgctaggg gccctgacct ggggtgtcat     2100
gaccgctgac accactcaga gctggaacca agatctagat agtccgtaga tagcacttag     2160
gacaagaatg tgcattgatg gggtggtgat gaggtgccag gcactgggta gagcacctgg     2220
tccacgtgga ttgtctcagg gaagccttga aaaccacgga ggtggatgcc aggaaagggc     2280
ccatgtggca gaaggcaaag tacaggccaa gaattggggg tgggggagat ggcttcccca     2340
ctatgggatg acgaggcgag agggaagccc ttgctgcctg ccattcccag accccagccc     2400
tttgtgctca ccctggttcc actggtctca aaagtcacct gcctacaaat gtacaaaagg     2460
cgaaggttct gatggctgcc ttgctccttg ctcccccacc cctgtgagg acttctctag       2520 gaagtccttc ctgactacct gtgcccagag tgcccctaca tgagactgta tgccctgcta     2580
tcagatgcca gatctatgtg tctgtctgtg tgtccatccc gccggcccc cagactaacc      2640 tccaggcatg gactgaatct ggttctcctc ttgtacaccc ctcaaccctta tgcagcctgg    2700 agtgggcatc aataaaatga actgtcgact gaacaaaaaa aaaaaaaaaa aa             2752
```

<210> SEQ ID NO 44
<211> LENGTH: 3093
<212> TYPE: DNA
<213> ORGANISM: Homo sapiens

<400> SEQUENCE: 44

```
cggggccgag gcgcgaggag gtgaggctgg agcgcggccc cctcgccttc cctgttccca     60
```

-continued

```
ggcaagctcc caaggcccgg gcggcggggc cgtcccgcgg gccagccaga tggcgacgtg      120
gcggttcccc gcccgccgcg accccaactc cgggacgcac gctgcggacg cctatcctcc      180
cccaggccgc tgacccgcct ccctgcccgg ccggctcccg ccgcggagga tatggaatat      240
tatcttgtaa aatggaaagg atggccagat tctacaaata cttgggaacc tttgcaaaat      300
ctgaagtgcc cgttactgct tcagcaattc tctaatgaca agcataatta tttatctcag      360
gtaaagaaag gcaaagcaat aactccaaaa gacaataaca aaactttgaa acctgccatt      420
gctgagtaca ttgtgaagaa ggctaaacaa aggatagctc tgcagagatg caagatgaa       480 ctcaacagaa gaaagaatca taaaggaatg atatttgttg aaaatactgt tgatttagag      540
ggcccacctt cagacttcta ttacattaac gaatacaaac cagctcctgg aatcagctta      600
gtcaatgaag ctacctttgg ttgttcatgc acagattgct tctttcaaaa atgttgtcct      660
gctgaagctg gagttctttt ggcttataat aaaaaccaac aaattaaaat cccacctggt      720
actcccatct atgaatgcaa ctcaaggtgt cagtgtggtc ctgattgtcc caataggatt      780
gtacaaaaag gcacacagta ttcgctttgc atctttcgaa ctagcaatgg acgtggctgg      840
ggtgtaaaga cccttgtgaa gattaaaaga atgagttttg tcatggaata tgttggagag      900
gtaatcacaa gtgaagaagc tgaaagacga ggacagttct atgacaacaa gggaatcacg      960
tatctctttg atctggacta tgagtctgat gaattcacag tggatgcggc tcgatacggc      1020
aatgtgtctc attttgtgaa tcacagctgt gacccaaatc ttcaggtgtt caatgttttc      1080
attgataacc tcgatactcg tcttccccga atagcattgt tttccacaag aaccataaat      1140
gctggagaag agctgacttt tgattatcaa atgaaaggtt ctggagatat atcttcagat      1200
tctattgacc acagcccagc caaaaagagg gtcagaacag tatgtaaatg tggagctgtg      1260
acttgcagag gttacctcaa ctgaacttttt tcaggaaata gagctgatga ttataatatt      1320
tttttcctaa tgttaacatt tttaaaaata catatttggg actcttatta tcaaggttct      1380
acctatgtta atttacaatt catgtttcaa gacatttgcc aaatgtatta ccgatgcctc      1440
tgaaaagggg gtcactgggt ctcatagact gatatgaagt cgacatattt atagtgctta      1500
gagaccaaac taatggaagg cagactattt acagcttagt atatgtgtac ttaagtctat      1560
gtgaacagag aaatgcctcc cgtagtgttt gaaagcgtta agctgataat gtaattaaca      1620
actgctgaga gatcaaagat tcaacttgcc atacacctca aattcggaga aacagttaat      1680
ttgggcaaat ctacagttct gttttttgcta ctctattgtc attcctgttt aatactcact      1740
gtacttgtat ttgagacaaa taggtgatac tgaatttat actgttttct acttttccat       1800
taaaacattg gcacctcaat gataaagaaa tttaaggtat aaaattaaat gtaaaaatta      1860
atttcagctt catttcgtat ttcgaagcaa tctagactgt tgtgatgagt gtatgtctga      1920
acctgtaatt cttaaaagac ttcttaatct tctagaagaa aaatctccga agagctctct      1980
ctagaagtcc aaaatggcta gccattatgc ttctttgaaa ggacatgata atgggaccag      2040
gatggttttt tggagtacca agcaagggga atggagcact ttaagggcgc ctgttagtaa      2100
catgaattgg aaatctgtgt cgagtacctc tgatctaaac ggtaaaacaa gctgcctgga      2160
gagcagctgt acctaacaat actgtaatgt acattaacat tacagcctct caatttcagg      2220
caggtgtaac agttcctttc caccagattt aatattttta tacttcctgc aggttcttct      2280
taaaaagtaa tctatatttt tgaactgata cttgttttat acataaattt tttttagatg      2340
tgataaagct aaacttggcc aaagtgtgtg cctgaattat tagacctttt tattagtcaa      2400
```

| | |
|---|---|
| cctacgaaga ctaaaataga atatattagt tttcaaggga gtgggaggct tccaacatag | 2460 |
| tattgaatct caggaaaaac tattctttca tgtctgattc tgagatttct aattgtgttg | 2520 |
| tgaaaatgat aaatgcagca aatctagctt tcagtattcc taattttac ctaagctcat | 2580 |
| tgctccaggc tttgattacc taaaataagc ttggataaaa ttgaaccaac ttcaagaatg | 2640 |
| cagcacttct taatctttag ctctttcttg ggagaagcta gactttattc attatattgc | 2700 |
| tatgacaact tcactctttc ataatatata ggataaattg tttacatgat tggaccctca | 2760 |
| gattctgtta accaaaattg cagaatgggg ggccaggcct gtgtggtggc tcacacctgt | 2820 |
| gatcccagca ctttgggagg ctgaggtagg aggatcacgt gaggtcggga gttcaagacc | 2880 |
| agcctggcca tcatggtgaa accctgtctc tactgaaaat acaaaaatta gccgggcgtg | 2940 |
| gtggcacacg cctgtagtcc cagctactca ggaggctgag gcaggagaat cacttgaatt | 3000 |
| caggaggcgg aggttgcagt gagccaagat cataccactg cactgcagcc tgagtgacac | 3060 |
| agtaagactg tctccaaaaa aaaaaaaaaa aaa | 3093 |

```
<210> SEQ ID NO 45
<211> LENGTH: 4449
<212> TYPE: DNA
<213> ORGANISM: Homo sapiens

<400> SEQUENCE: 45
```

| | |
|---|---|
| ggcactaaag gtttgcttcc gggcgtttct tttgcttccc cttccctctt tcacgcttcc | 60 |
| tccctcccc ctcctccctt atcccttcgc tttcgctctt ttccgtcgag gccgacccct | 120 |
| gagttgtgag tctgggggtct ggttggtgaa aagagccct tgaagctgga agacgggaga | 180 |
| ggacaaaagc atgtcttccc ttcctgggtg cattggtttg gatgcagcaa cagctacagt | 240 |
| ggagtctgaa gagattgcag agctgcaaca ggcagtggtt gaggaactgg gtatctctat | 300 |
| ggaggaactt cggcatttca tcgatgagga actggagaag atggattgtg tacagcaacg | 360 |
| caagaagcag ctagcagagt tagagacatg ggtaatacag aaagaatctg aggtggctca | 420 |
| cgttgaccaa ctctttgatg atgcatccag ggcagtgact aattgtgagt ctttggtgaa | 480 |
| ggacttctac tccaagctgg gactacaata ccgggacagt agctctgagg acgaatcttc | 540 |
| ccggcctaca gaaataattg agattcctga tgaagatgat gatgtcctca gtattgattc | 600 |
| aggtgatgct gggagcagaa ctccaaaaga ccagaagctc cgtgaagcta tggctgcctt | 660 |
| aagaaagtca gctcaagatg ttcagaagtt catggatgct gtcaacaaga gagcagttc | 720 |
| ccaggatctg cataaaggaa ccttgagtca gatgtctgga gaactaagca agatggtga | 780 |
| cctgatagtc agcatgcgaa ttctgggcaa gaagagaact aagacttggc acaaaggcac | 840 |
| ccttattgcc atccagacag ttgggccagg gaagaaatac aaggtgaaat ttgacaacaa | 900 |
| aggaaagagt ctactgtcgg ggaaccatat tgcctatgat taccaccctc ctgctgacaa | 960 |
| gctgtatgtg ggcagtcggg tggtcgccaa atacaaagat gggaatcagg tctggctcta | 1020 |
| tgctggcatt gtagctgaga caccaaacgt caaaaacaag ctcaggtttc tcattttctt | 1080 |
| tgatgatggc tatgcttcct atgtcacaca gtcggaactg tatcccattt gccggccact | 1140 |
| gaaaaagact tgggaggaca tagaagacat ctcctgccgt gacttcatag aggagtatgt | 1200 |
| cactgcctac cccaaccgcc ccatggtact gctcaagagt ggccagctta tcaagactga | 1260 |
| gtgggaaggc acgtggtgga agtcccgagt tgaggaggtg gatggcagcc tagtcaggat | 1320 |
| cctcttcctg gatgacaaaa gatgtgagtg gatctatcga ggctctacac ggctggagcc | 1380 |
| catgttcagc atgaaaacat cctcagcctc tgcactggag aagaagcaag gacagctcag | 1440 |

```
gacacgtcca aatatgggtg ctgtgaggag caaaggccct gttgtccagt acacacagga    1500
tctgaccggt actggaaccc agttcaagcc agtggaaccc ccacagccta cagctccacc    1560
tgccccacct ttcccacctg ctccacctct atccccccaa gcaggtgaca gtgacttgga    1620
aagccagctt gcccagtcac ggaagcaggt agccaaaaag agcacgtcct ttcgaccagg    1680
atctgtgggc tctggtcatt cctcccctac atctcctgca ctcagtgaaa atgtctctgg    1740
tgggaaacct gggatcaacc agacatatag atcaccttta ggctccacag cctctgcccc    1800
agcaccctca gcactcccgg cccctccagc accccagtc ttccatggca tgctggagcg    1860
ggccccagca gagccctcct accgtgctcc catggagaag cttttctact tacctcatgt    1920
ctgcagctat acctgtctgt ctcgagtcag acctatgagg aatgagcagt accggggcaa    1980
gaaccctctg ctggtcccgt tactatatga cttccggcgg atgacagccc ggcgtcgagt    2040
taaccgcaag atgggctttc atgttatcta taagacacct tgtggtctct gccttcggac    2100
aatgcaggag atagaacgct acctttcga gactggctgt gacttcctct tcctggagat    2160
gttctgtttg gatccatatg ttcttgtgga ccgaaagttt cagccctata agccttttta    2220
ctatattttg gacatcactt atgggaagga agatgttccc ctatcctgtg tcaatgagat    2280
tgacacaacc cctccacccc aggtggccta cagcaaggaa cgtatcccgg gcaagggtgt    2340
tttcattaac acaggccctg aatttctggt tggctgtgac tgcaaggatg ggtgtcggga    2400
caagtccaag tgtgcctgcc atcaactaac tatccaggct acagcctgta ccccaggagg    2460
ccaaatcaac cctaactctg ctaccagta caagagacta aagagtgtc tacccacagg    2520
ggtatatgag tgtaacaaac gctgcaaatg tgacccaaac atgtgcacaa accggttggt    2580
gcaacatgga ctacaagttc ggctacagct attcaagaca cagaacaagg ctggggtat    2640
ccgctgcttg gatgacattg ccaaaggctc ttttgtttgt atttatgcag gcaaaatcct    2700
gacagatgac tttgcagaca aggagggtct ggaaatgggt gatgagtact ttgcaaatct    2760
ggaccatatc gagagcgtgg agaacttcaa agaaggatat gagagtgatg cccctgttc    2820
ctctgacagc agtggtgtag acttgaagga ccaggaagat ggcaacagcg gtacagagga    2880
ccctgaagag tccaatgatg atagctcaga tgataacttc tgtaaggatg aggacttcag    2940
caccagttca gtgtggcgga gctatgctac ccggaggcag acccggggcc agaaagagaa    3000
cggactctct gagacaactt ccaaggactc ccaccccca gatcttggac ccccacatat    3060
tcctgttcct ccctcaatcc ctgtaggtgg ctgcaatcca ccttcctccg aagagacacc    3120
caagaacaag gtggcctcat ggttgagctg caatagtgtc agtgaaggtg gttttgctga    3180
ctctgatagc cattcatcct tcaagactaa tgaaggtggg gagggccggg ctggggaag    3240
ccgaatggag gctgagaagg cctccaccc aggactaggc atcaaggatg agggagacat    3300
caaacaggcc aagaaagagg acactgacga ccgaaacaag atgtcagtag ttactgaaag    3360
ctctcgaaat tacggttaca atccttctcc tgtgaagcct gaaggacttc gccgccacc    3420
tagtaagact agtatgcatc aaagccgaag actcatggct tctgctcagt ccaaccctga    3480
tgatgtcctg acactgtcca gcagcacaga aagtgagggg aaagtggga ccagccgaaa    3540
gcccactgct ggtcagactt cggctacagc ggttgacagt gatgatatcc agaccatatc    3600
ctctggctct gaaggggatg actttgagga caagaagaac atgactggtc aatgaagcg    3660
tcaagtggca gtaaaatcaa cccgaggctt tgctcttaaa tcaacccatg ggattgcaat    3720
taaatcaacc aacatggcct ctgtggacaa ggggagagc gcacctgttc gtaagaacac    3780
```

| | |
|---|---|
| acgccaattc tatgatggcg aggagtcttg ctacatcatt gatgccaagc ttgaaggcaa | 3840 |
| cctgggccgc tacctcaacc acagttgcag ccccaacctg tttgtccaga atgtcttcgt | 3900 |
| ggatacccat gatcttcgct tcccctgggt ggccttcttt gccagcaaaa gaatccgggc | 3960 |
| tgggacagaa cttacttggg actacaacta cgaggtgggc agtgtggaag caaggagct | 4020 |
| actctgttgc tgtggggcca ttgaatgcag aggacgtctt ctttagagga cagccttctt | 4080 |
| cccaacccTT cttgaactgt cgtttcctca ggaactgggt cttcctgatt gttgaaccct | 4140 |
| gacccgaagt ctctgggcta gctactcccc ccagctccta gttgatagaa atgggggttc | 4200 |
| tggaccagat gatcccttcc aatgtggtgc tagcaggcag gatcccttct ccacctccaa | 4260 |
| aggccctaaa gggtggggag agatcaccac tctaacctcg gcctgacatc cctcccatcc | 4320 |
| catatttgtc caagtgttcc tgcttctaac agactttgtt cttagaatgg agcctgtgta | 4380 |
| tctactatct ccagtttgta ttatttcttg aaagtctttt aacaatatga taaaactaag | 4440 |
| attgtgaaa | 4449 |

<210> SEQ ID NO 46
<211> LENGTH: 5123
<212> TYPE: DNA
<213> ORGANISM: Homo sapiens

<400> SEQUENCE: 46

| | |
|---|---|
| gcgcgggagg ggcggggcca cgctgcgggc ccgggccatg gccgccgccg atgccgaggc | 60 |
| agttccggcg agggggggagc ctcagcagga ttgctgtgtg aaaaccgagc tgctgggaga | 120 |
| agagacacct atggctgccg atgaaggctc agcagagaaa caggcaggag aggcccacat | 180 |
| ggctgcggac ggtgagacca atgggtcttg tgaaaacagc gatgccagca gtcatgcaaa | 240 |
| tgctgcaaag cacactcagg acagcgcaag ggtcaacccc caggatggca ccaacacact | 300 |
| aactcggata gcggaaaatg gggtttcaga aagagactca gaagcggcga agcaaaacca | 360 |
| cgtcactgcc gacgactttg tgcagacttc tgtcatcggc agcaacggat acatcttaaa | 420 |
| taagccggcc ctacaggcac agcccttgag gactaccagc actctggcct cttcgctgcc | 480 |
| tggccatgct gcaaaaaccc ttcctggagg ggctggcaaa gcaggactc caagcgcttt | 540 |
| tccccagacg ccagccgccc caccagccac ccttggggag gggagtgctg acacagagga | 600 |
| caggaagctc ccgccccctg cgccgacgt caaggtccac agggcacgca agaccatgcc | 660 |
| gaagtccgtc gtgggcctgc atgcagccag taaagatccc agagaagttc gagaagctag | 720 |
| agatcataag gaaccaaaag aggagatcaa caaaaacatt tctgactttg gacgacagca | 780 |
| gcttttaccc cccttcccat ccttcatca gtcgctacct cagaaccagt gctacatggc | 840 |
| caccacaaaa tcagacacag cttgcttgcc ttttgtttta gcagctgcag tatctcggaa | 900 |
| gaaaaacga agaatgggaa cctatagcct ggttcctaag aaaaagacca agtattaaa | 960 |
| acagaggacg tgattgaga tgtttaagag cataactcat tccactgtgg gttccaaggg | 1020 |
| ggagaaggac ctgggcgcca gcagcctgca cgtgaatggg gagagcctgg agatggactc | 1080 |
| ggatgaggac gactcagagg agctcgagga ggacgacggc catggtgcag agcaggcggc | 1140 |
| cgcgttcccc acagaggaca gcaggacttc aaggagagc atgtcggagg ctgatcgcgc | 1200 |
| ccagaagatg gacggggagt ccgaggagga gcaggagtcc gtggacaccg ggaggagga | 1260 |
| ggaaggcggt gacgagtctg acctgagttc ggaatccagc attaagaaga atttctcaa | 1320 |
| gaggaaagga aagaccgaca gtccctggat caagccagcc aggaaaagga ggcggagaag | 1380 |
| tagaaagaag cccagcggtg ccctcggttc tgagtcgtat aagtcatctg caggaagcgc | 1440 |

```
tgagcagacg gcaccaggag acagcacagg gtacatggaa gtttctctgg actccctgga    1500
tctccgagtc aaaggaattc tgtcttcaca agcagaaggg ttggccaacg gtccagatgt    1560
gctggagaca gacggcctcc aggaagtgcc tctctgcagc tgccggatgg aaacaccgaa    1620
gagtcgagag atcaccacac tggccaacaa ccagtgcatg gctacagaga gcgtggacca    1680
tgaattgggc cggtgcacaa acagcgtggt caagtatgag ctgatgcgcc cctccaacaa    1740
ggccccgctc ctcgtgctgt gtgaagacca ccggggccgc atggtgaagc accagtgctg    1800
tcctggctgt ggctacttct gcacagcggg taattttatg gagtgtcagc ccgagagcag    1860
catctctcac cgtttccaca agactgtgc ctctcgagtc aataacgcca gctattgtcc    1920
ccactgtggg gaggagagct ccaaggccaa agaggtgacg atagctaaag cagacaccac    1980
ctcgaccgtg acaccagtcc ccgggcagga aagggctcg gccctggagg cagggccga    2040 caccacaacg ggcagtgctg ccgggccacc actctcggag gacgacaagc tgcagggtgc    2100
agcctcccac gtgcccgagg ctttgatcc aacgggacct gctgggcttg ggaggccaac    2160
tcccggcctt tcccagggac cagggaagga aaccttggag agcgctctca tcgccctcga    2220
ctcggaaaaa cccaagaagc ttcgcttcca cccaaagcag ctgtacttct ccgccaggca    2280
aggggagctt cagaaggtgc tcctcatgct ggtggacgga attgaccca acttcaaaat    2340 ggagcaccag aataagcgct ctccactgca cgccgcggca gaggctggac acgtggacat    2400
ctgccacatg ctggttcagg cgggcgctaa tattgacacc tgctcagaag accagaggac    2460
cccgttgatg gaagcagccg aaaacaacca tctggaagca gtgaagtacc tcatcaaggc    2520
tggggccctg gtggatccca aggacgcaga gggctctacg tgtttgcacc tggctgccaa    2580
gaaaggccac tacgaagtgg tccagtacct gctttcaaat ggacagatgg acgtcaactg    2640
tcaggatgac ggaggctgga cacccatgat ctgggccaca gagtacaagc acgtggacct    2700
cgtgaagctg ctgctgtcca agggctctga catcaacatc cgagcaacg aggagaacat    2760 ttgcctgcac tgggcggcgt tctccggctg cgtggacata gccgagatcc tgctggctgc    2820
caagtgcgac ctccacgccg tgaacatcca cggagactcg ccactgcaca ttgccgcccg    2880
ggagaaccgc tacgactgtg tcgtcctctt tctttctcgg gattcagatg tcaccttaaa    2940
gaacaaggaa ggagagacgc ccctgcagtg tgcgagcctc aactctcagg tgtggagcgc    3000
tctgcagatg agcaaggctc tgcaggactc ggccccgac aggcccagcc ccgtggagag    3060
gatagtgagc agggacatcg ctcgaggcta cgagcgcatc cccatcccct gtgtcaacgc    3120 cgtgacagc gagccatgcc ccagcaacta caagtacgtc tctcagaact gcgtgacgtc    3180
ccccatgaac atcgacagaa atatcactca tctgcagtac tgcgtgtgca tcgacgactg    3240
ctcctccagc aactgcatgt gcggccagct cagcatgcgc tgctggtacg acaaggatgg    3300
ccggctcctg ccagagttca acatggcgga gcctcccttg atcttcgaat gcaaccacgc    3360
gtgctcctgc tggaggaact gccgaaatcg cgtcgtacag aatggtctca gggcaaggct    3420
gcagctctac cggacgcggg acatgggctg ggcgtgcgg tccctgcagg acatcccacc    3480
aggcaccttt gtctgcgagt atgttgggga gctgatttca gactcagaag ccgacgttcg    3540
agaggaagat tcttacctct ttgatctcga caataaggac ggggaggttt actgcatcga    3600
cgcgcggttc tacgggaacg tcagccggtt catcaaccac cactgcgagc ccaacctggt    3660
gcccgtgcgc gtgttcatgg cccaccagga cctgcggttc cccgatcg ccttcttcag    3720 cacccgcctg atcgaggccg gcgagcagct cgggtttgac tatggagagc gcttctggga    3780
```

| | |
|---|---|
| catcaaaggc aagctcttca gctgccgctg cggctccccc aagtgccggc actcgagcgc | 3840 |
| ggccctggcc cagcgtcagg ccagcgcggc ccaggaggcc caggaggacg gcttgcccga | 3900 |
| caccagctcc gcggctgccg ccgacccect atgagacgcc gccggccagc ggggcgctcg | 3960 |
| ggagccaggg accgccgcgt cgccgattag aggacgagga ggagagattc cgcacgcaac | 4020 |
| cgaaagggtc cttcggggct gcgccgccgg cttcctggag gggtcggagg tgaggctgca | 4080 |
| gcccctgcgg gcgggtgtgg atgcctccca gccaccttcc cagacctgcg gcctcaccgc | 4140 |
| gggcccagtg cccaggctgg agcgcacact ttggtccgcg cgccagagac gctgggagtc | 4200 |
| cgcactggca tcaccttctg agtttctgat gctgatttgt cgttgcgaag tttctcgttt | 4260 |
| cttcctctga cctccgaggt ccccgctgca ccacgggtt gctctgttct cctgtccggc | 4320 |
| ccagactctt ctgtgtggcg ccgccgaagc caccgttagc gcgagctgct ccgttcgccc | 4380 |
| tgcccacggc ctgcgtggct ggggccgagt cccaggggcc gcacggaggg cacagtctcc | 4440 |
| tgtcaggctc ggagaggtca ggagaccgac cccaccacta actttggaga aaatgtgggt | 4500 |
| ttgctttta aaggaatcct atatctagtc ctatatatca aacctctaac tgacgtttct | 4560 |
| tttcgaggaa gtggcttggt gggtgcagcc cccgccggtt ccgttgacgc tggcaccttc | 4620 |
| tgttgatttt ttaagccaca tgctatgatg aataaactga tttattttct accattactg | 4680 |
| aacattagga caaacacaaa ataaaaaaca aaacacagac aacggtgctg attctggtgt | 4740 |
| ggtttctact caccacgtga aataaactat caactgtata aagagaacaa agtgatttta | 4800 |
| gaataaaatg caggaaaaac ttttttaaag atgttagtct tgtagcgtga ataaatttgc | 4860 |
| catcaccttt tgtgtggtgg cctggcaggt catatacttt tttttggcat ataccttttt | 4920 |
| aaagactgta attagtgcag taacagtggg gttttttttg tgcaactctt ctaaaaacat | 4980 |
| tcataatgca gtcatgttta tttttttctg ttaaaatgtt tttgacagtt ttaagagcag | 5040 |
| tcttttggct ctgaccattt cttgttctgt ttccaatgaa atcaataaaa aaaagaagt | 5100 |
| actttaaaaa aaaaaaaaaa aaa | 5123 |

<210> SEQ ID NO 47
<211> LENGTH: 7970
<212> TYPE: DNA
<213> ORGANISM: Homo sapiens

<400> SEQUENCE: 47

| | |
|---|---|
| gtaaaagtga cattctaaat gttcctcact ctgcgaggct tatttttag ggactttgct | 60 |
| ataattctga aagacttagt tttacagtac atctgaaagt aggagttttc agaagtatgg | 120 |
| ctcttgggat aaatttagat tcttaattgt gaagctctgt taccacttgt tagaaggcag | 180 |
| gtcagctcac ctgcttgggg aggtaaatat atgaatgcac tctcgagtaa tttaatggag | 240 |
| ccctacctca atgtacagaa tgacagtatc acagatcaag aatggagtac gagtgatttt | 300 |
| cggctatggt gggggtaggt aggtcacttg tcccctgttg tctcttacta tttgtaaagt | 360 |
| gaagactatg attagtcttt ttgatcggga tggtttgaga tgaataaaga ataggcaggc | 420 |
| aatttggata cttaggcctt ttcaagaaca ttagtaacat tttttcttag atatttctcc | 480 |
| taatacaatg agtgttgtga aataacatgg cagttattgt tgagagaaaa gccttcccag | 540 |
| ttatgtattg agtccttagg cgttttgacc ttccctccac tcttacagaa cttggtggaa | 600 |
| ggggccacta tgttttctac ctccttccgt gcctttcaca aagccacatc ctgcaccgtc | 660 |
| tacccttctc tgtggatatt tttccgcttg gcaatttcct ttcctgaggc acccacttgg | 720 |
| gacatctgaa tctccatctc catgttgatg gcccgtttgt gcttggacgt gttcttccac | 780 |

-continued

```
ttgagactga gggttcatgt aatcaaagaa gtttctttgt tgtgtgtatc tttacagaac      840
acaacaggaa ttgaaaatga atcagaacac tactgagcct gtggcggcca ccgagaccct      900
ggctgaggta cccgaacatg tgctgcgagg acttccggag gaagtgaggc ttttcccttc      960
tgctgttgac aagacccgga ttggtgtctg ggccactaaa ccaattttaa aaggcaaaaa     1020
atttgggcca tttgttggtg ataagaaaaa aagatctcag gttaagaata atgtatacat     1080
gtgggaggtg tattacccaa atttgggatg gatgtgcatt gatgccactg atccagagaa     1140
gggaaactgg ctgcgatatg tgaattgggc ttgctcagga gaagagcaaa atttattccc     1200
actgaaaatc aacagagcca tttactataa aactttaaag ccaatcgcgc cgggcgagga     1260
gctcctggtc tggtacaatg gggaagacaa ccctgagata gcagctgcga ttgaggaaga     1320
gcgagccagc gcccggagca gcggagctc cccaagagc cggaaaggga agaaaaaatc       1380
ccaggaaaat aaaaacaaag gaaacaaaat ccaagacata caactgaaga caagtgagcc     1440
agatttcacc tctgcaaata tgagagattc tgcagaaggt cctaaagaag acgaagagaa     1500
gccttcagcc tcagcacttg agcagccggc caccctccag gaggtggcca gtcaggaggt     1560
gcctccagaa ctagcaaccc ctgccccctgc ctgggagcca cagccagaac cagacgagcg    1620
attagaagcg gcagcttgtg aggtgaatga tttgggggaa gaggaggagg aggaagagga    1680
ggaggatgaa gaagaagaag aagatgatga tgatgatgag ttggaagacg aggggggaaga   1740
agaagccagc atgccaaatg aaaattctgt gaaagagcca gaaatacggt gtgatgagaa    1800
gccagaagat ttattagagg aaccaaaaac aacttcagaa gaaactcttg aagactgctc    1860
agaggtaaca cctgccatgc aaatccccag aactaaagaa gaggccaatg gtgatgtatt    1920
tgaaacgttt atgtttccgt gtcaacattg tgaaaggaag tttacaacca acaggggct    1980
tgagcgtcac atgcatatcc atatatccac cgtcaatcat gctttcaaat gcaagtactg    2040
tgggaaagcc tttggcacac agattaaccg gcggcgacat gagcggcgcc atgaagcagg    2100
gttaaagcgg aaacccagcc aaaacactaca gccgtcagag gatctggctg atggcaaagc   2160
atctggagaa aacgttgctt caaaagatga ttcgagtcct cccagtcttg gccagactg    2220
tctgatcatg aattcagaga aggcttccca agacacaata aattcttctg tcgtagaaga    2280
gaatggggaa gttaaagaac ttcatccgtg caaatattgt aaaaaggttt ttggaactca    2340
tactaatatg agacggcatc agcgtagagt tcacgaacgt catctgattc ccaaaggtgt   2400
acggcgaaaa ggaggccttg aagagcccca gcctccagca gaacaggccc aggccaccca    2460
gaacgtgtat gtaccaagca cagagccgga ggaggaaggg gaagcagatg atgtgtacat    2520
catggacatt tctagcaata tctctgaaaa cttaaattac tatattgatg gtaaaattca    2580
aactaataac aacactagta actgtgatgt gattgagatg gagtctgctt cggcagattt    2640
gtatggtata aattgtctgc tcactccagt tacagtggaa attactcaaa atataaagac    2700
cacacaggtc cctgtaacag aagatcttcc taaagagcct ttgggcagca caaatagtga    2760
ggccaagaag cggagaactg cgagcccacc tgcactgccc aaaattaagg ccgaaacaga    2820
ctctgacccc atggtcccct cttgctcttt aagtcttcct cttagcatat caacaacaga    2880
ggcagtgtct ttccacaaag agaaagtgt ttatttgtca tcaaagctca acaacttct     2940
tcaaacccaa gataaactaa ctcctgcagg gatttcagca actgaaatag ctaaattagg    3000
tcctgttttgt gtgtctgctc ctgcatcaat gttgcctgtg acctcaagta ggtttaagag    3060
gcggaccagc tctcctccca gttctccaca gcacagtcct gcccttcgag actttggaaa    3120
```

```
gccaagtgat gggaaagcag catggaccga tgccgggctg acttccaaaa aatccaaatt    3180
agaaagtcac agcgactcac cagcatggag tttgtctggg agagatgaga gagaaactgt    3240
gagccctcca tgctttgatg aatataaaat gtctaaagag tggacagcta gttctgcttt    3300
tagcagtgtg tgcaaccagc agccactgga tttatccagc ggtgtcaaac agaaggctga    3360
gggtacaggc aagactccag tccagtggga atctgtctta gatctcagtg tgcataaaaa    3420
gcattgtagt gactctgaag gcaaggaatt caaagaaagt cattcagtgc agcctacgtg    3480
tagtgctgta aagaaaagga accaaccac ctgcatgctg cagaaggttc ttctcaatga    3540
atataatggc atcgatttac ctgtagaaaa ccctgcagat gggaccagga gcccaagtcc    3600
ttgtaaatcc ctagaagctc agccagatcc tgacctcggt ccgggctctg gtttccctgc    3660
ccctactgtt gagtccacac ctgatgtttg tccttcatca cctgccctgc agacaccctc    3720
cctttcatcc ggtcagctgc tcctctctt gatccccaca gatccctctt ccctccacc    3780 ctgtccccg gtattaactg ttgccactcc gccccctccc ctccttccta ccgtacctct    3840
tccagccccc tcttccagtg catctccaca cccatgcccc tctccactct caaatgccac    3900
cgcacagtcc ccacttccaa ttctgtcccc aacagtgtcc ccctctccct ctcccattcc    3960
tcccgtggag cccctgatgt ctgccgcctc acccgggcct ccaacacttt cttcttcctc    4020
ctcttcatct tcctcctcct cttcgttttc ttcttcatct tcctcctctt ctccttctcc    4080
acctcctctc tccgcaatat catctgttgt ttcctctggt gataatctgg aggcttctct    4140
ccccatgata tctttcaaac aggaggaatt agagaatgaa ggtctgaaac ccagggaaga    4200
gccccagtct gctgctgaac aggatgttgt tgttcaggaa acattcaaca aaaactttgt    4260
ttgcaacgtc tgtgaatcac cttttctttc cattaaagat ctaaccaaac atttatctat    4320
tcatgctgaa gaatggccct tcaaatgtga attttgtgtg cagctttta aggataaaac    4380 ggacttgtca gaacatcgct ttttgcttca tggagttggg aatatctttg tgtgttctgt    4440
ttgtaaaaaa gaatttgctt ttttgtgcaa tttgcagcag caccagcgag atctccaccc    4500
agataaggtg tgcacacatc acgagtttga aagcgggact ctgaggcccc agaactttac    4560
agatcccagc aaggcccatg tagagcatat gcagagcttg ccagaagatc ctttagaaac    4620
ttctaaagaa gaagaggagt taaatgattc ctctgaagag ctttacacga ctataaaaat    4680
aatggcttct ggaataaaga caaaagatcc agatgttcga ttgggcctca atcagcatta    4740
cccaagcttt aaaccacctc catttcagta ccatcaccgt aaccccatgg ggattggtgt    4800
gacagccaca aatttcacta cacacaatat tccacagact ttcactaccg ccattcgctg    4860
cacaaagtgt ggaaaggtg tcgacaatat gccggagttg cacaaacata tcctggcttg    4920
tgcttctgca agtgacaaga gaggtacac gcctaagaaa aacccagtac cattaaaaca    4980
aactgtgcaa cccaaaatg gcgtggtggt tttagataac tctgggaaaa atgccttccg    5040
acgaatggga cagcccaaaa ggcttaactt tagtgttgag ctcagcaaaa tgtcgtcgaa    5100
taagctcaaa ttaaatgcat tgaagaaaaa aaatcagcta gtacagaaag caattcttca    5160 gaaaacaaa tctgcaaagc agaaggccga cttgaaaaat gcttgtgagt catcctctca    5220
catctgccct tactgtaatc gagagttcac ttacattgga agcctgaata acacgccgc    5280 cttcagctgt cccaaaaaac ccctttctcc tcccaaaaaa aaagtttctc attcatctaa    5340
gaaaggtgga cactcatcac ctgcaagtag tgacaaaaac agtaacagca accaccgcag    5400
acggacagcg gatgcggaga ttaaaatgca aagcatgcag actccgttgg gcaagaccag    5460
agcccgcagc tcaggcccca cccaagtccc acttccctcc tcatccttca ggtccaagca    5520
```

```
gaacgtcaag tttgcagctt cggtgaaatc caaaaaacca agctcctcct ctttaaggaa   5580
ctccagcccg ataagaatgg ccaaaataac tcatgttgag gggaaaaaac ctaaagctgt   5640
ggccaagaat cattctgctc agctttccag caaaacatca cggagcctgc acgtgagggt   5700
acagaaaagc aaagctgttt tacaaagcaa atccaccttg gcgagtaaga aaagaacaga   5760
ccggttcaat ataaaatcta gagagcggag tgggggccca gtcacccgga gccttcagct   5820
ggcagctgct gctgacttga gtgagaacaa gagagaggac ggcagcgcca agcaggagct   5880
gaaggacttc agctacagcc tccgcttggc gtcccgatgc tctccaccag cggccccgta   5940
catcaccagg cagtatagga aggtcaaagc tccagctgca gcccagttcc agggaccatt   6000
cttcaaagag tagacactct ggctgctccc tgacagcacc tgaagtgacc tggaatcagt   6060
gaagccaaag ggactggcag tctgccctgc agggagtacc gacctatccc agttgtgtga   6120
ggctgcgaga gaaagggagt gcatgtgcgc gcgtgcatgt gtgcgtgcgt gtgtgttcac   6180
gtgttctcgt gcgggcgcgt gagtggtctt caaacgaggg tcccgatccc cggggcggca   6240
ggaaggggggc cgactccacg ctgtcctttg gatgatact tggatgcagc tcttgggacc   6300
gtgttctgca gccagccttt cctgttgggg tggggcctct cctactatgc aattttttcaa   6360
gagctccttg accctgcttt ttgcttcttg agttgtcttt tgccattatg gggactttgg   6420
tttgacccag gggtcagcct taggaaggcc ttcaggagga ggccgagttc cccttcagta   6480
ccacccctct ctccccacct tccctctccc ggcaacatct ctgggaatca acagcatatt   6540
gacacgttgg agccgagcct gaacatgccc ctcggcccca gcacatggaa aacccccttc   6600
cttgcctaag gtgtctgagt ttctggctct tgaggcattt ccagacttga aattctcatc   6660
agtccattgc tcttgagtct ttgcagagaa cctcagatca ggtgcacctg ggagaaagac   6720
tttgtcccca cttacagatc tatctcctcc cttgggaagg gcagggaatg gggacggtgt   6780
atggaggggga gggatctcct gcgcccttca ttgccacact tggtgggacc atgaacatct   6840
ttagtgtctg agcttctcaa attagctgca ataggaaaaa aacaaattgg gaaatgaaaa   6900
aaaaatggga agattaaaaa gcacaggggg aagaagaaga gatttcggag gccatcctgc   6960
caggggcgga cggggctgac tcctgctctc tggaggacgg tcagtccatg tctcggagaa   7020
acgggtgagc tgagcttggc gtttggaccc agttcagtga ggttcttggg ttttgtgcct   7080
ttgggggcaga ccccaggcaa ggatgtctga gaccacttgg gcgctgtttt ctcagctcca   7140
atttcaagag tgagctatca aacccagagc ggaaggaggg agctctgatg agcacggttt   7200
gtcacacgat aaagggattt ttttttttcag ggctactacg gttgatcttg caactctgta   7260
aatatgtatg tagacacttt taaaagcacg tatttatgtc cctgactgta aatgctccat   7320
ttttaaagtt ttataacttg tgttatttaa tgagtcagtc aatcggctgc agtatgggat   7380
ctgataagga tctaggagaa gggtctcatg cggaccctca catgggcaga aaaatggtgg   7440
tcattggccg acatcacagt tttcctgttt cccacccagc taaaaccgt tgtttgcttt    7500
aaatttttcat aaactggaat cctttcaccc gctcctacag ctaaccctca caagcatgaa   7560
gtgctgtggc tgttccttat cctaatgatg cgcttttgtc ccgtaaatgt taacactcat   7620
gaagcatacc ccggcctctc agttcttgag ggcctcccca ccgcagcagc aaggaaagct   7680
cacgaacccc aaacctggca agtcacctgc agcccatggt gagctctggg aagtgtggtt   7740
gaggccttgg ggtcactcct tttttgcatg tgcaaatgtg ctggtcaccc ttcaacgctc   7800
ccagacggtc aggaaaactg ttccaatcat gaaaaggggg gatgattttg taaaagtggc   7860
```

```
atttcctggt cagtggtggt cttcaagacg acagctctgt atctgccatg tgaagagaat    7920
taacaataaa agtgtgaaga gcgattgtga ggaacaaaaa aaaaaaaaaa               7970
```

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(31)
<223> OTHER INFORMATION: a, c, t, g, unknown or other

<400> SEQUENCE: 48

```
aannnnnnnn nnnnnnnnnn nnnnnnnnnn ntt                                   33
```

<210> SEQ ID NO 49
<211> LENGTH: 4526
<212> TYPE: DNA
<213> ORGANISM: Homo sapiens

<400> SEQUENCE: 49

```
acggctgcgc agatgccgac tttagaggag gcggagtttc ggccttcgcc tgctggaaaa     60
gcagtaggat cggccagtgg cgacagcagg agctgagcct aagccctggc ggggctttgg    120
gctgtagatt cctgtctgac taaagggacc tcaaaaagga gggaaaatgg cttctgagtc    180
tgaaactctg aatcccagtg ctaggataat gacctttat ccaactatgg aagagttccg    240
aaacttcagt agatacattg cctacattga atcccaagga gctcatcggg cagggctagc    300
caaggttgtt cctccaaaag agtggaagcc acgagcatcc tatgatgaca ttgatgattt    360
ggtcattcct gcccccattc aacagctggt gacggggcag tctggcctct ttactcagta    420
caacatacag aagaaagcca tgactgttcg agagttccgc aagatagcca atagcgataa    480
gtactgtacc ccacgctata gtgagtttga agagctcgag cggaaatact ggaaaaatct    540
tacattcaat cctccaatct atggtgcaga tgtgaatggt accctctatg aaaagcatgt    600
tgatgagtgg aatattggcc ggctgagaac aatcctggac ttggtggaaa aggagagtgg    660
gatcaccatt gagggtgtga acacccata cctgtacttt ggcatgtgga agacatcctt    720
tgcttggcac actgaagaca tggacctcta cagcatcaac tacctgcact ttggagaacc    780
aaagtcctgg tactctgttc cacctgagca tggaaagcgg ttggaacgcc tcgccaaagg    840 cttttttccca ggaagtgctc aaagctgtga ggcatttctc cgccacaaga tgaccctgat    900
ttccccgtta atgctgaaga aatatggaat tcccttttgac aaggtgactc aagaggctgg    960
agagtttatg atcactttcc cttatggtta ccatgccggc tttaaccatg ttttaactg     1020 tgcggagtct accaattttg ctacccgtcg gtggattgag tacggcaagc aagctgtgct    1080
gtgctcctgt agaaaggaca tggtgaagat ctccatggat gtgtttgtga aaagttcca    1140 gccagaaagg tacaaacttt ggaaagctgg gaaggacaac acagttattg accatactct    1200
gcccacgcca gaagcagctg agtttcttaa ggagagtgaa ctgcctccaa gagctggcaa    1260
cgaggaggag tgcccagagg aggacatgga aggggtggga gatggagagg aaggagacct    1320
gaagacaagc ctggccaagc accgaatagg acaaagagg caccgagttt gtcttgaaat    1380
accacaggag gtgagtcaga gtgagctctt ccccaaggag gatctgagtt ctgagcagta    1440
tgagatgacg gagtgcccgg cagccctcgc ccctgtgagg cccacccata gctctgtgcg    1500
```

-continued

```
gcaagttgag gatggtctta ccttcccaga ttattctgac tccactgaag tcaaatttga    1560
agagcttaaa aatgtcaaac tagaagagga ggatgaggag gaagaacaag cagcagctgc    1620
cttggatctt tctgtgaatc ctgcgtctgt aggggacgc cttgtcttct caggctccaa     1680
aaagaaatca tcttctagcc tgggctctgg ctcttcacgg gattctatct cttctgattc    1740
agaaactagt gagcctctct cctgccgagc ccaagggcaa acgggagttc tcactgtgca    1800
cagttatgcc aaaggggatg gcagggtcac tgtgggagag ccatgcacga ggaagaaagg    1860
aagcgccgct agaagtttca gtgagcggga gctggcagag gttgcagatg aatacatgtt    1920
ttccctagaa gagaataaga agtccaaggg acgccgtcag cctttaagca agctcccccg    1980
ccatcaccca cttgtgctgc aggagtgtgt cagtgatgat gagacatctg aacagctgac    2040
ccctgaggaa gaggctgagg agacagaggc ctgggccaag cctctgagcc aactgtggca    2100
gaaccgacct ccaaactttg aggctgagaa ggaattcaat gagaccatgg cccaacaggc    2160
ccctcactgc gctgtctgta tgatcttcca gacttatcat caggttgaat ttggaggctt    2220
taatcagaac tgtggaaatg cttcagattt agcccccag aagcagagga ccaagccatt     2280
gattccagaa atgtgcttca cttcgactgg ctgcagcacg gacatcaacc tttctactcc    2340
ttatcttgag gaggatggca ccagcatact cgtttcctgc aagaagtgca gcgtccgggt    2400
ccatgccagt tgctatgggg tcccccctgc aaaggcttct gaagactgga tgtgttctcg    2460
gtgttcagcc aatgccctag aggaggactg ctgtttatgc tcattacgag gaggggccct    2520
gcagagagca aatgatgaca ggtgggtcca cgtttcatgt gctgtggcaa ttctggaagc    2580
aaggtttgtc aacattgcag aaagaagtcc ggtggatgtg agcaaaatcc ccctgccccg    2640
cttcaaactg aaatgtatct tctgtaagaa gcggaggaaa agaactgctg ctgctgtgt     2700
gcagtgttct cacggccgct gcccaactgc cttccatgtg agctgcgccc aggctgccgg    2760
tgtgatgatg cagcctgacg actggccttt tgtggtcttc attacctgct ttcggcacaa    2820
gattcctaat ttggagcgtg ccaaggggggc cttgcaaagc atcactgcag ccagaaagt    2880
cattagcaag cataagaacg ggcgcttcta ccagtgtgaa gtggtcaggc tcaccaccga    2940
gaccttctat gaagtcaact ttgatgatgg ctccttcagc gacaatcttt atcctgagga    3000
catagtgagc caggactgtc tccagtttgg tcctcctgct gaaggggaag tggtccaagt    3060
gagatggaca gacggccaag tctatggagc caagtttgtg gcctcccacc ctatccaaat    3120
gtaccaggtg gagtttgagg atggctcaca acttgtggtt aagagagatg atgtatacac    3180
actggatgaa gagcttccca agagagtcaa atctagactg tcagtagcct cagacatgcg    3240
cttcaatgag attttcacag agaaagaggt taagcaagaa aagaaacggc aacgagttat    3300
caactcaaga taccgggaag attatattga gcctgcacta taccgggcca tcatggagta    3360
ggtgcttcca gggtccaagg gattctcagc catccaggca agagcactct gggttccaca    3420
gcacagcaga catggaacgc tgaagtctct gaaagtgaag ttgtaaaaag aaaaggaatg    3480
aaataaccga cccatcatct tctcacccac cctcattgca ttccgctgta gtgaaaggac    3540
gagccatttc tgggcacgtg gcagcagtcg ctgatctccc agctgagggg ctgagcactg    3600
gaatgctgtg gctgcactgg ccccagtcca tagaggggtc aactatgctg gctgactgg     3660
ctgccttgtt cctggcctag gacttagctt cataactatc acctgcaccg actaggctga    3720
ggtgctggta cttgccccaa cccctacttt tgtatttata tgtgtgtgtg tgtgtgcgtg    3780
cgtgcgtgcg tgcgtgtatg tttggtctgg accagcttct gccagcccct ggcctttact    3840
ttcttccttg cctatgcagg gcaaacaaaa tgtgaaattc tgccctcagc tgagctgagt    3900
```

```
aagggctcct gggggttggc tggagatggg tgtggcatct gtccaggcct ggaaccgtct   3960
caagacagtg ctggcaaagc tgcagtattg agatgctaag gagctgatgc cacctctttg   4020
tcttccccta aaggagaaca tggggataac atgggtgtgt gcccacaaca ctctaggtgc   4080
agagcccctg tggcaaagta ttacaggggtg tgggtgggga ttaccctgaa tcggggattt   4140
taatgatgga agcaggcaga gcctggtggg tgattctgtc aacagaaaat tgcaatcatg   4200
caggggctgg gagggttagg atgaaaaaac tggggccatt ggaggcccac tgtaggtggg   4260
agggagctga ttttggggtg ggggtggga  ctagagggca atactgaagg ggttaaacag   4320
gtttttgctc ctcaagaatt tgtttgcctg ggcccaggat tggagggctt cacaccaata   4380
ccctgtgtat acaagaatca gatttataat acttcccctt ttttgttacg tatgaacact   4440
ataaaccaaa ttattttgaa aactggtgca tcaccttgtc cttagcaata aaatgtgttg   4500
agcagaggaa aaaaaaaaaa aaaaaa                                        4526
```

<210> SEQ ID NO 50
<211> LENGTH: 1064
<212> TYPE: PRT
<213> ORGANISM: Homo sapiens

<400> SEQUENCE: 50

```
Met Ala Ser Glu Ser Glu Thr Leu Asn Pro Ser Ala Arg Ile Met Thr
1               5                   10                  15

Phe Tyr Pro Thr Met Glu Glu Phe Arg Asn Phe Ser Arg Tyr Ile Ala
            20                  25                  30

Tyr Ile Glu Ser Gln Gly Ala His Arg Ala Gly Leu Ala Lys Val Val
        35                  40                  45

Pro Pro Lys Glu Trp Lys Pro Arg Ala Ser Tyr Asp Asp Ile Asp Asp
    50                  55                  60

Leu Val Ile Pro Ala Pro Ile Gln Gln Leu Val Thr Gly Gln Ser Gly
65                  70                  75                  80

Leu Phe Thr Gln Tyr Asn Ile Gln Lys Lys Ala Met Thr Val Arg Glu
                85                  90                  95

Phe Arg Lys Ile Ala Asn Ser Asp Lys Tyr Cys Thr Pro Arg Tyr Ser
            100                 105                 110

Glu Phe Glu Glu Leu Glu Arg Lys Tyr Trp Lys Asn Leu Thr Phe Asn
        115                 120                 125

Pro Pro Ile Tyr Gly Ala Asp Val Asn Gly Thr Leu Tyr Glu Lys His
    130                 135                 140

Val Asp Glu Trp Asn Ile Gly Arg Leu Arg Thr Ile Leu Asp Leu Val
145                 150                 155                 160

Glu Lys Glu Ser Gly Ile Thr Ile Glu Gly Val Asn Thr Pro Tyr Leu
                165                 170                 175

Tyr Phe Gly Met Trp Lys Thr Ser Phe Ala Trp His Thr Glu Asp Met
            180                 185                 190

Asp Leu Tyr Ser Ile Asn Tyr Leu His Phe Gly Glu Pro Lys Ser Trp
        195                 200                 205

Tyr Ser Val Pro Pro Glu His Gly Lys Arg Leu Glu Arg Leu Ala Lys
    210                 215                 220

Gly Phe Phe Pro Gly Ser Ala Gln Ser Cys Glu Ala Phe Leu Arg His
225                 230                 235                 240

Lys Met Thr Leu Ile Ser Pro Leu Met Leu Lys Lys Tyr Gly Ile Pro
                245                 250                 255
```

```
Phe Asp Lys Val Thr Gln Glu Ala Gly Glu Phe Met Ile Thr Phe Pro
                260                 265                 270

Tyr Gly Tyr His Ala Gly Phe Asn His Gly Phe Asn Cys Ala Glu Ser
            275                 280                 285

Thr Asn Phe Ala Thr Arg Arg Trp Ile Glu Tyr Gly Lys Gln Ala Val
        290                 295                 300

Leu Cys Ser Cys Arg Lys Asp Met Val Lys Ile Ser Met Asp Val Phe
305                 310                 315                 320

Val Arg Lys Phe Gln Pro Glu Arg Tyr Lys Leu Trp Lys Ala Gly Lys
                325                 330                 335

Asp Asn Thr Val Ile Asp His Thr Leu Pro Thr Pro Glu Ala Ala Glu
            340                 345                 350

Phe Leu Lys Glu Ser Glu Leu Pro Pro Arg Ala Gly Asn Glu Glu Glu
        355                 360                 365

Cys Pro Glu Glu Asp Met Glu Gly Val Glu Asp Gly Glu Glu Gly Asp
370                 375                 380

Leu Lys Thr Ser Leu Ala Lys His Arg Ile Gly Thr Lys Arg His Arg
385                 390                 395                 400

Val Cys Leu Glu Ile Pro Gln Glu Val Ser Gln Ser Glu Leu Phe Pro
                405                 410                 415

Lys Glu Asp Leu Ser Ser Glu Gln Tyr Glu Met Thr Glu Cys Pro Ala
            420                 425                 430

Ala Leu Ala Pro Val Arg Pro Thr His Ser Ser Val Arg Gln Val Glu
        435                 440                 445

Asp Gly Leu Thr Phe Pro Asp Tyr Ser Asp Ser Thr Glu Val Lys Phe
        450                 455                 460

Glu Glu Leu Lys Asn Val Lys Leu Glu Glu Asp Glu Glu Glu Glu Glu
465                 470                 475                 480

Gln Ala Ala Ala Leu Asp Leu Ser Val Asn Pro Ala Ser Val Gly
                485                 490                 495

Gly Arg Leu Val Phe Ser Gly Ser Lys Lys Ser Ser Ser Ser Leu
            500                 505                 510

Gly Ser Gly Ser Ser Arg Asp Ser Ile Ser Ser Asp Ser Glu Thr Ser
        515                 520                 525

Glu Pro Leu Ser Cys Arg Ala Gln Gly Gln Thr Gly Val Leu Thr Val
530                 535                 540

His Ser Tyr Ala Lys Gly Asp Gly Arg Val Thr Val Gly Glu Pro Cys
545                 550                 555                 560

Thr Arg Lys Lys Gly Ser Ala Ala Arg Ser Phe Ser Glu Arg Glu Leu
                565                 570                 575

Ala Glu Val Ala Asp Glu Tyr Met Phe Ser Leu Glu Glu Asn Lys Lys
            580                 585                 590

Ser Lys Gly Arg Arg Gln Pro Leu Ser Lys Leu Pro Arg His His Pro
        595                 600                 605

Leu Val Leu Gln Glu Cys Val Ser Asp Asp Thr Ser Glu Gln Leu
610                 615                 620

Thr Pro Glu Glu Glu Ala Glu Glu Thr Glu Ala Trp Ala Lys Pro Leu
625                 630                 635                 640

Ser Gln Leu Trp Gln Asn Arg Pro Pro Asn Phe Glu Ala Glu Lys Glu
                645                 650                 655

Phe Asn Glu Thr Met Ala Gln Gln Ala Pro His Cys Ala Val Cys Met
            660                 665                 670

Ile Phe Gln Thr Tyr His Gln Val Glu Phe Gly Gly Phe Asn Gln Asn
```

|           |           |           | 675       |           |           |           | 680       |           |           |           | 685       |           |           |
|-----------|-----------|-----------|-----------|-----------|-----------|-----------|-----------|-----------|-----------|-----------|-----------|-----------|-----------|

Cys Gly Asn Ala Ser Asp Leu Ala Pro Gln Lys Gln Arg Thr Lys Pro
            690                 695                 700

Leu Ile Pro Glu Met Cys Phe Thr Ser Thr Gly Cys Ser Thr Asp Ile
705                 710                 715                 720

Asn Leu Ser Thr Pro Tyr Leu Glu Glu Asp Gly Thr Ser Ile Leu Val
                725                 730                 735

Ser Cys Lys Lys Cys Ser Val Arg Val His Ala Ser Cys Tyr Gly Val
            740                 745                 750

Pro Pro Ala Lys Ala Ser Glu Asp Trp Met Cys Ser Arg Cys Ser Ala
            755                 760                 765

Asn Ala Leu Glu Glu Asp Cys Cys Leu Cys Ser Leu Arg Gly Gly Ala
770                 775                 780

Leu Gln Arg Ala Asn Asp Asp Arg Trp Val His Val Ser Cys Ala Val
785                 790                 795                 800

Ala Ile Leu Glu Ala Arg Phe Val Asn Ile Ala Glu Arg Ser Pro Val
                805                 810                 815

Asp Val Ser Lys Ile Pro Leu Pro Arg Phe Lys Leu Lys Cys Ile Phe
            820                 825                 830

Cys Lys Lys Arg Arg Lys Arg Thr Ala Gly Cys Cys Val Gln Cys Ser
            835                 840                 845

His Gly Arg Cys Pro Thr Ala Phe His Val Ser Cys Ala Gln Ala Ala
            850                 855                 860

Gly Val Met Met Gln Pro Asp Asp Trp Pro Phe Val Val Phe Ile Thr
865                 870                 875                 880

Cys Phe Arg His Lys Ile Pro Asn Leu Glu Arg Ala Lys Gly Ala Leu
                885                 890                 895

Gln Ser Ile Thr Ala Gly Gln Lys Val Ile Ser Lys His Lys Asn Gly
            900                 905                 910

Arg Phe Tyr Gln Cys Glu Val Val Arg Leu Thr Thr Glu Thr Phe Tyr
            915                 920                 925

Glu Val Asn Phe Asp Asp Gly Ser Phe Ser Asp Asn Leu Tyr Pro Glu
930                 935                 940

Asp Ile Val Ser Gln Asp Cys Leu Gln Phe Gly Pro Pro Ala Glu Gly
945                 950                 955                 960

Glu Val Val Gln Val Arg Trp Thr Asp Gly Gln Val Tyr Gly Ala Lys
                965                 970                 975

Phe Val Ala Ser His Pro Ile Gln Met Tyr Gln Val Glu Phe Glu Asp
            980                 985                 990

Gly Ser Gln Leu Val Val Lys Arg Asp Asp Val Tyr Thr Leu Asp Glu
            995                 1000                1005

Glu Leu Pro Lys Arg Val Lys Ser Arg Leu Ser Val Ala Ser Asp
        1010                1015                1020

Met Arg Phe Asn Glu Ile Phe Thr Glu Lys Glu Val Lys Gln Glu
        1025                1030                1035

Lys Lys Arg Gln Arg Val Ile Asn Ser Arg Tyr Arg Glu Asp Tyr
        1040                1045                1050

Ile Glu Pro Ala Leu Tyr Arg Ala Ile Met Glu
        1055                1060

<210> SEQ ID NO 51
<211> LENGTH: 5675
<212> TYPE: DNA
<213> ORGANISM: Homo sapiens

<400> SEQUENCE: 51

```
agggctcggt cgccagcaac cgagcggggc ccggcccgag cggggcctgg gggtgcgacg    60
ccgagggcgg gggagagcgc gccgctgctc ccggaccggg ccgcgcacgc cgcctcagga   120
accatcactg ttgctggagg cacctgacaa atcctagcga atttttggag catctccacc   180
caggaacctc gccatccaga agtgtgcttc ccgcacagct gcagccatgg ggtctgagga   240
ccacggcgcc cagaacccca gctgtaaaat catgacgttt cgcccaacca tggaagaatt   300
taaagacttc aacaaatacg tggcctacat agagtcgcag ggagcccacc gggcgggcct   360
ggccaagatc atccccccga aggagtggaa gccgcggcag acgtatgatg acatcgacga   420
cgtggtgatc ccggcgccca tccagcaggt ggtgacgggc cagtcgggcc tcttcacgca   480
gtacaatatc cagaagaagg ccatgacagt gggcgagtac cgccgcctgg ccaacagcga   540
gaagtactgt accccgcggc accaggactt tgatgacctt gaacgcaaat actggaagaa   600
cctcaccttt gtctccccga tctacggggc tgacatcagc ggctctttgt atgatgacga   660
cgtggcccag tggaacatcg ggagcctccg gaccatcctg acatggtgg agcgcgagtg    720
cggcaccatc atcgagggcg tgaacacgcc ctacctgtac ttcggcatgt ggaagaccac   780
cttcgcctgg cacaccgagg acatggacct gtacagcatc aactacctgc actttgggga   840
gcctaagtcc tggtacgcca tcccaccaga gcacggcaag cgcctggagc ggctggccat   900
cggcttcttc cccgggagct cgcagggctg cgacgccttc ctgcggcata gatgacccct   960
catctcgccc atcatcctga agaagtacgg gatcccctte agccggatca cgcaggaggc  1020
cggggaattc atgatcacat tccctacgg ctaccacgcc ggcttcaatc acgggttcaa   1080
ctgcgcagaa tctaccaact tcgccaccct gcggtggatt gactacgca aagtggccac   1140
tcagtgcacg tgccggaagg acatggtcaa gatctccatg gacgtgttcg tgcgcatcct  1200
gcagcccgag cgctacgagc tgtggaagca gggcaaggac ctcacggtgc tggaccacac  1260
gcggcccacg gcgctcacca gccccgagct gagctcctgg agtgcatccc gggcctcgct  1320
gaaggccaag ctcctccgca ggtctcaccg gaaacggagc cagcccaaga agccgaagcc  1380
cgaagacccc aagttccctg ggagggtac ggctggggca cgctcctag aggaggctgg   1440
gggcagcgtg aaggaggagg ctgggccgga ggttgacccc gaggaggagg aggaggagcc  1500
gcagccactg ccacacggcc gggaggccga gggcgcagaa gaggacggga ggggcaagct  1560
gcggccaacc aaggccaaga gcgagcggaa gaagaagagc ttcggcctgc tgccccaca   1620
gctgccgccc ccgcctgctc acttcccctc agaggaggcg ctgtggctgc atccccact   1680
ggagcccccg gtgctgggcc caggccctgc agccatggag gagagccccc tgccggcacc  1740
ccttaatgtc gtgccccctg aggtgcccag tgaggagcta gaggccaagc ctcggcccat  1800
catccccatg ctgtacgtgg tgccgcggcc gggcaaggca gccttcaacc aggagcacgt  1860
gtcctgccag caggcctttg agcactttgc ccagaagggt ccgacctgga aggaaccagt  1920
ttcccccatg gagctgacgg ggccagagga cggtgcagcc agcagtgggg caggtcgcat  1980
ggagaccaaa gcccgggccg gagaggggca ggcaccgtcc acattttcca aattgaagat  2040
ggagatcaag aagagccggc gccatcccct gggccggccg cccacccggt ccccactgtc  2100
ggtggtgaag caggaggcct caagtgacga ggaggcatcc cctttctccg ggaggaaga   2160
tgtgagtgac ccggacgcct tgaggccgct gctgtctctg cagtgaaaga acagggcggc  2220
cagcttccag gccgagagga agttcaacgc agcggctgcg cgcacggagc cctactgcgc  2280
```

```
catctgcacg ctcttctacc cctactgcca ggccctacag actgagaagg aggcacccat    2340
agcctccctc ggagagggct gcccggccac attaccctcc aaaagccgtc agaagacccg    2400
accgctcatc cctgagatgt gcttcacctc tggcggtgag aacacggagc cgctgcctgc    2460
caactcctac atcggcgacg acgggaccag cccctgatc gcctgcggca agtgctgcct    2520
gcaggtccat gccagttgct atggcatccg tcccgagctg gtcaatgaag gctggacgtg    2580
ttcccggtgc gcggcccacg cctggactgc ggagtgctgc ctgtgcaacc tgcgaggagg    2640
tgcgctgcag atgaccaccg ataggaggtg gatccacgtg atctgtgcca tcgcagtccc    2700
cgaggcgcgc ttcctgaacg tgattgagcg ccaccctgtg gacatcagcg ccatccccga    2760
gcagcggtgg aagctgaaat gcgtgtactg ccggaagcgg atgaagaagg tgtcaggtgc    2820
ctgtatccag tgctcctacg agcactgctc cacgtccttc cacgtgacct gcgcccacgc    2880
cgcaggcgtg ctcatggagc cggacgactg gccctatgtg gtctccatca cctgcctcaa    2940
gcacaagtcg gggggtcacg ctgtccaact cctgagggcc gtgtccctag gccaggtggt    3000
catcaccaag aaccgcaacg ggctgtacta ccgctgtcgc gtcatcggtg ccgcctcgca    3060
gacctgctac gaagtgaact tcgacgatgg ctcctacagc gacaacctgt accctgagag    3120
catcacgagt agggactgtg tccagctggg accccttcc gaggggagc tggtggagct    3180
ccggtggact gacggcaacc tctacaaggc caagttcatc tcctccgtca ccagccacat    3240
ctaccaggtg gagtttgagg acgggtccca gctgacggtg aagcgtgggg acatcttcac    3300
cctggaggag gagctgccca agagggtccg ctctcggctg tcactgagca cgggggcacc    3360
gcaggagccc gccttctcgg gggaggaggc caaggccgcc aagcgccgc gtgtgggcac    3420
cccgcttgcc acggaggact ccggggcgag ccaggactac gtggccttcg tggagagcct    3480
cctgcaggtg cagggccggc ccggagcccc cttctaggac agctggccgc tcaggcgacc    3540
ctcagcccgg cggggaggcc atggcatgcc ccggcgttc gcttgctgtg aattcctgtc    3600
ctcgtgtccc cgaccccga gaggccacct ccaagccgcg ggtgccccct agggcgacag    3660
gagccagcgg gacgccgcac gcggccccag actcagggag cagggccagg cgggctcggg    3720
ggccggccag gggagcaccc cactcaacta ctcagaattt taaaccatgt aagctctctt    3780
cttctcgaaa aggtgctact gcaatgccct actgagcaac ctttgagatt gtcacttctg    3840
tacataaacc acctttgtga ggctctttct ataaatacat attgtttaaa aaaagcaag    3900
aaaaaagga aacaaagga aaatatcccc aaagttgttt tctagatttg tggctttaag    3960
aaaaacaaaa caaacaaac acattgtttt tctcagaacc aggattctct gagaggtcag    4020
agcatctcgc tgttttttg ttgttgtttt aaaatattat gatttggcta cagaccaggc    4080
agggaaagag accggtaat tggagggtga gcctcggggg ggggcagga cgccccggtt    4140
tcggcacagc ccggtcactc acggcctcgc tctcgcctca ccccggctcc tgggctttga    4200
tggtctggtg ccagtgcctg tgcccactct gtgcctgctg gaggaggcc caggctctct    4260
ggtggccgcc cctgtgcacc tggccagggg aagcccgggg gtctgggcc tccctccgtc    4320
tgcgcccacc tttgcagaat aaactctctc ctggggtttg tctatctttg tttctctcac    4380
ctgagagaaa cgcaggtgtt ccagaggctt ccttgcagac aaagcacccc tgcacctcct    4440
atggctcagg atgagggagg cccccaggcc cttctggttg gtagtgagtg tggacagctt    4500
cccagctctt cggtacaaac cctgagcagg tcggggaca cagggccgag gcaggccttc    4560
ggggccccctt tcgcctgctt ccgggcaggg acgaggcctg gtgtcctcgc tccacccacc    4620
cacgctgctg tcacctgagg ggaatctgct tcttaggagt gggttgagct gatagagaaa    4680
```

-continued

```
aaacggcctt cagcccaggc tgggaagcgc cttctccagg tgcctctccc tcaccagctc    4740 tgcaccccte tggggagcct tccccacctt agctgtctcc tgcccagggg agggatggag    4800
gagataattt gcttatatta aaacaaaaa atggctgagg caggagtttg ggaccagcct     4860
gggctatata gcaagacccc atcactacaa atttttaca aattagctag gtgtggtggt     4920
gcgcacctgt ggtcccagct actcgggagg ctgtggtggg aggattgctt gagtccagga   4980
ggttgaggct gcagtcagct cagattgcac cactgcactc cagcctgggc aacagagcga   5040
gaccctgtct ccaaaaaaaa aaaaagcaa tgtttatatt ataaagagt gtcctaacag     5100 tccccgggct agagaggact aaggaaaaca gagagagtgt tacgcaggag caagcctttc   5160
atttccttgg tggggaggg gggcggttgc cctggagagg gccggggtcg gggaggttgg    5220 gggtgtcag ccaaaacgtg gaggtgtccc tctgcacgca gccctcgccc ggcgtggcgc    5280
tgacactgta ttcttatgtt gtttgaaaat gctatttata ttgtaaagaa gcgggcgggt  5340 gccctgctg cccttgtccc ttggggtca cacccatccc ctggtgggct cctgggcggc    5400
ctgcgcagat gggccacaga agggcaggcc ggagctgcac actctcccca cgaaggtatc  5460
tctgtgtctt actctgtgca aagacgcggc aaaacccagt gccctggttt ttccccaccc  5520
gagatgaagg atacgctgta ttttttgcct aatgtccctg cctctaggtt cataatgaat  5580 taaggttca tgaacgctgc gaaaaaaaaa aaaaaaaaa aaaaaaaaa aaaaaaaaaa    5640 aaaaaaaaaa aaaaaaaaa aaaaaaaaa aaaaa                              5675
```

<210> SEQ ID NO 52
<211> LENGTH: 1096
<212> TYPE: PRT
<213> ORGANISM: Homo sapiens

<400> SEQUENCE: 52

```
Met Gly Ser Glu Asp His Gly Ala Gln Asn Pro Ser Cys Lys Ile Met
1               5                   10                  15

Thr Phe Arg Pro Thr Met Glu Glu Phe Lys Asp Phe Asn Lys Tyr Val
            20                  25                  30

Ala Tyr Ile Glu Ser Gln Gly Ala His Arg Ala Gly Leu Ala Lys Ile
        35                  40                  45

Ile Pro Pro Lys Glu Trp Lys Pro Arg Gln Thr Tyr Asp Asp Ile Asp
    50                  55                  60

Asp Val Val Ile Pro Ala Pro Ile Gln Gln Val Val Thr Gly Gln Ser
65                  70                  75                  80

Gly Leu Phe Thr Gln Tyr Asn Ile Gln Lys Lys Ala Met Thr Val Gly
                85                  90                  95

Glu Tyr Arg Arg Leu Ala Asn Ser Glu Lys Tyr Cys Thr Pro Arg His
            100                 105                 110

Gln Asp Phe Asp Asp Leu Glu Arg Lys Tyr Trp Lys Asn Leu Thr Phe
        115                 120                 125

Val Ser Pro Ile Tyr Gly Ala Asp Ile Ser Gly Ser Leu Tyr Asp Asp
    130                 135                 140

Asp Val Ala Gln Trp Asn Ile Gly Ser Leu Arg Thr Ile Leu Asp Met
145                 150                 155                 160

Val Glu Arg Glu Cys Gly Thr Ile Ile Glu Gly Val Asn Thr Pro Tyr
                165                 170                 175

Leu Tyr Phe Gly Met Trp Lys Thr Thr Phe Ala Trp His Thr Glu Asp
            180                 185                 190
```

```
Met Asp Leu Tyr Ser Ile Asn Tyr Leu His Phe Gly Glu Pro Lys Ser
            195                 200                 205
Trp Tyr Ala Ile Pro Pro Glu His Gly Lys Arg Leu Glu Arg Leu Ala
    210                 215                 220
Ile Gly Phe Phe Pro Gly Ser Ser Gln Gly Cys Asp Ala Phe Leu Arg
225                 230                 235                 240
His Lys Met Thr Leu Ile Ser Pro Ile Ile Leu Lys Lys Tyr Gly Ile
                245                 250                 255
Pro Phe Ser Arg Ile Thr Gln Glu Ala Gly Glu Phe Met Ile Thr Phe
            260                 265                 270
Pro Tyr Gly Tyr His Ala Gly Phe Asn His Gly Phe Asn Cys Ala Glu
        275                 280                 285
Ser Thr Asn Phe Ala Thr Leu Arg Trp Ile Asp Tyr Gly Lys Val Ala
    290                 295                 300
Thr Gln Cys Thr Cys Arg Lys Asp Met Val Lys Ile Ser Met Asp Val
305                 310                 315                 320
Phe Val Arg Ile Leu Gln Pro Glu Arg Tyr Glu Leu Trp Lys Gln Gly
                325                 330                 335
Lys Asp Leu Thr Val Leu Asp His Thr Arg Pro Thr Ala Leu Thr Ser
            340                 345                 350
Pro Glu Leu Ser Ser Trp Ser Ala Ser Arg Ala Ser Leu Lys Ala Lys
        355                 360                 365
Leu Leu Arg Arg Ser His Arg Lys Arg Ser Gln Pro Lys Lys Pro Lys
    370                 375                 380
Pro Glu Asp Pro Lys Phe Pro Gly Glu Gly Thr Ala Gly Ala Ala Leu
385                 390                 395                 400
Leu Glu Glu Ala Gly Gly Ser Val Lys Glu Glu Ala Gly Pro Glu Val
                405                 410                 415
Asp Pro Glu Glu Glu Glu Glu Pro Gln Pro Leu Pro His Gly Arg
            420                 425                 430
Glu Ala Glu Gly Ala Glu Asp Gly Arg Gly Lys Leu Arg Pro Thr
        435                 440                 445
Lys Ala Lys Ser Glu Arg Lys Lys Ser Phe Gly Leu Leu Pro Pro
    450                 455                 460
Gln Leu Pro Pro Pro Ala His Phe Pro Ser Glu Glu Ala Leu Trp
465                 470                 475                 480
Leu Pro Ser Pro Leu Glu Pro Val Leu Gly Pro Gly Pro Ala Ala
                485                 490                 495
Met Glu Glu Ser Pro Leu Pro Ala Pro Leu Asn Val Val Pro Glu
            500                 505                 510
Val Pro Ser Glu Glu Leu Glu Ala Lys Pro Arg Pro Ile Ile Pro Met
    515                 520                 525
Leu Tyr Val Val Pro Arg Pro Gly Lys Ala Ala Phe Asn Gln Glu His
    530                 535                 540
Val Ser Cys Gln Gln Ala Phe Glu His Phe Ala Gln Lys Gly Pro Thr
545                 550                 555                 560
Trp Lys Glu Pro Val Ser Pro Met Glu Leu Thr Gly Pro Glu Asp Gly
                565                 570                 575
Ala Ala Ser Ser Gly Ala Gly Arg Met Glu Thr Lys Ala Arg Ala Gly
            580                 585                 590
Glu Gly Gln Ala Pro Ser Thr Phe Ser Lys Leu Lys Met Glu Ile Lys
        595                 600                 605
Lys Ser Arg Arg His Pro Leu Gly Arg Pro Pro Thr Arg Ser Pro Leu
```

```
          610                 615                 620
Ser Val Val Lys Gln Glu Ala Ser Ser Asp Glu Ala Ser Pro Phe
625                 630                 635                 640

Ser Gly Glu Glu Asp Val Ser Asp Pro Asp Ala Leu Arg Pro Leu Leu
                645                 650                 655

Ser Leu Gln Trp Lys Asn Arg Ala Ala Ser Phe Gln Ala Glu Arg Lys
                660                 665                 670

Phe Asn Ala Ala Ala Arg Thr Glu Pro Tyr Cys Ala Ile Cys Thr
                675                 680                 685

Leu Phe Tyr Pro Tyr Cys Gln Ala Leu Gln Thr Glu Lys Glu Ala Pro
        690                 695                 700

Ile Ala Ser Leu Gly Glu Gly Cys Pro Ala Thr Leu Pro Ser Lys Ser
705                 710                 715                 720

Arg Gln Lys Thr Arg Pro Leu Ile Pro Glu Met Cys Phe Thr Ser Gly
                725                 730                 735

Gly Glu Asn Thr Glu Pro Leu Pro Ala Asn Ser Tyr Ile Gly Asp Asp
                740                 745                 750

Gly Thr Ser Pro Leu Ile Ala Cys Gly Lys Cys Cys Leu Gln Val His
                755                 760                 765

Ala Ser Cys Tyr Gly Ile Arg Pro Glu Leu Val Asn Glu Gly Trp Thr
                770                 775                 780

Cys Ser Arg Cys Ala Ala His Ala Trp Thr Ala Glu Cys Cys Leu Cys
785                 790                 795                 800

Asn Leu Arg Gly Gly Ala Leu Gln Met Thr Thr Asp Arg Arg Trp Ile
                805                 810                 815

His Val Ile Cys Ala Ile Ala Val Pro Glu Ala Arg Phe Leu Asn Val
                820                 825                 830

Ile Glu Arg His Pro Val Asp Ile Ser Ala Ile Pro Glu Gln Arg Trp
                835                 840                 845

Lys Leu Lys Cys Val Tyr Cys Arg Lys Arg Met Lys Lys Val Ser Gly
        850                 855                 860

Ala Cys Ile Gln Cys Ser Tyr Glu His Cys Ser Thr Ser Phe His Val
865                 870                 875                 880

Thr Cys Ala His Ala Ala Gly Val Leu Met Glu Pro Asp Asp Trp Pro
                885                 890                 895

Tyr Val Val Ser Ile Thr Cys Leu Lys His Lys Ser Gly Gly His Ala
                900                 905                 910

Val Gln Leu Leu Arg Ala Val Ser Leu Gly Gln Val Val Ile Thr Lys
        915                 920                 925

Asn Arg Asn Gly Leu Tyr Tyr Arg Cys Arg Val Ile Gly Ala Ala Ser
930                 935                 940

Gln Thr Cys Tyr Glu Val Asn Phe Asp Asp Gly Ser Tyr Ser Asp Asn
945                 950                 955                 960

Leu Tyr Pro Glu Ser Ile Thr Ser Arg Asp Cys Val Gln Leu Gly Pro
                965                 970                 975

Pro Ser Glu Gly Glu Leu Val Glu Leu Arg Trp Thr Asp Gly Asn Leu
                980                 985                 990

Tyr Lys Ala Lys Phe Ile Ser Ser Val Thr Ser His Ile Tyr Gln Val
                995                 1000                1005

Glu Phe Glu Asp Gly Ser Gln Leu Thr Val Lys Arg Gly Asp Ile
        1010                1015                1020

Phe Thr Leu Glu Glu Glu Leu Pro Lys Arg Val Arg Ser Arg Leu
        1025                1030                1035
```

Ser Leu Ser Thr Gly Ala Pro Gln Glu Pro Ala Phe Ser Gly Glu
        1040                1045                1050

Glu Ala Lys Ala Ala Lys Arg Pro Arg Val Gly Thr Pro Leu Ala
    1055                1060                1065

Thr Glu Asp Ser Gly Arg Ser Gln Asp Tyr Val Ala Phe Val Glu
    1070                1075                1080

Ser Leu Leu Gln Val Gln Gly Arg Pro Gly Ala Pro Phe
    1085                1090                1095

<210> SEQ ID NO 53
<211> LENGTH: 4687
<212> TYPE: DNA
<213> ORGANISM: Homo sapiens

<400> SEQUENCE: 53

| | | | | | |
|---|---|---|---|---|---|
| gccataggtg | cgcgtcggcg | cccaggagga | cgtgtggcgc | gtggactaca | tcaggtccag | 60 |
| ccctgcggga | ccccagccag | cgcttccggg | caaggttctg | tgcacctgtt | ttctccttct | 120 |
| acgcgagtat | ctttccccctc | cggaaagaat | gggatatgcc | tgtgtccaaa | ggacaagaag | 180 |
| atgcgcgcca | gcaagcctaa | gttaaccaca | gcgcggaagt | tgagcccaaa | gcaagagcgt | 240 |
| gccgggcacc | tttaagctgt | tgtaagccc | acgtgactca | ccaagtgcgg | gccccagcgg | 300 |
| tcacgtgacg | gcgcgcgcgc | cctcgcgcag | ggagagccgg | cggtgcgcgc | gccttcgccg | 360 |
| ctgcctccca | cccacccct | cgacgggagg | gtgaggcgcg | gcgcagtgat | cgggcggccg | 420 |
| gggtcctgtg | cgcgtgcgca | gcgaacagct | gtcacctagt | gcggaacaag | tctcccaaat | 480 |
| ttcccaaatc | tccctgggcc | ggaggccact | gtcttctctt | cctcctccac | cgagtcgtgc | 540 |
| tctcgcccca | accgcgcgc | cagacactgc | cctaaccatc | atggaggtgg | ccgaggtgga | 600 |
| aagtcctctg | aaccccagct | gtaagataat | gaccttcaga | ccctccatgg | aggagttccg | 660 |
| ggagttcaac | aaataccttg | catacatgga | gtctaaagga | gcccatcgtg | cgggtcttgc | 720 |
| aaaggtgatt | cctcctaagg | agtggaagcc | aagacagtgc | tatgatgaca | ttgataattt | 780 |
| gctcattcca | gcaccaattc | agcagatggt | cacagggcag | tcaggactgt | tcactcagta | 840 |
| caacatccag | aaaaaagcga | tgactgtgaa | ggagttcagg | cagctggcca | acagtggcaa | 900 |
| atattgtact | ccaagatact | tggattacga | agatttggag | cgcaagtact | ggaagaactt | 960 |
| aactttgtg | gcacctatct | atggtgcaga | tattaatggg | agcatatatg | atgagggtgt | 1020 |
| ggatgaatgg | aacatagctc | gcctcaatac | agtcttggat | gtggttgaag | aagagtgtgg | 1080 |
| catttctatt | gagggtgtaa | ataccccata | tctctatttt | ggcatgtgga | agaccacgtt | 1140 |
| tgcatggcac | accgaagaca | tggacctcta | tagcattaat | tatctccact | tggagagcc | 1200 |
| caagtcttgg | tatgctatac | ctccggagca | tggaaaacga | cttgaaagac | tagctcaagg | 1260 |
| tttttttccca | agcagctccc | aagggtgtga | tgcatttctt | cgccacaaga | tgacattgat | 1320 |
| ttctccatca | gtattgaaga | aatatggtat | tccctttgac | aagataaccc | aggaggctgg | 1380 |
| agaattcatg | atcactttcc | catatggcta | ccatgctggt | tttaatcatg | gtttcaactg | 1440 |
| tgcagaatct | acaaattttg | ctactgtcag | atggattgac | tatggaaaag | ttgccaaatt | 1500 |
| gtgcacttgc | aggaaagaca | tggtgaagat | ttcaatggat | atctttgtga | ggaaatttca | 1560 |
| gccagacaga | tatcagcttt | ggaaacaagg | aaaggatata | tacaccattg | atcacacgaa | 1620 |
| gcctactcca | gcatccaccc | ctgaagtaaa | agcatggctg | cagaggagga | ggaaagtaag | 1680 |
| aaaagcatcc | cgaagcttcc | agtgtgctag | gtctacctct | aaaaggccta | aggctgatga | 1740 |

```
ggaagaggaa gtgtcagatg aagtcgatgg ggcagaggtc cctaaccccg actcagtcac    1800
agatgacctc aaggtcagtg aaaagtcaga agcagcagtg aagctgagga acacagaagc    1860
atcttcagaa gaagagtcat ctgctagcag gatgcaggtg gagcagaatt tatcagatca    1920
tatcaaactc tcaggaaaca gctgcttaag tacatctgta acagaagaca taaaaactga    1980
ggatgacaaa gcttatgcat atagaagtgt accttctata tccagtgagg ctgatgattc    2040
cattccattg tctagtggct atgagaagcc cgagaaatca gacccatccg agctttcatg    2100
gccaaagtca cctgagtcat gctcatcagt ggcagagagt aatggtgtgt taacagaggg    2160
agaagagagt gatgtggaga gccatgggaa tggccttgaa cctggggaaa tcccagcggt    2220
ccccagtgga gagagaaata gcttcaaagt ccccagtata gcagagggag agaacaaaac    2280
ctctaagagt tggcgccatc cacttagcag gcctccagca agatctccga tgactcttgt    2340
gaagcagcag gcgccaagtg atgaagaatt gcctgaggtt ctgtccattg aggaggaagt    2400
ggaagaaaca gagtcttggg cgaaacctct catccacctt tggcagacga agtcccctaa    2460
cttcgcagct gagcaagagt ataatgcaac agtggccagg atgaagccac actgtgccat    2520
ctgcactctg ctcatgccgt accacaagcc agatagcagc aatgaagaaa atgatgctag    2580
atgggagaca aaattagatg aagtcgttac atcggaggga aagactaagc ccctcatacc    2640
agagatgtgt tttatttata gtgaagaaaa tatagaatat tctccaccca atgccttcct    2700
tgaagaggat ggaacaagtc tccttatttc ctgtgcaaag tgctgcgtac gggttcatgc    2760
aagttgttat ggtattcctt ctcatgagat ctgtgatgga tggctgtgtg cccggtgcaa    2820
aagaaatgcg tggacagcag aatgctgtct ctgcaatttg agaggaggtg ctcttaagca    2880
aacgaagaac aataagtggg cccatgtcat gtgcgccgtt gcggtcccag aagttcgatt    2940
cactaatgtc ccagaaagga cacaaataga tgtaggcaga ataccttttac agaggttaaa    3000 attgaaatgc atcttctgca gacaccgggt taagagggtc tctggagcct gcatccagtg    3060
ttcctacggt cgctgcccgg cctccttcca tgtcacttgt gcccatgctg ctgggggtact    3120 gatggagcct gatgactggc cttatgtggt gaacattaca tgctttcgac ataaggtcaa    3180
ccccaacgtg aagtccaagg cttgcgagaa ggtcattttcc gtgggtcaaa cggtcatcac    3240
gaagcatcgg aacacccggt attacagttg cagagtgatg gctgtgacat cgcagacctt    3300
ctatgaggtc atgtttgatg atggctcctt tagcagagac acatttcctg aggatatcgt    3360
gagccgagac tgtctgaagc tgggcccacc tgctgaggga gaagtcgtcc aagtcaagtg    3420
gcccgatggc aaactctatg gagcaaaata ttttggatca aatattgccc acatgtacca    3480
ggttgagttt gaagatggat cccagatagc aatgaagaga gaggacatct cactttaga    3540 tgaagagtta cccaagagag tgaaagctcg atttttccaca gcctctgaca tgcgatttga    3600
agacacgttt tatggagcag acattatcca aggggagaga aagagacaaa gagtgctgag    3660
ctccaggttt aagaatgaat atgtggccga ccctgtatac cgcactttttt tgaagagctc    3720 tttccagaag aagtgccaga agagacagta gtctgcatac atcgctgcag ccacagagc    3780 agcttgggtt ggaagagaga agatgaaggg acatccttgg ggctgtgccg tgagttttgc    3840
tggcataggt gacagggtgt gtctctgaca gtggtaaatc gggtttccag agtttggtca    3900
ccaaaaatac aaaatacacc caatgaattg gacgcagcaa tctgaaatca tctctagtct    3960
tgctttcact tgtgagcagt tgtcttctat gatcccaaag aagttttcta agtgaaggaa    4020
aatactagta aatcacccac aaggaaaagc cactgccaca gaggaggcgg gtcccttgt    4080 gcggcttagg gccctgtcag gaaacacacg gggacctctc tctctagctc cagcaggtgg    4140
```

-continued

```
cacctcggta cccagcgggt agggcgataa tttatatatt ttccacagtc agggaaggac    4200
tctcacttat ttgtttcaaa ttgcagtttt tataaaacat ttttaaaaca caaatggcat    4260
gtatgctaat gagatttacc cgtgtgctat ctgtatttcc cttgtacaga acttttacat    4320
ttttgaatat tcctattact tttgattgtg tctgatggga actgagttgt tggcctttgt    4380
gaaatgaaat ttttggctct tgagaaagaa ttcttatgaa ttgttatgcg aattttatat    4440
atttaaagag ggagatctgg ggctgttatt tttaaacact tttttttcata atacatattc    4500 cgagtagata tttataaaat atatgtttct ttcattatgt gtttgtaaaa ttagagttta    4560
aataaatatg ctttgatgca tagttttgaa ctaatgtaac atgattttc tttttttaaaa    4620 cagcctgaaa atgtactagt gtttaaaaat aaagatttcc attttctcca aaaaaaaaaa    4680
aaaaaaa                                                              4687
```

<210> SEQ ID NO 54
<211> LENGTH: 1056
<212> TYPE: PRT
<213> ORGANISM: Homo sapiens

<400> SEQUENCE: 54

```
Met Glu Val Ala Glu Val Glu Ser Pro Leu Asn Pro Ser Cys Lys Ile
1               5                   10                  15

Met Thr Phe Arg Pro Ser Met Glu Glu Phe Arg Glu Phe Asn Lys Tyr
            20                  25                  30

Leu Ala Tyr Met Glu Ser Lys Gly Ala His Arg Ala Gly Leu Ala Lys
        35                  40                  45

Val Ile Pro Pro Lys Glu Trp Lys Pro Arg Gln Cys Tyr Asp Asp Ile
    50                  55                  60

Asp Asn Leu Leu Ile Pro Ala Pro Ile Gln Gln Met Val Thr Gly Gln
65                  70                  75                  80

Ser Gly Leu Phe Thr Gln Tyr Asn Ile Gln Lys Lys Ala Met Thr Val
                85                  90                  95

Lys Glu Phe Arg Gln Leu Ala Asn Ser Gly Lys Tyr Cys Thr Pro Arg
            100                 105                 110

Tyr Leu Asp Tyr Glu Asp Leu Glu Arg Lys Tyr Trp Lys Asn Leu Thr
        115                 120                 125

Phe Val Ala Pro Ile Tyr Gly Ala Asp Ile Asn Gly Ser Ile Tyr Asp
    130                 135                 140

Glu Gly Val Asp Glu Trp Asn Ile Ala Arg Leu Asn Thr Val Leu Asp
145                 150                 155                 160

Val Val Glu Glu Glu Cys Gly Ile Ser Ile Glu Gly Val Asn Thr Pro
                165                 170                 175

Tyr Leu Tyr Phe Gly Met Trp Lys Thr Thr Phe Ala Trp His Thr Glu
            180                 185                 190

Asp Met Asp Leu Tyr Ser Ile Asn Tyr Leu His Phe Gly Glu Pro Lys
        195                 200                 205

Ser Trp Tyr Ala Ile Pro Pro Glu His Gly Lys Arg Leu Glu Arg Leu
    210                 215                 220

Ala Gln Gly Phe Phe Pro Ser Ser Gln Gly Cys Asp Ala Phe Leu
225                 230                 235                 240

Arg His Lys Met Thr Leu Ile Ser Pro Ser Val Leu Lys Lys Tyr Gly
                245                 250                 255

Ile Pro Phe Asp Lys Ile Thr Gln Glu Ala Gly Glu Phe Met Ile Thr
            260                 265                 270
```

```
Phe Pro Tyr Gly Tyr His Ala Gly Phe Asn His Gly Phe Asn Cys Ala
            275                 280                 285

Glu Ser Thr Asn Phe Ala Thr Val Arg Trp Ile Asp Tyr Gly Lys Val
        290                 295                 300

Ala Lys Leu Cys Thr Cys Arg Lys Asp Met Val Lys Ile Ser Met Asp
305                 310                 315                 320

Ile Phe Val Arg Lys Phe Gln Pro Asp Arg Tyr Gln Leu Trp Lys Gln
                325                 330                 335

Gly Lys Asp Ile Tyr Thr Ile Asp His Thr Lys Pro Thr Pro Ala Ser
                340                 345                 350

Thr Pro Glu Val Lys Ala Trp Leu Gln Arg Arg Lys Val Arg Lys
            355                 360                 365

Ala Ser Arg Ser Phe Gln Cys Ala Arg Ser Thr Ser Lys Arg Pro Lys
            370                 375                 380

Ala Asp Glu Glu Glu Val Ser Asp Glu Val Asp Gly Ala Glu Val
385                 390                 395                 400

Pro Asn Pro Asp Ser Val Thr Asp Asp Leu Lys Val Ser Glu Lys Ser
                405                 410                 415

Glu Ala Ala Val Lys Leu Arg Asn Thr Glu Ala Ser Ser Glu Glu Glu
            420                 425                 430

Ser Ser Ala Ser Arg Met Gln Val Glu Gln Asn Leu Ser Asp His Ile
            435                 440                 445

Lys Leu Ser Gly Asn Ser Cys Leu Ser Thr Ser Val Thr Glu Asp Ile
            450                 455                 460

Lys Thr Glu Asp Asp Lys Ala Tyr Ala Tyr Arg Ser Val Pro Ser Ile
465                 470                 475                 480

Ser Ser Glu Ala Asp Asp Ser Ile Pro Leu Ser Ser Gly Tyr Glu Lys
                485                 490                 495

Pro Glu Lys Ser Asp Pro Ser Glu Leu Ser Trp Pro Lys Ser Pro Glu
                500                 505                 510

Ser Cys Ser Ser Val Ala Glu Ser Asn Gly Val Leu Thr Glu Gly Glu
            515                 520                 525

Glu Ser Asp Val Glu Ser His Gly Asn Gly Leu Glu Pro Gly Glu Ile
            530                 535                 540

Pro Ala Val Pro Ser Gly Glu Arg Asn Ser Phe Lys Val Pro Ser Ile
545                 550                 555                 560

Ala Glu Gly Glu Asn Lys Thr Ser Lys Ser Trp Arg His Pro Leu Ser
                565                 570                 575

Arg Pro Pro Ala Arg Ser Pro Met Thr Leu Val Lys Gln Gln Ala Pro
                580                 585                 590

Ser Asp Glu Glu Leu Pro Glu Val Leu Ser Ile Glu Glu Glu Val Glu
            595                 600                 605

Glu Thr Glu Ser Trp Ala Lys Pro Leu Ile His Leu Trp Gln Thr Lys
            610                 615                 620

Ser Pro Asn Phe Ala Ala Glu Gln Glu Tyr Asn Ala Thr Val Ala Arg
625                 630                 635                 640

Met Lys Pro His Cys Ala Ile Cys Thr Leu Leu Met Pro Tyr His Lys
                645                 650                 655

Pro Asp Ser Ser Asn Glu Glu Asn Asp Ala Arg Trp Glu Thr Lys Leu
                660                 665                 670

Asp Glu Val Val Thr Ser Glu Gly Lys Thr Lys Pro Leu Ile Pro Glu
            675                 680                 685
```

```
Met Cys Phe Ile Tyr Ser Glu Glu Asn Ile Glu Tyr Ser Pro Pro Asn
690                 695                 700
Ala Phe Leu Glu Glu Asp Gly Thr Ser Leu Leu Ile Ser Cys Ala Lys
705                 710                 715                 720
Cys Cys Val Arg Val His Ala Ser Cys Tyr Gly Ile Pro Ser His Glu
                725                 730                 735
Ile Cys Asp Gly Trp Leu Cys Ala Arg Cys Lys Arg Asn Ala Trp Thr
                740                 745                 750
Ala Glu Cys Cys Leu Cys Asn Leu Arg Gly Gly Ala Leu Lys Gln Thr
                755                 760                 765
Lys Asn Asn Lys Trp Ala His Val Met Cys Ala Val Ala Val Pro Glu
770                 775                 780
Val Arg Phe Thr Asn Val Pro Glu Arg Thr Gln Ile Asp Val Gly Arg
785                 790                 795                 800
Ile Pro Leu Gln Arg Leu Lys Leu Lys Cys Ile Phe Cys Arg His Arg
                805                 810                 815
Val Lys Arg Val Ser Gly Ala Cys Ile Gln Cys Ser Tyr Gly Arg Cys
                820                 825                 830
Pro Ala Ser Phe His Val Thr Cys Ala His Ala Ala Gly Val Leu Met
                835                 840                 845
Glu Pro Asp Asp Trp Pro Tyr Val Val Asn Ile Thr Cys Phe Arg His
850                 855                 860
Lys Val Asn Pro Asn Val Lys Ser Lys Ala Cys Glu Lys Val Ile Ser
865                 870                 875                 880
Val Gly Gln Thr Val Ile Thr Lys His Arg Asn Thr Arg Tyr Tyr Ser
                885                 890                 895
Cys Arg Val Met Ala Val Thr Ser Gln Thr Phe Tyr Glu Val Met Phe
                900                 905                 910
Asp Asp Gly Ser Phe Ser Arg Asp Thr Phe Pro Glu Asp Ile Val Ser
                915                 920                 925
Arg Asp Cys Leu Lys Leu Gly Pro Pro Ala Glu Gly Glu Val Val Gln
                930                 935                 940
Val Lys Trp Pro Asp Gly Lys Leu Tyr Gly Ala Lys Tyr Phe Gly Ser
945                 950                 955                 960
Asn Ile Ala His Met Tyr Gln Val Glu Phe Glu Asp Gly Ser Gln Ile
                965                 970                 975
Ala Met Lys Arg Glu Asp Ile Tyr Thr Leu Asp Glu Glu Leu Pro Lys
                980                 985                 990
Arg Val Lys Ala Arg Phe Ser Thr Ala Ser Asp Met Arg Phe Glu Asp
                995                 1000                1005
Thr Phe Tyr Gly Ala Asp Ile Ile Gln Gly Glu Arg Lys Arg Gln
        1010                1015                1020
Arg Val Leu Ser Ser Arg Phe Lys Asn Glu Tyr Val Ala Asp Pro
        1025                1030                1035
Val Tyr Arg Thr Phe Leu Lys Ser Ser Phe Gln Lys Lys Cys Gln
        1040                1045                1050
Lys Arg Gln
1055

<210> SEQ ID NO 55
<211> LENGTH: 523
<212> TYPE: PRT
<213> ORGANISM: Homo sapiens

<400> SEQUENCE: 55
```

```
Met Glu Thr Met Lys Ser Lys Ala Asn Cys Ala Gln Asn Pro Asn Cys
1               5                   10                  15

Asn Ile Met Ile Phe His Pro Thr Lys Glu Glu Phe Asn Asp Phe Asp
            20                  25                  30

Lys Tyr Ile Ala Tyr Met Glu Ser Gln Gly Ala His Arg Ala Gly Leu
        35                  40                  45

Ala Lys Ile Ile Pro Pro Lys Glu Trp Lys Ala Arg Glu Thr Tyr Asp
    50                  55                  60

Asn Ile Ser Glu Ile Leu Ile Ala Thr Pro Leu Gln Gln Val Ala Ser
65                  70                  75                  80

Gly Arg Ala Gly Val Phe Thr Gln Tyr His Lys Lys Lys Ala Met
                85                  90                  95

Thr Val Gly Glu Tyr Arg His Leu Ala Asn Ser Lys Lys Tyr Gln Thr
            100                 105                 110

Pro Pro His Gln Asn Phe Glu Asp Leu Glu Arg Lys Tyr Trp Lys Asn
        115                 120                 125

Arg Ile Tyr Asn Ser Pro Ile Tyr Gly Ala Asp Ile Ser Gly Ser Leu
    130                 135                 140

Phe Asp Glu Asn Thr Lys Gln Trp Asn Leu Gly His Leu Gly Thr Ile
145                 150                 155                 160

Gln Asp Leu Leu Glu Lys Glu Cys Gly Val Val Ile Glu Gly Val Asn
                165                 170                 175

Thr Pro Tyr Leu Tyr Phe Gly Met Trp Lys Thr Thr Phe Ala Trp His
            180                 185                 190

Thr Glu Asp Met Asp Leu Tyr Ser Ile Asn Tyr Leu His Leu Gly Glu
            195                 200                 205

Pro Lys Thr Trp Tyr Val Val Pro Glu His Gly Gln Arg Leu Glu
        210                 215                 220

Arg Leu Ala Arg Glu Leu Phe Pro Gly Ser Ser Arg Gly Cys Gly Ala
225                 230                 235                 240

Phe Leu Arg His Lys Val Ala Leu Ile Ser Pro Thr Val Leu Lys Glu
                245                 250                 255

Asn Gly Ile Pro Phe Asn Arg Ile Thr Gln Glu Ala Gly Glu Phe Met
            260                 265                 270

Val Thr Phe Pro Tyr Gly Tyr His Ala Gly Phe Asn His Gly Phe Asn
            275                 280                 285

Cys Ala Glu Ala Ile Asn Phe Ala Thr Pro Arg Trp Ile Asp Tyr Gly
        290                 295                 300

Lys Met Ala Ser Gln Cys Ser Cys Gly Glu Ala Arg Val Thr Phe Ser
305                 310                 315                 320

Met Asp Ala Phe Val Arg Ile Leu Gln Pro Glu Arg Tyr Asp Leu Trp
                325                 330                 335

Lys Arg Gly Gln Asp Arg Ala Val Val Asp His Met Glu Pro Arg Val
            340                 345                 350

Pro Ala Ser Gln Glu Leu Ser Thr Gln Lys Glu Val Gln Leu Pro Arg
        355                 360                 365

Arg Ala Ala Leu Gly Leu Arg Gln Leu Pro Ser His Trp Ala Arg His
    370                 375                 380

Ser Pro Trp Pro Met Ala Ala Arg Ser Gly Thr Arg Cys His Thr Leu
385                 390                 395                 400

Val Cys Ser Ser Leu Pro Arg Arg Ser Ala Val Ser Gly Thr Ala Thr
                405                 410                 415
```

-continued

```
Gln Pro Arg Ala Ala Val His Ser Ser Lys Lys Pro Ser Ser Thr
            420                 425                 430
Pro Ser Ser Thr Pro Gly Pro Ser Ala Gln Ile Ile His Pro Ser Asn
        435                 440                 445
Gly Arg Arg Gly Arg Gly Arg Pro Pro Gln Lys Leu Arg Ala Gln Glu
450                 455                 460
Leu Thr Leu Gln Thr Pro Ala Lys Arg Pro Leu Leu Ala Gly Thr Thr
465                 470                 475                 480
Cys Thr Ala Ser Gly Pro Glu Pro Glu Pro Leu Pro Glu Asp Gly Ala
                485                 490                 495
Leu Met Asp Lys Pro Val Pro Leu Ser Pro Gly Leu Gln His Pro Val
            500                 505                 510
Lys Ala Ser Gly Cys Ser Trp Ala Pro Val Pro
        515                 520

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
catggccttc cgtgttccta                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcctgcttca ccaccttctt                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgtgatgcca ggcacttggt                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgggctccac ctttgtggtt                                               20

<210> SEQ ID NO 60
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 60
ttggagtcca ggcagagtg                                                   19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cactgtcatc ggggcttgtg                                                  20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tttctggttg gctgtgactg                                                  20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gagttagggt tgacttggcc                                                  20

<210> SEQ ID NO 64
<211> LENGTH: 423
<212> TYPE: PRT
<213> ORGANISM: Homo sapiens

<400> SEQUENCE: 64
```

Met Glu Thr Met Lys Ser Lys Ala Asn Cys Ala Gln Asn Pro Asn Cys
1               5                   10                  15

Asn Ile Met Ile Phe His Pro Thr Lys Glu Glu Phe Asn Asp Phe Asp
            20                  25                  30

Lys Tyr Ile Ala Tyr Met Glu Ser Gln Gly Ala His Arg Ala Gly Leu
        35                  40                  45

Ala Lys Ile Ile Pro Pro Lys Glu Trp Lys Ala Arg Glu Thr Tyr Asp
    50                  55                  60

Asn Ile Ser Glu Ile Leu Ile Ala Thr Pro Leu Gln Gln Val Ala Ser
65                  70                  75                  80

Gly Arg Ala Gly Val Phe Thr Gln Tyr His Lys Lys Lys Lys Ala Met
                85                  90                  95

Thr Val Gly Glu Tyr Arg His Leu Ala Asn Ser Lys Lys Tyr Gln Thr
            100                 105                 110

-continued

```
Pro Pro His Gln Asn Phe Glu Asp Leu Glu Arg Lys Tyr Trp Lys Asn
        115                 120                 125
Arg Ile Tyr Asn Ser Pro Ile Tyr Gly Ala Asp Ile Ser Gly Ser Leu
    130                 135                 140
Phe Asp Glu Asn Thr Lys Gln Trp Asn Leu Gly His Leu Gly Thr Ile
145                 150                 155                 160
Gln Asp Leu Leu Glu Lys Glu Cys Gly Val Val Ile Glu Gly Val Asn
                165                 170                 175
Thr Pro Tyr Leu Tyr Phe Gly Met Trp Lys Thr Thr Phe Ala Trp His
                180                 185                 190
Thr Glu Asp Met Asp Leu Tyr Ser Ile Asn Tyr Leu His Leu Gly Glu
                195                 200                 205
Pro Lys Thr Trp Tyr Val Val Pro Pro Glu His Gly Gln Arg Leu Glu
                210                 215                 220
Arg Leu Ala Arg Glu Leu Phe Pro Gly Ser Ser Arg Gly Cys Gly Ala
225                 230                 235                 240
Phe Leu Arg His Lys Val Ala Leu Ile Ser Pro Thr Val Leu Lys Glu
                245                 250                 255
Asn Gly Ile Pro Phe Asn Arg Ile Thr Gln Glu Ala Gly Glu Phe Met
                260                 265                 270
Val Thr Phe Pro Tyr Gly Tyr His Ala Gly Phe Asn His Gly Phe Asn
                275                 280                 285
Cys Ala Glu Ala Ile Asn Phe Ala Thr Pro Arg Trp Ile Asp Tyr Gly
                290                 295                 300
Lys Met Ala Ser Gln Cys Ser Cys Gly Glu Ala Arg Val Thr Phe Ser
305                 310                 315                 320
Met Asp Ala Phe Val Arg Ile Leu Gln Pro Glu Arg Tyr Asp Leu Trp
                325                 330                 335
Lys Arg Gly Gln Asp Arg Ala Val Val Asp His Met Glu Pro Arg Val
                340                 345                 350
Pro Ala Ser Gln Glu Leu Ser Thr Gln Lys Glu Val Gln Leu Pro Arg
                355                 360                 365
Arg Ala Ala Leu Gly Leu Arg Gln Leu Pro Ser His Trp Ala Arg His
            370                 375                 380
Ser Pro Trp Pro Met Ala Ala Arg Ser Gly Thr Arg Cys His Thr Leu
385                 390                 395                 400
Val Cys Ser Ser Leu Pro Arg Arg Ser Ala Val Ser Gly Thr Ala Thr
                405                 410                 415
Gln Pro Arg Ala Ala Ala Val
            420

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gly Gly Gly Cys
1               5
```